United States Patent
Semizarov et al.

(10) Patent No.: US 10,047,403 B2
(45) Date of Patent: Aug. 14, 2018

(54) DIAGNOSTIC METHODS FOR DETERMINING PROGNOSIS OF NON-SMALL CELL LUNG CANCER

(71) Applicant: Abbott Molecular Inc., Des Plaines, IL (US)

(72) Inventors: Dimitri Semizarov, Chicago, IL (US); Xin Lu, Libertyville, IL (US); Ke Zhang, Grand Forks, ND (US); Rick R. Lesniewski, Collegeville, PA (US); John S. Coon, Oak Park, IL (US)

(73) Assignee: Abbott Molecular Inc., Des Plaines, IL (US)

( * ) Notice: Subject to any disclaimer, the term of this patent is extended or adjusted under 35 U.S.C. 154(b) by 0 days.

(21) Appl. No.: 15/019,829

(22) Filed: Feb. 9, 2016

(65) Prior Publication Data
US 2016/0237504 A1    Aug. 18, 2016

Related U.S. Application Data

(63) Continuation of application No. 12/910,891, filed on Oct. 25, 2010, now Pat. No. 9,291,625.
(Continued)

(51) Int. Cl.
*C12Q 1/68* (2018.01)
*C12Q 1/6886* (2018.01)
*G01N 33/574* (2006.01)

(52) U.S. Cl.
CPC ..... *C12Q 1/6886* (2013.01); *G01N 33/57423* (2013.01); *C12Q 2600/106* (2013.01);
(Continued)

(58) Field of Classification Search
CPC ............ C12Q 1/6886; C12Q 2600/106; C12Q 2600/112; C12Q 2600/118;
(Continued)

(56) References Cited

U.S. PATENT DOCUMENTS 4,683,195 A    7/1987    Mullis et al.
4,683,202 A    7/1987    Mullis
(Continued)

FOREIGN PATENT DOCUMENTS

CN    1384207 A    12/2002
EP    320308 A2    6/1989
(Continued)

OTHER PUBLICATIONS

Hirsch et al., Increased Epidermal Growth Factor Receptor Gene Copy Number Detected by Fluorescence In Situ Hybridization Associates With Increased Sensitivity to Gefitinib in Patients With Bronchioloalveolar Carcinoma Subtypes: A Southwest Oncology Group Study, J. Clinical Oncology, vol. 23 _ No. 28 _ Oct. 1, 2005.*
(Continued)

*Primary Examiner* — Reza Ghafoorian
(74) *Attorney, Agent, or Firm* — Melissa E. Kolom; Casimir Jones, S.C.

(57) ABSTRACT

The present disclosure provides methods for identifying early stage non-small-cell lung cancer (NSCLC) patients who will have an unfavorable prognosis for the recurrence of lung cancer after surgical resection. The methods are based in part on the discovery of chromosomal copy number abnormalities that can be used for prognostic classification. The methods preferably use fluorescence in situ hybridization with fluorescently labeled nucleic acid probes to hybridize to patient samples to quantify the chromosomal copy number of these genetic loci.

11 Claims, 162 Drawing Sheets

Figure 24 is a Kaplan-Meier plot showing the overall survival (OS) in days for a 78 patient cohort with NSCLC stage Ia-IIa.

Related U.S. Application Data

(60) Provisional application No. 61/254,968, filed on Oct. 26, 2009.

(52) U.S. Cl.
CPC .. *C12Q 2600/112* (2013.01); *C12Q 2600/118* (2013.01); *C12Q 2600/156* (2013.01); *C12Q 2600/178* (2013.01); *G01N 2800/52* (2013.01); *G01N 2800/54* (2013.01); *G01N 2800/56* (2013.01); *G01N 2800/60* (2013.01)

(58) Field of Classification Search
CPC ........ C12Q 2600/156; C12Q 2600/178; G01N 33/57423; G01N 2800/52; G01N 2800/54; G01N 2800/56
See application file for complete search history.

(56) References Cited

U.S. PATENT DOCUMENTS

| | | |
|---|---|---|
| 5,322,770 A | 6/1994 | Gelfand |
| 5,491,224 A | 2/1996 | Bittner et al. |
| 5,756,696 A | 5/1998 | Gray et al. |
| 5,776,688 A | 7/1998 | Bittner et al. |
| 6,174,681 B1 | 1/2001 | Halling et al. |
| 7,897,329 B2 | 3/2011 | Nakamura et al. |
| 2003/0087248 A1 | 5/2003 | Morrison et al. |
| 2006/0024692 A1 | 2/2006 | Nakamura et al. |
| 2006/0063194 A1 | 3/2006 | Morrison et al. |
| 2006/0078885 A1 | 4/2006 | Katz et al. |

FOREIGN PATENT DOCUMENTS

| | | |
|---|---|---|
| EP | 439182 B1 | 4/1996 |
| WO | WO-05117553 A2 | 12/2005 |
| WO | WO-2006128195 A2 | 11/2006 |
| WO | WO-2007055553 A1 | 5/2007 |
| WO | WO-2008050356 A1 | 5/2008 |
| WO | WO-2008095049 A2 | 8/2008 |
| WO | WO-2009129154 A1 | 10/2009 |

OTHER PUBLICATIONS

Aviel-Ronen S., et al., "Genomic Markers for Malignant Progression in Pulmonary Adenocarcinoma with Bronchioloalveolar Features," Proceedings of the National Academy of Science, USA, 2008, vol. 105 (29), pp. 10155-10160.

Bions H., et al., "Genome Wide Snp Comparative Analysis Between Egfr and Kras Mutated Nscic and Characterization of Two Models of Oncogenic Cooperation in Non-small Cell Lung Carcinoma," BMC Medical Genomics, 2008, vol. 1, pp. 25.

Broet P., et al., "Prediction of Clinical Outcome in Multiple Lung Cancer Cohorts by Integrative Genomics: Implications for Chemotherapy Selection," Cancer Research, 2009, vol. 69 (3), pp. 1055-1062.

Cappuzzo F., et al., "Increased MET Gene Copy Number Negatively Affects Survival of Surgically Resected Non-Small-Cell Lung Cancer Patients," Journal of Clinical Oncology, 2009, vol. 27 (10), pp. 1667-1674.

Chen L., et al., "Lysine Acetyltransferase GCN5 Potentiates the Growth of Non-Small Cell Lung Cancer via Promotion of E2F1, Cyclin D1, and Cyclin E1 Expression," Journal of Biological Chemistry, 2013, vol. 288 (20), pp. 14510-14521.

ELF® 97 mRNA In Situ Hybridization Kits, Product Information, by Molecular Probes, Revised: Feb. 2, 2001, MP 06604.

Erlanson M., et al., "Expression of Cyclin E and the Cyclin-dependent Kinase Inhibitor p27 in Malignant lymphomas-prognostic Implications," Blood, 1998, vol. 92 (3), pp. 770-777.

Etemadmoghadam D., et al., "Integrated Genome-Wide DNA Copy Number and Expression Analysis Identifies Distinct Mechanisms of Primary Chemoresistance in Ovarian Carcinomas," Clinical Cancer Research, 2009, vol. 15 (4), pp. 1417-1427.

European Search Report for Application No. EP13187129, dated Oct. 25, 2013, 10 pages.

Final Office Action dated Jan. 7, 2015 for U.S. Appl. No. 12/910,891, filed Oct. 25, 2010.

Final Office Action dated Jul. 31, 2013 for U.S. Appl. No. 12/910,891, filed Oct. 25, 2010.

Final Office Action dated Jan. 4, 2013 for U.S. Appl. No. 12/910,892, filed Oct. 25, 2010.

Final Office Action dated Jan. 7, 2015 for U.S. Appl. No. 12/910,892, filed Oct. 25, 2010.

Fong K.M., et al., "MYCL Genotypes and Loss of Heterozygosity in Non-Small-Cell Lung Cancer," British Journal of Cancer, 1996, vol. 74 (12), pp. 1975-1978.

Freier K., et al., "Recurrent Copy Number Gain of Transcription Factor SOX2 and Corresponding High Protein Expression in Oral Squamous Cell Carcinoma," Genes, Chromosomes and Cancer, 2010, vol. 49 (1), pp. 9-16.

Galimberti F., et al., "Targeting the Cyclin E-Cdk-2 Complex Represses Lung Cancer Growth by Triggering Anaphase Catastrophe," Clinical Cancer Research, 2010, vol. 16 (1), pp. 109-120.

Gallegos Ruiz M.I., et al., "Integration of Gene Dosage and Gene Expression in Non-small Cell Lung Cancer, Identification of HSP90 as Potential Target," Plos One, 2008, vol. 3 (3), pp. E1722.

Gasparian A.V., et al., "Allelic Imbalance and Instability of Microsatellite Loci on Chromosome 1p in Human Non-Small-Cell Lung Cancer," British Journal of Cancer, 1998, vol. 77 (10), pp. 1604-1611.

Halling K.C., et al., "Fluorescence In Situ Hybridization in Diagnostic Cytology," Human Pathology, 2007, vol. 38, pp. 1137-1144.

Hirsch F.R., et al., "Epidermal Growth Factor Receptor in Non-Small-Cell Lung Carcinomas: Correlation Between Gene Copy Number and Protein Expression and Impact on Prognosis," Journal of Clinical Oncology, 2003, vol. 21 (20), pp. 3798-3807.

Huang L.N., et al., "Meta-Analysis for Cyclin E in Lung Cancer Survival," Clinica Chimica Acta, 2012, vol. 413 (7-8), pp. 663-668.

International Preliminary Report on Patentability for Application No. PCT/US2010/053893, dated May 1, 2012, 1 page.

International Preliminary Report on Patentability for Application No. PCT/US2010/053900, dated May 1, 2012, 1 page.

International Search Report and Written Opinion for Application No. PCT/US2010/053893, dated Jun. 10, 2011, 12 pages.

International Search Report and Written Opinion for Application No. PCT/US2010/053900, dated Feb. 11, 2011, 12 pages.

Invitation to Pay Additional Fees for Application No. PCT/US2010/053893, dated Mar. 28, 2011, 6 pages.

Kim T.M., et al., "Genome-Wide Screening of Genomic Alterations and their Clinicopathologic Implications in Non-Small Cell Lung Cancers," Clinical Cancer Research, 2005, vol. 11 (23), pp. 8235-8242.

Leung S.Y., et al., "Comprehensive Analysis of 19q12 Amplicon in Human Gastric Cancers," Modern Pathology, 2006, vol. 19 (6), pp. 854-863.

Marone M., et al., "Analysis of Cyclin E and CDK2 in Ovarian Cancer: Gene Amplification and RNA Overexpression," International Journal of Cancer, 1998, vol. 75, pp. 34-39.

Marshall R.L., et al., "Detection of HCV RNA by the Asymmetric Gap Ligase Chain Reaction," PCR Methods and Applications, 1994, vol. 4 (2), pp. 80-84.

Matsuzaki H., et al., "Genotyping Over 100,000 SNPs on a Pair of Oligonucleotide Arrays," Nature Methods, 2004, vol. 1 (2), pp. 109-111.

Michelland S., et al., "Comparison of Chromosomal Imbalances in Neuroendocrine and Non-small-cell Lung Carcinomas," Cancer Genetics and Cytogenetics, 1999, vol. 114 (1), pp. 22-30.

Mishina T., et al., "Cyclin E Expression, a Potential Prognostic Marker for Non-Small Cell Lung Cancers," Clinical Cancer Research, 2000, vol. 6 (1), pp. 11-16.

Morrison, L.E. et al., "Labeling Fluorescence In Situ Hybridization Probes for Genomic Targets," Methods in Molecular Biology, 2002, vol. 204, pp. 21-40.

(56) References Cited

OTHER PUBLICATIONS

Muller, et al., "Cyclin E is the Only Cyclin-dependent Kinase 2-associated Cyclin that Predicts Metastasis and Survival in Early Stage Non-Small Cell Lung Cancer," Cancer Research, 2001, vol. 61, pp. 647-653.
Muller K.M., et al., "New Aspects of Lung Tumor Pathology," Verhandlungen der Deutschen Gesellschaft fur Pathology, 1999, vol. 83, pp. 168-183.
Nakayama K., et al., "Amplicon Profiles in Ovarian Serous Carcinomas," International Journal of Cancer, 2007, vol. 120 (12), pp. 2613-2617.
Nath J., et al., "Fluorescence in Situ Hybridization (FISH): DNA Probe Production and Hybridization Criteria," Biotechnic & Histochemistry, 1998, vol. 73 (1), pp. 6-22.
Non-Final Office Action dated May 7, 2015 for U.S. Appl. No. 12/910,891, filed Oct. 25, 2010.
Non-Final Office Action dated Jul. 9, 2014 for U.S. Appl. No. 12/910,891, filed Oct. 25, 2010.
Non-Final Office Action dated Oct. 12, 2012 for U.S. Appl. No. 12/910,891, filed Oct. 25, 2010.
Non-Final Office Action dated Jun. 21, 2013 for U.S. Appl. No. 12/910,892, filed Oct. 25, 2010.
Non-Final Office Action dated Jan. 29, 2014 for U.S. Appl. No. 12/910,891, filed Oct. 25, 2010.
Non-Final Office Action dated May 7, 2015 for U.S. Appl. No. 12/910,892, filed Oct. 25, 2010.
Non-Final Office Action dated May 8, 2012 for U.S. Appl. No. 12/910,892, filed Oct. 25, 2010.
Non-Final Office Action dated Jul. 10, 2014 for U.S. Appl. No. 12/910,892, filed Oct. 25, 2010.
Non-Final Office Action dated Dec. 30, 2013 for U.S. Appl. No. 12/910,892, filed Oct. 25, 2010.
Peng W.X., et al., "Array-Based Comparative Genomic Hybridization Analysis of High-Grade Neuroendocrine Tumors of the Lung," Cancer Science, 2005, vol. 96 (10), pp. 661-667.
Schrami P., et al., "Cyclin E Overexpression and Amplification in Human Tumours," The Journal of Pathology, 2003, vol. 200 (3), pp. 375-382.
Scott W.J., et al., "Treatment of Non-Small Cell Lung Cancer Stage I and Stage II: ACCP Evidence-Based Clinical Practice Guidelines," Chest, 2007, vol. 132 (3 Suppl.), pp. 234S-242S.
Singhal S., et al., "Prognostic Implications of Cell Cycle, Apoptosis, and Angiogenesis Biomarkers in Non-Small Cell Lung Cancer: A Review," Clinical Cancer Research, 2005, vol. 11 (11), pp. 3974-3986.
Wheeless L.L., et al., "Bladder Irrigation Specimens Assayed by Fluorescence In Situ Hybridization to Interphase Nuclei," Cytometry, 1994, vol. 17 (4), pp. 319-326.
Wrage M., et al., "Genomic Profiles Associated with Early Micrometastasis in Lung Cancer: Relevance of 4q Deletion," Clinical Cancer Research, 2009, vol. 15 (5), pp. 1566-1574.
Yasmeen A., et al., "E- and A-Type Cyclins as Markers for Cancer Diagnosis and Prognosis," Expert Review of Molecular Diagnostics, 2003, vol. 3 (5), pp. 617-633.
Zhao X., et al., "Homozygous Deletions and Chromosome Amplifications in Human Lung Carcinomas Revealed by Single Nucleotide Polymorphism Array Analysis," Cancer Research, 2005, vol. 65 (13), pp. 5561-5570.
United States Patent Office Action for U.S. Appl. No. 15/019,689 dated May 18, 2017 (19 pages).
United States Patent Office Action for U.S. Appl. No. 15/019,689 dated Oct. 20, 2017 (9 pages).

\* cited by examiner

Figure 1 is a Kaplan-Meier plot showing the overall survival (OS) in days for a 78 patient cohort with NSCLC stage Ia-IIa.

Figure 2 is a Kaplan-Meier plot showing the overall survival (OS) in days for a 78 patient cohort with NSCLC stage Ia-IIa.

Figure 3 is a Kaplan-Meier plot showing the overall survival (OS) in days for a 78 patient cohort with NSCLC stage Ia-IIa.

Figure 4 is a Kaplan-Meier plot showing the overall survival (OS) in days for a 71 patient cohort with NSCLC stage Ib-IIb.

Figure 5 is a Kaplan-Meier plot showing the overall survival (OS) in days for a 102 patient cohort with NSCLC stage Ia-IIb.

Figure 6 is a Kaplan-Meier plot showing the overall survival (OS) in days for a 78 patient cohort with NSCLC stage Ia-IIa.

Figure 7 is a Kaplan-Meier plot showing the time to recurrence (TTR) in days for a 74 patient cohort with NSCLC stage Ia-IIa.

Figure 8 is a Kaplan-Meier plot showing the overall survival (OS) in days for a 78 patient cohort with NSCLC stage Ia-IIa.

Figure 9 is a Kaplan-Meier plot showing the overall survival (OS) in days for a 78 patient cohort with NSCLC stage Ia-IIa.

Figure 10 is a Kaplan-Meier plot showing the overall survival (OS) in days for a 78 patient cohort with NSCLC stage Ia-IIa.

Figure 11 is a Kaplan-Meier plot showing the time to recurrence (TTR) in days for a 74 patient cohort with NSCLC stage Ia-IIa.

Figure 12 is a Kaplan-Meier plot showing the overall survival (OS) in days for a 78 patient cohort with NSCLC stage Ia-IIa.

Figure 13 is a Kaplan-Meier plot showing the overall survival (OS) in days for a 78 patient cohort with NSCLC stage Ia-IIa.

Figure 14 is a Kaplan-Meier plot showing the overall survival (OS) in days for a 78 patient cohort with NSCLC stage Ia-IIa.

Figure 15 is a Kaplan-Meier plot showing the time to recurrence (TTR) in days for a 74 patient cohort with NSCLC stage Ia-IIa.

Figure 16 is a Kaplan-Meier plot showing the overall survival (OS) in days for a 78 patient cohort with NSCLC stage Ia-IIa.

Figure 17 is a Kaplan-Meier plot showing the time to recurrence (TTR) in days for a 74 patient cohort with NSCLC stage Ia-IIa.

Figure 18 is a Kaplan-Meier plot showing the overall survival (OS) in days for a 78 patient cohort with NSCLC stage Ia-IIa.

Figure 19 is a Kaplan-Meier plot showing the overall survival (OS) in days for a 78 patient cohort with NSCLC stage Ia-IIb.

Figure 20 is a Kaplan-Meier plot showing the overall survival (OS) in days for a 78 patient cohort with NSCLC stage Ia-IIa.

Figure 21 is a Kaplan-Meier plot showing the time to recurrence (TTR) in days for a 74 patient cohort with NSCLC stage Ia-IIa.

Figure 22 is a Kaplan-Meier plot showing the overall survival (OS) in days for a 78 patient cohort with NSCLC stage Ia-IIa.

Figure 23 is a Kaplan-Meier plot showing the overall survival (OS) in days for a 78 patient cohort with NSCLC stage Ia-IIa.

Figure 24 is a Kaplan-Meier plot showing the overall survival (OS) in days for a 78 patient cohort with NSCLC stage Ia-IIa.

Figure 24 is a Kaplan-Meier plot showing the overall survival (OS) in days for a 78 patient cohort with NSCLC stage Ia-IIa.

Figure 26 is a Kaplan-Meier plot showing the time to recurrence (TTR) in days for a 66 patient cohort with NSCLC stage Ib-IIb.

Figure 27 is a Kaplan-Meier plot showing the overall survival (OS) in days for a 78 patient cohort with NSCLC stage Ia-IIa.

Figure 28 is a Kaplan-Meier plot showing the overall survival (OS) in days for a 71 patient cohort with NSCLC stage Ib-IIb.

Figure 29 is a Kaplan-Meier plot showing the overall survival (OS) in days for a 102 patient cohort with NSCLC stage Ia-IIb.

Figure 30 is a Kaplan-Meier plot showing the overall survival (OS) in days for a 102 patient cohort with NSCLC stage Ia-IIb.

Figure 31 is a Kaplan-Meier plot showing the overall survival (OS) in days for a 78 patient cohort with NSCLC stage Ia-IIa.

Figure 32 is a Kaplan-Meier plot showing the overall survival (OS) in days for a 78 patient cohort with NSCLC stage Ia-IIa.

Figure 33 is a Kaplan-Meier plot showing the overall survival (OS) in days for a 78 patient cohort with NSCLC stage Ia-IIa.

Figure 34 is a Kaplan-Meier plot showing the overall survival (OS) in days for a 78 patient cohort with NSCLC stage Ia-IIa.

Figure 35 is a Kaplan-Meier plot showing the overall survival (OS) in days for a 102 patient cohort with NSCLC stage Ia-IIb.

Figure 36 is a Kaplan-Meier plot showing the overall survival (OS) in days for a 78 patient cohort with NSCLC stage Ia-IIa.

Figure 37 is a Kaplan-Meier plot showing the overall survival (OS) in days for a 102 patient cohort with NSCLC stage Ia-IIb.

Figure 38 is a Kaplan-Meier plot showing the time to recurrence (TTR) in days for a 97 patient cohort with NSCLC stage Ia-IIb.

Figure 39 is a Kaplan-Meier plot showing the time to recurrence (TTR) in days for a 97 patient cohort with NSCLC stage Ia-IIb.

Figure 40 is a Kaplan-Meier plot showing the time to recurrence (TTR) in days for a 97 patient cohort with NSCLC stage Ia-IIb.

Figure 41 is a Kaplan-Meier plot showing the overall survival (OS) in days for a 78 patient cohort with NSCLC stage Ia-IIa.

Figure 42 is a Kaplan-Meier plot showing the overall survival (OS) in days for a 78 patient cohort with NSCLC stage Ia-IIa.

Figure 43 is a Kaplan-Meier plot showing the overall survival (OS) in days for a 102 patient cohort with NSCLC stage Ia-IIb.

Figure 44 is a Kaplan-Meier plot showing the time to recurrence (TTR) in days for a 97 patient cohort with NSCLC stage Ia-IIb.

Figure 45 is a Kaplan-Meier plot showing the overall survival (OS) in days for a 78 patient cohort with NSCLC stage Ia-IIa.

Figure 46 is a Kaplan-Meier plot showing the overall survival (OS) in days for a 78 patient cohort with NSCLC stage Ia-IIa.

Figure 47 is a Kaplan-Meier plot showing the time to recurrence (TTR) in days for a 97 patient cohort with NSCLC stage Ia-IIb.

Figure 48 is a Kaplan-Meier plot showing the overall survival (OS) in days for a 78 patient cohort with NSCLC stage Ia-IIa.

Figure 49 is a Kaplan-Meier plot showing the overall survival (OS) in days for a 78 patient cohort with NSCLC stage Ia-IIa.

Figure 50 is a Kaplan-Meier plot showing the time to recurrence (TTR) in days for a 97 patient cohort with NSCLC stage Ia-IIb.

Figure 51 is a Kaplan-Meier plot showing the overall survival (OS) in days for a 78 patient cohort with NSCLC stage Ia-IIa.

Figure 52 is a Kaplan-Meier plot showing the time to recurrence (TTR) in days for a 74 patient cohort with NSCLC stage Ia-IIa.

Figure 53 is a Kaplan-Meier plot showing the overall survival (OS) in days for a 78 patient cohort with NSCLC stage Ia-IIa.

Figure 53 is a Kaplan-Meier plot showing the overall survival (OS) in days for a 78 patient cohort with NSCLC stage Ia-IIa.

Figure 55 is a Kaplan-Meier plot showing the time to recurrence (TTR) in days for a 97 patient cohort with NSCLC stage Ia-IIb.

Figure 56 is a Kaplan-Meier plot showing the time to recurrence (TTR) in days for a 97 patient cohort with NSCLC stage Ia-IIb.

Figure 57 is a Kaplan-Meier plot showing the time to recurrence (TTR) in days for a 97 patient cohort with NSCLC stage Ia-IIb.

Figure 58 is a Kaplan-Meier plot showing the overall survival (OS) in days for a 78 patient cohort with NSCLC stage Ia-IIa.

Figure 59 is a Kaplan-Meier plot showing the overall survival (OS) in days for a 78 patient cohort with NSCLC stage Ia-IIa.

Figure 60 is a Kaplan-Meier plot showing the overall survival (OS) in days for a 102 patient cohort with NSCLC stage Ia-IIb.

Figure 61 is a plot indicating average copy number, comparing the average copy number pattern obtained using a training (100K array) data set and a validating (SNP 6.0 array) data set.

Figure 62 is a Kaplan-Meier plot showing the overall survival (OS) in days for a 78 patient cohort with NSCLC stage Ia-IIa.

Figure 63 is a Kaplan-Meier plot showing the time to recurrence (TTR) in days for a 74 patient cohort with NSCLC stage Ia-IIa.

Figure 64 is a Kaplan-Meier plot showing the overall survival (OS) in days for a 74 patient cohort with NSCLC stage Ia-IIa.

Figure 65 is a Kaplan-Meier plot showing the time to recurrence (TTR) in days for a 74 patient cohort with NSCLC stage Ia-IIa.

Figure 66 is a Kaplan-Meier plot showing the overall survival (OS) in days for a 74 patient cohort with NSCLC stage Ia-IIa.

Figure 67 is a Kaplan-Meier plot showing the time to recurrence (TTR) in days for a 74 patient cohort with NSCLC stage Ia-IIa.

Figure 68 is a Kaplan-Meier plot showing the time to recurrence (TTR) in days for a 74 patient cohort with NSCLC stage Ia-IIa.

Figure 69 is a Kaplan-Meier plot showing the overall survival (OS) in days for a 74 patient cohort with NSCLC stage Ia-IIa.

Figure 70 is a Kaplan-Meier plot showing the time to recurrence (TTR) in days for a 74 patient cohort with NSCLC stage Ia-IIa.

Figure 71 is a Kaplan-Meier plot showing the overall survival (OS) in days for a 74 patient cohort with NSCLC stage Ia-IIa.

Figure 72 is a Kaplan-Meier plot showing the time to recurrence (TTR) in days for a 74 patient cohort with NSCLC stage Ia-IIa.

Figure 73 is a Kaplan-Meier plot showing the overall survival (OS) in days for a 74 patient cohort with NSCLC stage Ia-IIa.

Figure 74 is a Kaplan-Meier plot showing the time to recurrence (TTR) in days for a 74 patient cohort with NSCLC stage Ia-IIa.

Figure 75 is a Kaplan-Meier plot showing the overall survival (OS) in days for a 74 patient cohort with NSCLC stage Ia-IIa.

Figure 76 is a Kaplan-Meier plot showing the time to recurrence (TTR) in days for a 74 patient cohort with NSCLC stage Ia-IIa.

Figure 77 is a Kaplan-Meier plot showing the overall survival (OS) in days for a 74 patient cohort with NSCLC stage Ia-IIa.

Figure 78 is a Kaplan-Meier plot showing the time to recurrence (TTR) in days for a 74 patient cohort with NSCLC stage Ia-IIa.

Figure 79 is a Kaplan-Meier plot showing the overall survival (OS) in days for a 74 patient cohort with NSCLC stage Ia-IIa.

Figure 80 is a Kaplan-Meier plot showing the time to recurrence (TTR) in days for a 74 patient cohort with NSCLC stage Ia-IIa.

Figure 81 is a Kaplan-Meier plot showing the overall survival (OS) in days for a 74 patient cohort with NSCLC stage Ia-IIa.

Figure 82 is a Kaplan-Meier plot showing the time to recurrence (TTR) in days for a 74 patient cohort with NSCLC stage Ia-IIa.

Figure 83 is a Kaplan-Meier plot showing the overall survival (OS) in days for a 74 patient cohort with NSCLC stage Ia-IIa.

Figure 84 is a Kaplan-Meier plot showing the time to recurrence (TTR) in days for a 74 patient cohort with NSCLC stage Ia-IIa.

Figure 85 is a Kaplan-Meier plot showing the overall survival (OS) in days for a 74 patient cohort with NSCLC stage Ia-IIa.

Figure 86 is a Kaplan-Meier plot showing the time to recurrence (TTR) in days for a 74 patient cohort with NSCLC stage Ia-IIa.

Figure 87 is a Kaplan-Meier plot showing the overall survival (OS) in days for a 74 patient cohort with NSCLC stage Ia-IIa.

Figure 88 is a Kaplan-Meier plot showing the overall survival (OS) in days for a 74 patient cohort with NSCLC stage Ia-IIa.

Figure 89 is a Kaplan-Meier plot showing the time to recurrence (TTR) in days for a 74 patient cohort with NSCLC stage Ia-IIa.

Figure 89 is a Kaplan-Meier plot showing the time to recurrence (TTR) in days for a 74 patient cohort with NSCLC stage Ia-IIa.

Figure 91 is a Kaplan-Meier plot showing the overall survival (OS) in days for a 74 patient cohort with NSCLC stage Ia-IIa.

Figure 92 is a Kaplan-Meier plot showing the time to recurrence (TTR) in days for a 74 patient cohort with NSCLC stage Ia-IIa.

Figure 93 is a Kaplan-Meier plot showing the overall survival (OS) in days for a 74 patient cohort with NSCLC stage Ia-IIa.

Figure 94 is a Kaplan-Meier plot showing the time to recurrence (TTR) in days for a 74 patient cohort with NSCLC stage Ia-IIa.

Figure 95 is a Kaplan-Meier plot showing the overall survival (OS) in days for a 74 patient cohort with NSCLC stage Ia-IIa.

Figure 96 is a Kaplan-Meier plot showing the time to recurrence (TTR) in days for a 74 patient cohort with NSCLC stage Ia-IIa.

Figure 97 is a Kaplan-Meier plot showing the overall survival (OS) in days for a 74 patient cohort with NSCLC stage Ia-IIa.

Figure 98 is a Kaplan-Meier plot showing the time to recurrence (TTR) in days for a 74 patient cohort with NSCLC stage Ia-IIa.

Figure 99 is a Kaplan-Meier plot showing the overall survival (OS) in days for a 74 patient cohort with NSCLC stage Ia-IIa.

Figure 100 is a Kaplan-Meier plot showing the time to recurrence (TTR) in days for a 74 patient cohort with NSCLC stage Ia-IIa.

Figure 101 is a Kaplan-Meier plot showing the overall survival (OS) in days for a 74 patient cohort with NSCLC stage Ia-IIa.

Figure 102 is a Kaplan-Meier plot showing the time to recurrence (TTR) in days for a 74 patient cohort with NSCLC stage Ia-IIa.

Figure 103 is a Kaplan-Meier plot showing the overall survival (OS) in days for a 74 patient cohort with NSCLC stage Ia-IIa.

Figure 104 is a Kaplan-Meier plot showing the time to recurrence (TTR) in days for a 74 patient cohort with NSCLC stage Ia-IIa.

Figure 105 is a Kaplan-Meier plot showing the overall survival (OS) in days for a 74 patient cohort with NSCLC stage Ia-IIa.

Figure 106 is a Kaplan-Meier plot showing the time to recurrence (TTR) in days for a 74 patient cohort with NSCLC stage Ia-IIa.

Figure 107 is a Kaplan-Meier plot showing the overall survival (OS) in days for a 74 patient cohort with NSCLC stage Ia-IIa.

Figure 108 is a Kaplan-Meier plot showing the time to recurrence (TTR) in days for a 74 patient cohort with NSCLC stage Ia-IIa.

Figure 109 is a Kaplan-Meier plot showing the overall survival (OS) in days for a 74 patient cohort with NSCLC stage Ia-IIa.

Figure 110 is a Kaplan-Meier plot showing the time to recurrence (TTR) in days for a 74 patient cohort with NSCLC stage Ia-IIa.

Figure 111 is a Kaplan-Meier plot showing the overall survival (OS) in days for a 74 patient cohort with NSCLC stage Ia-IIa.

Figure 112 is a Kaplan-Meier plot showing the time to recurrence (TTR) in days for a 74 patient cohort with NSCLC stage Ia-IIa.

Figure 113 is a Kaplan-Meier plot showing the overall survival (OS) in days for a 74 patient cohort with NSCLC stage Ia-IIa.

Figure 114 is a Kaplan-Meier plot showing the time to recurrence (TTR) in days for a 74 patient cohort with NSCLC stage Ia-IIa.

Figure 115 is a Kaplan-Meier plot showing the overall survival (OS) in days for a 74 patient cohort with NSCLC stage Ia-IIa.

Figure 116 is a Kaplan-Meier plot showing the time to recurrence (TTR) in days for a 74 patient cohort with NSCLC stage Ia-IIa.

Figure 117 is a Kaplan-Meier plot showing the overall survival (OS) in days for a 74 patient cohort with NSCLC stage Ia-IIa.

Figure 118 is a Kaplan-Meier plot showing the time to recurrence (TTR) in days for a74 patient cohort with NSCLC stage Ia-IIa.

Figure 119 is a Kaplan-Meier plot showing the overall survival (OS) in days for a 74 patient cohort with NSCLC stage Ia-IIa.

Figure 120 is a Kaplan-Meier plot showing the time to recurrence (TTR) in days for a 74 patient cohort with NSCLC stage Ia-IIa.

Figure 121 is a Kaplan-Meier plot showing the overall survival (OS) in days for a 74 patient cohort with NSCLC stage Ia-IIa.

Figure 122 is a Kaplan-Meier plot showing the overall survival (OS) in days for a 74 patient cohort with NSCLC stage Ia-IIa.

Figure 123 is a Kaplan-Meier plot showing the time to recurrence (TTR) in days for a 74 patient cohort with NSCLC stage Ia-IIa.

Figure 124 is a Kaplan-Meier plot showing the time to recurrence (TTR) in days for a 74 patient cohort with NSCLC stage Ia-IIa.

Figure 125 is a Kaplan-Meier plot showing the overall survival (OS) in days for a 74 patient cohort with NSCLC stage Ia-IIa.

Figure 126 is a Kaplan-Meier plot showing the time to recurrence (TTR) in days for a 74 patient cohort with NSCLC stage Ia-IIa.

Figure 127 is a Kaplan-Meier plot showing the overall survival (OS) in days for a 74 patient cohort with NSCLC stage Ia-IIa.

Figure 128 is a Kaplan-Meier plot showing the time to recurrence (TTR) in days for a 74 patient cohort with NSCLC stage Ia-IIa.

Figure 129 is a Kaplan-Meier plot showing the overall survival (OS) in days for a 74 patient cohort with NSCLC stage Ia-IIa.

Figure 130 is a Kaplan-Meier plot showing the overall survival (OS) in days for a 74 patient cohort with NSCLC stage Ia-IIa.

Figure 131 is a Kaplan-Meier plot showing the overall survival (OS) in days for a 74 patient cohort with NSCLC stage Ia-IIa.

Figure 132 is a Kaplan-Meier plot showing the time to recurrence (TTR) in days for 74 patient cohort with NSCLC stage Ia-IIa.

Figure 133 is a Kaplan-Meier plot showing the overall survival (OS) in days for a 74 patient cohort with NSCLC stage Ia-IIa.

Figure 134 is a Kaplan-Meier plot showing the time to recurrence (TTR) in days for a 74 patient cohort with NSCLC stage Ia-IIa.

Figure 135 is a Kaplan-Meier plot showing the overall survival (OS) in days for a 74 patient cohort with NSCLC stage Ia-IIa.

Figure 136 is a Kaplan-Meier plot showing the time to recurrence (TTR) in days for a 74 patient cohort with NSCLC stage Ia-IIa.

Figure 137 is a Kaplan-Meier plot showing the overall survival (OS) in days for a 74 patient cohort with NSCLC stage Ia-IIa.

Figure 138 is a Kaplan-Meier plot showing the time to recurrence (TTR) in days for a 74 patient cohort with NSCLC stage Ia-IIa.

Figure 139 is a Kaplan-Meier plot showing the overall survival (OS) in days for a 74 patient cohort with NSCLC stage Ia-IIa.

Figure 140 is a Kaplan-Meier plot showing the time to recurrence (TTR) in days for a 74 patient cohort with NSCLC stage Ia-IIa.

Figure 141 is a Kaplan-Meier plot showing the overall survival (OS) in days for a 74 patient cohort with NSCLC stage Ia-IIa.

Figure 142 is a Kaplan-Meier plot showing the time to recurrence (TTR) in days for a 74 patient cohort with NSCLC stage Ia-IIa.

Figure 143 is a Kaplan-Meier plot showing the overall survival (OS) in days for a 74 patient cohort with NSCLC stage Ia-IIa.

Figure 144 is a Kaplan-Meier plot showing the time to recurrence (TTR) in days for a 74 patient cohort with NSCLC stage Ia-IIa.

Figure 145 is a Kaplan-Meier plot showing the overall survival (OS) in days for a 74 patient cohort with NSCLC stage Ia-IIa.

Figure 146 is a Kaplan-Meier plot showing the time to recurrence (TTR) in days for a 74 patient cohort with NSCLC stage Ia-IIa.

Figure 147 is a Kaplan-Meier plot showing the overall survival (OS) in days for a 74 patient cohort with NSCLC stage Ia-IIa.

Figure 148 is a Kaplan-Meier plot showing the overall survival (OS) in days for a 74 patient cohort with NSCLC stage Ia-IIa.

Figure 149 is a Kaplan-Meier plot showing the time to recurrence (TTR) in days for a 74 patient cohort with NSCLC stage Ia-IIa.

Figure 150 v is a Kaplan-Meier plot showing the overall survival (OS) in days for a 74 patient cohort with NSCLC stage Ia-IIa.

Figure 151 is a Kaplan-Meier plot showing the time to recurrence (TTR) in days for a 74 patient cohort with NSCLC stage Ia-IIa.

Figure 152 is a Kaplan-Meier plot showing the time to recurrence (TTR) in days for a 74 patient cohort with NSCLC stage Ia-IIa.

Figure 153 is a Kaplan-Meier plot showing the time to recurrence (TTR) in days for a 74 patient cohort with NSCLC stage Ia-IIa.

Figure 154 is a Kaplan-Meier plot showing the time to recurrence (TTR) in days for a 74 patient cohort with NSCLC stage Ia-IIa.

Figure 155 is a Kaplan-Meier plot showing the time to recurrence (TTR) in days for a 74 patient cohort with NSCLC stage Ia-IIa.

Figure 156 is a Kaplan-Meier plot showing the time to recurrence (TTR) in days for a 74 patient cohort with NSCLC stage Ia-IIa.

Figure 157 is a Kaplan-Meier plot showing the time to recurrence (TTR) in days for a 74 patient cohort with NSCLC stage Ia-IIa.

Figure 158 is a Kaplan-Meier plot showing the time to recurrence (TTR) in days for a 74 patient cohort with NSCLC stage Ia-IIa.

Figure 159 is a Kaplan-Meier plot showing the time to recurrence (TTR) in days for a 74 patient cohort with NSCLC stage Ia-IIa.

Figure 160 is a Kaplan-Meier plot showing the time to recurrence (TTR) in days for a 74 patient cohort with NSCLC stage Ia-IIa.

Figure 161 is a Kaplan-Meier plot showing the time to recurrence (TTR) in days for a 74 patient cohort with NSCLC stage Ia-IIa.

Figure 162 is a Kaplan-Meier plot showing the time to recurrence (TTR) in days for a 74 patient cohort with NSCLC stage Ia-IIa.

DIAGNOSTIC METHODS FOR DETERMINING PROGNOSIS OF NON-SMALL CELL LUNG CANCER

CROSS-REFERENCE TO RELATED APPLICATION(S)

This is a continuation of U.S. patent application Ser. No. 12/910,891, filed on Oct. 25, 2010, which claims priority to U.S. Provisional Patent Application No. 61/254,968, filed on Oct. 26, 2009, the entire contents of all of which are fully incorporated herein by reference.

FIELD OF THE INVENTION

The present disclosure relates to in vitro diagnostic assays of tissue samples from lung cancer patients for determining patient prognosis, and in particular relates to an in vitro assay for determining prognosis of early stage patients, such as those diagnosed with Stage I or Stage II non-small cell lung cancer.

BACKGROUND OF THE INVENTION

Lung cancer accounted for almost one third of cancer deaths in the United States in 2005, and is broadly classified into two types: non-small cell lung cancer and small cell lung cancer. Non-small cell lung cancer (NSCLC) comprises 80-85% of lung cancer cases in the United States. NSCLC comprises three major types: (i) Squamous cell carcinoma, which begins in squamous cells, that are thin, flat cells that look like fish scales. Squamous cell carcinoma is also called epidermoid carcinoma; (ii) Large cell carcinoma, which begins in several types of large lung cells; (iii) Adenocarcinoma, which begins in the cells that line the alveoli of the lung and make substances such as mucus. Other less common types of NSCLC include pleomorphic carcinoma, carcinoid tumor and unclassified carcinoma.

Diagnosis of NSCLC is done by a pathologist's examination of suspected tissue, such as a biopsy sample. After NSCLC diagnosis, the patient's disease is assigned a prognosis (the chance of recovery) using the patient's overall health and age, the severity of symptoms such as coughing and difficulty in breathing, the particular type of NSCLC, and the staging of the cancer. Staging takes into account the size of the tumor and whether the tumor is present in the lung only or has spread to other places in the body. The particular treatment options for a NSCLC patient are then selected based upon these considerations, and the cancer staging is an important component for treatment selection. Patients with early stage NSCLC can potentially be cured by surgical resection to remove the tumor, but the current diagnostic modalities are not able to predict which patients will recur after surgery. Cancer is a frequently fatal disease with a low cure rate, for which the majority of treatments are directed at improving the quality and duration of life. Because cancer cells are human cells, frequently distinguished only by the accumulation of a relatively small number of genetic aberrations or protein mutations, drug therapies that are useful in killing cancer cells are commonly also detrimental to many normal human cells and cause typically significant toxicities in patients who are treated. Furthermore, because cancers frequently recur locally or metastasize to tissues and organs remote from their tissue of origin, it is critical to know which patients with early stage cancers need drug treatment after surgical removal of their primary tumor. This is an especially critical issue in patients with early stage NSCLC, whose tumors were detected early and removed surgically, specifically patients with Stage I and IIa disease. Under-treating these patients with anti-cancer drugs results in an unacceptably high rate of patients developing recurrent or metastatic disease, ultimately leading to increased morbidity and death. Over-treating this population results in an unacceptably high number of patients who, not needing drug therapy, experience the toxic side effects from the drugs given to them.

The National Comprehensive Cancer Network internet web site describes NSCLC staging as follows. "The system most often used in United States clinical practice to describe the growth and spread of non-small cell lung cancer (NSCLC) is the TNM staging system, also known as the American Joint Committee on Cancer (AJCC) system. In TNM staging, information about the tumor (T), any spread into nearby lymph nodes (N), and any distant organ metastases (M) is combined and a stage is assigned to specific TNM groupings. The grouped stages are described using the number 0 and Roman numerals from I to IV.

"T categories are based on the lung cancer's size, its spread and location within the lungs, and its spread to nearby tissues. In the Tis category, the cancer is found only in the layer of cells lining the air passages. It has not spread into other lung tissues. This category is also known as carcinoma in situ.

"In the T1 category, the cancer is no larger than 3 centimeters (slightly less than 1 to 1¼ inches), has not spread to the visceral pleura (membranes that surround the lungs), and does not affect the main branches of the bronchi.

"In the T2 category, the cancer has one or more of the following features: (i) it is larger than 3 cm; (ii) it involves a main bronchus of a lung but is not closer than 2 cm (about 3¼ to 4 inches) to the point where the trachea (windpipe) branches into the left and right main bronchi; or (iii) has spread to the visceral pleura. The cancer may partially block the airways, but this has not caused the entire lung to collapse or develop pneumonia.

"In the T3 category, the cancer has one or more of the following features: (i) it has spread to the chest wall, the diaphragm (the breathing muscle that separates the chest from the abdomen), the mediastinal pleura (the membranes surrounding the space between the 2 lungs), or parietal pericardium (the membranes of the sac surrounding the heart); (ii) it involves a main bronchus of a lung, and it is closer than 2 cm to the point where the trachea (or windpipe) branches into the left and right main bronchi, but does not involve this area; or (iii) It has grown into the airways enough to cause one lung to entirely collapse or to cause pneumonia of the entire lung.

"In the T4 category, the cancer has one or more of the following features: (i) It has spread to the mediastinum (the space behind the chest bone and in front of the heart), the heart, the trachea (windpipe), the esophagus (the tube connecting the throat to the stomach), the backbone, or the point where the trachea branches into the left and right main bronchi; (ii) Two or more separate tumor nodules are present in the same lobe; or (iii) a malignant pleural effusion is present, which is the existence of fluid containing cancer cells in the space surrounding the lung.

"The N category depends on which, if any, of the lymph nodes near the lungs are affected by the cancer. In the N0 category, the cancer has not spread to any lymph node. In the N1 category, the cancer has spread to lymph nodes within the lung or into the hilar lymph nodes (those located around the area where the bronchus enters the lung). In N1 category the affected lymph nodes are only on the same side as the cancerous lung. In the N2 category, the cancer has spread to subcarinal lymph nodes (those which are around the point where the trachea branches into the left and right bronchi) or to lymph nodes in the mediastinum (the space behind the chest bone and in front of the heart). In the N2 category, the affected lymph nodes are on the same side of the cancerous lung. In the N3 category, the cancer has spread to lymph nodes near the collarbone on either side, and/or to the hilar or mediastinal lymph nodes on the side opposite the cancerous lung.

"The M category depends on whether the cancer has metastasized and spread to any distant tissues and organs. In the M0 category, there is no distant cancer spread. In the M1 category, the cancer has spread to 1 or more distant sites. Sites which are considered distant include other lobes of the lungs, lymph nodes further than those used to determine the N category of the cancer, and other organs or tissues such as the liver, bones, or brain.

Once the T, N, and M categories have been assigned for the particular NSCLC, this information is combined (stage grouping) to assign an overall stage of 0, I, II, III, or IV (see Table 1). Various combinations of the T and N categories are combined into stages. The stages identify tumor types that have a similar prognosis and are treated in a similar way. As noted in Table 1, a tumor with distant spread (i.e., an M1 category cancer) is considered Stage IV, regardless of tumor size of involvement of lymph nodes." The following Table from the NCCN internet web site shows the combined category and stage classification for NSCLC.

TABLE 1

| Overall Stage | T Category | N Category | M Category |
|---|---|---|---|
| Stage 0 | Tis | N0 | M0 |
| Stage IA | T1 | N0 | M0 |
| Stage IB | T2 | N0 | M0 |
| Stage IIA | T1 | N1 | M0 |
| Stage IIB | T2 | N1 | M0 |
|  | T3 | N0 | M0 |
| Stage IIIA | T1 | N2 | M0 |
|  | T2 | N2 | M0 |
|  | T3 | N1 | M0 |
|  | T3 | N2 | M0 |
| Stage IIIB | Any T | N3 | M0 |
|  | T4 | Any N | M0 |
| Stage IV | Any T | Any N | M1 |

NSCLC patients with lower stage numbers generally have a more favorable prognosis and outlook for survival, and these patients are generally treated by surgical resection of the tumor. However, even for early stage patients, such as those with Stage 1B, Stage IIA or IIB NSCLC, a significant percentage of these patients will recur after surgical resection with more aggressive disease and die. The current clinical diagnostic methods are incapable of identifying early stage NSCLC prognosis with sufficient accuracy to direct more aggressive therapy against those patients more likely to recur. Better in vitro diagnostic methods are needed to identify higher risk, early stage NSCLC patients who should receive neoadjuvant or adjuvant chemotherapy or generally have treatment opinions re-evaluated.

Molecular in vitro diagnostic assays based on fluorescence in situ hybridization (FISH) using fluorescently labeled DNA hybridization probes to identify chromosomal abnormalities have been disclosed for use in the selection of chemotherapy for NSCLC patients, (PCT/US2005/018879, "Methods for prediction of clinical outcome to epidermal growth factor inhibitors by cancer patients", M. Garcia et al.). FISH assays have been described as an initial diagnostic assay for NSCLC in U.S. Patent Application 20060063194, "Methods and probes for the detection of cancer", L. Morrison et al., published Mar. 23, 2006 (hereafter referred to as "Morrison '194"), the disclosure of which is incorporated herein by reference in its entirety. The Morrison '194 application describes multiple FISH probe sets useful for screening and diagnosis of NSCLC, and one probe set described in Morrison '194 is commercially available as the LAVysion™ probe set from Abbott Molecular, Inc. (Des Plaines, Ill., U.S.A.) under ASR (Analyte Specific Reagent) labeling for use by clinical laboratories to produce clinical diagnostic assays. Under the U.S. Food and Drug Administration ASR labeling requirements, the ASR labeling must not include any claims as to the medical utility of the ASR. The LAVysion ASR probe set comprises four FISH probes: a chromosome 5p15 locus specific probe labeled with the SpectrumGreen green fluorophore, a chromosome 8q24 locus specific probe labeled with the SpectrumGold yellow fluorophore, a chromosome 6 enumeration probe labeled with the SpectrumAqua blue fluorophore, and a chromosome 7p12 locus specific probe labeled with the SpectrumRed red fluorophore. Research performed using the LAVysion probe set has been described and is reviewed for example in K. Halling et al., "Fluorescence in situ hybridization in diagnostic cytology", Hum. Path. (2007) 38: 1137-1144.

Overexpression of cyclin E has previously been associated with poor outcome in lung cancer (reviewed in Singhal et al., Clin. Cancer Res., 2005, 11, pp. 3974-3986). However, no copy number alterations at the cyclin E locus have been established as predictive markers.

Moreover, no previous reports on FISH assays for NSCLC have disclosed the use of FISH probes to more accurately identify prognosis for early stage NSCLC, in particular, those classified as Stage IB or Stage II.

SUMMARY OF THE INVENTION

In one aspect, the present disclosure provides a method of predicting disease outcome in a patient being treated for lung cancer, the method comprising the steps of: a) providing a test sample from a patient; b) determining a copy number of a cancer outcome marker in the test sample; c) comparing the copy number of the cancer outcome marker in the test sample against a baseline copy number of two, thereby determining the presence or absence of a copy number change for the cancer outcome marker in the test sample; and d) based on the presence or absence of a copy number change for the cancer outcome marker in the test sample, identifying the patient as having an increased risk of a poor disease outcome when compared to a baseline measure of disease outcome in patients having no copy number change in the cancer outcome marker, wherein the presence of a copy number change in the cancer outcome marker is predictive of poor disease outcome. In one embodiment, the poor disease outcome is for example at least one of a decreased overall survival time, when compared to an overall survival time of patients having no copy number change for the cancer outcome marker, and a shorter time to recurrence, when compared to the time to recurrence for patients having no copy number change for the cancer outcome marker.

In another aspect, the present disclosure provides a method of predicting treatment outcome in a patient being treated for lung cancer, the method comprising: a) providing a test sample from a patient; b) determining the presence or absence of a copy number change for a cancer outcome marker in the test sample, wherein the cancer outcome marker is a region of chromosomal DNA, the change in copy number of which is associated with a poor disease outcome; and c) based on the presence or absence of a copy number change for the cancer outcome marker, determining whether the patient has a higher risk of a decreased overall survival time or a shorter time to recurrence, when compared to an overall survival time of patients having no copy number gain for the cancer outcome marker.

In any of the methods, the cancer outcome marker is for example a region of chromosomal DNA, the amplification of which produces a copy number gain of the cancer outcome marker, wherein the copy number gain is associated with a poor disease outcome. Such cancer outcome markers include any selected from the group consisting of Chr 19, 34.7 Mb-35.6 Mb; Chr 19, 38.9-40.7 Mb; Chr 17, 69.2-71.3 Mb; Chr 6, 70.8-71.1 Mb; Chr 12, 93.7 kb-1.9 Mb; Chr 11, 64.3-64.8 Mb; Chr 19, 57.0-62.2 Mb; Chr 6, 39.1-39.9 Mb; Chr 11, 64.8-65.7 Mb; Chr 11, 61.4-64.3 Mb; Chr 17, 51.5-53.2 Mb; Chr 17, 43.5-44.9 Mb; Chr 2, 147.6-151.1 Mb; Chr 6, 123.7-135.6 Mb; Chr 8, 6.9-8.8 Mb; Chr 2, 159.9-161.4 Mb; Chr 2, 200.9-204.2 Mb; Chr 6, 36.3-36.7 Mb; Chr 2, 205.9-208.1 Mb; and Chr 1, 109.5-111.1 Mb. In a method wherein the cancer outcome marker is Chr 19, 34.7 Mb-35.6 Mb, the marker includes nucleotide sequences encoding C19orf12; C19orf12; cyclin E1; PLEKHF1; POP4; and ZNF536. In a method wherein the cancer outcome marker is Chr 19, 38.9-40.7 Mb, the marker includes nucleotide sequences encoding ATP4A ATPase; CHST8, DMKN FAR1, 2, 3; FXYD1, 3, 5, 7; GAPDHS; GPI; GPR42; GRAMD1A; HAMP; HPN; KCTD15 KIAA0355; KRTDAP; LGI4; LSM14A; LSR; MAG; PDCD2L; SAE2 SUMO1; SBSN; SCN1B; TMEM147,162; USF2; WTIP; and ZNF181, 30, 302, 599, 792. In a method wherein the cancer outcome marker is Chr 17, 69.2-71.3 Mb, the marker includes nucleotide sequences encoding. ARMC7 (armadillo repeat containing 7); ATP5H ATP synthase (H+ transporting, mitochondrial F0 complex, subunit d); CASKIN2 (CASK interacting protein 2); CD300A (CD300a molecule); CD300C (CD300c molecule); CD300E (CD300e molecule); CD300LB (CD300 molecule-like family member b); CD300LF (CD300 molecule-like family member f); CDR2L (cerebellar degeneration-related protein 2-like); DNAI2 (dynein, axonemal, intermediate chain 2); (FADS6 fatty acid desaturase domain family, member 6); FDXR (ferredoxin reductase); GALK1 (galactokinase 1); GGA3 (golgi associated, gamma adaptin ear containing, ARF binding protein): GPR142 (G protein-coupled receptor 142); GPRC5C (G protein-coupled receptor, family C, group 5, member C); GRB2 (growth factor receptor-bound protein 2); GRIN2C (glutamate receptor, ionotropic, N-methyl D-aspartate 2C); H3F3B (H3 histone, family 3B (H3.3B)); HN1 (hematological and neurological expressed 1 ICT1 immature colon carcinoma transcript 1); ITGB4 (integrin, beta 4); KCTD2 (potassium channel tetramerisation domain containing 2); KIAA0195; KIF19 (kinesin family member 19); LLGL2 (lethal giant larvae homolog 2 (*Drosophila*)); LOC388419 (galectin-3-binding protein-like); MIF4GD (MIF4G domain containing); MRPS7 (mitochondrial ribosomal protein S7); NAT9 (N-acetyltransferase 9); NT5C (5',3'-nucleotidase, cytosolic); NUP85 (nucleoporin 85 kDa); OTOP2 (otopetrin 2); OTOP3 (otopetrin 3); RAB37 (RAB37, member RAS oncogene family); RECQL5 (RecQ protein-like 5); RPL38 ribosomal protein L38; SAP30BP (SAP30 binding protein); SLC16A5 (solute carrier family 16, member 5 (monocarboxylic acid transporter 6)); SLC25A19 (solute carrier family 25 (mitochondrial thiamine pyrophosphate carrier), member 19); SLC9A3R1 (solute carrier family 9 (sodium/hydrogen exchanger), member 3 regulator 1); SUMO2 (SMT3 suppressor of mif two 3 homolog 2 (*S. cerevisiae*)); TMEM104 (transmembrane protein 104); TTYH2 (tweety homolog 2 (*Drosophila*)); UNK (unkempt homolog (*Drosophila*)); and USH1G (Usher syndrome 1G (autosomal recessive) [Marker 3]. In a method wherein the cancer outcome marker is Chr 6, 70.8-71.1 Mb, the marker includes nucleotide sequences encoding COL19A1 (collagen, type XIX, alpha 1), and COL9A1 (collagen, type IX, alpha 1). [Marker 4]. In a method wherein the cancer outcome marker is Chr 12, 93.7 kb-1.9 Mb, the marker includes nucleotide sequences encoding ADIPOR2 (adiponectin receptor 2); B4GALNT3 (beta-1,4-N-acetyl-galactosaminyl transferase 3); CACNA2D4 (calcium channel, voltage-dependent, alpha 2/delta subunit 4); CCDC77 (coiled-coil domain containing 77); ERCT (ELKS/RAB6-interacting/CAST family member 1); FBXL14 (F-box and leucine-rich repeat protein 14); HSN2 (hereditary sensory neuropathy, type II); IQSEC3 (IQ motif and Sec7 domain 3); JARID1A (jumonji, AT rich interactive domain 1A); LRTM2 (leucine-rich repeats and transmembrane domains 2); NINJ2 (ninjurin 2); RAD52 (RAD52 homolog (*S. cerevisiae*)); SLC6A12 (solute carrier family 6 (neurotransmitter transporter, betaine/GABA), member 12); SLC6A13 (solute carrier family 6 (neurotransmitter transporter, GABA), member 13); WNK1 (WNK lysine deficient protein kinase 1); and WNT5B (wingless-type MMTV integration site family, member 5B). [Marker 5]. In a method wherein the cancer outcome marker is Chr 11, 64.3-64.8 Mb, the marker includes nucleotide sequences encoding ARL2 (ADP-ribosylation factor-like 2); ATG2A ATG2 (autophagy related 2 homolog A (*S. cerevisiae*)); BATF2 (basic leucine zipper transcription factor, ATF-like 2; CAPN1 calpain 1, (mu/I) large subunit); CDC42BPG (CDC42 binding protein kinase gamma (DMPK-like)); CDCA5 (cell division cycle associated 5); EHD1 (EH-domain containing 1); FAU (Finkel-Biskis-Reilly murine sarcoma virus (FBR-MuSV) ubiquitously expressed); GPHA2 (glycoprotein hormone alpha 2); MAP4K2 mitogen-activated protein kinase kinase kinase kinase 2; MEN1 multiple endocrine neoplasia I; MRPL49 mitochondrial ribosomal protein L49; NAALADL1 N-acetylated alpha-linked acidic dipeptidase-like 1; POLA2 polymerase (DNA directed), alpha 2 (70 kD subunit); PPP2R5B protein phosphatase 2, regulatory subunit B', beta isoform; SAC3D1 SAC3 domain containing 1 SLC22A20 solute carrier family 22, member 20; SNX15 sorting nexin 15; SPDYC speedy homolog C (*Drosophila*); SYVN1 synovial apoptosis inhibitor 1, synoviolin; TM7SF2 transmembrane 7 superfamily member 2; ZFPL1 zinc finger protein-like 1; ZNHIT2 zinc finger, HIT type 2; hsa-mir-192; and hsa-mir-194-2. [Marker 6]. In a method wherein the cancer outcome marker is Chr 19, 57.0-62.2 Mb, the marker includes nucleotide sequences encoding BIRC8 (baculoviral IAP repeat-containing 8); BRSK1 (BR serine/threonine kinase 1); CACNG6, 7, 8 calcium channel, voltage-dependent, gamma subunit 6, 7, 8; CCDC106 coiled-coil domain containing 106; CDC42EP5 CDC42 effector protein (Rho GTPase binding) 5; CNOT3 CCR4-NOT transcription complex, subunit 3; COX6B2 cytochrome c oxidase subunit VIb polypeptide 2 (testis); DPRX divergent-paired related homeobox; EPN1 epsin 1; EPS8L1 EPS8-like 1; FCAR Fc fragment of IgA, receptor for; FIZZ FLT3-interacting zinc finger 1; GALP galanin-like peptide; GP6 glycoprotein VI (platelet); HSPBP1 hsp70-interacting protein; IL11 interleukin 11; ISOC2 isochorismatase domain containing 2; KIR2DL1, KIR2DL4, KIR2DS4 KIR3DL1, KIR3DL3, KIR3DX1 killer cell immunoglobulin-like receptor; LAIR1,2 leukocyte-associated immunoglobulin-like receptor 1,2; LENG1, 4, 8, 9 leukocyte receptor cluster (LRC) member 1, 4, 8, 9; LILRA2, 3, 4 leukocyte immunoglobulin-like receptor, subfamily A (with TM domain), member 2, 3, 4; LILRB1, 2, 3, 4, 5 leukocyte immunoglobulin-like receptor, subfamily B (with TM and ITIM domains), member 1, 2, 3, 4, 5; MYADM myeloid-associated differentiation marker; NAT14 N-acetyltransferase 14; NCR1 natural cytotoxicity triggering receptor 1; NDUFA3 NADH dehydrogenase (ubiquinone) 1 alpha subcomplex, 3, 9 kDa; NLRP2, 4, 5, 7, 8, 9, 11, 12, 13 NLR family, pyrin domain containing 2, 4, 5, 7, 8, 9, 11, 12, 13; OSCAR osteoclast associated, immunoglobulin-like receptor; PEG3 paternally expressed 3; PPP1R12C protein phosphatase 1, regulatory (inhibitor) subunit 12C; PPP2R1A protein phosphatase 2 (formerly 2A), regulatory subunit A, alpha isoform; PRKCG protein kinase C, gamma; PRPF31 PRP31 pre-mRNA processing factor 31 homolog (S. cerevisiae); PTPRH protein tyrosine phosphatase, receptor type, H; RDH13 retinol dehydrogenase 13 (all-trans/9-cis); RPL28 ribosomal protein L28; RPS9 ribosomal protein S9; SAPS1 SAPS domain family, member 1; SUV420H2 suppressor of variegation 4-20 homolog 2 (Drosophila); SYT5 synaptotagmin V; TFPT TCF3 (E2A) fusion partner (in childhood Leukemia); TMC4 transmembrane channel-like 4; TMEM190 transmembrane protein 190; TMEM86B transmembrane protein 86B; TNNI3 troponin I type 3 (cardiac); TNNT1 troponin T type 1 (skeletal, slow); TSEN34 tRNA splicing endonuclease 34 homolog (S. cerevisiae); TTYH1 tweety homolog 1 (Drosophila); U2AF2 U2 small nuclear RNA auxiliary factor 2; UBE2S ubiquitin-conjugating enzyme E2S; VN1R2 vomeronasal 1 receptor 2; VN1R4 vomeronasal 1 receptor 4; VSTM1 V-set and transmembrane domain containing 1; ZNF28, 160, 320, 321, 331, 347, 350, 415, 432, 444, 468, 470 zinc finger protein 28, 160, 320, 321, 331, 347, 350, 415, 432, 444, 468, 470; and miRNA's including hsa-mir-643, hsa-mir-512-1, hsa-mir-512-2, hsa-mir-498, hsa-mir-520e, hsa-mir-515-1, hsa-mir-519e, hsa-mir-520f, hsa-mir-515-2, hsa-mir-519c, hsa-mir-520a, hsa-mir-526b, hsa-mir-519b, hsa-mir-525, hsa-mir-523, hsa-mir-518f, hsa-mir-520b, hsa-mir-518b, hsa-mir-526a-1, hsa-mir-520c, hsa-mir-518c, hsa-mir-524, hsa-mir-517a, hsa-mir-519d, hsa-mir-521-2, hsa-mir-520d, hsa-mir-517b, hsa-mir-520g, hsa-mir-516-3, hsa-mir-526a-2, hsa-mir-518e, hsa-mir-518a-1, hsa-mir-518d, hsa-mir-516-4, hsa-mir-518a-2, hsa-mir-517c, hsa-mir-520h, hsa-mir-521-1, hsa-mir-522, hsa-mir-519a-1, hsa-mir-527, hsa-mir-516-1, hsa-mir-516-2, hsa-mir-519a-2, hsa-mir-371, hsa-mir-372, hsa-mir-373, hsa-mir-516a-1, hsa-mir-516a-2, hsa-mir-516b-1, hsa-mir-516b-2, hsa-mir-517a-1, hsa-mir-517a-2, hsa-mir-520c-1, and hsa-mir-520c-2 [Marker 7]. In a method wherein the cancer outcome marker is Chr 6, 39.1-39.9 Mb, the marker includes nucleotide sequences encoding C6orf64 (chromosome 6 open reading frame 64); DNAH8 dynein, axonemal, heavy chain 8; GLP1R glucagon-like peptide 1 receptor; KCNK16 potassium channel, subfamily K, member 16; KCNK17 potassium channel, subfamily K, member 17; KCNK5 potassium channel, subfamily K, member 5; and KIF6 kinesin family member 6. [Marker 8]. In a method wherein the cancer outcome marker is Chr 11, 64.8-65.7 Mb, the marker includes nucleotide sequences encoding BANF1 (barrier to autointegration factor 1); CATSPER1 cation channel, sperm associated 1 CCDC85B coiled-coil domain containing 85B; CDC42EP2CDC42 effector protein (Rho GTPase binding) 2; CFL1 cofilin 1 (non-muscle); CST6 cystatin E/M; CTSW cathepsin W; DPF2 D4, zinc and double PHD fingers family 2; DRAP1 DR1-associated protein 1 (negative cofactor 2 alpha); EFEMP2 EGF-containing fibulin-like extracellular matrix protein 2; EHBP1L1 EH domain binding protein 1-like 1; FAM89B family with sequence similarity 89, member B; FIBP fibroblast growth factor (acidic) intracellular binding protein; FOSL1 FOS-like antigen 1; FRMD8 FERM domain containing 8; GAL3ST3 galactose-3-O-sulfotransferase 3; HTATIP HIV-1 Tat interacting protein, 60 kDa. KCNK7 potassium channel, subfamily K, member 7; LTBP3 latent transforming growth factor beta binding protein 3; MAP3K11 mitogen-activated protein kinase kinase kinase 11; MGC11102 hypothetical protein MGC11102; MUS81 MUS81 endonuclease homolog (S. cerevisiae); OVOL1 ovo-like 1 (Drosophila); PACS1 phosphofurin acidic cluster sorting protein 1; PCNXL3 pecanex-like 3 (Drosophila); POLA2 polymerase (DNA directed) alpha 2 (70 kD subunit); RELA v-rel reticuloendotheliosis viral oncogene homolog A, nuclear factor of kappa light polypeptide gene enhancer in B-cells 3, p65 (avian); RNASEH2C ribonuclease H2, subunit C; SART1 squamous cell carcinoma antigen recognized by T cells; SCYL1 SCY1-like 1 (S. cerevisiae); SF3B2 splicing factor 3b, subunit 2, 145 kDa; SIPA1 signal-induced proliferation-associated gene 1; SLC25A45 solute carrier family 25, member 45; SSSCA1 Sjogren syndrome/scleroderma autoantigen 1; TIGD3 tigger transposable element derived 3; and TSGA10IP testis specific, 10 interacting protein [Marker 9]. In a method wherein the cancer outcome marker is Chr 11, 61.4-64.3 Mb, the marker includes nucleotide sequences encoding AHNAK (AHNAK nucleoprotein); ASRGL1 asparaginase like 1; B3GAT3 beta-1,3-glucuronyltransferase 3 (glucuronosyltransferase I); BAD BCL2-antagonist of cell death; BEST1 bestrophin 1; BSCL2 Bernardinelli-Seip congenital lipodystrophy 2 (seipin); CCDC88B coiled-coil domain containing 88B; CHRM1 cholinergic receptor, muscarinic 1; COX8A cytochrome c oxidase subunit 8A (ubiquitous); DKFZP564J0863 DKFZP564J0863 protein; DKFZP566E164 DKFZP566E164 protein; DNAJC4 DnaJ (Hsp40) homolog, subfamily C, member 4; EEF1G eukaryotic translation elongation factor 1 gamma; EML3 echinoderm microtubule associated protein like 3; ESRRA estrogen-related receptor alpha; FADS2, 3 fatty acid desaturase 2,3; FKBP2 FK506 binding protein 2, 13 kDa; FLRT1 fibronectin leucine rich transmembrane protein1; FTH1 ferritin, heavy polypeptide 1; GANAB glucosidase, alpha; neutral AB; GNG3 guanine nucleotide binding protein (G protein), gamma 3; GPR137 G protein-coupled receptor 137; HRASLS2, 3, 5 HRAS-like suppressor 2, 3, 5; INCENP inner centromere protein antigens 135/155 kDa; INTS5 integrator complex subunit 5; KCNK4 potassium channel, subfamily K, member 4; LGALS12 lectin, galactoside-binding, soluble, 12 (galectin 12); MACROD1 MACRO domain containing 1; MARK2 MAP/microtubule affinity-regulating kinase 2; MGC3196 hypothetical protein MGC3196; MTA2 metastasis associated 1 family, member 2; NAT11 N-acetyltransferase 11; NRXN2 neurexin 2; NUDT22 nudix (nucleoside diphosphate linked moiety X)-type motif 22; NXF1 nuclear RNA export factor 1; OTUB1 OTU domain, ubiquitin aldehyde binding 1; PLCB3 phospholipase C, beta 3 (phosphatidylinositol-specific); POLR2G polymerase (RNA) II (DNA directed) polypeptide G; PPP1R14B protein phosphatase 1, regulatory (inhibitor) subunit 14B; PRDX5 peroxiredoxin 5; PYGM phosphorylase, glycogen; muscle (McArdle syndrome, glycogen storage disease type V); RAB3IL1 RAB3A interacting protein (rabin3)-like 1; RARRES3 retinoic acid receptor responder (tazarotene induced) 3; RASGRP2 RAS guanyl releasing protein 2 (calcium and DAG-regulated); RCOR2 REST corepressor 2; ROM1 retinal outer segment membrane protein 1; RPS6KA4 ribosomal protein S6 kinase, 90 kDa, polypeptide 4; RTN3 reticulon 3; SCGB1A1, 1D1, 1D2, 1D4, 2A1, 2A1 secretoglobin, family; SF1 splicing factor 1; SLC22A10, 11, 12, 6, 8, 9 solute carrier family 22 (organic anion/cation transporter) SLC3A2 solute carrier family 3 (activators of dibasic and neutral amino acid transport), member 2; STIP1 stress-induced-phosphoprotein 1 (Hsp70/Hsp90-organizing protein); STX5 syntaxin 5; TAF6L TAF6-like RNA polymerase II, p300/CBP-associated factor (PCAF)-associated factor, 65 kDa; TRPT1 tRNA phosphotransferase 1; TTC9C tetratricopeptide repeat domain 9C; TUT1 terminal uridylyl transferase 1; U6 snRNA-specific RP2 UNC-112 related protein 2; UST6 putative UST1-like organic anion transporter; VEGFB vascular endothelial growth factor B; WDR74 WD repeat domain 74; and ZBTB3 zinc finger and BTB domain containing 3. [Marker 10]. In a method wherein the cancer outcome marker is Chr 17, 51.5-53.2 Mb, the marker includes nucleotide sequences encoding AKAP1 (A kinase (PRKA) anchor protein 1); ANKFN1 (ankyrin-repeat and fibronectin type III domain containing 1); C17orf67 chromosome 17 open reading frame 67; COIL coilin; DGKE diacylglycerol kinase, epsilon 64 kDa; MSI2 musashi homolog 2 (Drosophila); NOG noggin; SCPEP1 serine carboxypeptidase 1; and TRIM25 tripartite motif-containing 25. [Marker 11]. In a method wherein the cancer outcome marker is Chr 17, 43.5-44.9 Mb, the marker includes nucleotide sequences encoding hsa-mir-10a; hsa-mir-196a-1; ABI3 (ABI gene family, member 3); ATP5G1 (ATP synthase, H+ transporting, mitochondrial F0 complex, subunit C1 (subunit 9)); B4GALNT2 beta-1,4-N-acetyl-galactosaminyl transferase 2; CALCOCO2 calcium binding and coiled-coil domain 2; CBX1 chromobox homolog 1 (HP1 beta homolog Drosophila); GIP gastric inhibitory polypeptide; GNGT2 guanine nucleotide binding protein (G protein), gamma transducing activity polypeptide 2; HOXB1, 2, 3, 4, 5, 6, 7, 8, 9, 13 homeobox B1, 2, 3, 4, 5, 6, 7, 8, 9, 13; IGF2BP1 insulin-like growth factor 2 mRNA binding protein 1; NFE2L1 nuclear factor (erythroid-derived 2)-like 1; NGFR nerve growth factor receptor (TNFR superfamily, member 16); PHB prohibitin PHOSPHO1 phosphatase, orphan 1; PRAC small nuclear protein PRAC; SKAP1 src kinase associated phosphoprotein 1; SNF8 SNF8, ESCRT-II complex subunit, homolog (S. cerevisiae); SNX11 sorting nexin 11; TTLL6 tubulin tyrosine ligase-like family, member 6; UBE2Z (ubiquitin-conjugating enzyme E2Z); and ZNF652 (zinc finger protein 652). [Marker 12]. In a method wherein the cancer outcome marker is Chr 2, 147.6-151.1 Mb, the marker includes nucleotide sequences encoding ACVR2A activin A receptor, type IIA; C2orf25 chromosome 2 open reading frame 25; EPC2 enhancer of polycomb homolog 2 (Drosophila); KIF5C kinesin family member 5C; LOC130576 hypothetical protein LOC130576; LYPD6 LY6/PLAUR domain containing 6; MBD5 methyl-CpG binding domain protein 5; ORC4L origin recognition complex, subunit 4-like (yeast); and RND3 Rho family GTPase 3. [Marker 13]. In a method wherein the cancer outcome marker is Chr 6, 123.7-135.6 Mb, the marker includes nucleotide sequences encoding hsa-mir-588; AKAP7 (A kinase (PRKA) anchor protein 7); ALDH8A1 aldehyde dehydrogenase 8 family, member A1; ARG1 arginase, liver; ARHGAP18 Rho GTPase activating protein 18; CTGF connective tissue growth factor; ECHDC1 enoyl Coenzyme A hydratase domain containing 1; ENPP1,3 ectonucleotide pyrophosphatase/phosphodiesterase 1,3; EPB41L2 erythrocyte membrane protein band 4.1-like 2; EYA4 eyes absent homolog 4 (Drosophila); HDDC2 HD domain containing 2; HEY2 hairy/enhancer-of-split related with YRPW motif 2; HINT3 histidine triad nucleotide binding protein 3; KIAA1913 KIAA1913; LAMA2 laminin, alpha 2 (merosin, congenital muscular dystrophy); MED23 mediator complex subunit 23; MOXD1 monooxygenase, DBH-like 1; MYB v-myb myeloblastosis viral oncogene homolog (avian); NCOA7 nuclear receptor coactivator 7; NKAIN2 Na+/K+ transporting ATPase interacting 2; OR2A4 olfactory receptor, family 2, subfamily A, member 4; PTPRK protein tyrosine phosphatase, receptor type, K; RNF146 ring finger protein 146; RNF217 ring finger protein 217; RPS12 ribosomal protein S12; SAMD3 sterile alpha motif domain containing 3; SGK serum/glucocorticoid regulated kinase; SLC2A12 solute carrier family 2 (facilitated glucose transporter), member 12; STX7 syntaxin 7; TAAR1, 2, 5, 6, 8, 9 trace amine associated receptor 1, 2, 5, 6, 8, 9; TBPL1 TBP-like 1; TCF21 transcription factor 21; TPD52L1 tumor protein D52-like 1; TRDN triadin; TRMT11 tRNA methyltransferase 11 homolog (S. cerevisiae)); and VNN1, 2, 3 (vanin 1, 2, 3). [Marker 14]. In a method wherein the cancer outcome marker is Chr 8, 6.9-8.8 Mb, the marker includes nucleotide sequences encoding CLDN23 claudin 23; DEFA5 defensin, alpha 5, Paneth cell-specific; DEFB103B defensin, beta 103B; DEFB104A defensin, beta 104A; DEFB104B defensin, beta 104B; DEFB105B defensin, beta 105B; DEFB106A defensin, beta 106A; DEFB106B defensin, beta 106B; DEFB107A defensin, beta 107A; DEFB107B defensin, beta 107B; DEFB4 defensin, beta 4; MFHAS1 malignant fibrous histiocytoma amplified sequence 1; PRAGMIN homolog of rat pragma of Rnd2; SPAG11A sperm associated antigen 11A; and SPAG11B sperm associated antigen 11B. [Marker 15]. In a method wherein the cancer outcome marker is Chr 2, 159.9-161.4 Mb, the marker includes nucleotide sequences encoding BAZ2B bromodomain adjacent to zinc finger domain, 2B; CD302 CD302 molecule; ITGB6 integrin, beta 6; LY75 lymphocyte antigen 75; MARCH7 (membrane-associated ring finger (C3HC4) 7); PLA2R1 (phospholipase A2 receptor 1, 180 kDa); and RBMS1 (RNA binding motif, single stranded interacting protein 1). [Marker 16]. In a method wherein the cancer outcome marker is Chr 2, 200.9-204.2 Mb, the marker includes nucleotide sequences encoding ABI2 abl interactor 2; ALS2 amyotrophic lateral sclerosis 2 (juvenile); ALS2CR2, 4, 7, 8, 11, 12, 13 amyotrophic lateral sclerosis 2 (juvenile) chromosome region, candidate 2, 4, 7, 8, 11, 12, 13; AOX1 aldehyde oxidase 1; BMPR2 bone morphogenetic protein receptor, type II (serine/threonine kinase); BZW1 basic leucine zipper and W2 domains 1; CASP10 caspase 10, apoptosis-related cysteine peptidase; CASP8 caspase 8, apoptosis-related cysteine peptidase; CFLAR CASP8 and FADD-like apoptosis regulator; CLK1 CDC-like kinase 1; CYP20A1 cytochrome P450, family 20, subfamily A, polypeptide 1; FAM126B family with sequence similarity 126, member B; FZD7 frizzled homolog 7 (Drosophila) ICA1L islet cell autoantigen 1.69 kDa-like; KCTD18 potassium channel tetramerisation domain containing 18; LOC26010 viral DNA polymerase-transactivated protein 6; MPP4 membrane protein, palmitoylated 4 (MAGUK p55 subfamily member 4). NBEAL1 neurobeachin-like 1; NDUFB3 NADH dehydrogenase (ubiquinone) 1 beta subcomplex, 3, 12 kDa; NIF3L1 NIF3 NGG1 interacting factor 3-like 1 (S. pombe); NOP5/NOP58 nucleolar protein NOP5/NOP58; ORC2L origin recognition complex, subunit 2-like (yeast); PPIL3 peptidylprolyl isomerase (cyclophilin)-like 3; RAPH1 Ras association (RalGDS/AF- 6) and pleckstrin homology domains 1; SGOL2 shugoshin-like 2 (*S. pombe*); SUMO1 SMT3 suppressor of mif two 3 homolog 1 (*S. cerevisiae*); TRAK2 trafficking protein, kinesin binding 2; and WDR12 (WD repeat domain 12). [Marker 17]. In a method wherein the cancer outcome marker is Chr 6, 36.3-36.7 Mb, the marker includes nucleotide sequences encoding BRPF3 (bromodomain and PHD finger containing, 3); DKFZp779B1540 hypothetical protein DKFZp779B1540; ETV7 ets variant gene 7 (TEL2 oncogene); KCTD20 potassium channel tetramerisation domain containing 20; PNPLA1 patatin-like phospholipase domain containing 1; PXT1 peroxisomal, testis specific 1; SFRS3 splicing factor, arginine/serine-rich 3; and STK38 (serine/threonine kinase 38). [Marker 18]. In a method wherein the cancer outcome marker is Chr 2, 205.9-208.1 Mb, the marker includes nucleotide sequences encoding ADAM23 (ADAM metallopeptidase domain 23); CPO carboxypeptidase O; DYTN dystrotelin; EEF1B2 eukaryotic translation elongation factor 1 beta 2; FASTKD2 FAST kinase domains 2; FLJ20309 hypothetical protein FLJ20309; GPR1 G protein-coupled receptor 1; KLF7 Kruppel-like factor 7 (ubiquitous); MDH1B malate dehydrogenase 1B, NAD (soluble); NDUFS1 NADH dehydrogenase (ubiquinone) Fe—S protein 1, 75 kDa (NADH-coenzyme Q reductase); NRP2 neuropilin 2; PARD3B par-3 partitioning defective 3 homolog B (*C. elegans*); ZDBF2 (zinc finger, DBF-type containing 2); and hCG_1657980 hCG1657980. [Marker 19]. In a method wherein the cancer outcome marker is Chr 1, 109.5-111.1 Mb, the marker includes nucleotide sequences encoding hsa-mir-197; AHCYL1 S-adenosylhomocysteine hydrolase-like 1); ALX3 aristaless-like homeobox 3; AMIGO1 adhesion molecule with Ig-like domain 1; AMPD2 adenosine monophosphate deaminase 2 (isoform L); ATXN7L2 ataxin 7-like 2; CELSR2 cadherin, EGF LAG seven-pass G-type receptor 2 (flamingo homolog, *Drosophila*); CSF1 colony stimulating factor 1 (macrophage); CYB561D1 cytochrome b-561 domain containing 1; EPS8L3 EPS8-like 3; FAM40A family with sequence similarity 40, member A; GNAI3 guanine nucleotide binding protein (G protein), alpha inhibiting activity polypeptide 3; GNAT2 guanine nucleotide binding protein (G protein), alpha transducing activity polypeptide 2; GPR61 G protein-coupled receptor 61; GSTM1, M2, M3, M4, M5 glutathione S-transferase M1, M2 (muscle), M3 (brain), M4, M5; HBXIP hepatitis B virus x interacting protein; KCNA2, 3, 4, 10 potassium voltage-gated channel, shaker-related subfamily, member 2, 3, 4, 10; KIAA1324 KIAA1324; MYBPHL myosin binding protein H-like; PROK1 prokineticin 1; PSMA5 proteasome (prosome, macropain) subunit, alpha type, 5; PSRC1 proline/serine-rich coiled-coil 1; RBM15 RNA binding motif protein 15; SARS seryl-tRNA synthetase; SLC16A4 solute carrier family 16, member 4 (monocarboxylic acid transporter 5); SLC6A17 solute carrier family 6, member 17; SORT1 sortilin 1; SYPL2 synaptophysin-like 2; and UBL4B (ubiquitin-like 4B). [Marker 20].

Alternatively, in any of the methods the cancer outcome marker is for example a region of chromosomal DNA, the deletion of which produces a copy number loss of the cancer outcome marker, wherein the copy number loss is associated with a poor disease outcome. Such cancer outcome markers can be selected from the group consisting of Chr 5, 62.9-67.8 Mb; Chr 5, 53.3-53.8 Mb; Chr 4, 105.8-107.2 Mb; Chr 16, 45.8-46.3 Mb; Chr 5, 50.7-52.0 Mb; Chr 5, 94.2-96.1 Mb; Chr 9, 36.1-37.0 Mb; Chr 5, 94.2-96.1 Mb; Chr14, 51.1-52.8 Mb; Chr 14, 61.5-68.6 Mb; Chr 9, 28.1 Mb; Chr 4, 43.7-44.2 Mb; Chr 5, 60.8-62.9 Mb; Chr 3, 120.0-121.1 Mb; Chr 4, 46.2-48.0 Mb; Chr 14, 38.9-40.0 Mb; Chr 4, 44.2-44.6 Mb; Chr 2, 213.7-214.3 Mb; Chr14, 43.9-46.6 Mb; Chr 14, 27.6-28.6 Mb; Chr 3, 98.0-98.3 Mb; Chr14, 55.2-60.0 Mb; Chr14, 48.7-51.1 Mb; Chr 4, 81.4-83.2 Mb; Chr 10, 51.9-54.2 Mb; Chr 5, 55.2-58.6 Mb; and Chr 5, 67.8-68.5 Mb. In a method wherein the cancer outcome marker is Chr 5, 62.9-67.8 Mb, the marker includes nucleotide sequences encoding ADAMTS6 ADAM metallopeptidase with thrombospondin type 1 motif, 6; CD180 CD180 molecule; CENPK centromere protein K; ERBB2IP erbb2 interacting protein; F1113611 hypothetical protein F1113611; HTR1A 5-hydroxytryptamine (serotonin) receptor 1A; MAST4 microtubule associated serine/threonine kinase family member 4; NLN neurolysin (metallopeptidase M3 family); P18SRP P18SRP protein; PIK3R1 phosphoinositide-3-kinase, regulatory subunit 1 (p85 alpha); PPWD1 peptidylprolyl isomerase domain and WD repeat containing 1; RGS7BP regulator of G-protein signaling 7 binding protein; RNF180 ring finger protein 180; SDCCAG10 serologically defined colon cancer antigen 10; SFRS12 splicing factor, arginine/serine-rich 12; SGTB small glutamine-rich tetratricopeptide repeat (TPR)-containing, beta0; and TRIM23 tripartite motif-containing 23. [Deletion Marker 1]. In a method wherein the cancer outcome marker is Chr 5, 53.3-53.8 Mb, the marker includes nucleotide sequences encoding ARL15 (ADP-ribosylation factor-like 15); HSPB3 (heat shock 27 kDa protein 3) and hsa-miR-581. [Deletion Marker 2]. In a method wherein the cancer outcome marker is Chr 4, 105.8-107.2 Mb, the marker includes nucleotide sequences encoding F1120184 (hypothetical protein F1120184); GSTCD (glutathione S-transferase, C-terminal domain containing); INTS12 integrator complex subunit 12; KIAA1546 KIAA1546; MGC16169 hypothetical protein MGC16169; NPNT (nephronectin); and PPA2 pyrophosphatase (inorganic) 2. [Deletion Marker 3]. In a method wherein the cancer outcome marker is Chr 16, 45.8-46.3 Mb, the marker includes nucleotide sequences encoding ITFG1 (integrin alpha FG-GAP repeat containing 1) and PHKB (phosphorylase kinase, beta). [Deletion Marker 4]. In a method wherein the cancer outcome marker is Chr 5, 50.7-52.0 Mb, the marker includes a nucleotide sequence encoding ISL1 (ISL LIM homeobox). [Deletion Marker 5]. In a method wherein the cancer outcome marker is Chr 5, 94.2-96.1 Mb, the marker includes nucleotide sequences encoding ARSK (arylsulfatase family, member K); CAST (calpastatin); ELL2 (elongation factor, RNA polymerase II, 2); FAM81B family with sequence similarity 81, member B; GLRX glutaredoxin (thioltransferase); GPR150 G protein-coupled receptor 150; KIAA0372 KIAA0372; MCTP1 multiple C2 domains, transmembrane 1; PCSK1 proprotein convertase subtilisin/kexin type 1; RFESD (Rieske (Fe—S) domain containing); RHOBTB3 Rho-related BTB domain containing 3; SPATA9 (spermatogenesis associated 9); and hsa-miR-583. [Deletion Marker 6]. In a method wherein the cancer outcome marker is Chr 9, 36.1-37.0 Mb, the marker includes nucleotide sequences encoding C9orf19 chromosome 9 open reading frame 19; CCIN calicin; CLTA clathrin, light chain (Lca); GNE glucosamine (UDP-N-acetyl)-2-epimerase/N-acetylmannosamine kinase; MELK maternal embryonic leucine zipper kinase; PAX5 paired box 5; RECK reversion-inducing-cysteine-rich protein with kazal motifs; and RNF38 ring finger protein 38. [Deletion Marker 7]. In a method wherein the cancer outcome marker is Chr 5, 94.2-96.1 Mb, the marker includes nucleotide sequences encoding ARSK arylsulfatase family, member K; CAST calpastatin; ELL2 elongation factor, RNA polymerase II, 2; FAM81B family with sequence similarity 81, member B; GLRX glutaredoxin (thioltransferase); GPR150 G protein-coupled receptor 150; KIAA0372 KIAA0372; MCTP1 multiple C2 domains, transmembrane 1; PCSK1 proprotein convertase subtilisin/kexin type 1; RFESD Rieske (Fe—S) domain containing; RHOBTB3 Rho-related BTB domain containing 3; SPATA9 spermatogenesis associated 9. [Deletion Marker 8]. In a method wherein the cancer outcome marker is Chr14, 51.1-52.8 Mb, the marker includes nucleotide sequences encoding; C14orf166 chromosome 14 open reading frame 166; DDHD1 DDHD domain containing 1; ERO1L ERO1-like (S. cerevisiae); FRMD6 FERM domain containing 6; GNG2 guanine nucleotide binding protein (G protein), gamma 2; GNPNAT1 glucosamine-phosphate N-acetyltransferase 1; GPR137C G protein-coupled receptor 137C; NID2 nidogen 2 (osteonidogen); PLEKHC1 pleckstrin homology domain containing, family C (with FERM domain) member 1; PSMC6 proteasome (prosome, macropain) 26S subunit, ATPase, 6; PTGDR prostaglandin D2 receptor (DP); PTGER2 prostaglandin E receptor 2 (subtype EP2), 53 kDa; STYX serine/threonine/tyrosine interacting protein; TXNDC16 thioredoxin domain containing 16. [Deletion Marker 9]. In a method wherein the cancer outcome marker is Chr 14, 61.5-68.6 Mb, the marker includes nucleotide sequences encoding ACTN1 actinin, alpha 1; AKAP5 A kinase (PRKA) anchor protein 5; ARG2 arginase, type II; ATP6V1D ATPase, H+ transporting, lysosomal 34 kDa, V1 subunit D; C14orf50 chromosome 14 open reading frame 50; C14orf54 chromosome 14 open reading frame 54; C14orf83 chromosome 14 open reading frame 83; CHURC1 churchill domain containing 1; EIF2S1 eukaryotic translation initiation factor 2, subunit 1 alpha, 35 kDa; ESR2 estrogen receptor 2 (ER beta); FLJ39779 FLJ39779 protein; FNTB farnesyltransferase, CAAX box, beta; FUT8 fucosyltransferase 8 (alpha (1,6) fucosyltransferase); GPHB5 glycoprotein hormone beta 5; GPHN gephyrin; GPX2 glutathione peroxidase 2 (gastrointestinal); HSPA2 heat shock 70 kDa protein 2; KCNH5 potassium voltage-gated channel, subfamily H (eag-related), member 5; MAX MYC associated factor X; MPP5 membrane protein, palmitoylated 5 (MAGUK p55 subfamily member 5); MTHFD1 methylenetetrahydrofolate dehydrogenase (NADP+ dependent) 1, methenyltetrahydrofolate cyclohydrolase, formyltetrahydrofolate synthetase; PIGH phosphatidylinositol glycan anchor biosynthesis, class H; PLEK2 pleckstrin 2; PLEKHG3 pleckstrin homology domain containing, family G (with RhoGef domain) member 3; PLEKHH1 pleckstrin homology domain containing, family H (with MyTH4 domain) member 1; PPP2R5E protein phosphatase 2, regulatory subunit B', epsilon isoform; RAB15 RAB15, member RAS oncogene family; RAD51L1 RAD51-like 1 (S. cerevisiae); RDH11 retinol dehydrogenase 11 (all-trans/9-cis/11-cis); RDH12 retinol dehydrogenase 12 (all-trans/9-cis/11-cis); RHOJ ras homolog gene family, member J; SGPP1 sphingosine-1-phosphate phosphatase 1; SPTB spectrin, beta, erythrocytic (includes spherocytosis, clinical type I); SYNE2 spectrin repeat containing, nuclear envelope 2; SYT16 synaptotagmin XVI; VTI1B vesicle transport through interaction with t-SNAREs homolog 1B (yeast); WDR22 WD repeat domain 22; WDR89 WD repeat domain 89; ZBTB1 zinc finger and BTB domain containing 1; ZBTB25 zinc finger and BTB domain containing 25; ZFP36L1 zinc finger protein 36, C3H type-like 1; ZFYVE26 zinc finger, FYVE domain containing 26 and hsa-miR-625. [Deletion Marker 10]. In a method wherein the cancer outcome marker is Chr 9, 28.1 Mb, the marker includes a nucleotide sequence encoding LINGO2 (leucine rich repeat and Ig domain containing 2). [Deletion Marker 11]. In a method wherein the cancer outcome marker is Chr 4, 43.7-44.2 Mb, the marker includes a nucleotide sequence encoding KCTD8 (potassium channel tetramerisation domain containing 8). [Deletion Marker 12]. In a method wherein the cancer outcome marker is Chr 5, 60.8-62.9 Mb, the marker includes nucleotide sequences encoding DIMT1L DIM1 dimethyladenosine transferase 1-like (S. cerevisiae); FLJ37543 hypothetical protein FLJ37543; IPO11 importin 11; ISCA1L iron-sulfur cluster assembly 1 homolog (S. cerevisiae)-like; and KIF2A kinesin heavy chain member 2A. [Deletion Marker 13]. In a method wherein the cancer outcome marker is Chr 3, 120.0-121.1 Mb, the marker includes nucleotide sequences encoding ADPRH ADP-ribosylarginine hydrolase; B4GALT4 UDP-Gal:betaGlcNAc beta 1,4-galactosyltransferase, polypeptide 4; C3orf1 chromosome 3 open reading frame 1; C3orf15 chromosome 3 open reading frame 15; C3orf30 chromosome 3 open reading frame 30; CD80 CD80 molecule; CDGAP Cdc42 GTPase-activating protein; COX17 COX17 cytochrome c oxidase assembly homolog (S. cerevisiae); GSK3B glycogen synthase kinase 3 beta; IGSF11 immunoglobulin superfamily, member 11; KTELC1 KTEL (Lys-Tyr-Glu-Leu) containing 1; NR1I2 nuclear receptor subfamily 1, group I, member 2; PLA1A phospholipase A1 member A; POPDC2 popeye domain containing 2; TMEM39A transmembrane protein 39A; and UPK1B uroplakin 1B. [Deletion Marker 14]. In a method wherein the cancer outcome marker is Chr 4, 46.2-48.0 Mb, the marker includes nucleotide sequences encoding ATP10D ATPase, class V, type 10D; CNGA1 cyclic nucleotide gated channel alpha 1; COMMD8 COMM domain containing 8; CORIN corin, serine peptidase; COX7B2 cytochrome c oxidase subunit VIIb2; GABRA4 gamma-aminobutyric acid (GABA) A receptor, alpha 4; GABRB1 gamma-aminobutyric acid (GABA) A receptor, beta 1; NFXL1 nuclear transcription factor, X-box binding-like 1; NPAL1 NIPA-like domain containing 1; TEC tec protein tyrosine kinase; and TXK TXK tyrosine kinase. [Deletion Marker 15]. In a method wherein the cancer outcome marker is Chr 14, 38.9-40.0 Mb, the marker includes a nucleotide sequence encoding FBXO33 (F-box protein 33). [Deletion Marker 16]. In a method wherein the cancer outcome marker is Chr 4, 44.2-44.6 Mb, the marker includes nucleotide sequences encoding GNPDA2 (glucosamine-6-phosphate deaminase 2); GUF1 (GUF1 GTPase homolog (S. cerevisiae)); and YIPF7 (Yip1 domain family, member 7). [Deletion Marker 17]. In a method wherein the cancer outcome marker is Chr 2, 213.7-214.3 Mb, the marker includes nucleotide sequences encoding IKZF2 IKAROS family zinc finger 2 (Helios); and SPAG16 sperm associated antigen 16. [Deletion Marker 18]. In a method wherein the cancer outcome marker is Chr14, 43.9-46.6 Mb, the marker includes nucleotide sequences encoding C14orf106 chromosome 14 open reading frame 106; C14orf155 chromosome 14 open reading frame 155; C14orf28 chromosome 14 open reading frame 28; FANCM Fanconi anemia, complementation group M; FKBP3 FK506 binding protein 3, 25 kDa; KIAA0423 KIAA0423; KLHL28 kelch-like 28 (Drosophila); MDGA2 MAM domain containing glycosylphosphatidylinositol anchor 2; PRPF39 PRP39 pre-mRNA processing factor 39 homolog (S. cerevisiae); and RPL10L ribosomal protein L10-like. [Deletion Marker 19]. In a method wherein the cancer outcome marker is Chr 14, 27.6-28.6 Mb, the marker includes a nucleotide sequence encoding FOXG1 (forkhead box G1). [Deletion Marker 20]. In a method wherein the cancer outcome marker is Chr 3, 98.0-98.3 Mb, the marker includes nucleotide sequences encoding EPHA6 (EPH receptor A6). [Deletion Marker 21]. In a method wherein the cancer outcome marker is Chr14, 55.2-60.0 Mb, the marker includes nucleotide sequences encoding ACTR10 actin-related protein 10 homolog (*S. cerevisiae*); ARID4A AT rich interactive domain 4A (RBP1-like); C14orf100 chromosome 14 open reading frame 100; C14orf101 chromosome 14 open reading frame 101; C14orf105 chromosome 14 open reading frame 105; C14orf108 chromosome 14 open reading frame 108; C14orf135 chromosome 14 open reading frame 135; C14orf149 chromosome 14 open reading frame 149; C14orf37 chromosome 14 open reading frame 37; C14orf39 chromosome 14 open reading frame 39; DAAM1 dishevelled associated activator of morphogenesis 1; DACT1 dapper, antagonist of beta-catenin, homolog 1 (*Xenopus laevis*); DHRS7 dehydrogenase/reductase (SDR family) member 7; EXOC5 exocyst complex component 5; GPR135 G protein-coupled receptor 135; KIAA0586 KIAA0586; NAT12 N-acetyltransferase 12; OTX2 orthodenticle homeobox 2; *PELI2* pellino homolog 2 (*Drosophila*); PPM1A protein phosphatase 1A (formerly 2C), magnesium-dependent, alpha isoform; PSMA3 proteasome (prosome, macropain) subunit, alpha type, 3; RTN1 reticulon 1; SLC35F4 solute carrier family 35, member F4; TIMM9 translocase of inner mitochondrial membrane 9 homolog (yeast); and UNQ9438 TIMM. [Deletion Marker 22]. In a method wherein the cancer outcome marker is Chr14, 48.7-51.1 Mb, the marker includes nucleotide sequences encoding ABHD12B abhydrolase domain containing 12B; ARF6 ADP-ribosylation factor 6; ATP5S ATP synthase, H+ transporting, mitochondrial F0 complex, subunit s (factor B); C14orf104 chromosome 14 open reading frame 104; C14orf138 chromosome 14 open reading frame 138; CDKL1 cyclin-dependent kinase-like 1 (CDC2-related kinase); FRMD6 FERM domain containing 6; KLHDC1 kelch domain containing 1; KLHDC2 kelch domain containing 2; L2HGDH L-2-hydroxyglutarate dehydrogenase; LOC196913 hypothetical protein LOC196913; LOC283551 hypothetical protein LOC283551; MAP4K5 mitogen-activated protein kinase kinase kinase kinase 5; MGAT2 mannosyl (alpha-1,6)-glycoprotein beta-1,2-N-acetylglucosaminyltransferase; NIN ninein (GSK3B interacting protein); POLE2 polymerase (DNA directed), epsilon 2 (p59 subunit); PPIL5 peptidylprolyl isomerase (cyclophilin)-like 5 PYGL phosphorylase, glycogen; liver (Hers disease, glycogen storage disease type VI); RPL36AL ribosomal protein L36a-like; and RPS29 ribosomal protein S29. [Deletion Marker 23]. In a method wherein the cancer outcome marker is Chr 4, 81.4-83.2 Mb, the marker includes nucleotide sequences encoding BMP3 bone morphogenetic protein 3 (osteogenic); C4orf22 chromosome 4 open reading frame 22; FGF5 fibroblast growth factor 5; PRKG2 protein kinase, cGMP-dependent, type II; and RASGEF1B RasGEF domain family, member 1B. [Deletion Marker 24]. In a method wherein the cancer outcome marker is Chr 10, 51.9-54.2 Mb, the marker includes nucleotide sequences encoding ACF apobec-1 complementation factor; ASAH2B N-acylsphingosine amidohydrolase (non-lysosomal ceramidase) 2B; CSTF2T cleavage stimulation factor, 3' pre-RNA, subunit 2, 64 kDa, tau variant; DKK1 dickkopf homolog 1 (*Xenopus laevis*); MBL2 mannose-binding lectin (protein C) 2, soluble (opsonic defect); PRKG1 protein kinase, cGMP-dependent, type I; SGMS1 sphingomyelin synthase 1; and hsa-miR-605. [Deletion Marker 25]. In a method wherein the cancer outcome marker is Chr 5, 55.2-58.6 Mb, the marker includes nucleotide sequences encoding ANKRD55 ankyrin repeat domain 55; C5orf29 chromosome 5 open reading frame 29; C5orf35 chromosome 5 open reading frame 35; DKFZp686D0972 similar to RIKEN cDNA 4732495G21 gene; GPBP1 GC-rich promoter binding protein 1; IL31RA interleukin 31 receptor A; IL6ST interleukin 6 signal transducer (gp130, oncostatin M receptor); MAP3K1 mitogen-activated protein kinase kinase kinase 1; MIER3 mesoderm induction early response 1, family member 3; PDE4D phosphodiesterase 4D, cAMP-specific (phosphodiesterase E3 dunce homolog, *Drosophila*); PLK2 polo-like kinase 2 (*Drosophila*); and RAB3C RAB3C, member RAS oncogene family. [Deletion Marker 26]. In a method wherein the cancer outcome marker is Chr 5, 67.8-68.5 Mb, the marker includes nucleotide sequences encoding CCNB1 (cyclin B1) and SLC30A5 (solute carrier family 30 (zinc transporter), member 5). [Deletion Marker 27].

In any of the methods, the test sample can be a tissue sample that may contain tumor cells, such as for example a blood sample, a tumor tissue or a suspected tumor tissue, a thin layer cytological sample, a fine needle aspirate sample, a lung wash sample, a pleural effusion sample, a fresh frozen tissue sample, a paraffin embedded tissue sample or an extract or processed sample produced from any of the preceding. In exemplary embodiments, the tissue sample is a lung tissue sample or a peripheral blood sample comprising circulating tumor cells. In any of the methods, the determining step (b) can be performed by in situ hybridization. The in situ hybridization can be performed with a nucleic acid probe that is fluorescently labeled, with at least two nucleic acid probes, or a peptide nucleic acid probe. The determining step (b) may be performed by polymerase chain reaction, a nucleic acid sequencing assay, or nucleic acid microarray assay. In an exemplary embodiment, the lung cancer is non-small-cell lung cancer, which can be for example squamous cell carcinoma, large cell carcinoma or adenocarcinoma. In any of the methods, the patient can receiving treatment with chemotherapy, radiation, surgery or any combination thereof.

In another aspect, the present disclosure provides a method of selecting a treatment for a patient suffering from lung cancer, the method comprising the steps of: a) providing a test sample from the patient wherein treatment with a chemotherapy agent is at least one treatment option for the patient; b) determining a copy number of the cancer outcome marker in the test sample; c) comparing the copy number of the cancer outcome marker in the test sample against a baseline copy number of two thereby determining the presence or absence of a copy number change for the cancer outcome marker in the test sample; and d) determining a chemotherapy treatment regimen based on the comparison in step c). The step of determining a treatment regimen based on the comparison in step c) includes for example selecting a chemotherapy agent and determining a frequency of chemotherapy treatment when a copy number change is present for the cancer outcome marker.

In another aspect, the present disclosure provides a method of classifying a patient as having a lung cancer that is resistant to treatment comprising the steps of: a) providing a test sample from a patient; b) determining a copy number for the cancer outcome marker; c) comparing the copy number for the cancer outcome marker in the test sample against a baseline copy number of two for the cancer outcome marker to determine the presence or absence of a copy number change in the cancer outcome marker in the patient; and d) classifying the patient as having a lung cancer that is resistant to treatment based on the presence of a copy number change in the cancer outcome marker.

In another aspect, the present disclosure provides a kit comprising: a) reagents for determining the presence or absence of a copy number change for the cancer outcome marker; and b) instructions for performing the test. The reagents to determine the presence or absence of a copy number change for the cancer outcome marker can include for example detectably-labeled polynucleotides that hybridize to at least a portion of the cancer outcome marker. The cancer outcome marker can be a region of chromosomal DNA, the amplification of which produces a copy number gain of the cancer outcome marker, wherein the copy number gain is associated with a poor disease outcome. Such cancer outcome markers can be selected from the group consisting of Chr 19, 34.7 Mb-35.6 Mb; Chr 19, 38.9-40.7 Mb; Chr 17, 69.2-71.3 Mb; Chr 6, 70.8-71.1 Mb; Chr 12, 93.7 kb-1.9 Mb; Chr 11, 64.3-64.8 Mb; Chr 19, 57.0-62.2 Mb; Chr 6, 39.1-39.9 Mb; Chr 11, 64.8-65.7 Mb; Chr 11, 61.4-64.3 Mb; Chr 17, 51.5-53.2 Mb; Chr 17, 43.5-44.9 Mb; Chr 2, 147.6-151.1 Mb; Chr 6, 123.7-135.6 Mb; Chr 8, 6.9-8.8 Mb; Chr 2, 159.9-161.4 Mb; Chr 2, 200.9-204.2 Mb; Chr 6, 36.3-36.7 Mb; Chr 2, 205.9-208.1 Mb; and Chr 1, 109.5-111.1 Mb. The cancer outcome marker can be a region of chromosomal DNA, the deletion of which produces a copy number loss of the cancer outcome marker, wherein the copy number loss is associated with a poor disease outcome. Such cancer outcome markers can be selected from the group consisting of Chr 5, 62.9-67.8 Mb; Chr 5, 53.3-53.8 Mb; Chr 4, 105.8-107.2 Mb; Chr 16, 45.8-46.3 Mb; Chr 5, 50.7-52.0 Mb; Chr 5, 94.2-96.1 Mb; Chr 9, 36.1-37.0 Mb; Chr 5, 94.2-96.1 Mb; Chr14, 51.1-52.8 Mb; Chr 14, 61.5-68.6 Mb; Chr 9, 28.1 Mb; Chr 4, 43.7-44.2 Mb; Chr 5, 60.8-62.9 Mb; Chr 3, 120.0-121.1 Mb; Chr 4, 46.2-48.0 Mb; Chr 14, 38.9-40.0 Mb; Chr 4, 44.2-44.6 Mb; Chr 2, 213.7-214.3 Mb; Chr14, 43.9-46.6 Mb; Chr 14, 27.6-28.6 Mb; Chr 3, 98.0-98.3 Mb; Chr14, 55.2-60.0 Mb; Chr14, 48.7-51.1 Mb; Chr 4, 81.4-83.2 Mb; Chr 10, 51.9-54.2 Mb; Chr 5, 55.2-58.6 Mb; and Chr 5, 67.8-68.5 Mb.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 119 is a Kaplan-Meier plot showing the overall survival (OS) in days for a 74 patient cohort with NSCLC stage Ia-IIa, classified by presence or absence of a copy number gain in SSSCA1.

FIG. 120 is a Kaplan-Meier plot showing the time to recurrence (TTR) in days for a 74 patient cohort with NSCLC stage Ia-IIa, classified by presence or absence of a copy number gain in SSSCA1.

FIG. 121 is a Kaplan-Meier plot showing the overall survival (OS) in days for a 74 patient cohort with NSCLC stage Ia-IIa, classified by presence or absence of a copy number gain in BAD.

FIG. 122 is a Kaplan-Meier plot showing the overall survival (OS) in days for a 74 patient cohort with NSCLC stage Ia-IIa, classified by presence or absence of a copy number gain in C11orf20.

FIG. 123 is a Kaplan-Meier plot showing the time to recurrence (TTR) in days for a 74 patient cohort with NSCLC stage Ia-IIa, classified by presence or absence of a copy number gain in BAD.

FIG. 124 is a Kaplan-Meier plot showing the time to recurrence (TTR) in days for a 74 patient cohort with NSCLC stage Ia-IIa, classified by presence or absence of a copy number gain in C11orf20.

FIG. 125 is a Kaplan-Meier plot showing the overall survival (OS) in days for a 74 patient cohort with NSCLC stage Ia-IIa, classified by presence or absence of a copy number gain in DNAJC4.

FIG. 126 is a Kaplan-Meier plot showing the time to recurrence (TTR) in days for a 74 patient cohort with NSCLC stage Ia-IIa, classified by presence or absence of a copy number gain in DNAJC4.

FIG. 127 is a Kaplan-Meier plot showing the overall survival (OS) in days for a 74 patient cohort with NSCLC stage Ia-IIa, classified by presence or absence of a copy number gain in ESRRA.

FIG. 128 is a Kaplan-Meier plot showing the time to recurrence (TTR) in days for a 74 patient cohort with NSCLC stage Ia-IIa, classified by presence or absence of a copy number gain in ESRRA.

FIG. 129 is a Kaplan-Meier plot showing the overall survival (OS) in days for a 74 patient cohort with NSCLC stage Ia-IIa, classified by presence or absence of a copy number gain in FADS2.

FIG. 130 is a Kaplan-Meier plot showing the overall survival (OS) in days for a 74 patient cohort with NSCLC stage Ia-IIa, classified by presence or absence of a copy number gain in FADS3.

Figure 131:
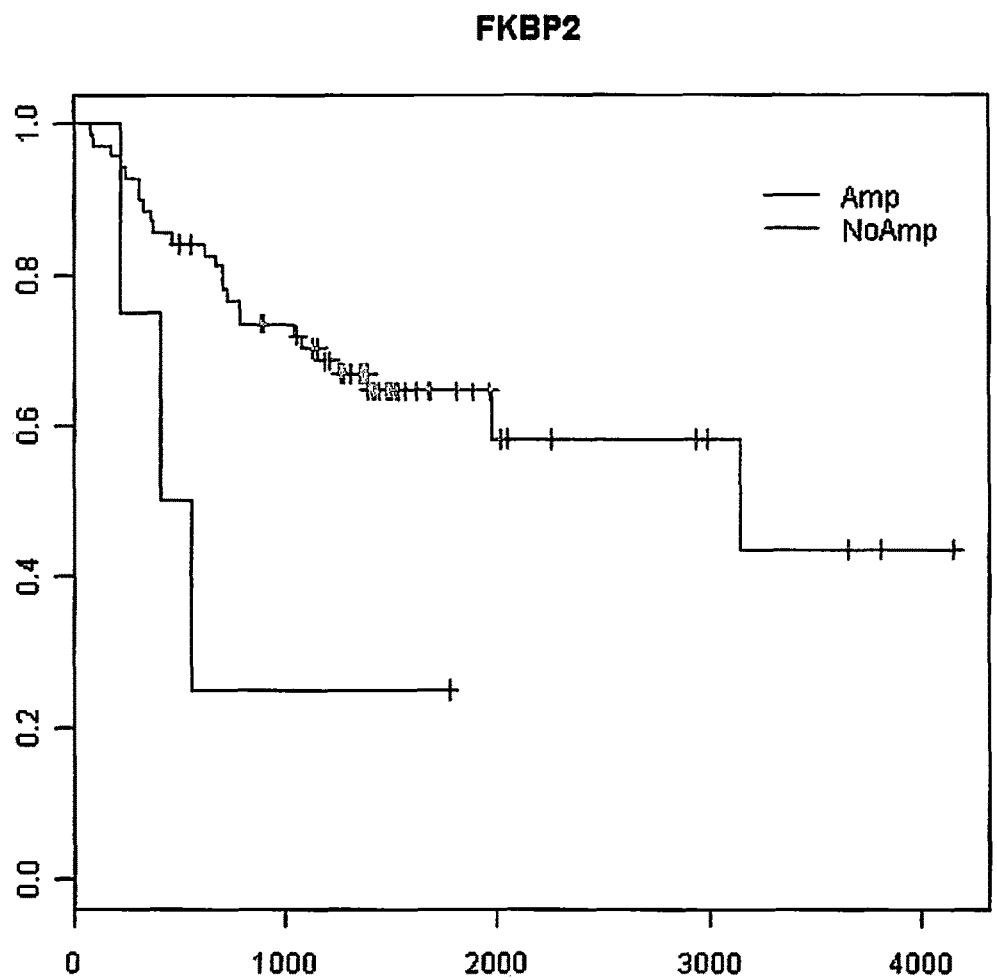

FIG. 131 is a Kaplan-Meier plot showing the overall survival (OS) in days for a 74 patient cohort with NSCLC stage Ia-IIa, classified by presence or absence of a copy number gain in FKBP2.

Figure 132:
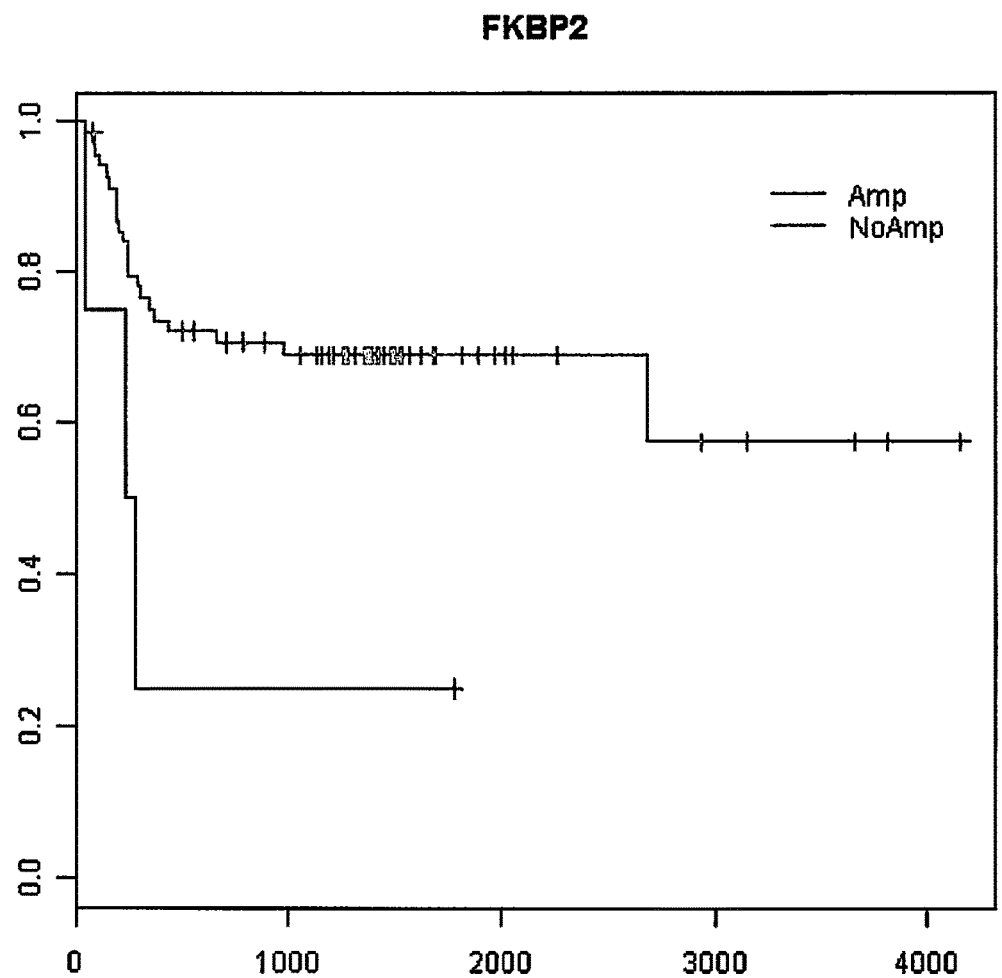

FIG. 132 is a Kaplan-Meier plot showing the time to recurrence (TTR) in days for a 74 patient cohort with NSCLC stage Ia-IIa, classified by presence or absence of a copy number gain in FKBP2.

Figure 133:
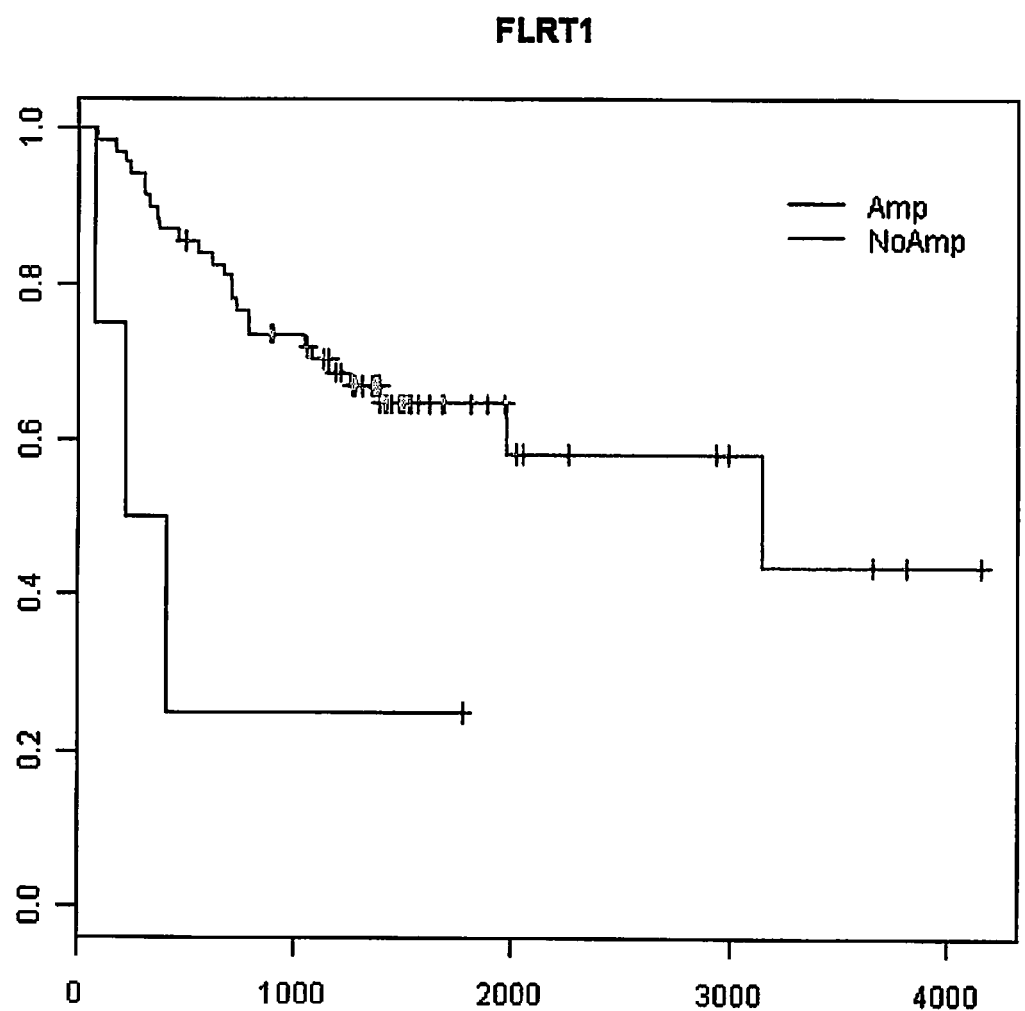

FIG. 133 is a Kaplan-Meier plot showing the overall survival (OS) in days for a 74 patient cohort with NSCLC stage Ia-IIa, classified by presence or absence of a copy number gain in FLRT1.

Figure 134:
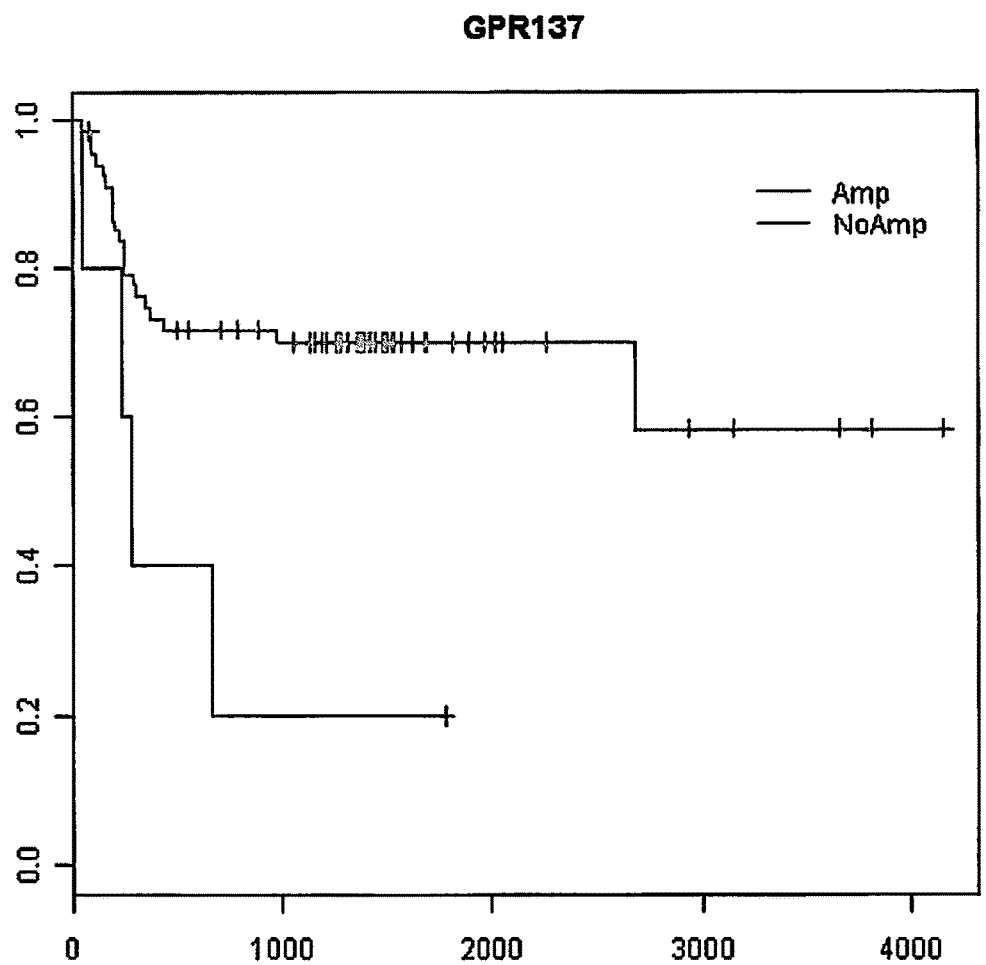

FIG. 134 is a Kaplan-Meier plot showing the time to recurrence (TTR) in days for a 74 patient cohort with NSCLC stage Ia-IIa, classified by presence or absence of a copy number gain in GPR137.

Figure 135:
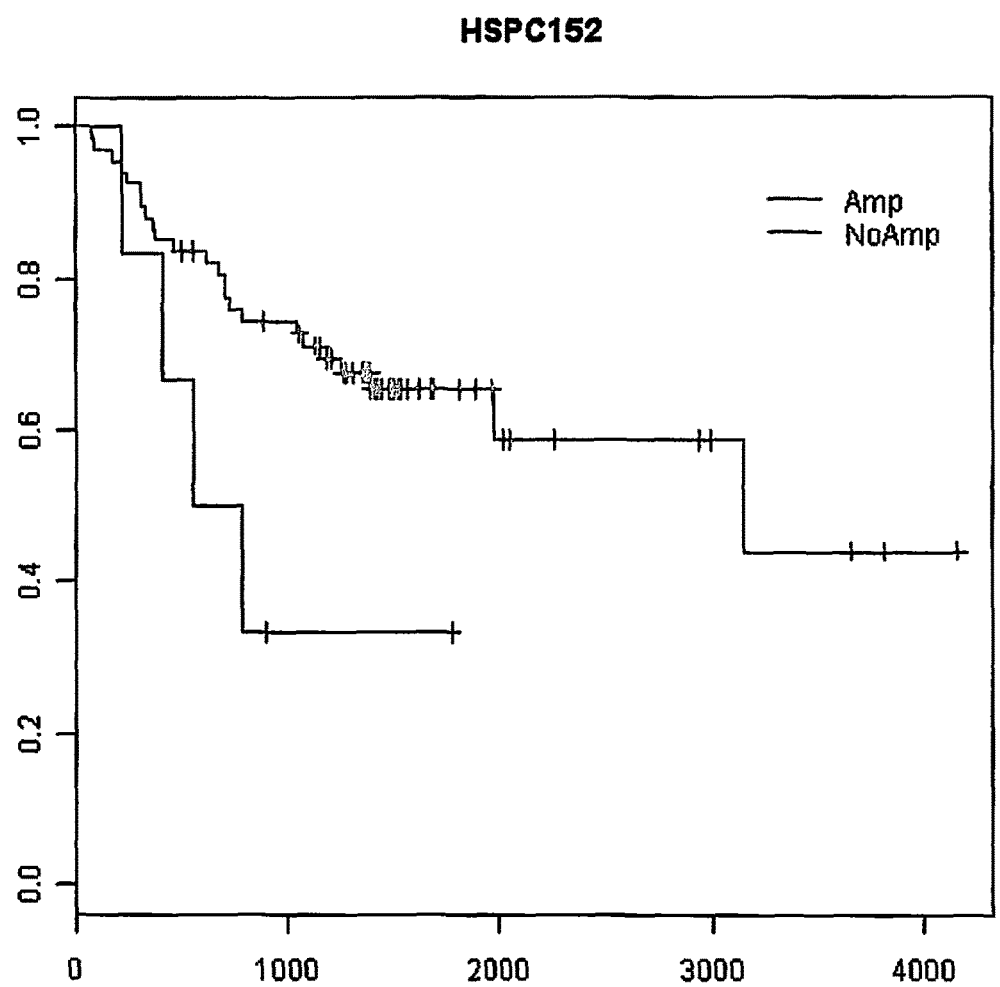

FIG. 135 is a Kaplan-Meier plot showing the overall survival (OS) in days for a 74 patient cohort with NSCLC stage Ia-IIa, classified by presence or absence of a copy number gain in HSPC152.

Figure 136:
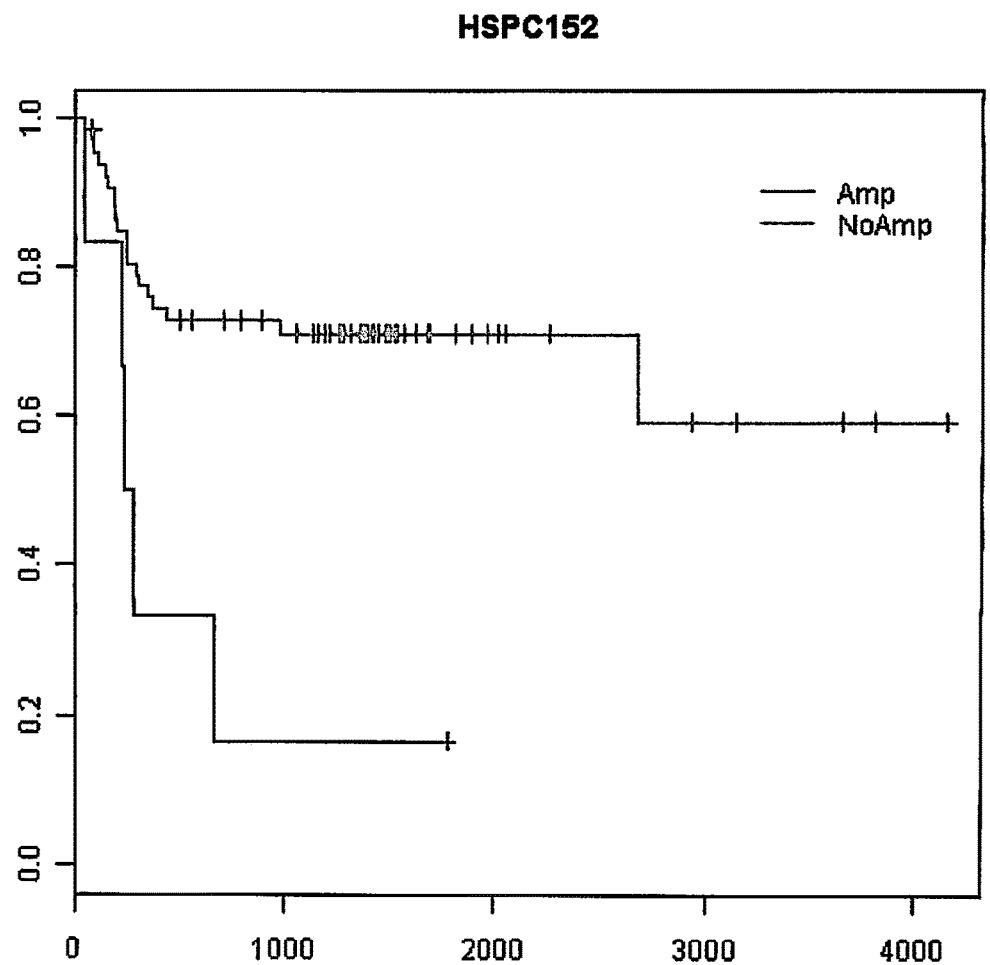

FIG. 136 is a Kaplan-Meier plot showing the time to recurrence (TTR) in days for a 74 patient cohort with NSCLC stage Ia-IIa, classified by presence or absence of a copy number gain in HSPC152.

Figure 137:
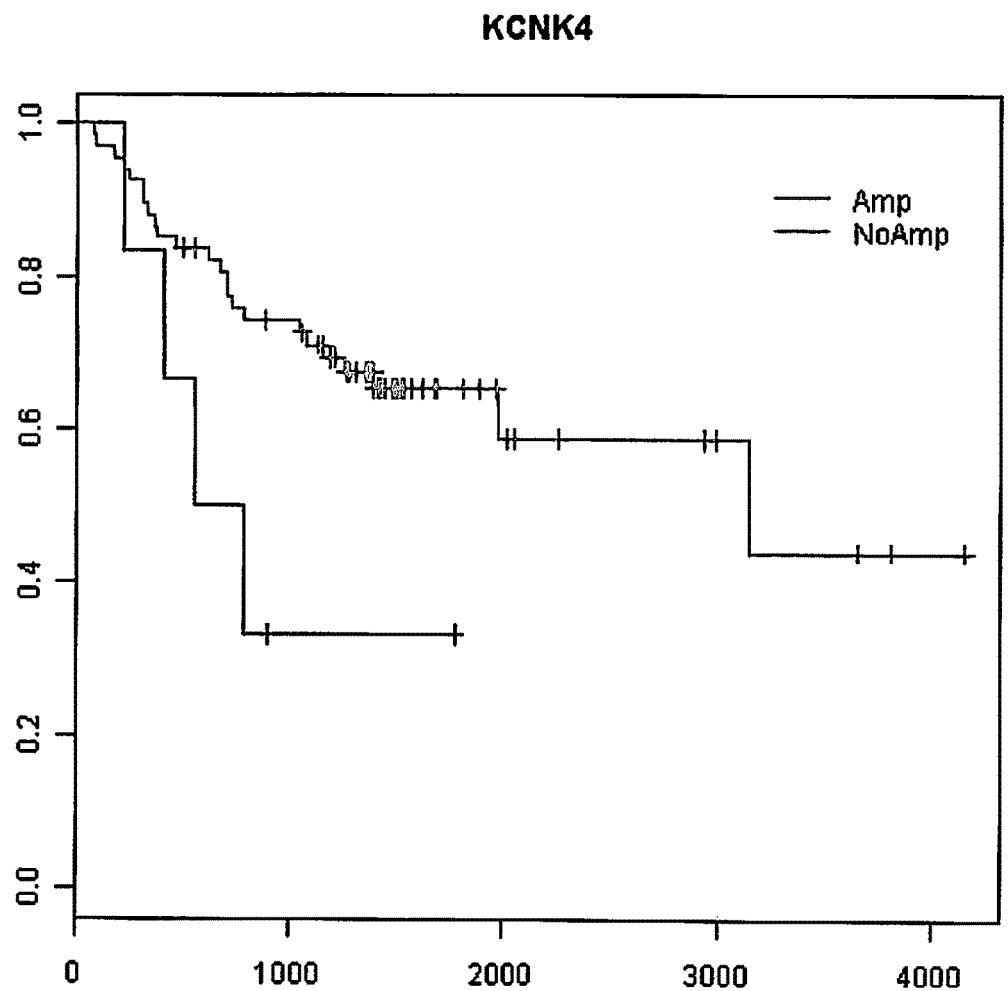

FIG. 137 is a Kaplan-Meier plot showing the overall survival (OS) in days for a 74 patient cohort with NSCLC stage Ia-IIa, classified by presence or absence of a copy number gain in KCNK4.

Figure 138:
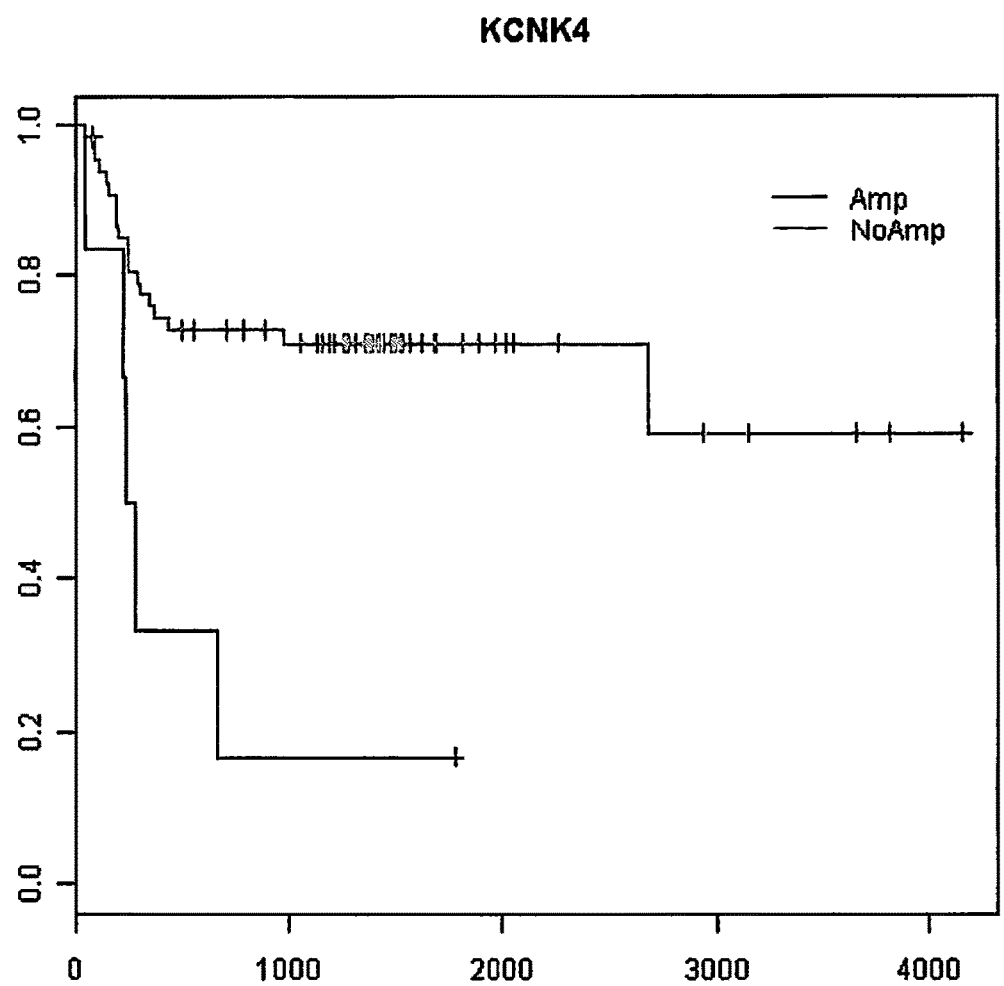

FIG. 138 is a Kaplan-Meier plot showing the time to recurrence (TTR) in days for a 74 patient cohort with NSCLC stage Ia-IIa, classified by presence or absence of a copy number gain in KCNK4.

Figure 139:
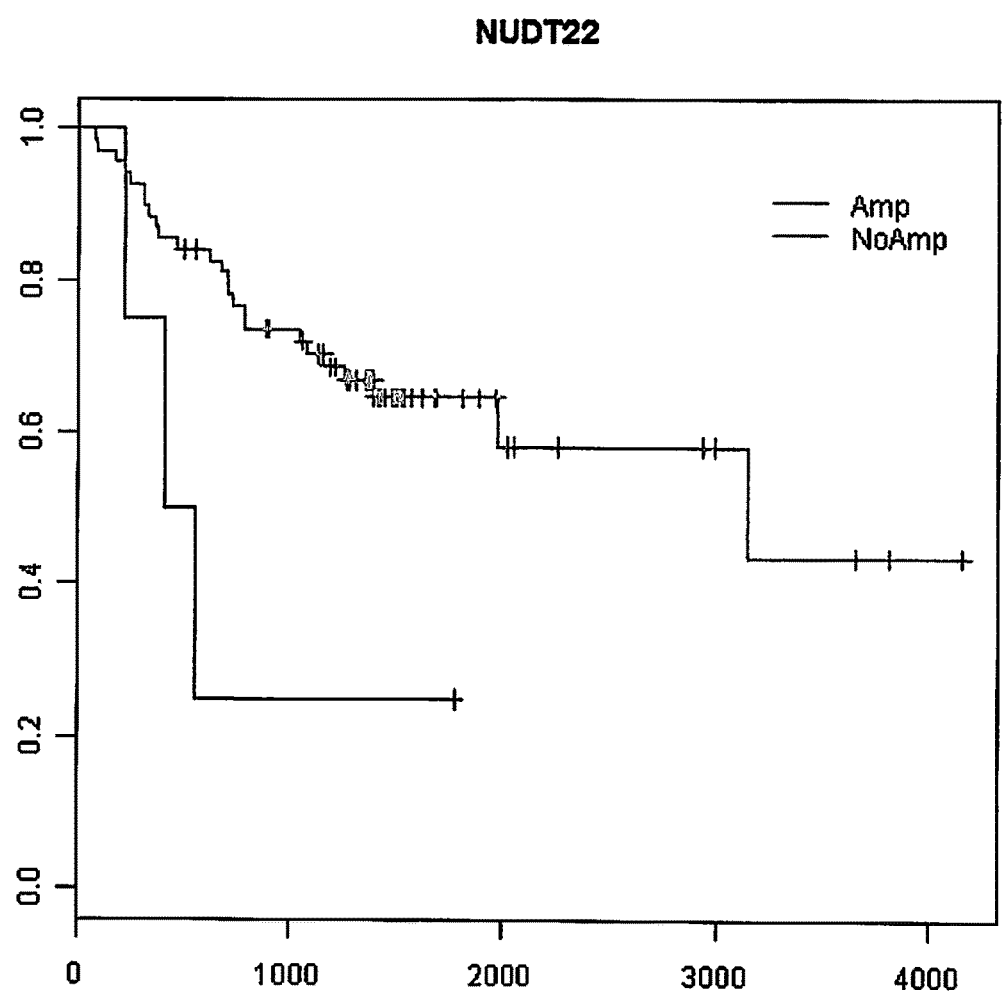

FIG. 139 is a Kaplan-Meier plot showing the overall survival (OS) in days for a 74 patient cohort with NSCLC stage Ia-IIa, classified by presence or absence of a copy number gain in NUDT22.

Figure 140:
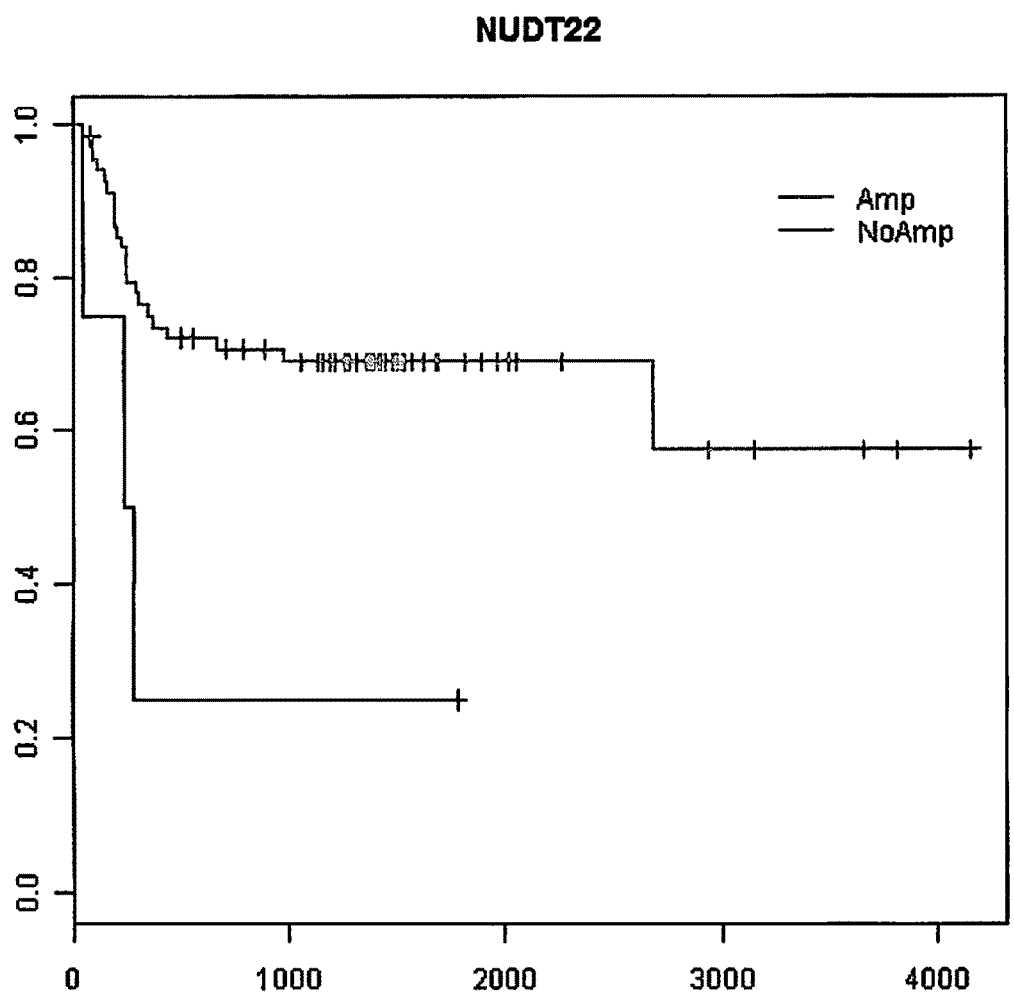

FIG. 140 is a Kaplan-Meier plot showing the time to recurrence (TTR) in days for a 74 patient cohort with NSCLC stage Ia-IIa, classified by presence or absence of a copy number gain in NUDT22.

Figure 141:
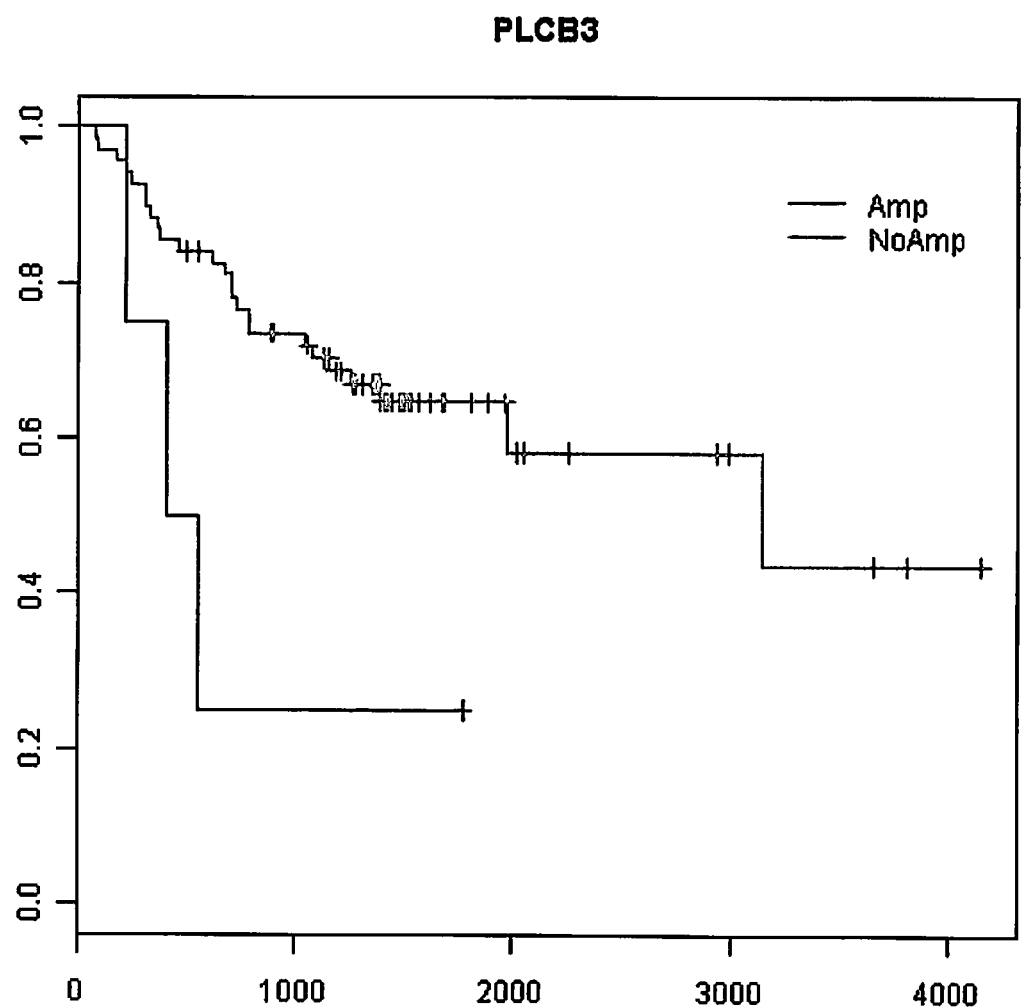

FIG. 141 is a Kaplan-Meier plot showing the overall survival (OS) in days for a 74 patient cohort with NSCLC stage Ia-IIa, classified by presence or absence of a copy number gain in PLCB3.

Figure 142:
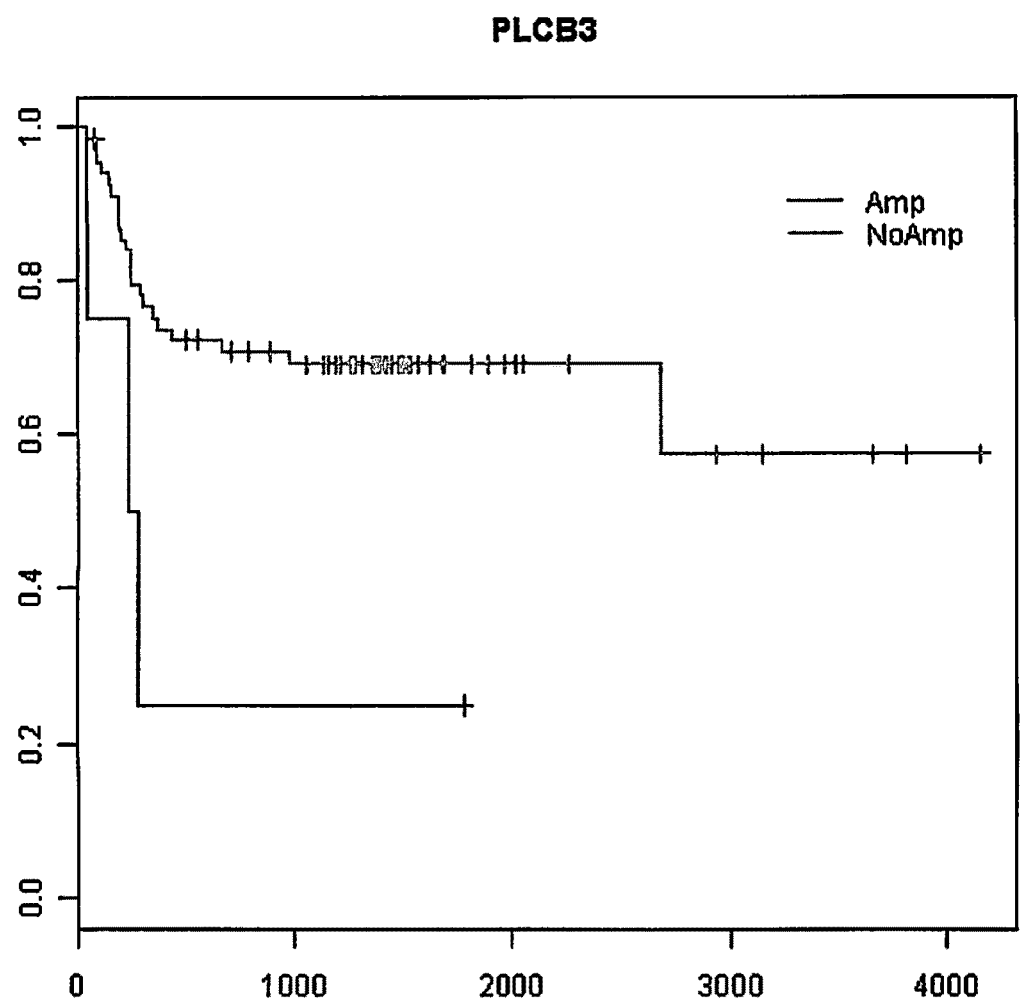

FIG. 142 is a Kaplan-Meier plot showing the time to recurrence (TTR) in days for a 74 patient cohort with NSCLC stage Ia-IIa, classified by presence or absence of a copy number gain in PLCB3.

Figure 143:
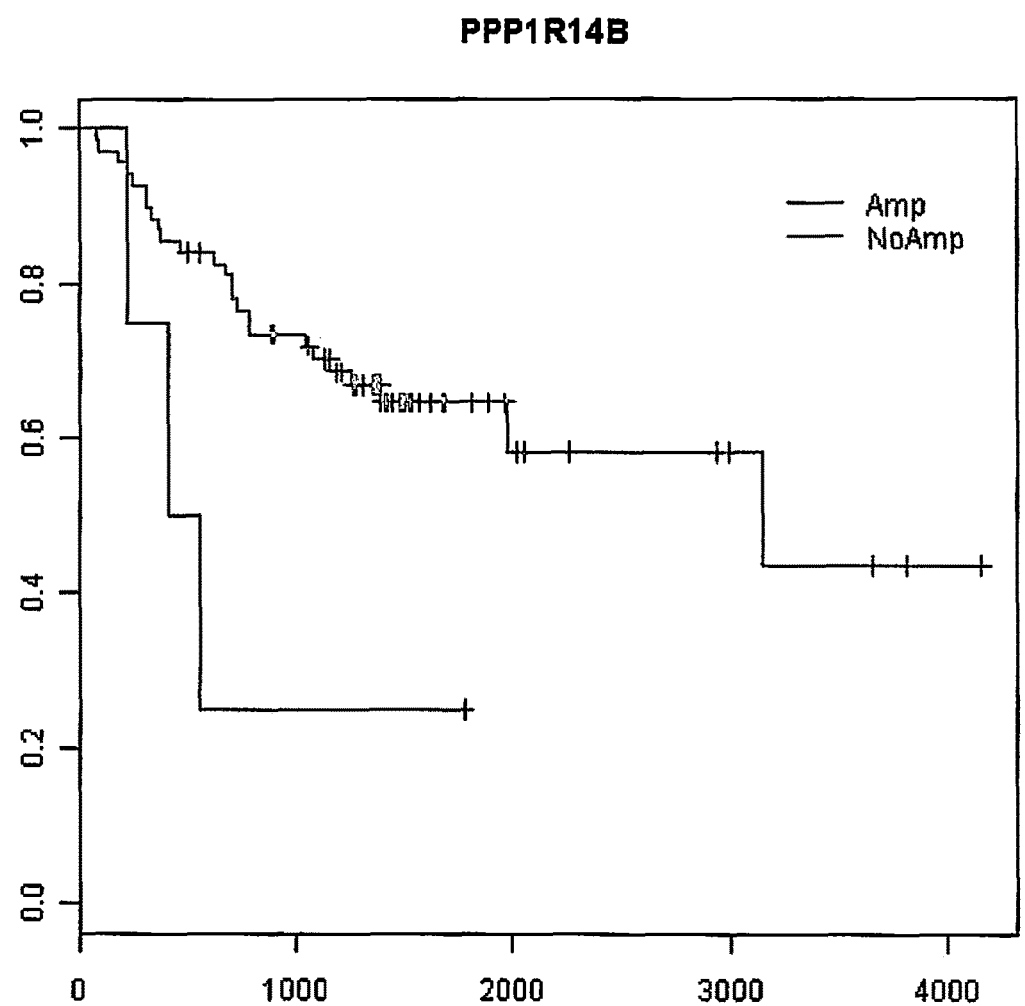

FIG. 143 is a Kaplan-Meier plot showing the overall survival (OS) in days for a 74 patient cohort with NSCLC stage Ia-IIa, classified by presence or absence of a copy number gain in PPP1R14B.

Figure 144:
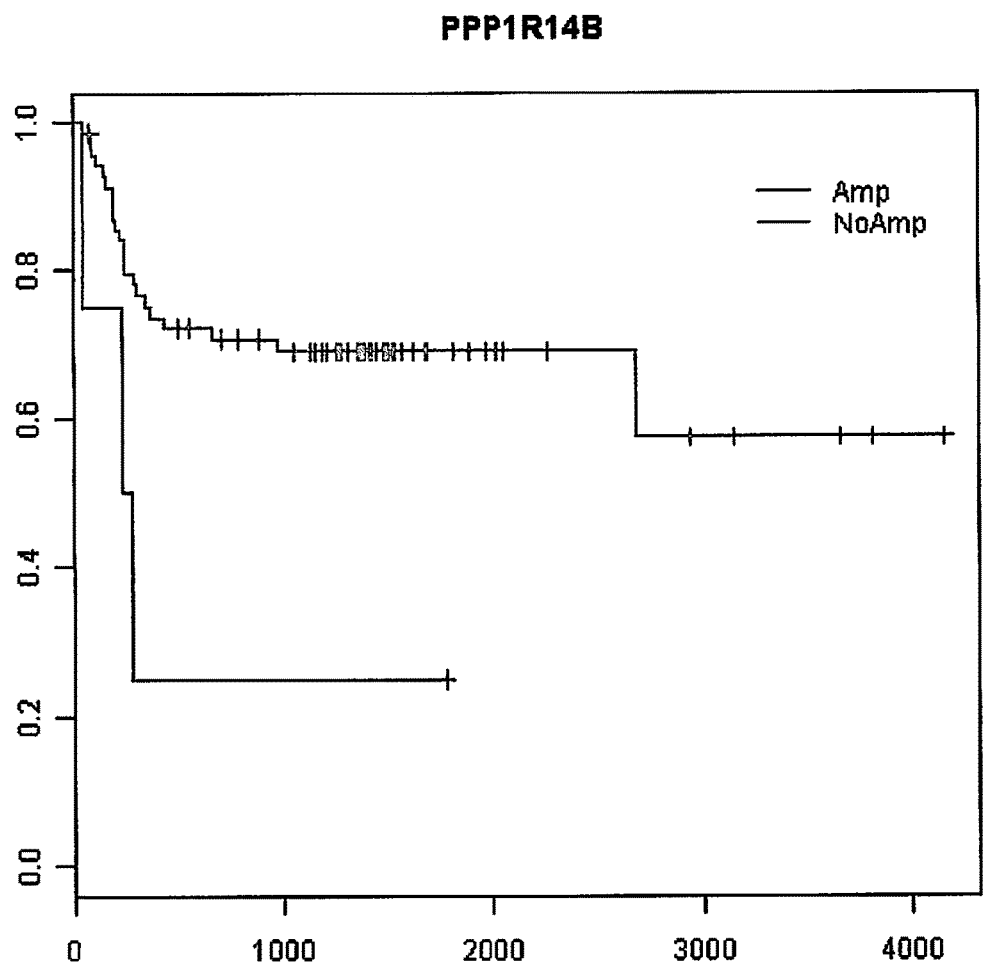

FIG. 144 is a Kaplan-Meier plot showing the time to recurrence (TTR) in days for a 74 patient cohort with NSCLC stage Ia-IIa, classified by presence or absence of a copy number gain in PPP1R14B.

Figure 145:
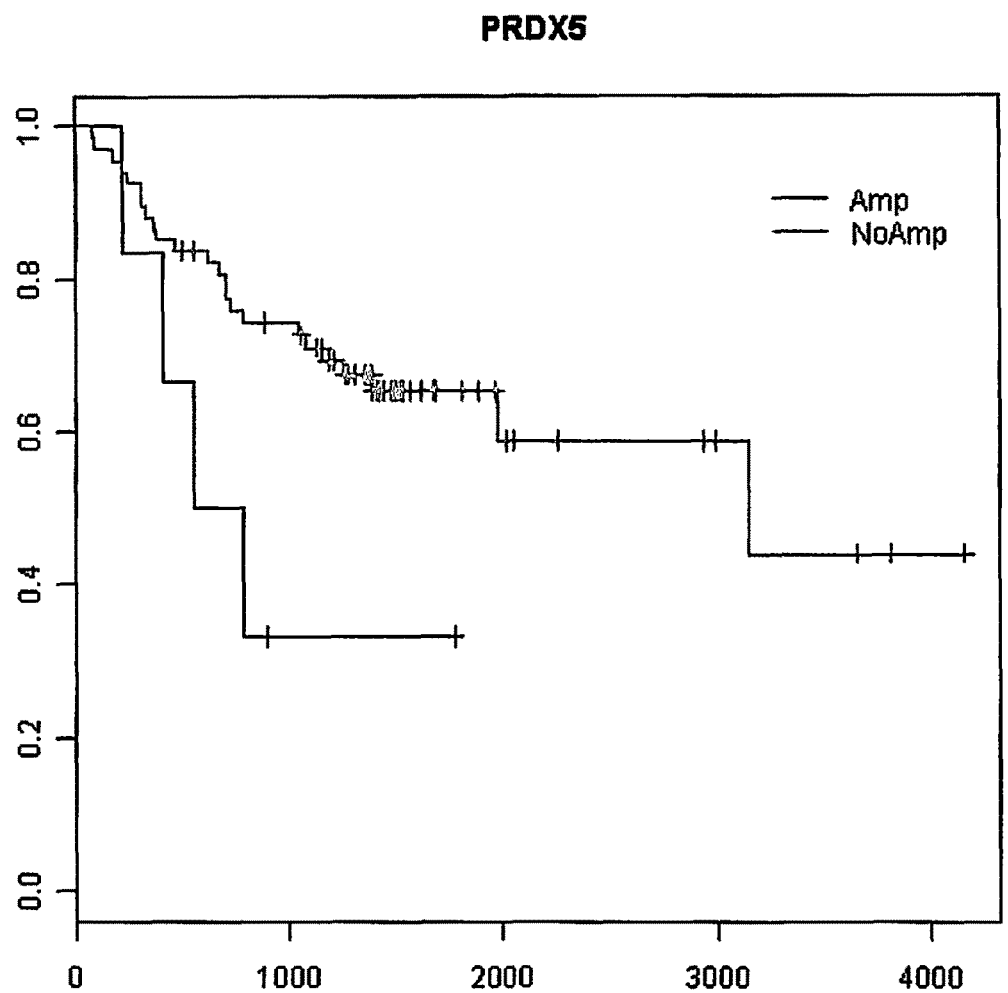

FIG. 145 is a Kaplan-Meier plot showing the overall survival (OS) in days for a 74 patient cohort with NSCLC stage Ia-IIa, classified by presence or absence of a copy number gain in PRDX5.

Figure 146:
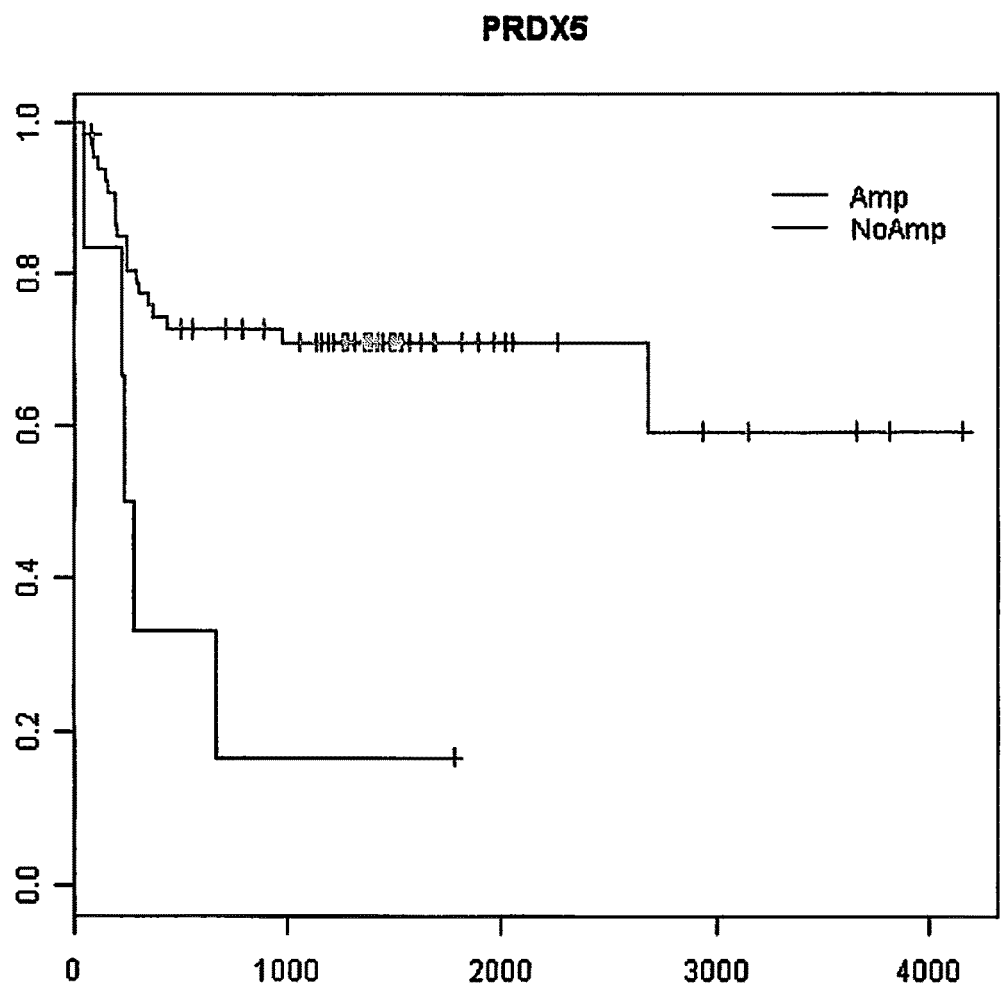

FIG. 146 is a Kaplan-Meier plot showing the time to recurrence (TTR) in days for a 74 patient cohort with NSCLC stage Ia-IIa, classified by presence or absence of a copy number gain in PRDX5.

Figure 147:
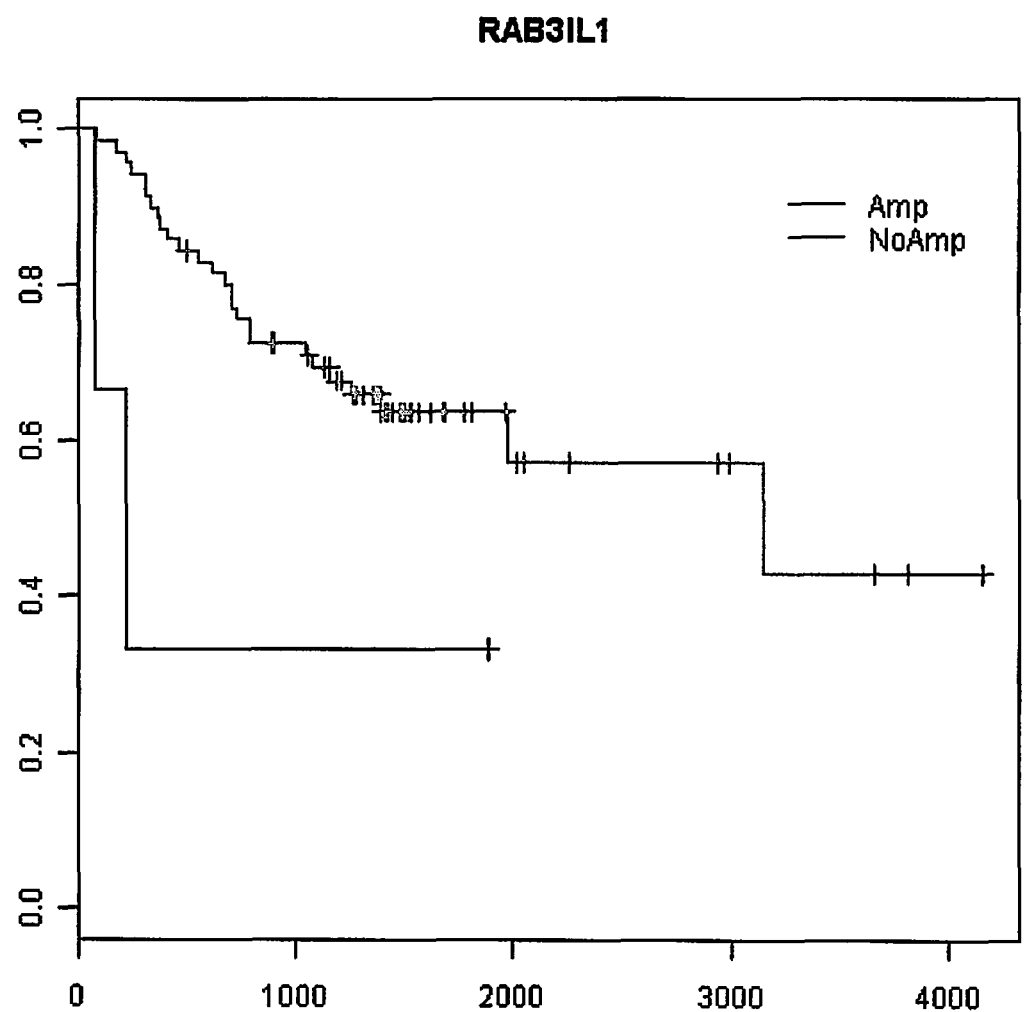

FIG. 147 is a Kaplan-Meier plot showing the overall survival (OS) in days for a 74 patient cohort with NSCLC stage Ia-IIa, classified by presence or absence of a copy number gain in RAB3IL1.

Figure 148:
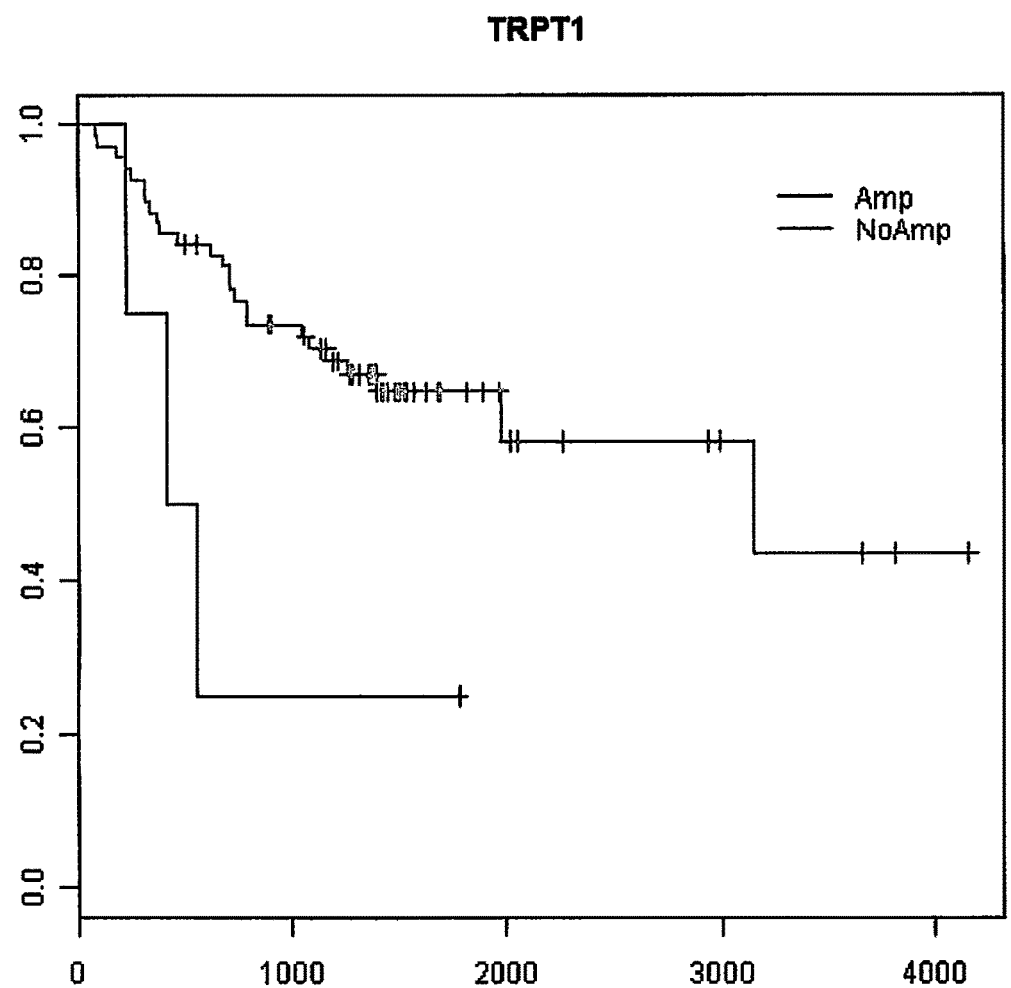

FIG. 148 is a Kaplan-Meier plot showing the overall survival (OS) in days for a 74 patient cohort with NSCLC stage Ia-IIa, classified by presence or absence of a copy number gain in TRPT1.

Figure 149:
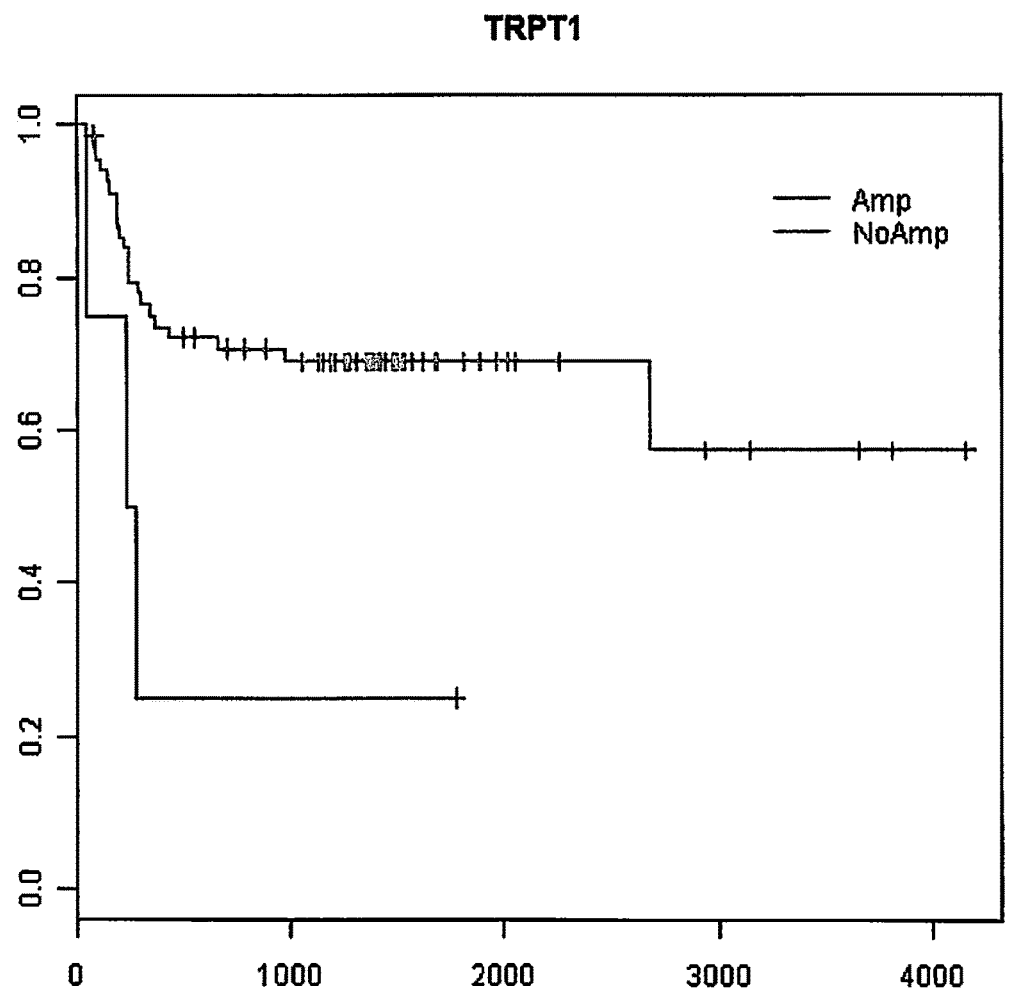

FIG. 149 is a Kaplan-Meier plot showing the time to recurrence (TTR) in days for a 74 patient cohort with NSCLC stage Ia-IIa, classified by presence or absence of a copy number gain in TRPT1.

Figure 150:
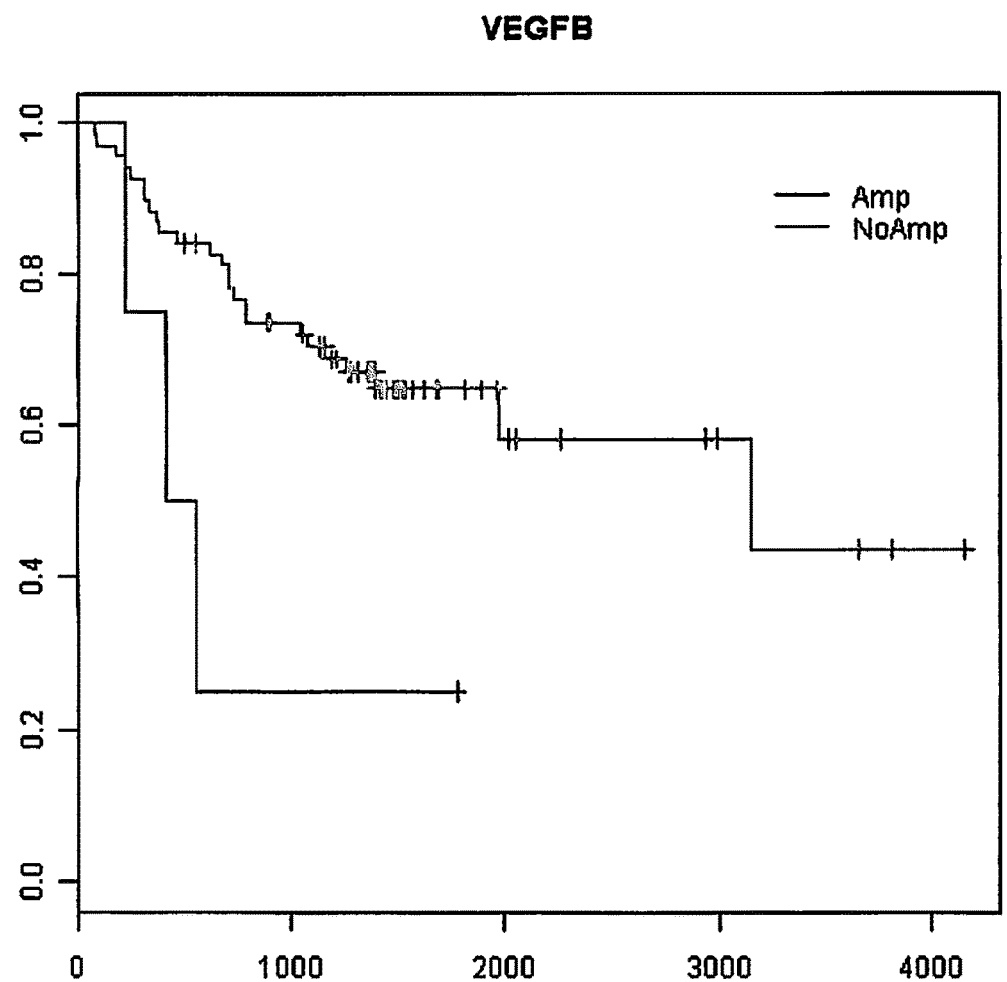

FIG. 150 v is a Kaplan-Meier plot showing the overall survival (OS) in days for a 74 patient cohort with NSCLC stage Ia-IIa, classified by presence or absence of a copy number gain in VEGFB.

Figure 151:
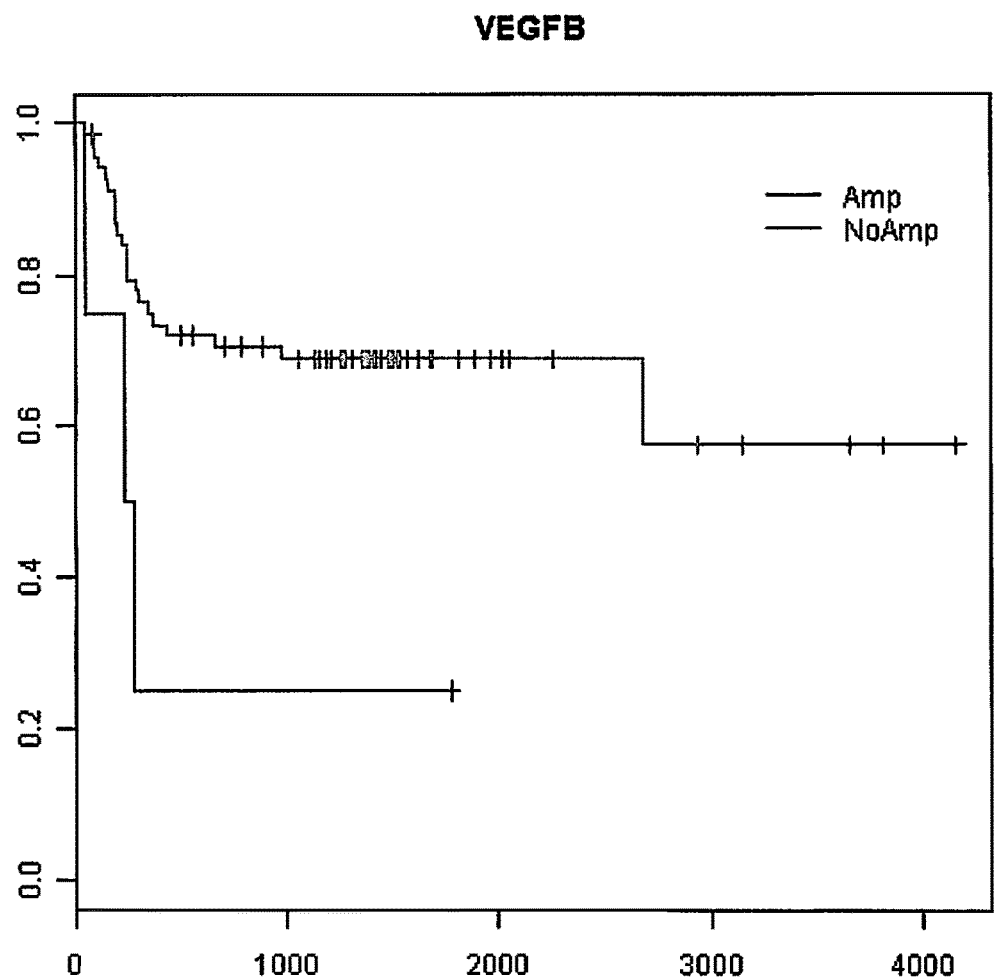

FIG. 151 is a Kaplan-Meier plot showing the time to recurrence (TTR) in days for a 74 patient cohort with NSCLC stage Ia-IIa, classified by presence or absence of a copy number gain in VEGFB.

Figure 152:
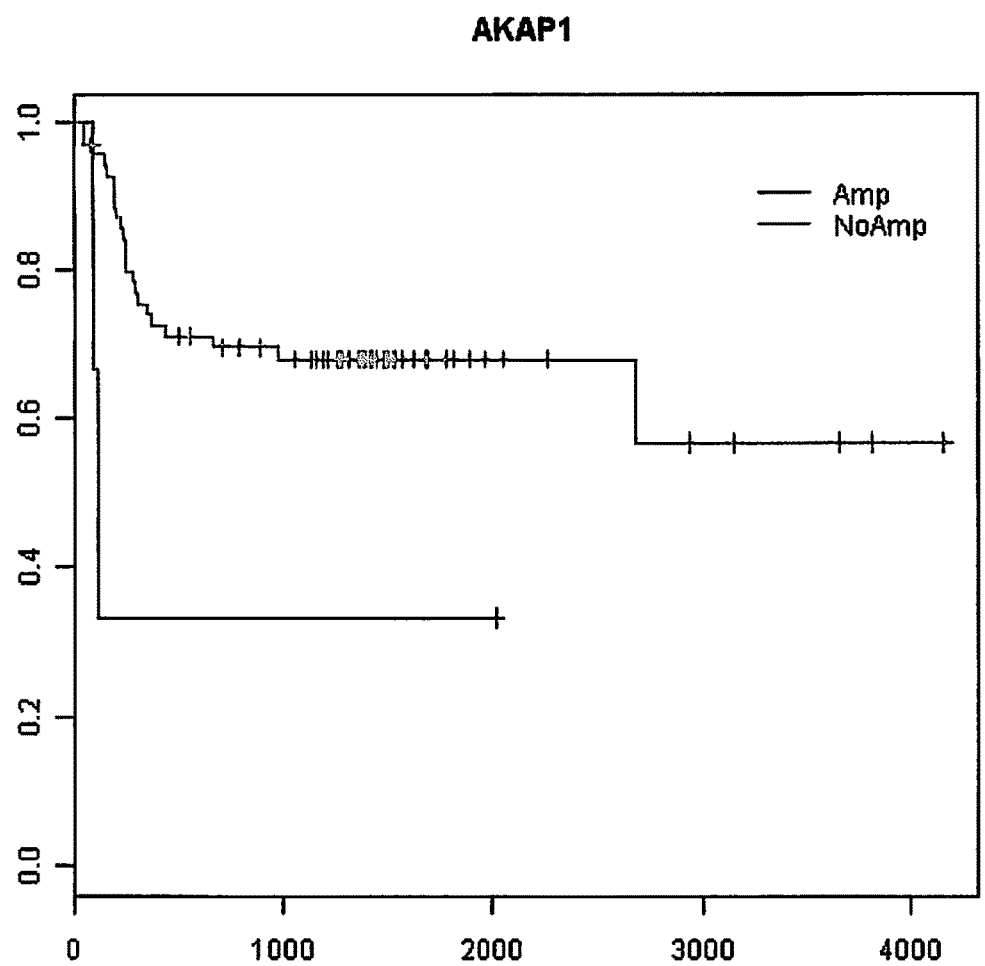

FIG. 152 is a Kaplan-Meier plot showing the time to recurrence (TTR) in days for a 74 patient cohort with NSCLC stage Ia-IIa, classified by presence or absence of a copy number gain in AKAP1.

Figure 153:
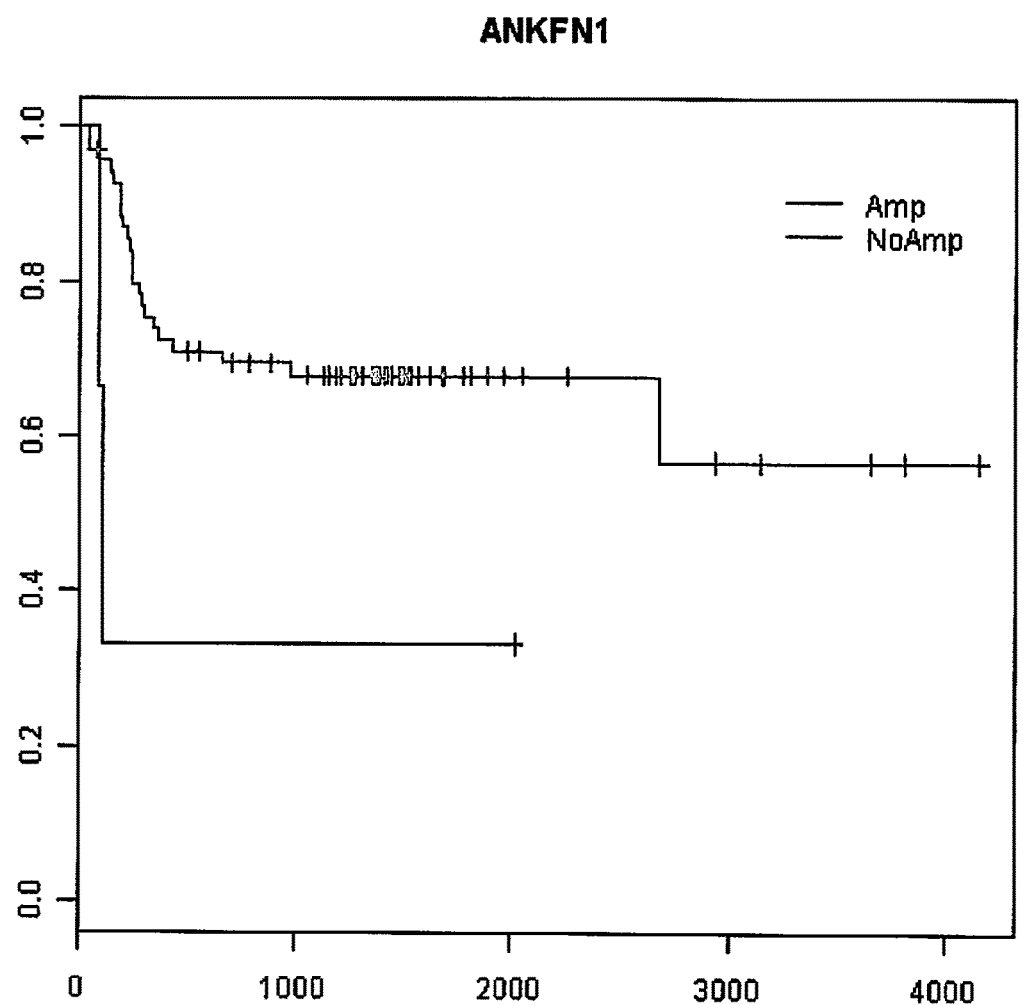

FIG. 153 is a Kaplan-Meier plot showing the time to recurrence (TTR) in days for a 74 patient cohort with NSCLC stage Ia-IIa, classified by presence or absence of a copy number gain in ANKFN1.

Figure 154:
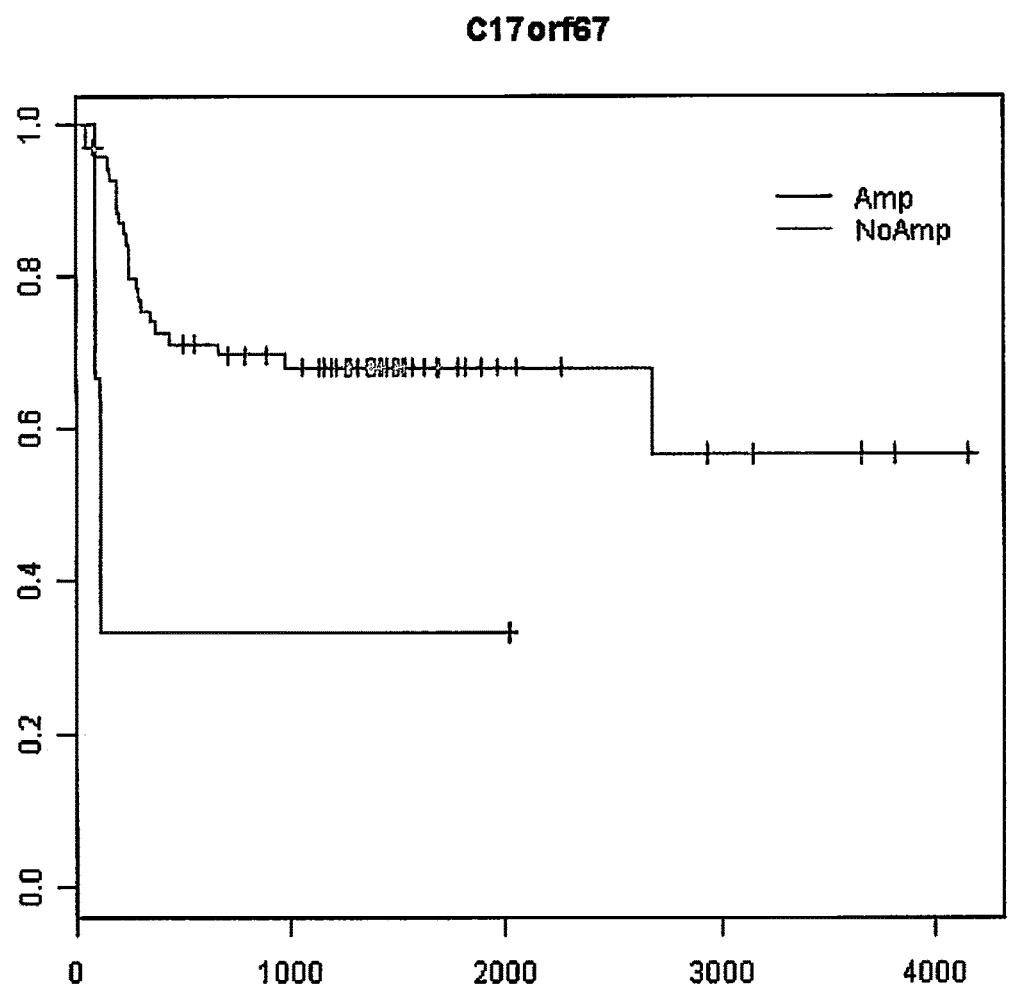

FIG. 154 is a Kaplan-Meier plot showing the time to recurrence (TTR) in days for a 74 patient cohort with NSCLC stage Ia-IIa, classified by presence or absence of a copy number gain in C17orf67.

Figure 155:
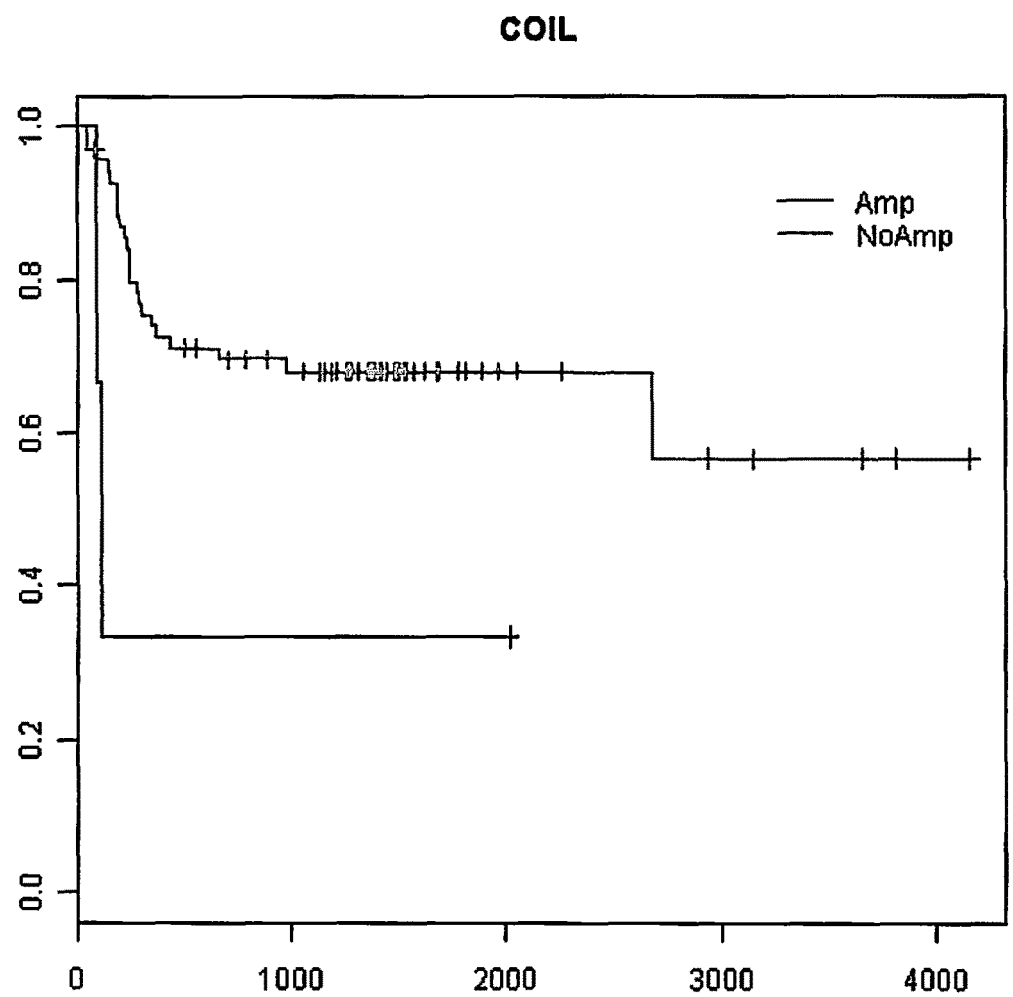

FIG. 155 is a Kaplan-Meier plot showing the time to recurrence (TTR) in days for a 74 patient cohort with NSCLC stage Ia-IIa, classified by presence or absence of a copy number gain in COIL.

Figure 156:
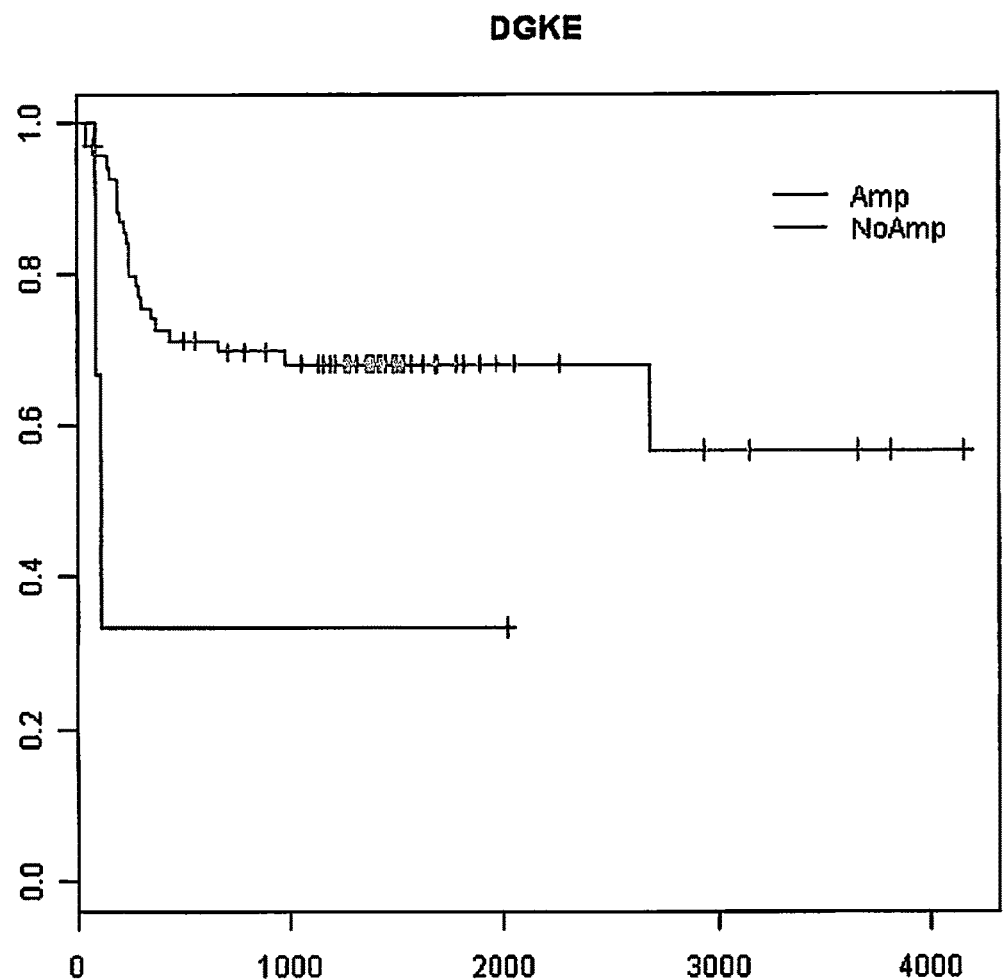

FIG. 156 is a Kaplan-Meier plot showing the time to recurrence (TTR) in days for a 74 patient cohort with NSCLC stage Ia-IIa, classified by presence or absence of a copy number gain in DGKE.

Figure 157:
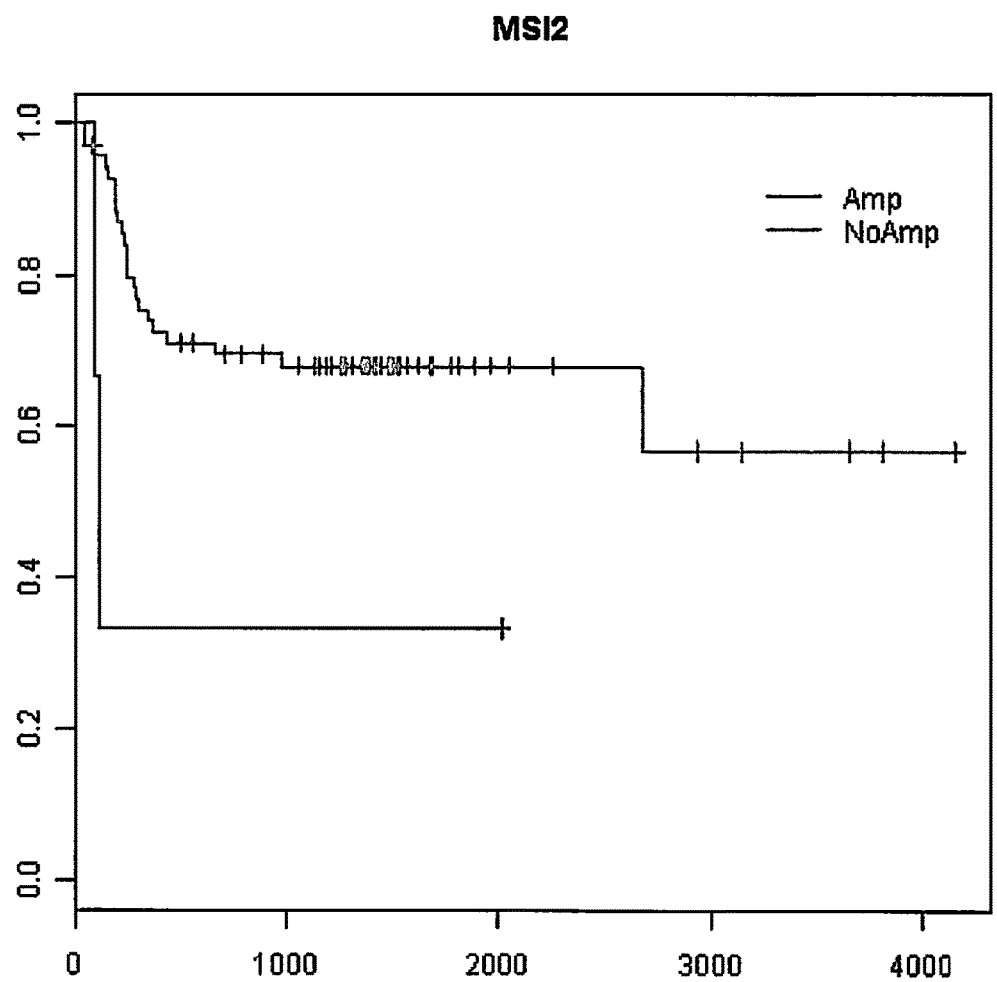

FIG. 157 is a Kaplan-Meier plot showing the time to recurrence (TTR) in days for a 74 patient cohort with NSCLC stage Ia-IIa, classified by presence or absence of a copy number gain in MSI2.

Figure 158:
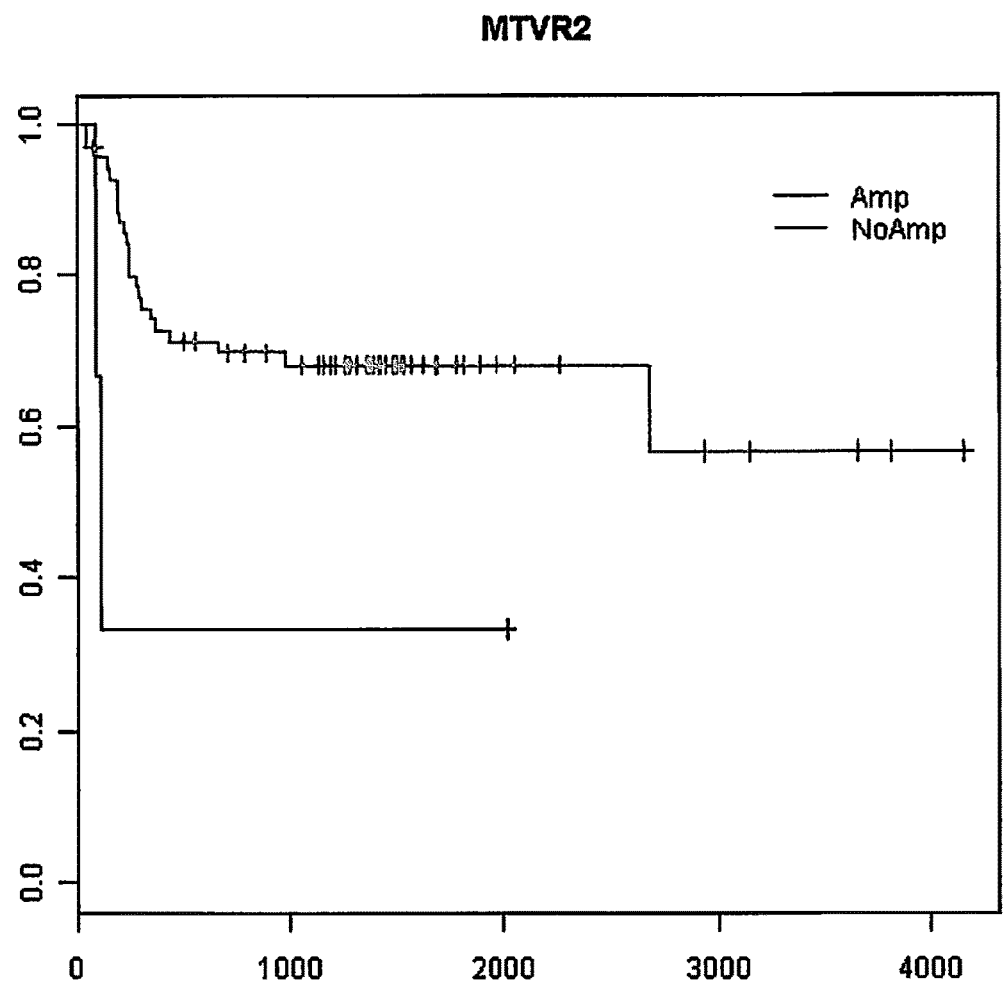

FIG. 158 is a Kaplan-Meier plot showing the time to recurrence (TTR) in days for a 74 patient cohort with NSCLC stage Ia-IIa, classified by presence or absence of a copy number gain in MTVR2.

Figure 159:
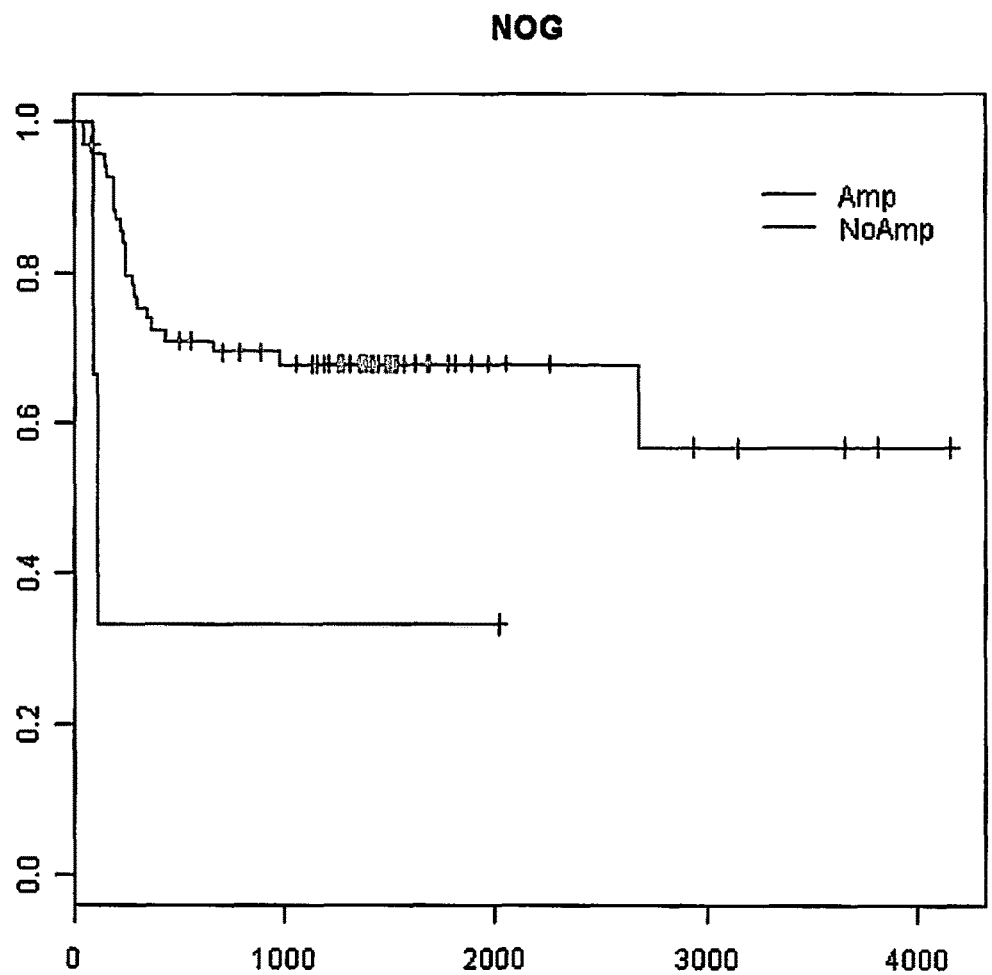

FIG. 159 is a Kaplan-Meier plot showing the time to recurrence (TTR) in days for a 74 patient cohort with NSCLC stage Ia-IIa, classified by presence or absence of a copy number gain in NOG.

Figure 160:
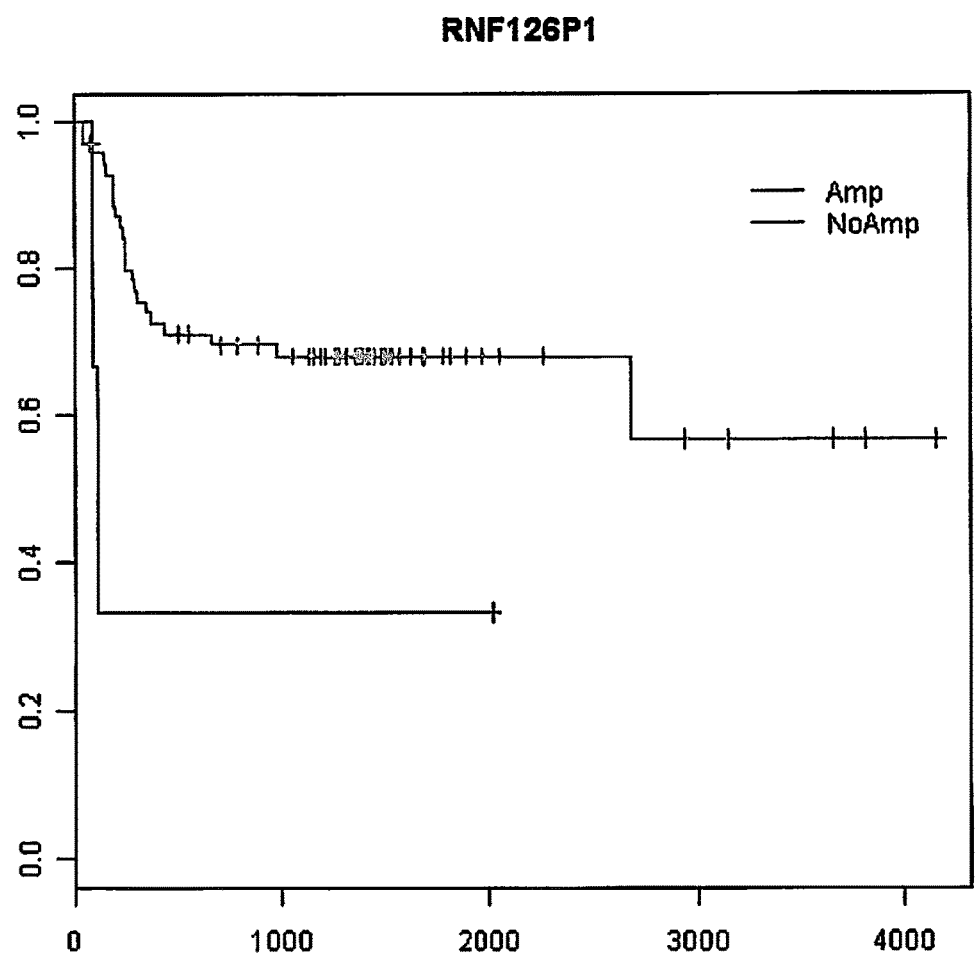

FIG. 160 is a Kaplan-Meier plot showing the time to recurrence (TTR) in days for a 74 patient cohort with NSCLC stage Ia-IIa, classified by presence or absence of a copy number gain in RNF126P1.

Figure 161:
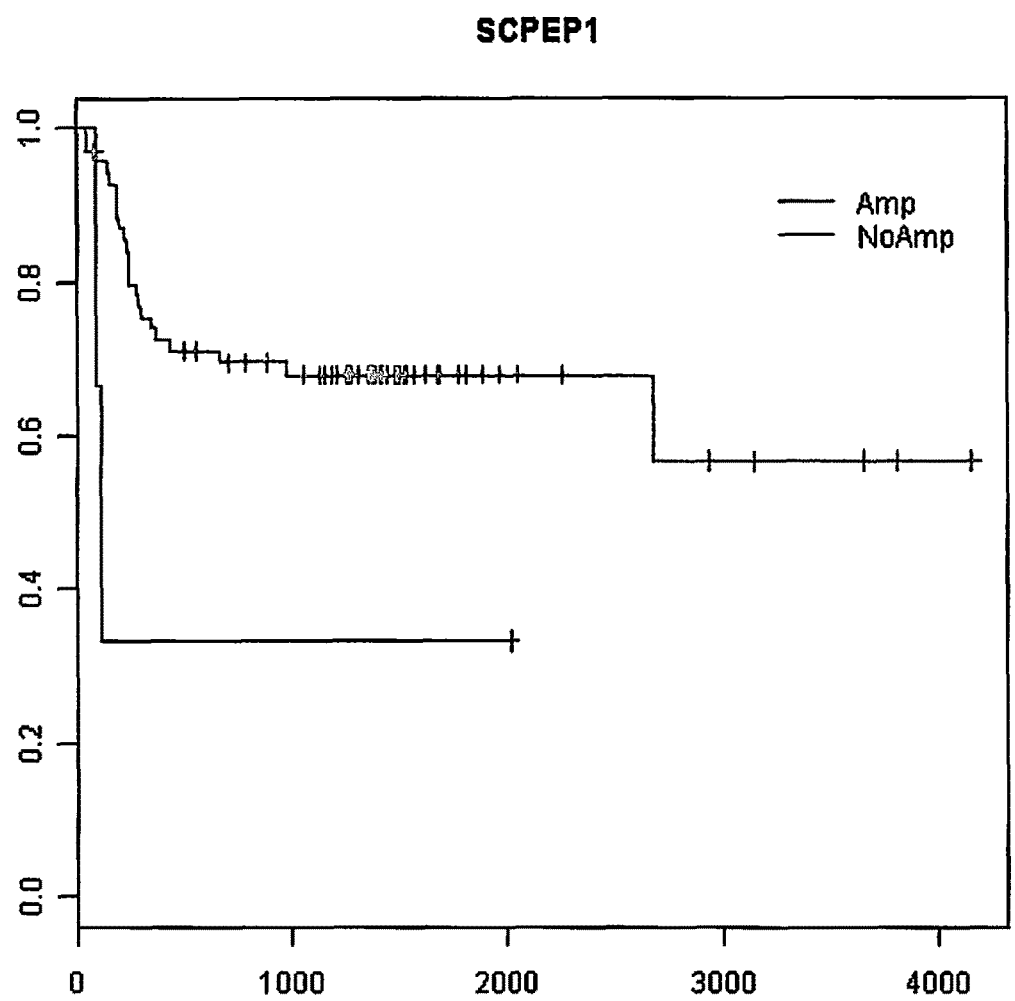

FIG. 161 is a Kaplan-Meier plot showing the time to recurrence (TTR) in days for a 74 patient cohort with NSCLC stage Ia-IIa, classified by presence or absence of a copy number gain in SCPEP1.

Figure 162:
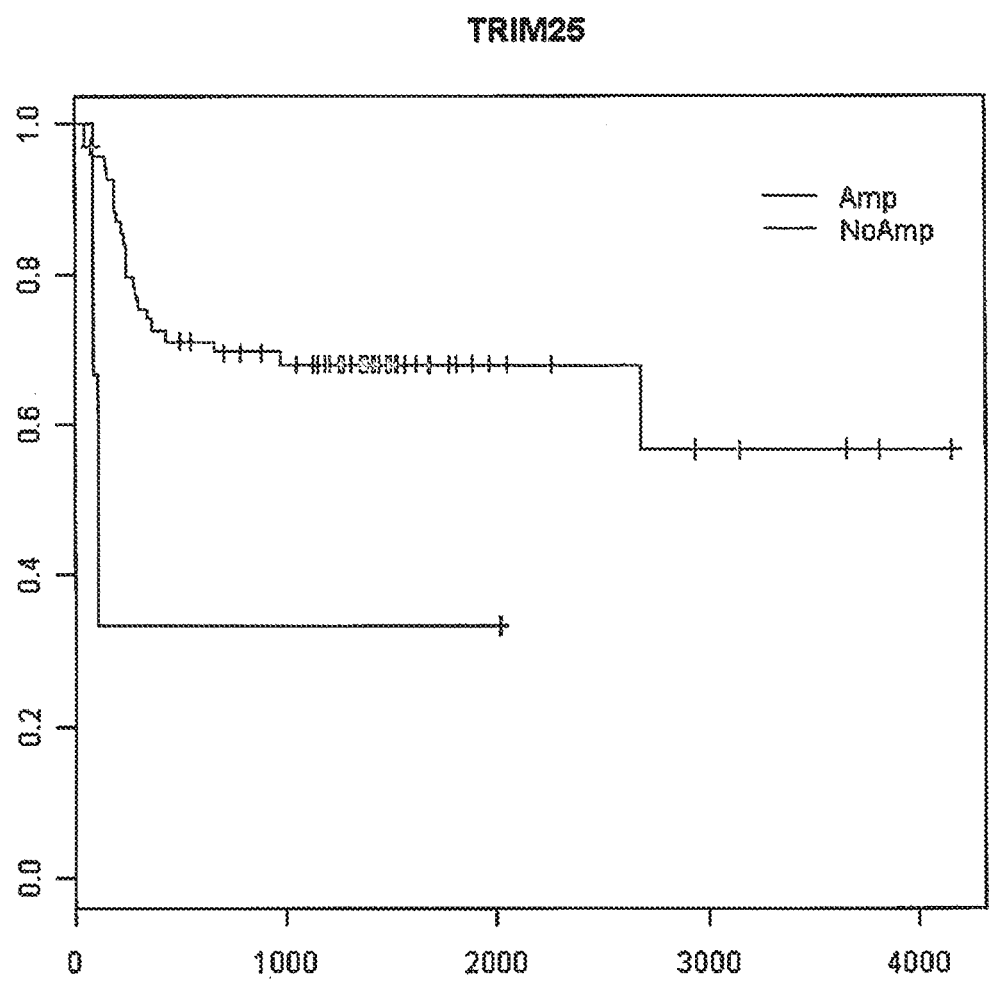

FIG. 162 is a Kaplan-Meier plot showing the time to recurrence (TTR) in days for a 74 patient cohort with NSCLC stage Ia-IIa, classified by presence or absence of a copy number gain in TRIM25.

DETAILED DESCRIPTION OF THE INVENTION

Previously described expression-based markers of poor outcome in cancer cannot be measured with FISH, a well-established clinical diagnostic tool. Until now, no gene amplifications/deletions have been identified that can predict disease outcome. The inventors have discovered copy number changes in certain chromosomal sequences in certain cancer patients. Moreover, the inventors have determined that the copy number changes are statistically significantly associated with shorter overall survival or reduced time to recurrence in stage I-II NSCLC.

Accordingly, the present disclosure provides methods of determining prognosis of early stage non-small cell lung cancer (NSCLC) in a human by assessment of the copy number of chromosomal DNA at any one of forty-seven markers. For each of these markers, a change in copy number is associated with a poorer prognosis in cancer. Copy number change was either a copy number gain of one or more, or a copy number loss. Poorer prognosis was assessed in patients having either a copy number gain or a copy number loss when compared to the normal baseline complement of two copies. Poorer prognosis was determined using measures of Overall Survival and Time to Recurrence. The present disclosure is particularly beneficial for providing improved prognostic information for early stage NSCLC patients and enables improved therapy selection for those early-stage NSCLC patients at higher risk of cancer recurrence.

The present disclosure includes methods for determining prognosis of NSCLC patients classified as early-stage cancers, in particular those classified as Stage IA, Stage IB, Stage IIA or Stage IIB (Stage IIA and IIB are collectively referred to as Stage II) using the widely used TNM staging system. Alternate NSCLC staging systems based upon other diagnostic classifications can be used to identify the patients whose tissue sample may be assayed by the methods disclosed herein. As used herein, an early stage NSCLC refers to a NSCLC tumor that has not spread to more than one lymph node, nor metastasized to any other organ. Early-stage NSCLC patients are almost always treated by surgical resection seeking complete tumor removal, yet a significant risk of recurrence exists for these early stage patients even where the tumor is believed to be completely resected. Current diagnostic modalities do not permit accurate prediction of which of these early stage cancers are high risk for recurrence and thus should be treated post-resection with adjuvant chemotherapy or before the resection using neo-adjuvant chemotherapy. The present disclosure provides prognostic identification of those early stage patients at higher risk by determining the gene copy number in the patient sample.

Thus in one aspect, the methods encompass a method of predicting disease outcome in a patient being treated for lung cancer. A test sample, which is a biological sample from the patient, is provided, and a copy number for a selected cancer outcome marker in the test sample is determined. The copy number from the test sample is compared against a baseline copy number of two, thereby determining the presence or absence of a copy number change for the cancer outcome marker. Based on the presence or absence of a copy number change for the cancer outcome marker in the test sample, the patient is identified as having an increased risk of a poor disease outcome when compared to a baseline measure of disease outcome in patients having no copy number change for the cancer outcome marker. The presence of a copy number change for the cancer outcome marker, i.e., a copy number of greater than 2 due to amplification, or less than 2 due to deletion, is predictive of poor disease outcome. The poor disease outcome is at least one of a decreased overall survival time when compared to an overall survival time of patients having no copy number change in the cancer outcome marker, and a shorter time to recurrence when compared to the time to recurrence for patients having no copy number change in the cancer outcome marker. The methods also encompass a method of predicting disease outcome in a patient being treated for lung cancer, in which based on the presence or absence of a copy number change in the cancer outcome marker, a determination is made as to whether the patient has a higher risk of a decreased overall survival time or a shorter time to recurrence when compared to an overall survival time of patients having no copy number change in the cancer outcome marker.

In any of the methods, the cancer outcome marker can be a region of chromosomal DNA, the amplification of which produces a copy number gain of the cancer outcome marker, wherein the copy number gain is associated with a poor disease outcome. Such cancer outcome markers include Chr 19, 34.7 Mb-35.6 Mb; Chr 19, 38.9-40.7 Mb; Chr 17, 69.2-71.3 Mb; Chr 6, 70.8-71.1 Mb; Chr 12, 93.7 kb-1.9 Mb; Chr 11, 64.3-64.8 Mb; Chr 19, 57.0-62.2 Mb; Chr 6, 39.1-39.9 Mb; Chr 11, 64.8-65.7 Mb; Chr 11, 61.4-64.3 Mb; Chr 17, 51.5-53.2 Mb; Chr 17, 43.5-44.9 Mb; Chr 2, 147.6-151.1 Mb; Chr 6, 123.7-135.6 Mb; Chr 8, 6.9-8.8 Mb; Chr 2, 159.9-161.4 Mb; Chr 2, 200.9-204.2 Mb; Chr 6, 36.3-36.7 Mb; Chr 2, 205.9-208.1 Mb; and Chr 1, 109.5-111.1 Mb. Alternatively, the cancer outcome marker can be a region of chromosomal DNA, the deletion of which produces a copy number loss of the cancer outcome marker, wherein the copy number loss is associated with a poor disease outcome. Such cancer outcome markers include Chr 5, 62.9-67.8 Mb; Chr 5, 53.3-53.8 Mb; Chr 4, 105.8-107.2 Mb; Chr 16, 45.8-46.3 Mb; Chr 5, 50.7-52.0 Mb; Chr 5, 94.2-96.1 Mb; Chr 9, 36.1-37.0 Mb; Chr 5, 94.2-96.1 Mb; Chr14, 51.1-52.8 Mb; Chr 14, 61.5-68.6 Mb; Chr 9, 28.1 Mb; Chr 4, 43.7-44.2 Mb; Chr 5, 60.8-62.9 Mb; Chr 3, 120.0-121.1 Mb; Chr 4, 46.2-48.0 Mb; Chr 14, 38.9-40.0 Mb; Chr 4, 44.2-44.6 Mb; Chr 2, 213.7-214.3 Mb; Chr14, 43.9-46.6 Mb; Chr 14, 27.6-28.6 Mb; Chr 3, 98.0-98.3 Mb; Chr14, 55.2-60.0 Mb; Chr14, 48.7-51.1 Mb; Chr 4, 81.4-83.2 Mb; Chr 10, 51.9-54.2 Mb; Chr 5, 55.2-58.6 Mb; and Chr 5, 67.8-68.5 Mb.

The methods can also be applied to the problem of selecting a treatment for a patient suffering from lung cancer. For example, the method can include determining a chemotherapy treatment regimen based on the presence or absence of a copy number change of a cancer outcome marker in the sample from the patient. The step of determining a treatment regimen based on the comparison in step c) includes for example selecting a chemotherapy agent and determining a frequency of chemotherapy treatment when a copy number change is present for the cancer outcome marker. For example, an unfavorable copy number change of a cancer outcome marker in an individual patient, which may be a copy number gain or loss depending on the marker as described herein, indicates a lung cancer that is resistant to treatment. In such cases a treatment provider may wish to consider a more aggressive than usual chemotherapy treatment regimen, including use of a stronger chemotherapy agent or more frequent chemotherapy treatment, or both.

Accordingly, the methods can also be used to classify a patient as having a lung cancer that is resistant to treatment. For example, given a determination that a copy change is present in the sample from the patient, the patient is classified as having a lung cancer that is resistant to further treatment. The patient may be currently undergoing treatment with chemotherapy, radiation, surgery or any combination thereof, or may be currently under consideration for any one of chemotherapy, radiation, surgery treatment or any combination thereof.

The determining step (b) can be performed, for example, using in situ hybridization and, more preferably, fluorescent in situ hybridization (FISH) with fluorescently labeled nucleic acid probes or fluorescently labeled probes comprising nucleic acid analogs. Preferably at least two nucleic acid probes are used. A peptide nucleic acid probe can be used. The determining step (b) can also be performed by polymerase chain reaction, a nucleic acid sequencing assay, or a nucleic acid microarray assay as known in the art.

The testing of early stage NSCLC is preferably done on an appropriate biological sample obtained from the patient, preferably by in situ hybridization. In general, in situ hybridization includes the steps of fixing a biological sample, hybridizing one or more chromosomal probes to target DNA contained within the fixed sample, washing to remove non-specifically bound probe, and detecting the hybridized probe. The in situ hybridization can also be carried out with the specimen cells from the biological sample in liquid suspension, followed by detection by flow cytometry. The method preferably uses a FISH assay with a two probe set comprising a probe specific to the marker region to evaluate chromosomal copy number abnormalities in a biological sample from a patient. Preferred FISH probes for use according to the present disclosure comprise a pair of probes specific to the cancer outcome marker nucleotide sequence, which may include any portion of the nucleotide sequence.

The identification of NSCLC prognosis can also be used with other prognostic in vitro diagnostic assays, such as evaluating the expression in the patient sample of suitable proteins known to be encoded in the marker region. Patients whose samples are found with expression of such proteins in conjunction with an abnormal chromosomal copy number pattern, that is associated with an unfavorable outcome (poor prognosis), may be eligible for more aggressive postsurgery treatment, such as chemotherapy.

Typically for a lung cancer patient the biological sample is a tissue sample such as a peripheral blood sample that contains circulating tumor cells, or a lung tumor tissue biopsy or resection. Other suitable tissue samples include for example a thin layer cytological sample, a fine needle aspirate sample, a lung wash sample, a pleural effusion sample, a fresh frozen tissue sample, a paraffin embedded tissue sample or an extract or processed sample produced from any of a peripheral blood sample. Preferably, the sample has been classified as an early stage cancer, for example, such as any of Stage IA, Stage IB, Stage IIA or Stage IIB, according to generally accepted staging practice, for example using pathological stages.

Probes constructed according to the polynucleotide sequences of the cancer outcome markers described herein can be used in various assay methods to provide various types of analysis. For example, such probes can be used in fluorescent in situ hybridization (FISH) technology to perform chromosomal analysis, including copy number profiling, and used to identify cancer-specific copy number changes in the cancer outcome markers. Probes also can be labeled with radioisotopes, directly- or indirectly-detectable haptens, or fluorescent molecules, and utilized for in situ hybridization studies to evaluate copy number of the cancer outcome markers in tissue specimens or cells.

Probes bind selectively to a target polynucleotide sequence, which is at least a portion of the sequence of a cancer outcome marker as described herein, i.e., a chromosomal region that is amplified in certain individuals. The nucleotide sequences of the cancer outcome markers provided herein, or any portion thereof, may be used to produce probes which can be used in various assays for copy number profiling in test samples. The probes may be designed from conserved nucleotide regions of the cancer outcome marker of interest, or from non-conserved nucleotide regions of the cancer outcome marker of interest, or any portion thereof including genes contained therein and portions thereof. The design of such probes for optimization in assays is within the skill of the routineer. Generally, nucleic acid probes are developed from non-conserved or unique regions when maximum specificity is desired, and nucleic acid probes are developed from conserved regions when assaying for nucleotide regions that are closely related to, for example, different members of a multi-gene family or in related species like mouse and man.

The polymerase chain reaction (PCR) is a technique for amplifying a desired nucleic acid sequence (target) contained in a nucleic acid or mixture thereof. In PCR, a pair of primers is employed in excess to hybridize to the complementary strands of the target nucleic acid. The primers are each extended by a polymerase using the target nucleic acid as a template. The extension products become target sequences themselves, following dissociation from the original target strand. New primers then are hybridized and extended by a polymerase, and the cycle is repeated to geometrically increase the number of target sequence molecules. PCR is disclosed in U.S. Pat. Nos. 4,683,195 and 4,683,202, which are incorporated herein by reference.

The Ligase Chain Reaction (LCR) is an alternate method for nucleic acid amplification. In LCR, probe pairs are used which include two primary (first and second) and two secondary (third and fourth) probes, all of which are employed in molar excess to target. The first probe hybridizes to a first segment of the target strand, and the second probe hybridizes to a second segment of the target strand, the first and second segments being contiguous so that the primary probes abut one another in 5' phosphate-3' hydroxyl relationship, and so that a ligase can covalently fuse or ligate the two probes into a fused product. In addition, a third (secondary) probe can hybridize to a portion of the first probe and a fourth (secondary) probe can hybridize to a portion of the second probe in a similar abutting fashion. Of course, if the target is initially double stranded, the secondary probes also will hybridize to the target complement in the first instance. Once the ligated strand of primary probes is separated from the target strand, it will hybridize with the third and fourth probes that can be ligated to form a complementary, secondary ligated product. It is important to realize that the ligated products are functionally equivalent to either the target or its complement. By repeated cycles of hybridization and ligation, amplification of the target sequence is achieved. This technique is described more completely in EP-A-320 308 to K. Backman published Jun. 16, 1989 and EP-A-439 182 to K. Backman et al., published Jul. 31, 1991, both of which are incorporated herein by reference.

For amplification of mRNAs, it is within the scope of the present disclosure to reverse transcribe mRNA into cDNA followed by polymerase chain reaction (RT-PCR); or, to use a single enzyme for both steps as described in U.S. Pat. No. 5,322,770, which is incorporated herein by reference; or reverse transcribe mRNA into cDNA followed by asymmetric gap ligase chain reaction (RT-AGLCR) as described by R. L. Marshall et al., PCR Methods and Applications 4:80-84 (1994), which also is incorporated herein by reference.

Chromosomal Probes. Suitable probes for in situ hybridization techniques fall into three broad groups: chromosome enumeration probes, which hybridize to a chromosomal region and indicate the presence or absence of a chromosome; chromosome arm probes, which hybridize to a chromosomal region and indicate the presence or absence of an arm of a chromosome; and locus specific probes, which hybridize to a specific locus on a chromosome and detect the presence or absence of a specific locus. Chromosomal probes and combinations thereof are chosen for sensitivity and/or specificity when used in the methods. Probe sets can include any number of probes, e.g., at least 2, 3, 4, 5, 6, 7, 8, 9, 10, 15, or 20 probes. The selection of individual probes and probe sets can be performed according to routine in the art, for example as described in US 20060063194, the entire disclosure of which is herein incorporated by reference. Such selection methods make use of discriminate and/or combinatorial analysis to select probes and probes sets that are useful for copy number profiling of the cancer outcome markers.

Suitable probes for use in in situ hybridization methods according to the present disclosure for the detection of abnormal copy number pattern (aneusomy or polysomy) are a combination of a chromosome enumeration probe and a chromosome locus-specific probe hybridizable to a portion of the marker sequence, with each probe labeled to be distinguishable from the other. As is well known in the art, a chromosome enumeration probe can hybridize to a repetitive sequence, located either near or removed from a centromere, or can hybridize to a unique sequence located at any position on a chromosome. For example, a chromosome enumeration probe can hybridize with repetitive DNA associated with the centromere of a chromosome. Centromeres of primate chromosomes contain a complex family of long tandem repeats of DNA comprised of a monomer repeat length of about 171 base pairs, that are referred to as alpha-satellite DNA. A non-limiting example of a specific chromosome enumeration probe is the SpectrumGreen™ CEP® 10 probe (Abbott Molecular, Inc., Des Plaines, Ill.). For example, the chromosome 19 enumeration probe is used with a locus specific probe for detecting copy number abnormalities at Chr19, 34.7 Mb-35.6 Mb, for example to determine the status of deletion and/or polysomy of loci contained therein. A locus specific probe hybridizes to a specific, non-repetitive locus on a chromosome. A suitable probe includes for example at least a portion of the any gene for which the marker sequence includes the nucleotide sequence encoding the gene. Locus specific probes are available commercially from Abbott Molecular Inc. in a probe set, for example mixed with the Vysis CEP® 10 SpectrumGreen probe.

Probes that hybridize with centromeric DNA are available commercially from Abbott Molecular Inc. (Des Plaines, Ill.) and Molecular Probes, Inc. (Eugene, Oreg.). Alternatively, probes can be made non-commercially using well known techniques. Sources of DNA for use in constructing DNA probes include genomic DNA, cloned DNA sequences such as bacterial artificial chromosomes (BAC), somatic cell hybrids that contain one or a part of a human chromosome along with the normal chromosome complement of the host, and chromosomes purified by flow cytometry or microdissection. The region of interest can be isolated through cloning or by site-specific amplification via the polymerase chain reaction (PCR). See, for example, Nath, et al., Biotechnic Histochem, 1998, 73 (1): 6-22; Wheeless, et al., Cytometry, 1994, 17:319-327; and U.S. Pat. No. 5,491,224. The starting human DNA used to manufacture useful locus specific probes can be obtained by obtaining a nucleic acid sequence for the locus from the Human Genome database, such as that maintained by the University of California Santa Cruz, and then using that sequence to screen in silico a BAC human DNA library, such as that maintained by the Roswell Park Cancer Center or Invitrogen, to identify useful BAC clones. Synthesized oligomeric DNA probes or probes made from nucleic acid analogs, such as peptide nucleic acid (PNA) probes, can also be used.

The size of the chromosomal region detected by the probes according to the present disclosure can vary in size, for example, from a short couple hundred base pair probe sequence to a large segment of 900,000 bases. Locus-specific probes that are directly labeled are preferably at least 100,000 bases in complexity, and use unlabeled blocking nucleic acid, as disclosed in U.S. Pat. No. 5,756,696, herein incorporated by reference, to avoid non-specific binding of the probe. It is also possible to use unlabeled, synthesized oligomeric nucleic acid or unlabeled nucleic acid analogs, such as a peptide nucleic acid, as the blocking nucleic acid.

The chromosomal probes can contain any detection moiety that facilitates the detection of the probe when hybridized to a chromosome. Effective detection moieties include both direct and indirect labels as described herein. Examples of detectable labels include fluorophores (i.e., organic molecules that fluoresce after absorbing light), radioactive isotopes (e.g., $^{32}P$, and $^{3}H$) and chromophores (e.g., enzymatic markers that produce a visually detectable marker). Fluorophores are preferred and can be directly labeled following covalent attachment to a nucleotide by incorporating the labeled nucleotide into the probe with standard techniques such as nick translation, random priming, and PCR labeling. Alternatively, deoxycytidine nucleotides within the probe can be transaminated with a linker. The fluorophore can then be covalently attached to the transaminated deoxycytidine nucleotides. See, e.g., U.S. Pat. No. 5,491,224 to Bittner, et al., which is incorporated herein by reference. Useful probe labeling techniques are described in Molecular Cytogenetics: Protocols and Applications, Y.-S. Fan, Ed., Chap. 2, "Labeling Fluorescence In Situ Hybridization Probes for Genomic Targets", L. Morrison et. al., p. 21-40, Humana Press, © 2002, incorporated herein by reference.

Examples of fluorophores that can be used in the methods described herein are: 7-amino-4-methylcoumarin-3-acetic acid (AMCA), Texas Red™ (Molecular Probes, Inc., Eugene, Oreg.); 5-(and-6)-carboxy-X-rhodamine, lissamine rhodamine B, 5-(and-6)-carboxyfluorescein; fluorescein-5-isothiocyanate (FITC); 7-diethylaminocoumarin-3-carboxylic acid, tetramethylrhodamine-5-(and-6)-isothiocyanate; 5-(and-6)-carboxytetramethylrhodamine; 7-hydroxycoumarin-3-carboxylic acid; 6-[fluorescein 5-(and-6)-carboxamido]hexanoic acid; N-(4,4-difluoro-5,7-dimethyl-4-bora-3a, 4a diaza-3-indacenepropionic acid; eosin-5-isothiocyanate; erythrosine-5-isothiocyanate; 5-(and-6)-carboxyrhodamine 6G; and Cascade™ blue acetylazide (Molecular Probes, Inc., Eugene, Oreg.). In the preferred probe set, fluorophores of different colors are used such that each chromosomal probe in the set can be distinctly visualized.

After hybridization, the probes can be viewed with a fluorescence microscope and an appropriate filter for each fluorophore, or by using dual or triple band-pass filter sets to observe multiple fluorophores. See, e.g., U.S. Pat. No. 5,776,688 to Bittner, et al., which is incorporated herein by reference. Any suitable microscopic imaging method can be used to visualize the hybridized probes, including automated digital imaging systems, such as those available from MetaSystems or Applied Imaging. Alternatively, techniques such as flow cytometry can be used to examine the hybridization pattern of the chromosomal probes.

Probes can also be labeled indirectly, e.g., with biotin or digoxygenin by means well known in the art. However, secondary detection molecules or further processing are then required to visualize the labeled probes. For example, a probe labeled with biotin can be detected by avidin (e.g. streptavidin) conjugated to a detectable marker, e.g., a fluorophore. Additionally, avidin can be conjugated to an enzymatic marker such as alkaline phosphatase or horseradish peroxidase. Such enzymatic markers can be detected in standard colorimetric reactions using a substrate for the enzyme. Substrates for alkaline phosphatase include 5-bromo-4-chloro-3-indolylphosphate and nitro blue tetrazolium. Diaminobenzidine can be used as a substrate for horseradish peroxidase.

The probes and probe sets useful with the methods can be packaged with other reagents into kits to be used in carrying out the methods as described herein.

Preferred Probe Set. An exemplary probe composition comprises a mixture of directly labeled DNA FISH probes. For example, such a probe set would include a Vysis SpectrumOrange probe and a Vysis SpectrumGreen probe. Suitable probe sets are available commercially premixed in a suitable hybridization buffer.

Preparation of Samples. A biological sample is a sample that contains cells or cellular material, including cell-containing extracts from a patient sample. For example, lung samples are typically cells or cellular material derived from pulmonary structures, including but not limited to lung parenchyma, bronchioles, bronchial, bronchi, and trachea. Non-limiting examples of biological samples useful for the detection of lung cancer include bronchial specimens, resected lung tissue, lung biopsies, and sputum samples. Examples of bronchial specimens include bronchial secretions, washings, lavage, aspirations, and brushings. Lung biopsies can be obtained by methods including surgery, bronchoscopy, fine needle aspiration (FNA), and transthoracic needle biopsy. In one example, touch preparations can be made from lung biopsies. The inventive assays can also be performed on a circulating tumor cell sample derived from a blood sample from an early stage NSCLC patient. A circulating tumor cell sample can be prepared using the immunomagnetic separation technology available from Immunicon.

Tissues can be fixed with a fixative such as formaldehyde and then embedded in paraffin. Sections are then cut using a microtome and are applied to a microscope slide. Cytology specimens can be prepared from cellular suspensions derived from FNA, bronchial washings, bronchial lavage, or sputum, or disseminated tissue cells. Cytology specimens can be prepared by fixation of cells in ethanol or methanol: acetic acid combined with cytocentrifugation, thin layer deposition methods (e.g. ThinPrep, Cytyc Corp.), smears, or pipetting onto microscope slides. In addition, biological samples can include effusions, e.g., pleural effusions, pericardial effusions, or peritoneal effusions.

Hybridization Methods. Any suitable in situ hybridization method can be used. Prior to in situ hybridization, chromosomal probes and chromosomal DNA contained within the cell each are denatured. If the chromosomal probes are prepared as a single-stranded nucleic acid, then denaturation of the probe is not required. Denaturation typically is performed by incubating in the presence of high pH, heat (e.g., temperatures from about 70° C. to about 95° C.), organic solvents such as formamide and tetraalkylammonium halides, or combinations thereof. For example, chromosomal DNA can be denatured by a combination of temperatures above 70° C. (e.g., about 73° C.) and a denaturation buffer containing 70% formamide and 2×SSC (0.3M sodium chloride and 0.03 M sodium citrate). Denaturation conditions typically are established such that cell morphology is preserved. For example, chromosomal probes can be denatured by heat, e.g., by heating the probes to about 73° C. for about five minutes.

After removal of denaturing chemicals or conditions, probes are annealed to the chromosomal DNA under hybridizing conditions. "Hybridizing conditions" are conditions that facilitate annealing between a probe and target chromosomal DNA. Hybridization conditions vary, depending on the concentrations, base compositions, complexities, and lengths of the probes, as well as salt concentrations, temperatures, and length of incubation. For example, in situ hybridizations are typically performed in hybridization buffer containing 1-2×SSC, 50-55% formamide, a hybridization accelerant (e.g. 10% dextran sulfate), and unlabeled blocking DNA to suppress non-specific hybridization. In general, hybridization conditions, as described above, include temperatures of about 25° C. to about 55° C., and incubation lengths of about 0.5 hours to about 96 hours. More particularly, hybridization can be performed at about 32° C. to about 45° C. for about 2 to about 16 hours.

Non-specific binding of chromosomal probes to DNA outside of the target region can be removed by a series of washes with a salt solution. Temperature and concentration of salt in each wash depend on the desired stringency. For example, for high stringency conditions, washes can be carried out at about 65° C. to about 80° C., using 0.2× to about 2×SSC, and about 0.1% to about 1% of a non-ionic detergent such as Nonidet P-40 (NP40). Stringency can be lowered by decreasing the temperature of the washes or by increasing the concentration of salt in the washes.

The hybridization of the probes to the tissue sample can be performed manually, or with the assistance of instruments, such as the ThermoBrite hybridization oven, the VP 2000 Processor, or the XMatrix™ processing instrument (all available commercially from Abbott Molecular, Inc.).

Pre-Selection of Cells. Cell samples can be evaluated preliminarily by a variety of methods and using a variety of criteria. The probes and methods described herein are not limited to usage with a particular screening methodology. One example is the "scanning method" wherein the observer scans hundreds to thousands of cells for cytologic abnormalities, e.g., as viewed with a DAPI filter. The number of cells assessed will depend on the cellularity of the specimen, which varies from patient to patient. Cytologic abnormalities commonly but not invariably associated with dysplastic and neoplastic cells include nuclear enlargement, nuclear irregularity, and abnormal DAPI staining (frequently mottled and lighter in color). In the scanning step, the observer preferably focuses the evaluation of the cells for chromosomal abnormalities (as demonstrated by FISH) to those cells that also exhibit cytological abnormalities. In addition, a proportion of the cells that do not have obvious cytologic abnormalities can be evaluated since chromosomal abnormalities also occur in the absence of cytologic abnormalities. This scanning method is described in further detail in U.S. Pat. No. 6,174,681 to Halling, et al., which is incorporated herein by reference. Lung cancer cells can be selected for evaluation using the method described in US Patent Pub. 2003/0087248 A1 by Morrison, et al., which is incorporated herein by reference.

Regions of the specimen may also be selected for evaluation using conventional stains, such as stains containing hematoxylin and eosin. For example, a pathologist can stain a section of a paraffin-embedded specimen with a hematoxylin/eosin stain, identify a region as probably cancerous by tissue morphology and staining pattern, and outline that region with a felt tip ink pen or glass scribe. The marked region is then transferred to the corresponding location on a serial section of the paraffin-embedded specimen with a glass scribe, and FISH is performed on that slide. Cells within the scribed region are then evaluated for FISH signals.

Detection of Classification Patterns of Chromosomal Abnormality. Abnormal cells are characterized by the presence of one or more patterns of chromosomal copy number abnormalities. The presence of a copy number abnormality pattern in a cell in the patient sample is assessed by examining the hybridization pattern of the chromosomal probe (e.g., the number of signals for each probe) in the cell, and recording the number of signals. Aneusomy is typically intended to mean abnormal copy number, either of the whole chromosome or a locus on a chromosome. Abnormal copy number includes both monosomy (one copy) and nullsomy (zero copies) of the autosomes, also referred to as a deletion, and greater than 2 copies, which for a particular chromosomal locus is sometimes referred to as gene amplification (alternatively, amplification is reserved for the situation in which the gene copy number exceeds the copy number of the chromosome in which it is contained). However, sectioning of paraffin-embedded specimens (typically 4-6 μm) may result in truncation of cell nuclei such that the number of FISH signals per cell for some cells will be somewhat lower than the actual number of copies in an intact nucleus. In the methods as described herein, the absolute number of particular FISH probe hybridization signals for each probe is determined and then used in various ratio comparisons.

Test samples can comprise any number of cells that is sufficient for a clinical diagnosis, and in a preferred paraffin-embedded tissue sample, the hybridization pattern is typically assessed in about 20 to about 200 cells. It is preferred to assess the hybridization pattern in about 40 to about 120 cells per sample.

The present disclosure thus describes new findings (DNA copy number changes of a cancer outcome marker) that may solve recognized treatment dilemmas by providing methods of determining which patients with early stage disease are at highest risk of disease recurrence or metastasis and who should be definitively treated with drug (or alternatives like radiation) therapies to maximize their chances of long term survival. In turn, the present disclosure describes findings enabling of a specific DNA test that detects a chromosomal copy number change in any one of a number of cancer outcome markers. Consequently when a test for a copy number change is negative, or normal copy number is present, this identifies patients who have low or no risk of disease recurrence or metastasis who do not need follow-up therapy after resection of their initial tumors. These testing strategies can significantly impact both the morbidity and mortality in patients with early stage NSCLC. The methods used herein also suggest application to other cancers to similarly detect DNA copy number gains of the cancer outcome markers that significantly associate with time to disease progression and/or overall survival. As such, the methods described herein have the potential to solve the question of which early-stage NSCLC patients should receive drug therapy after surgery and can broadly impact cancer treatment decisions and patient outcomes.

Kits. In another aspect, the present disclosure provides a kit comprising reagents for determining the presence or absence of a copy number change for the cancer outcome marker. The kit includes instructions for using the reagents to perform the test. The reagents to determine the presence or absence of a copy number change for the cancer outcome marker can include for example detectably-labeled polynucleotides that hybridize to at least a portion of the cancer outcome marker. The polynucleotides (probes) can be selected for sequences that hybridize, for example, to any portion of the cancer outcome marker. The cancer outcome marker can be a region of chromosomal DNA, the amplification of which produces a copy number gain of the cancer outcome marker, wherein the copy number gain is associated with a poor disease outcome. Such cancer outcome markers can be selected from the group consisting of Chr 19, 34.7 Mb-35.6 Mb; Chr 19, 38.9-40.7 Mb; Chr 17, 69.2-71.3 Mb; Chr 6, 70.8-71.1 Mb; Chr 12, 93.7 kb-1.9 Mb; Chr 11, 64.3-64.8 Mb; Chr 19, 57.0-62.2 Mb; Chr 6, 39.1-39.9 Mb; Chr 11, 64.8-65.7 Mb; Chr 11, 61.4-64.3 Mb; Chr 17, 51.5-53.2 Mb; Chr 17, 43.5-44.9 Mb; Chr 2, 147.6-151.1 Mb; Chr 6, 123.7-135.6 Mb; Chr 8, 6.9-8.8 Mb; Chr 2, 159.9-161.4 Mb; Chr 2, 200.9-204.2 Mb; Chr 6, 36.3-36.7 Mb; Chr 2, 205.9-208.1 Mb; and Chr 1, 109.5-111.1 Mb. The cancer outcome marker can instead be a region of chromosomal DNA, the deletion of which produces a copy number loss of the cancer outcome marker, wherein the copy number loss is associated with a poor disease outcome. Such cancer outcome markers can be selected from the group consisting of Chr 5, 62.9-67.8 Mb; Chr 5, 53.3-53.8 Mb; Chr 4, 105.8-107.2 Mb; Chr 16, 45.8-46.3 Mb; Chr 5, 50.7-52.0 Mb; Chr 5, 94.2-96.1 Mb; Chr 9, 36.1-37.0 Mb; Chr 5, 94.2-96.1 Mb; Chr14, 51.1-52.8 Mb; Chr 14, 61.5-68.6 Mb; Chr 9, 28.1 Mb; Chr 4, 43.7-44.2 Mb; Chr 5, 60.8-62.9 Mb; Chr 3, 120.0-121.1 Mb; Chr 4, 46.2-48.0 Mb; Chr 14, 38.9-40.0 Mb; Chr 4, 44.2-44.6 Mb; Chr 2, 213.7-214.3 Mb; Chr14, 43.9-46.6 Mb; Chr 14, 27.6-28.6 Mb; Chr 3, 98.0-98.3 Mb; Chr14, 55.2-60.0 Mb; Chr14, 48.7-51.1 Mb; Chr 4, 81.4-83.2 Mb; Chr 10, 51.9-54.2 Mb; Chr 5, 55.2-58.6 Mb; and Chr 5, 67.8-68.5 Mb. Accordingly, the probes can be selected for sequences that hybridize, for example, to any portion of any of the listed markers, including any portion of any of the genes encoded therein as set forth elsewhere herein.

Details of the present disclosure are further described in the following example, which is not intended to limit the scope of the invention as claimed. One of skill in the art will recognize that variations and modifications of the invention may be apparent upon reviewing the instant specification. It is therefore an object to provide for such modifications and variations of the embodiments described herein, without departing from the scope or the spirit of the invention.

EXAMPLES

Example 1

Analysis of NSCLC Patient Samples

Experimental Methods: Specimens A total of 178 NSCLC clinically annotated samples were profiled for copy number alterations using high-density SNP genotyping microarrays (100K array set by Affymetrix). All samples were carefully dissected to maximize tumor/normal tissue ratio and verify histopathological type and stage. Only samples from patients with stage I and II samples were analyzed. All of these were from patients treated with surgical resection without any follow-up or neoadjuvant chemotherapy. Clinical information collected for each patient included race, age, date of birth, sex, clinical stage, pathological stage, location, surgical procedure (SP) date, histology, differentiation, diagnosis date, node positivity, smoking status, chemotherapy status, radiation status, recurrence status, recurrence date, recurrence location, time to recurrence, date of last follow up, status at the last follow up, alive/dead, overall survival and cause of death. Time to Recurrence (TTR) and Overall Survival (OS) were chosen as the parameters of outcome. Other clinical parameters (node status, stage, etc) were considered as confounding variables. Times to recurrence of lung cancer and the overall survival times were obtained from the patient charts.

Tables 2 and 3 provide the figures for Overall Survival and Total Time to Recurrence, respectively, for the patient cohort studied.

TABLE 2

| | | OS | |
|---|---|---|---|
| Stage | deaths | alive (censored) | total |
| 1a | 6 | 25 | 31 |
| 1b | 6 | 40 | 46 |
| 2a | 0 | 1 | 1 |
| 2b | 7 | 17 | 24 |
| total | 19 | 83 | 102 |

TABLE 3

| | | TTR | |
|---|---|---|---|
| Stage | recurred | recurrence free (censored) | total |
| 1a | 10 | 21 | 31 |
| 1b | 9 | 34 | 43 |
| 2a | 1 | 0 | 1 |
| 2b | 9 | 13 | 22 |
| total | 29 | 68 | 97 |

Copy Number Profiling. Approximately 30 mg tissue from each tumor were used to extract high molecular weight, genomic DNA using the Qiagen DNAeasy kit (Qiagen, Valencia, Calif.) following the instructions by the manufacturer. The quality of DNA was checked by agarose gel electrophoresis. Two hundred and fifty nanograms of DNA were processed for hybridization to each of the two microarrays comprising the Genechip Human Mapping 100K set (Matsuzaki H, Dong S, Loi H, et al. Genotyping over 100,000 SNPs on a pair of oligonucleotide arrays. Nat Methods 2004; 1:109-11)-arrays (Affymetrix, Inc., Santa Clara, Calif.), which covers 116,204 single-nucleotide polymorphism (SNP) loci in the human genome with a mean intermarker distance of 23.6 kb. The microarrays were processed according to recommendations of the manufacturer (www.affymetrix.com). Copy number was calculated by comparing the chip signal to the average of 48 normal female samples. Samples with normal tissue contamination were removed by QC.

Statistical Methods. Univariate analysis was used to test the following parameters as potential confounding factors: Pathological stage, Clinical stage, Smoking status, Age, Sex, Node status, Histology (adenocarcinoma vs squamous cell carcinoma). No significant effects were detected. In survival analysis, interaction of clinical stage and marker regions was tested. No copy number abnormalities had significant interaction with stage (FDR p value<0.05).

Figure 1:
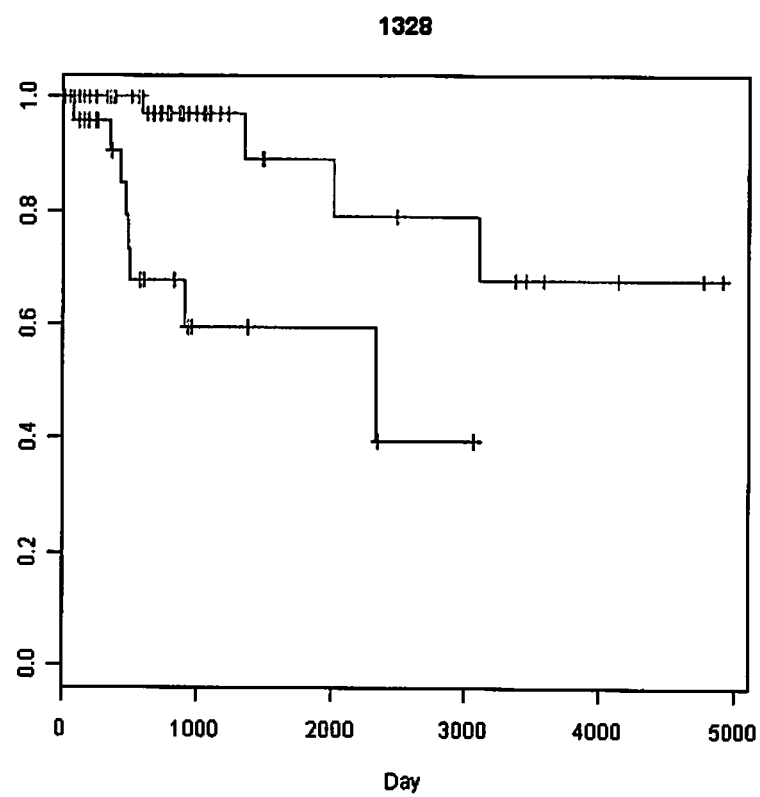
FIG. 1 is a Kaplan-Meier plot showing the overall survival (OS) in days for a 78 patient cohort with NSCLC stage Ia-IIa, classified by presence or absence of a copy number gain in Chr19, 34.7 Mb-35.6 Mb. [marker 1]

Results: Only patients with stage I-II disease were analyzed. FIGS. 1-28 are each a Kaplan-Meier plot showing the difference in OS or TTR between patients with and without amplification of a selected marker as indicated (i.e., a copy number gain of at least one). FIGS. 29-60 are each a Kaplan-Meier plot showing the difference in OS or TTR between patients with and without deletion (i.e., a copy number loss of at least one) of a selected marker as indicated to either overall survival time (OS). In all FIGS. 1-60, the upper line always shows data from patients with a normal baseline complement of two. In FIGS. 1-28, data for patients with a copy number gain for the marker are shown in red, and data for patients with the normal baseline complement of two are shown in green. In FIGS. 29-60, data for patients with the normal baseline complement of two are always shown in the upper line, in some figures shown in green (FIGS. 29, 30, 35, 37-40, 43, 44, 47, 50, 55-57 and 60), and in other figures shown in red (FIGS. 31-34, 36, 41, 42, 45, 46, 48, 49, 51-54, 58 and 59), while data for patients with a copy number loss for the marker are shown in certain figures in blue (FIGS. 29, 30, 35, 37-40, 43, 44, 47, 50, 55-57 and 60), and in other figures in green (FIGS. 31-34, 36, 41, 42, 45, 46, 48, 49, 51-54, 58 and 59). More specifically, the figures show results as follows:

FIG. 1 is a Kaplan-Meier plot showing the overall survival (OS) in days for a 78 patient cohort with NSCLC stage Ia-IIa, classified by presence or absence of a copy number gain in Chr19, 34.7 Mb-35.6 Mb. [marker 1]. FDR adjusted p-value=0.0299. 17 samples: 3 copies, 3 samples: 4 copies, 7 samples: 5 or more copies.

Figure 2:
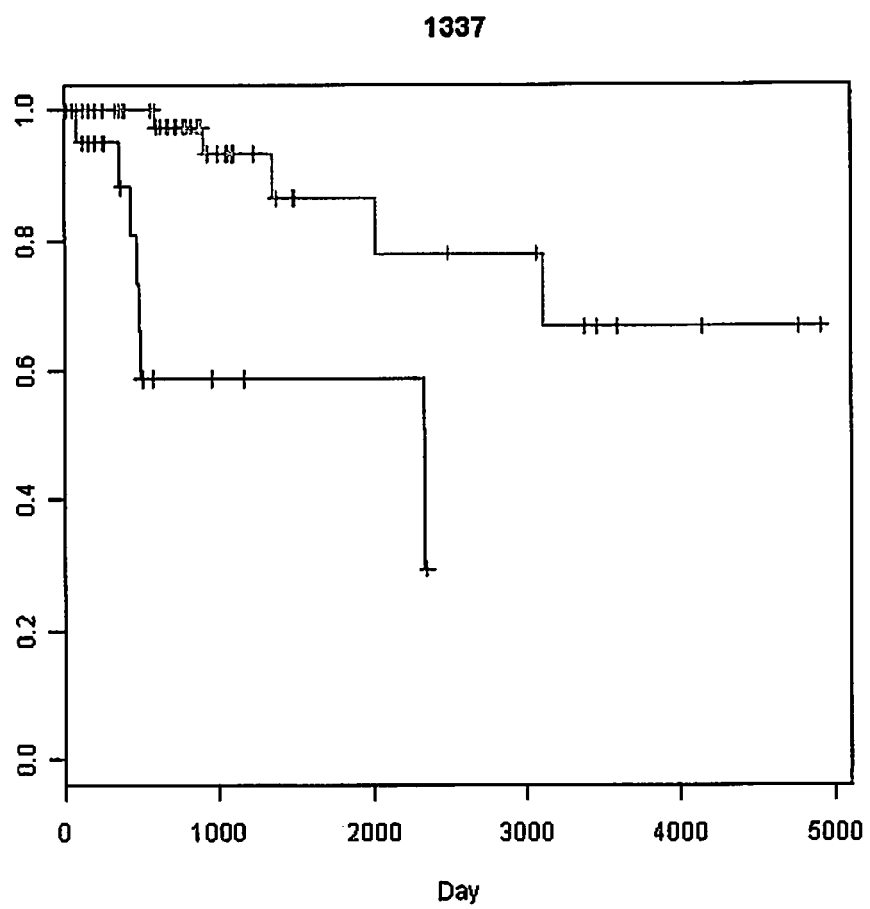
FIG. 2 is a Kaplan-Meier plot showing the overall survival (OS) in days for a 78 patient cohort with NSCLC stage Ia-IIa, classified by presence or absence of a copy number gain in Chr 19; 38.9-40.7 Mb. [marker 2]

FIG. 2 is a Kaplan-Meier plot showing the overall survival (OS) in days for a 78 patient cohort with NSCLC stage Ia-IIa, classified by presence or absence of a copy number gain in Chr 19; 38.9-40.7 Mb. [marker 2]. FDR p-value=0.0085. 17 samples: 3 copies; 3 samples: 4 copies; 4 samples: >=5 copies.

Figure 3:
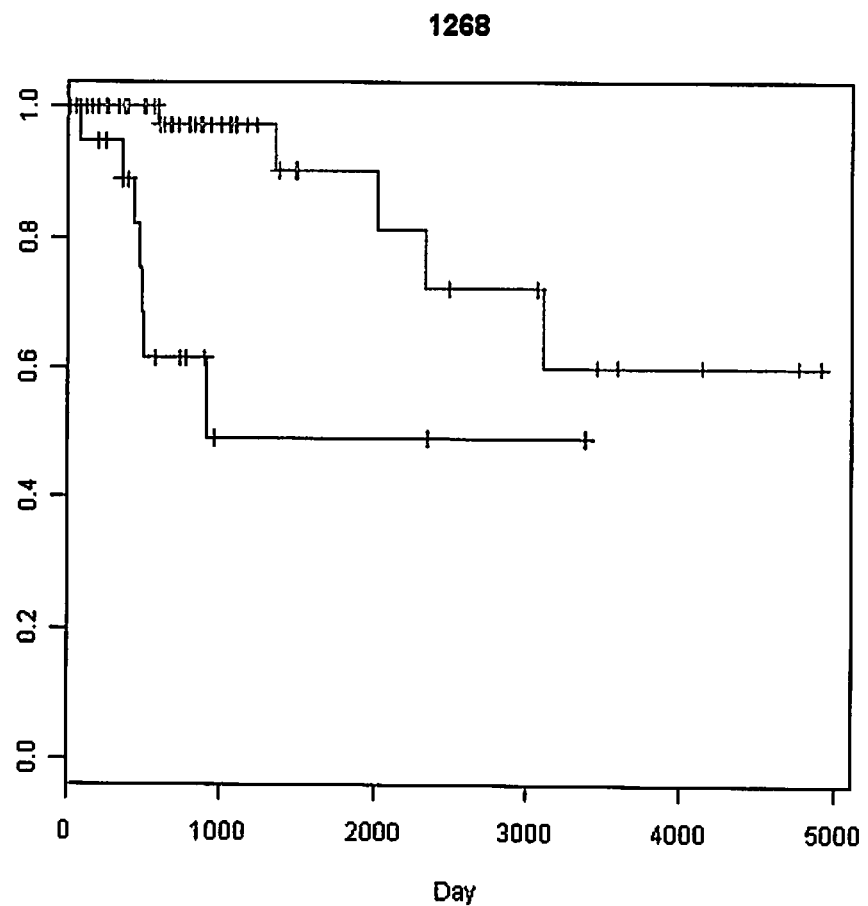
FIG. 3 is a Kaplan-Meier plot showing the overall survival (OS) in days for a 78 patient cohort with NSCLC stage Ia-IIa, classified by presence or absence of a copy number gain in Chr 17; 69.2-71.3 Mb. [marker 3]

FIG. 3 is a Kaplan-Meier plot showing the overall survival (OS) in days for a 78 patient cohort with NSCLC stage Ia-IIa, classified by presence or absence of a copy number gain in Chr 17; 69.2-71.3 Mb. [marker 3]. FDR p-value=0.0304. 16 samples: 3 copies; 5 samples: 4 copies.

Figure 4:
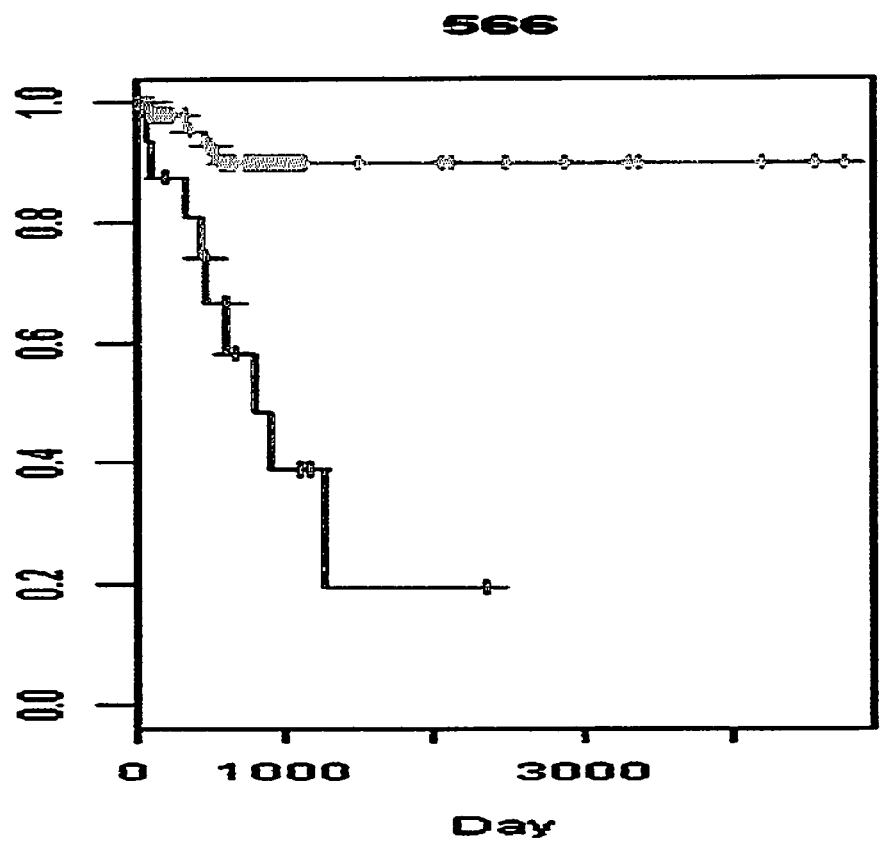
FIG. 4 is a Kaplan-Meier plot showing the overall survival (OS) in days for a 71 patient cohort with NSCLC stage Ib-IIb, classified by presence or absence of a copy number gain in Chr 6, 70.8-71.1 Mb. [marker 4]

FIG. 4 is a Kaplan-Meier plot showing the overall survival (OS) in days for a 71 patient cohort with NSCLC stage Ib-IIb, classified by presence or absence of a copy number gain in Chr 6, 70.8-71.1 Mb. [marker 4]. FDR p-value=0.0116. 15 samples: 3 copies, 1 sample: 4 copies, 1 sample: >=5 copies.

Figure 5:
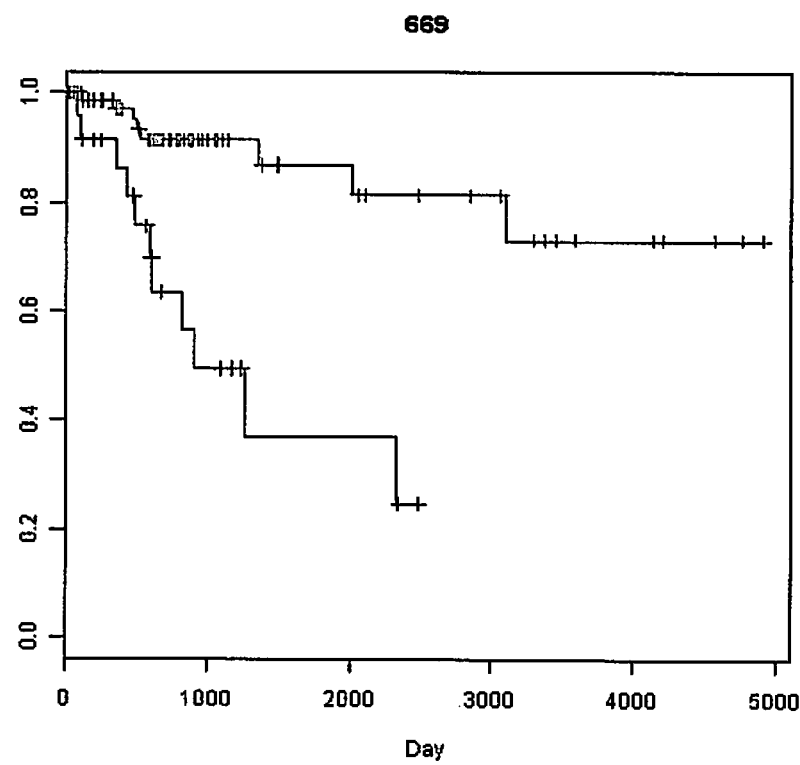
FIG. 5 is a Kaplan-Meier plot showing the overall survival (OS) in days for a 102 patient cohort with NSCLC stage Ia-IIb, classified by presence or absence of a copy number gain in Chr 6, 70.8-71.1 Mb. [marker 4]

FIG. 5 is a Kaplan-Meier plot showing the overall survival (OS) in days for a 102 patient cohort with NSCLC stage Ia-IIb, classified by presence or absence of a copy number gain in Chr 6, 70.8-71.1 Mb. [marker 4]. FDR p-value 0.0110. 15 samples: 3 copies, 1 sample: 4 copies, 1 sample: >=5 copies.

Figure 6:
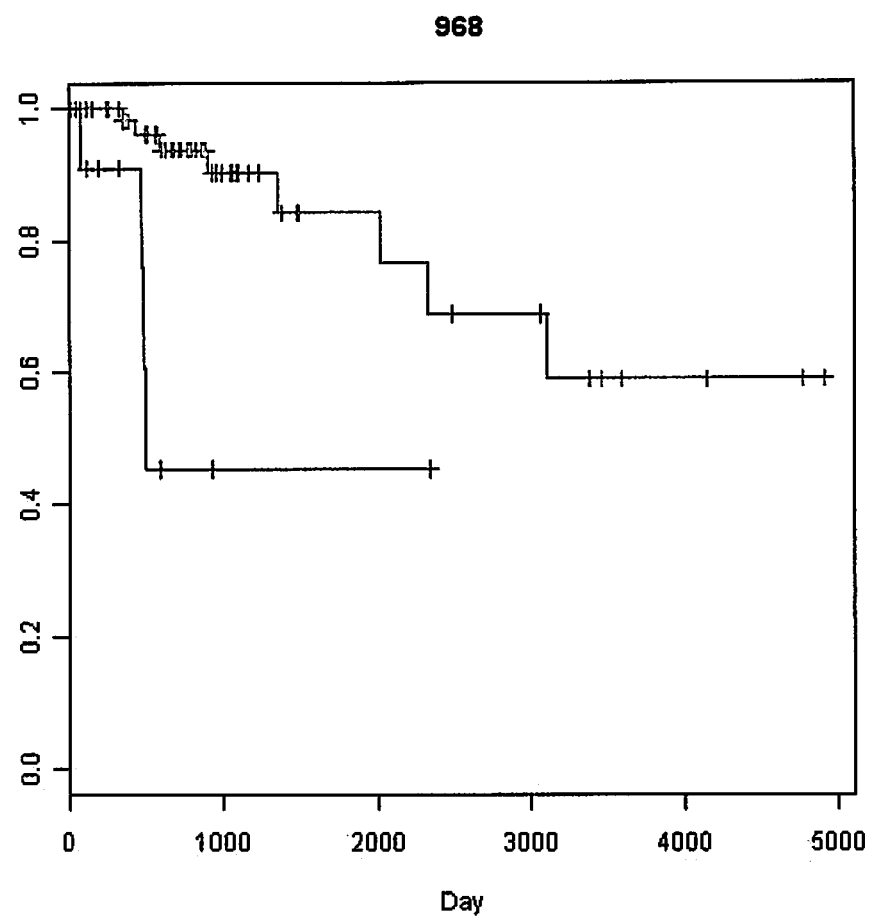
FIG. 6 is a Kaplan-Meier plot showing the overall survival (OS) in days for a 78 patient cohort with NSCLC stage Ia-IIa, classified by presence or absence of a copy number gain in Chr 12, 93.7 kb-1.9 Mb. [marker 5]

FIG. 6 is a Kaplan-Meier plot showing the overall survival (OS) in days for a 78 patient cohort with NSCLC stage Ia-IIa, classified by presence or absence of a copy number gain in Chr 12, 93.7 kb-1.9 Mb. [marker 5]. FDR p-value=0.0493. 5 samples: 3 copies, 5 samples: 4 copies, 1 sample: >=5 copies.

Figure 7:
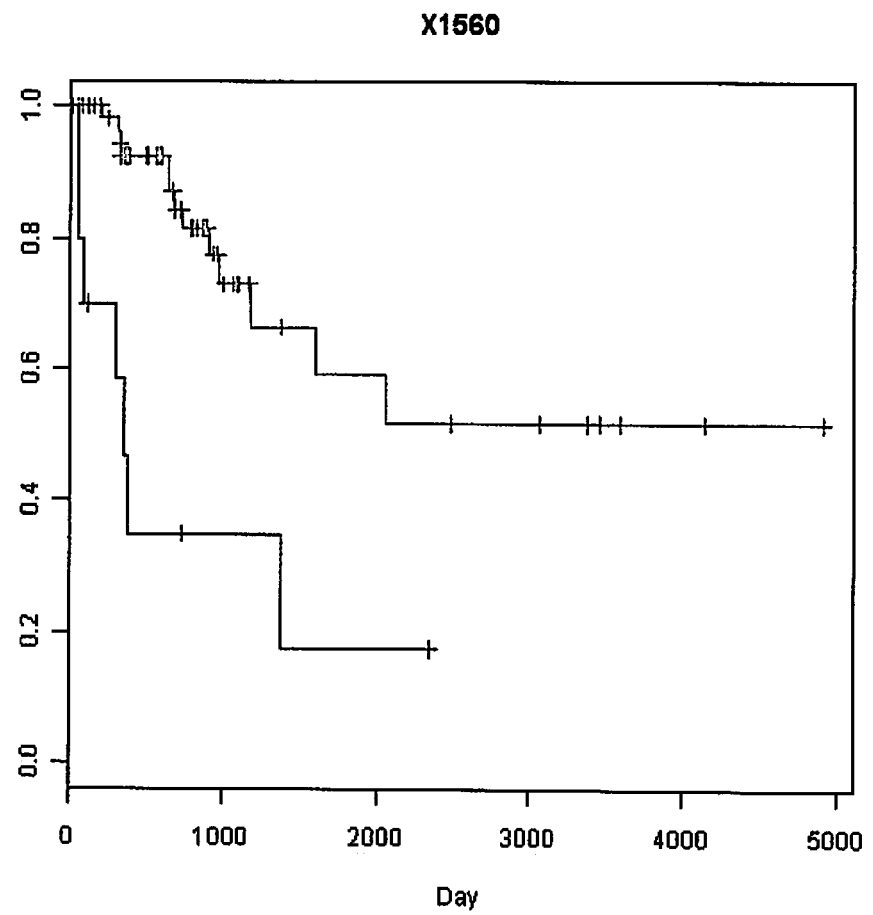
FIG. 7 is a Kaplan-Meier plot showing the time to recurrence (TTR) in days for a 74 patient cohort with NSCLC stage Ia-IIa, classified by presence or absence of a copy number gain in Chr 11, 64.3-64.8 Mb. [marker 6]

FIG. 7 is a Kaplan-Meier plot showing the time to recurrence (TTR) in days for a 74 patient cohort with NSCLC stage Ia-IIa, classified by presence or absence of a copy number gain in Chr 11, 64.3-64.8 Mb. [marker 6]. FDR p-value=0.0413. 9 samples: 3 copies, 2 samples: >=5 copies.

Figure 8:
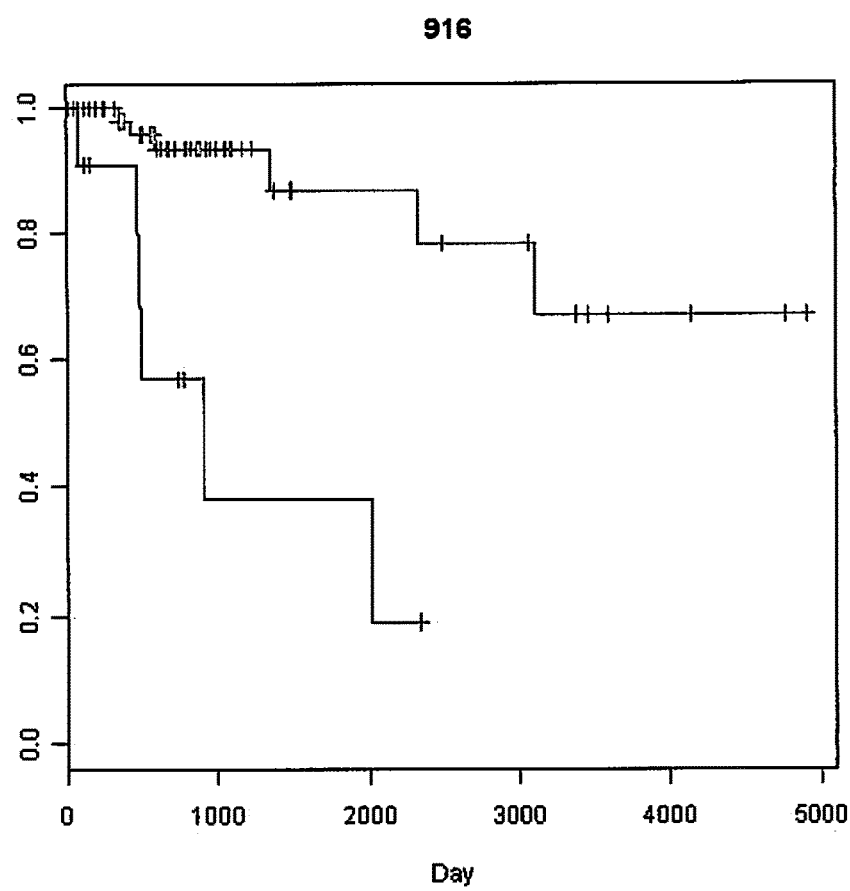
FIG. 8 is a Kaplan-Meier plot showing the overall survival (OS) in days for a 78 patient cohort with NSCLC stage Ia-IIa, classified by presence or absence of a copy number gain in Chr 11, 64.3-64.8 Mb. [marker 6]

FIG. 8 is a Kaplan-Meier plot showing the overall survival (OS) in days for a 78 patient cohort with NSCLC stage Ia-IIa, classified by presence or absence of a copy number gain in Chr 11, 64.3-64.8 Mb. [marker 6]. FDR p-value=0.0040. 9 samples: 3 copies, 2 sample: >=5 copies.

Figure 9:
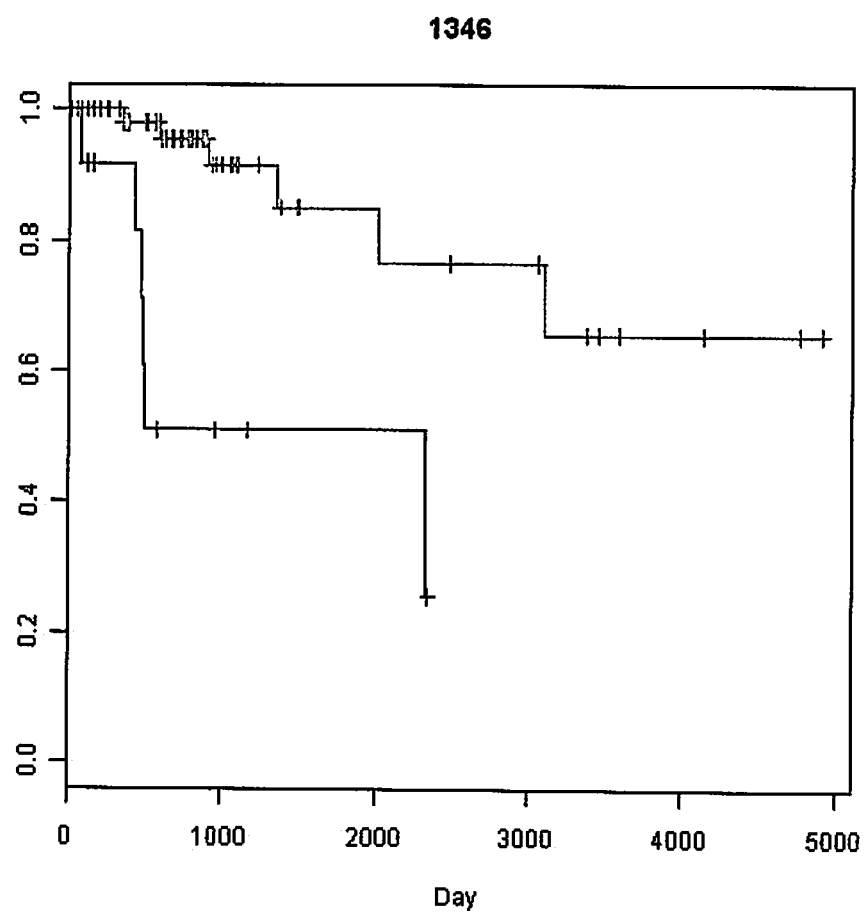
FIG. 9 is a Kaplan-Meier plot showing the overall survival (OS) in days for a 78 patient cohort with NSCLC stage Ia-IIa, classified by presence or absence of a copy number gain in Chr 19, 57.0-62.2 Mb. [marker 7]

FIG. 9 is a Kaplan-Meier plot showing the overall survival (OS) in days for a 78 patient cohort with NSCLC stage Ia-IIa, classified by presence or absence of a copy number gain in Chr 19, 57.0-62.2 Mb. [marker 7]. FDR p-value=0.0091. 10 samples: 3 copies, 3 samples: 4 copies.

Figure 10:
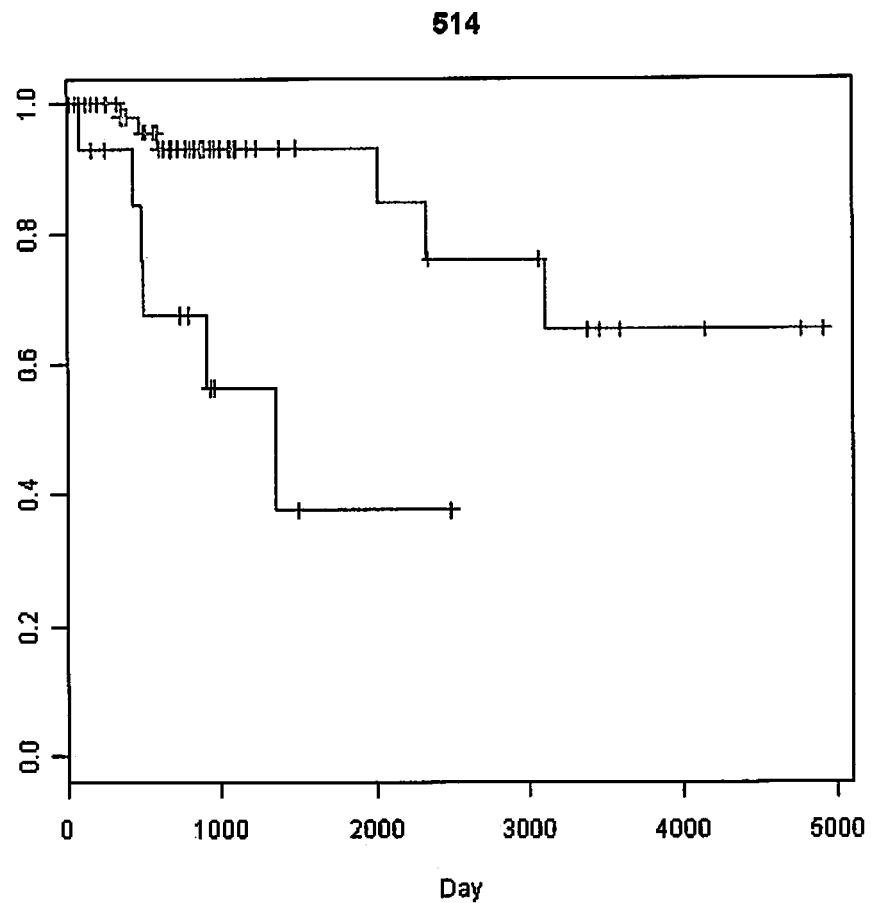
FIG. 10 is a Kaplan-Meier plot showing the overall survival (OS) in days for a 78 patient cohort with NSCLC stage Ia-IIa, classified by presence or absence of a copy number gain in Chr 6, 39.1-39.9 Mb. [marker 8]

FIG. 10 is a Kaplan-Meier plot showing the overall survival (OS) in days for a 78 patient cohort with NSCLC stage Ia-IIa, classified by presence or absence of a copy number gain in Chr 6, 39.1-39.9 Mb. [marker 8]. FDR p-value=0.0356. 13 samples: 3 copies, 1 sample: 4 copies.

Figure 11:
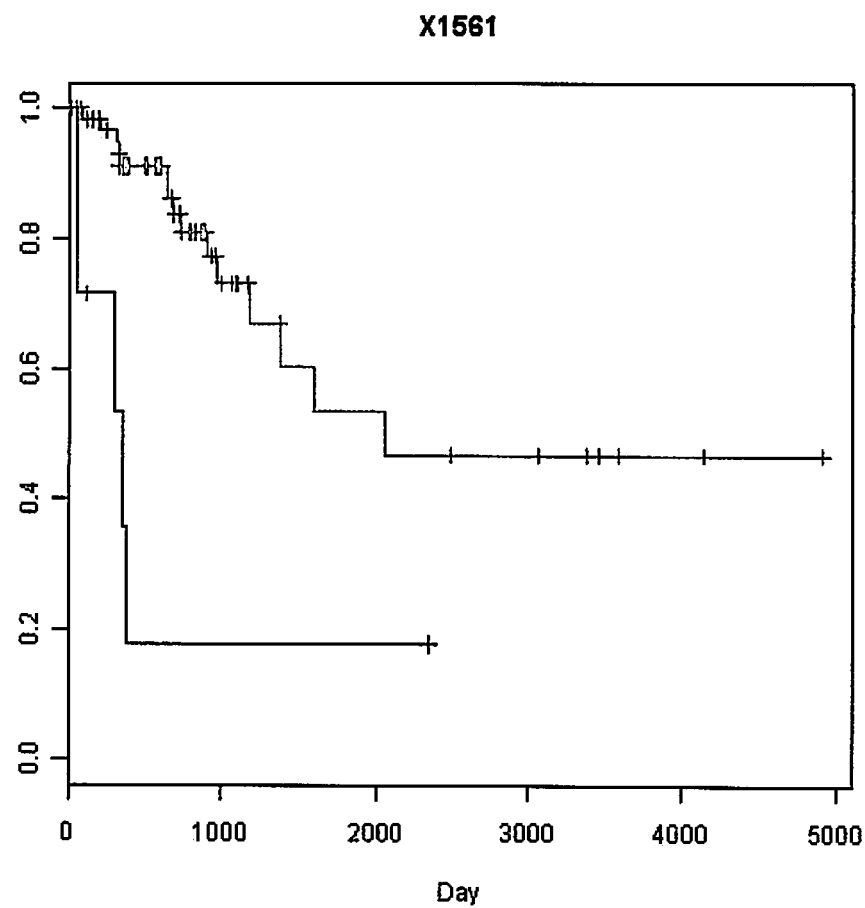
FIG. 11 is a Kaplan-Meier plot showing the time to recurrence (TTR) in days for a 74 patient cohort with NSCLC stage Ia-IIa, classified by presence or absence of a copy number gain in Chr 11, 64.8-65.7 Mb. [marker 9]

FIG. 11 is a Kaplan-Meier plot showing the time to recurrence (TTR) in days for a 74 patient cohort with NSCLC stage Ia-IIa, classified by presence or absence of a copy number gain in Chr 11, 64.8-65.7 Mb. [marker 9]. FDR p-value=0.0484. 5 samples: 3 copies, 2 samples: >=5 copies.

Figure 12:
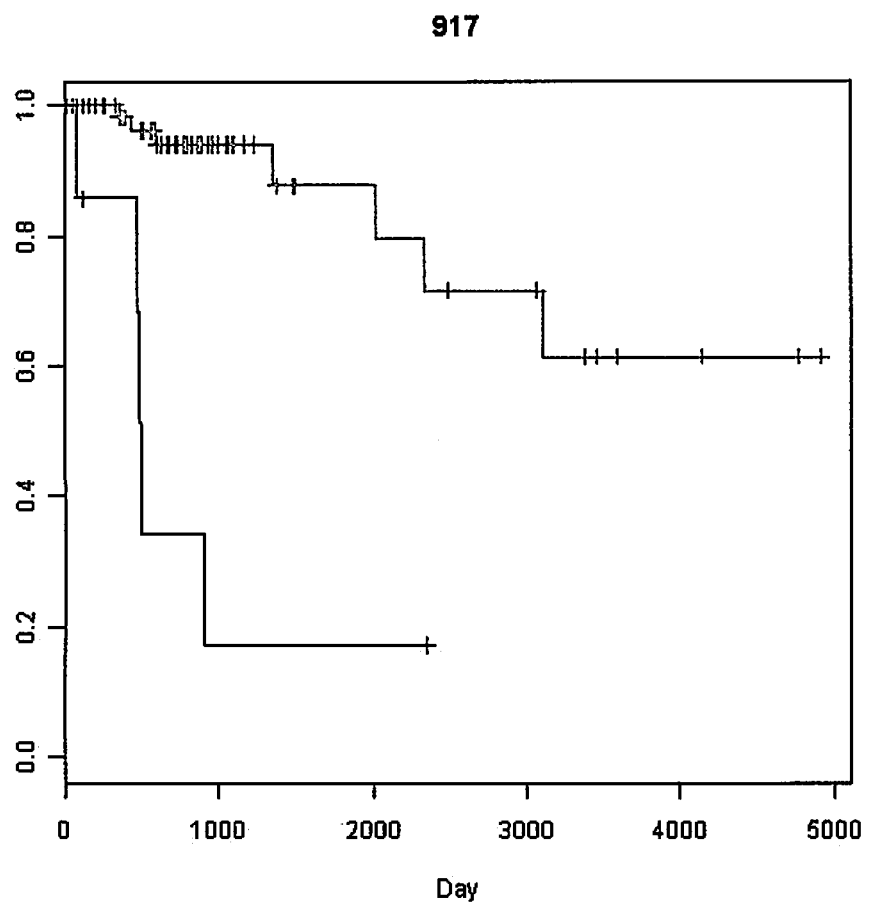
FIG. 12 is a Kaplan-Meier plot showing the overall survival (OS) in days for a 78 patient cohort with NSCLC stage Ia-IIa, classified by presence or absence of a copy number gain in Chr 11, 64.8-65.7 Mb. [marker 9]

FIG. 12 is a Kaplan-Meier plot showing the overall survival (OS) in days for a 78 patient cohort with NSCLC stage Ia-IIa, classified by presence or absence of a copy number gain in Chr 11, 64.8-65.7 Mb. [marker 9]. FDR p-value=0.0004. 5 samples: 3 copies, 2 samples: >=5 copies.

Figure 13:
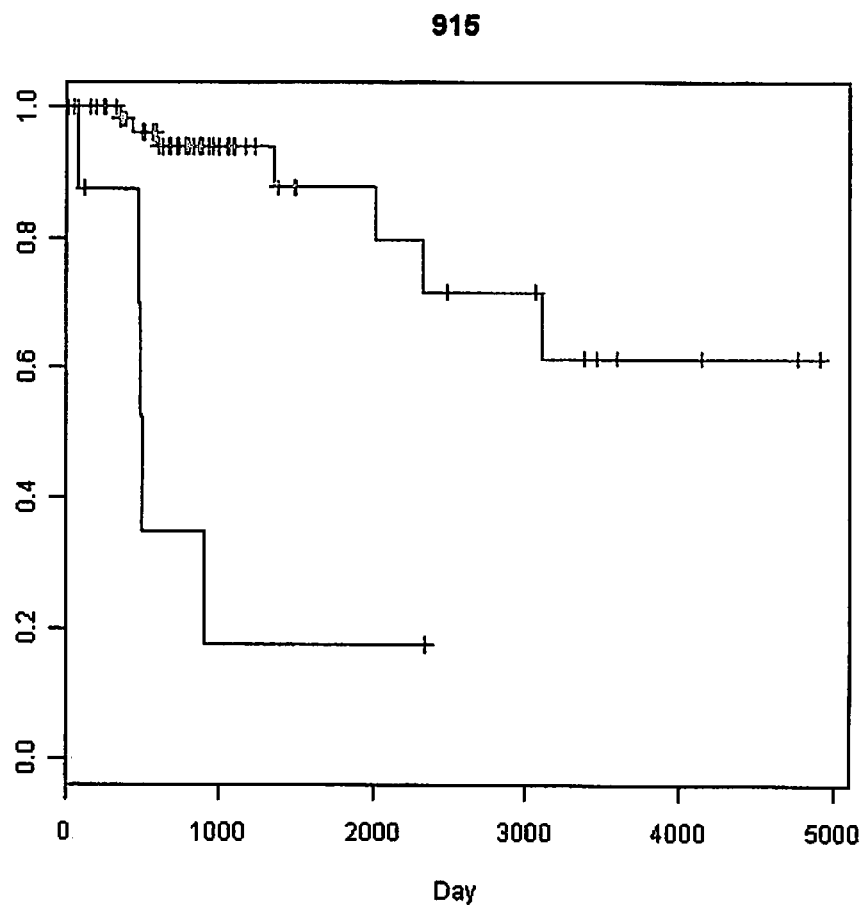
FIG. 13 is a Kaplan-Meier plot showing the overall survival (OS) in days for a 78 patient cohort with NSCLC stage Ia-IIa, classified by presence or absence of a copy number gain in Chr 11, 61.4-64.3 Mb. [marker 10]

FIG. 13 is a Kaplan-Meier plot showing the overall survival (OS) in days for a 78 patient cohort with NSCLC stage Ia-IIa, classified by presence or absence of a copy number gain in Chr 11, 61.4-64.3 Mb. [marker 10]. FDR p-value=0.0004; 8 samples; 3 copies, 1 sample: 4 copy.

Figure 14:
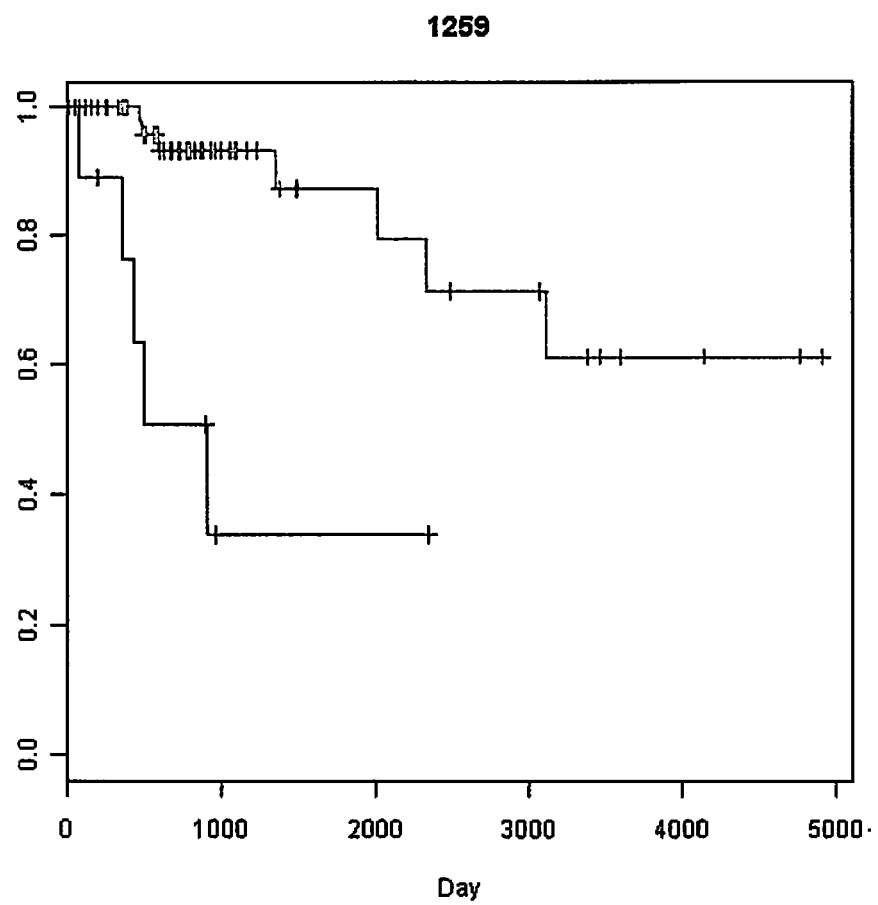
FIG. 14 is a Kaplan-Meier plot showing the overall survival (OS) in days for a 78 patient cohort with NSCLC stage Ia-IIa, classified by presence or absence of a copy number gain in Chr 17, 51.5-53.2 Mb. [marker 11]

FIG. 14 is a Kaplan-Meier plot showing the overall survival (OS) in days for a 78 patient cohort with NSCLC stage Ia-IIa, classified by presence or absence of a copy number gain in Chr 17, 51.5-53.2 Mb. [marker 11]. FDR p-value=0.0054. 8 samples: 3 copies, 1 sample: 4 copies.

Figure 15:
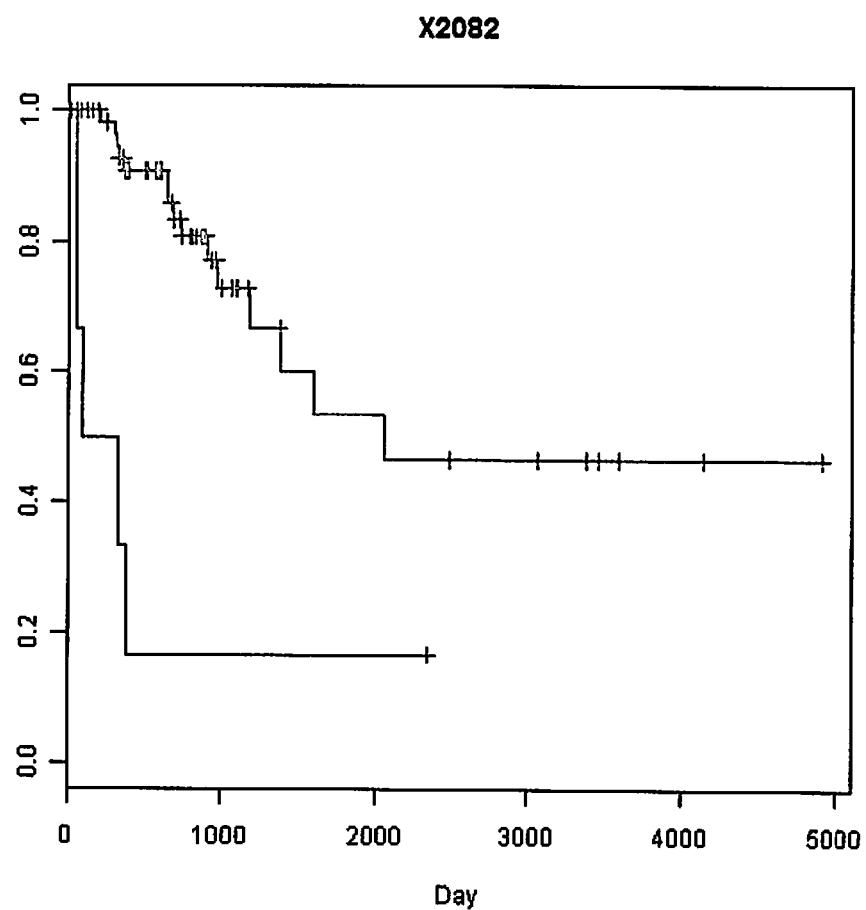
FIG. 15 is a Kaplan-Meier plot showing the time to recurrence (TTR) in days for a 74 patient cohort with NSCLC stage Ia-IIa, classified by presence or absence of a copy number gain in Chr 17, 43.5-44.9 Mb. [marker 12]

FIG. 15 is a Kaplan-Meier plot showing the time to recurrence (TTR) in days for a 74 patient cohort with NSCLC stage Ia-IIa, classified by presence or absence of a copy number gain in Chr 17, 43.5-44.9 Mb. [marker 12]. FDR p-value=0.0269. 4 samples: 3 copies, 2 samples: 4 copies.

Figure 16:
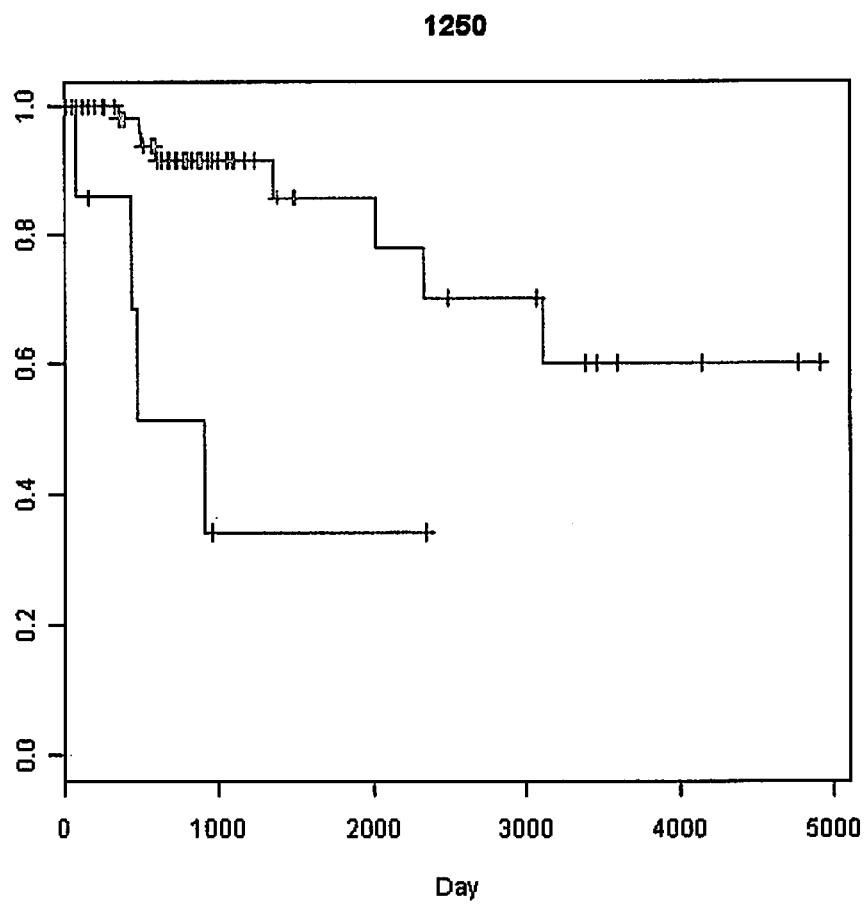
FIG. 16 is a Kaplan-Meier plot showing the overall survival (OS) in days for a 78 patient cohort with NSCLC stage Ia-IIa, classified by presence or absence of a copy number gain in Chr 17, 43.5-44.9 Mb. [marker 12]

FIG. 16 is a Kaplan-Meier plot showing the overall survival (OS) in days for a 78 patient cohort with NSCLC stage Ia-IIa, classified by presence or absence of a copy number gain in Chr 17, 43.5-44.9 Mb. [marker 12]. FDR p-value=0.0040. 5 samples: 3 copies, 2 samples: 4 copies.

Figure 17:
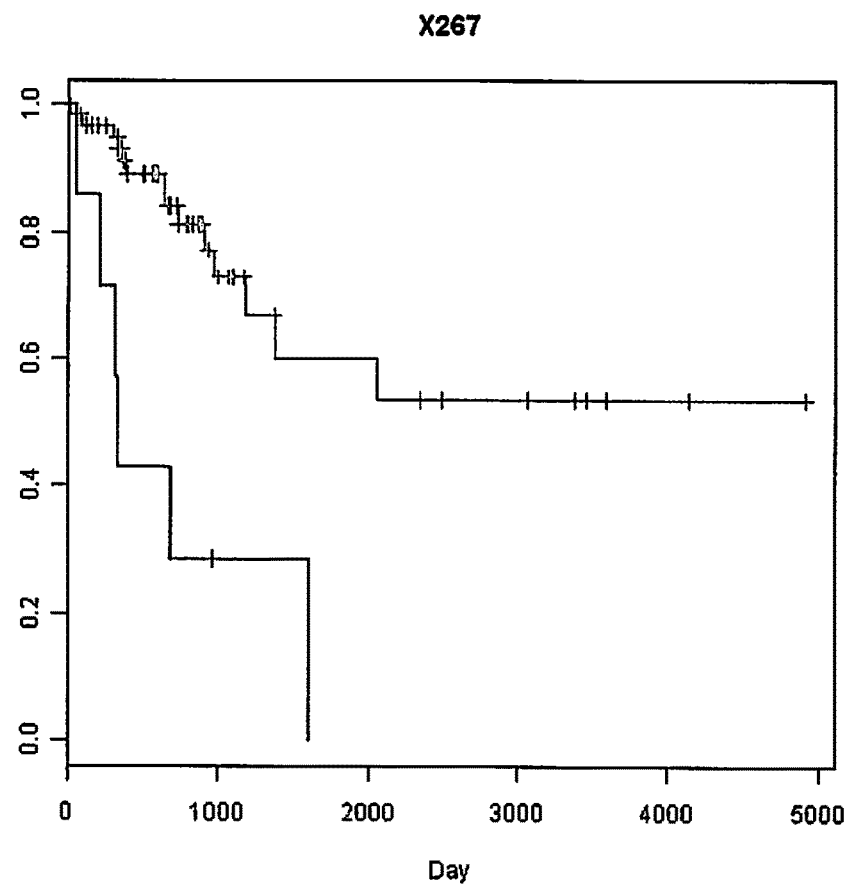
FIG. 17 is a Kaplan-Meier plot showing the time to recurrence (TTR) in days for a 74 patient cohort with NSCLC stage Ia-IIa, classified by presence or absence of a copy number gain in Chr 2, 147.6-151.1 Mb. [marker 13]

FIG. 17 is a Kaplan-Meier plot showing the time to recurrence (TTR) in days for a 74 patient cohort with NSCLC stage Ia-IIa, classified by presence or absence of a copy number gain in Chr 2, 147.6-151.1 Mb. [marker 13]. FDR p-value=0.0210. 7 samples: 3 copies.

Figure 18:
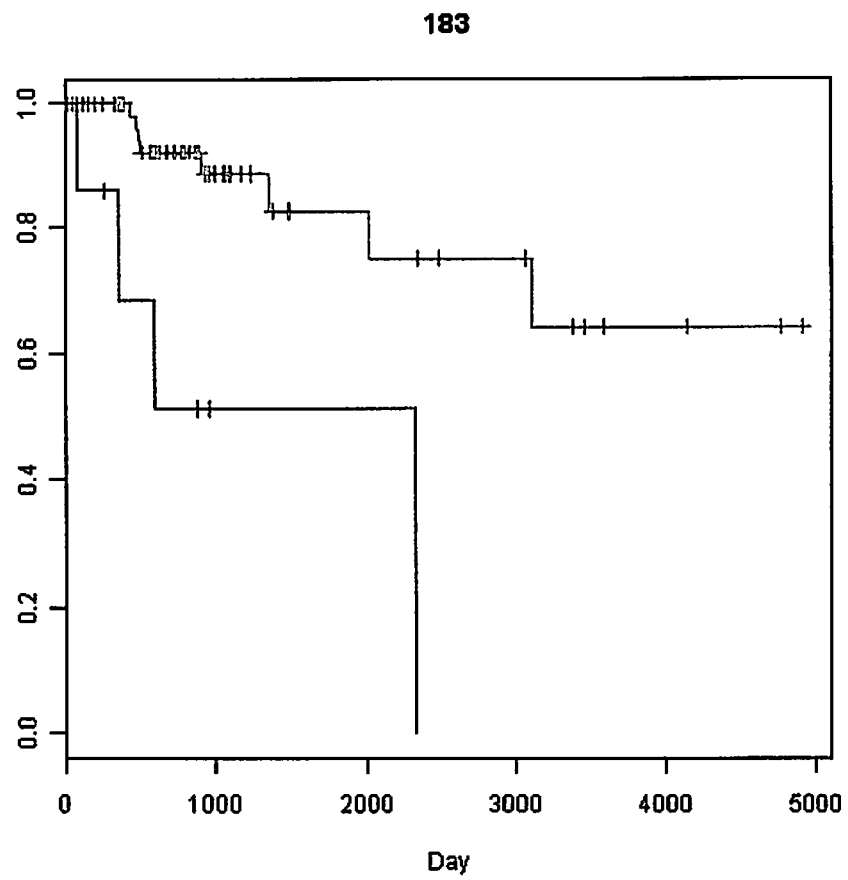
FIG. 18 is a Kaplan-Meier plot showing the overall survival (OS) in days for a 78 patient cohort with NSCLC stage Ia-IIa, classified by presence or absence of a copy number gain in Chr 2, 147.6-151.1 Mb. [marker 13]

FIG. 18 is a Kaplan-Meier plot showing the overall survival (OS) in days for a 78 patient cohort with NSCLC stage Ia-IIa, classified by presence or absence of a copy number gain in Chr 2, 147.6-151.1 Mb. [marker 13]. FDR p-value=0.0233. 7 samples: 3 copies.

Figure 19:
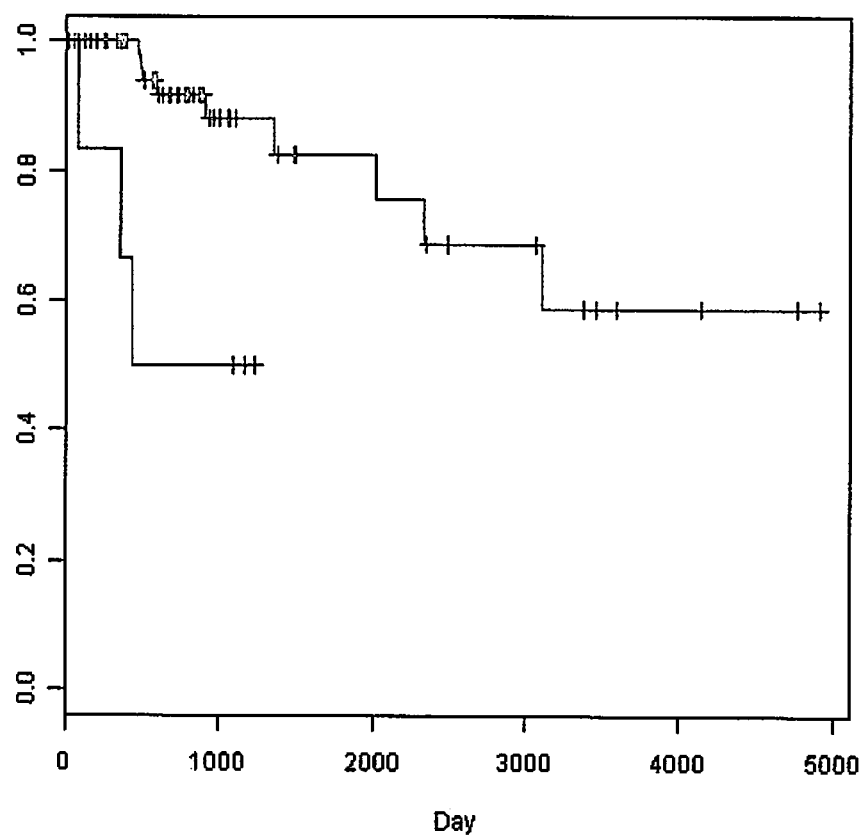
FIG. 19 is a Kaplan-Meier plot showing the overall survival (OS) in days for a 78 patient cohort with NSCLC stage Ia-IIb, classified by presence or absence of a copy number gain in Chr 6, 123.7-135.6 Mb. [marker 14]

FIG. 19 is a Kaplan-Meier plot showing the overall survival (OS) in days for a 78 patient cohort with NSCLC stage Ia-IIb, classified by presence or absence of a copy number gain in Chr 6, 123.7-135.6 Mb. [marker 14]. FDR p-value=0.0377. 7 samples: 3 copies.

Figure 20:
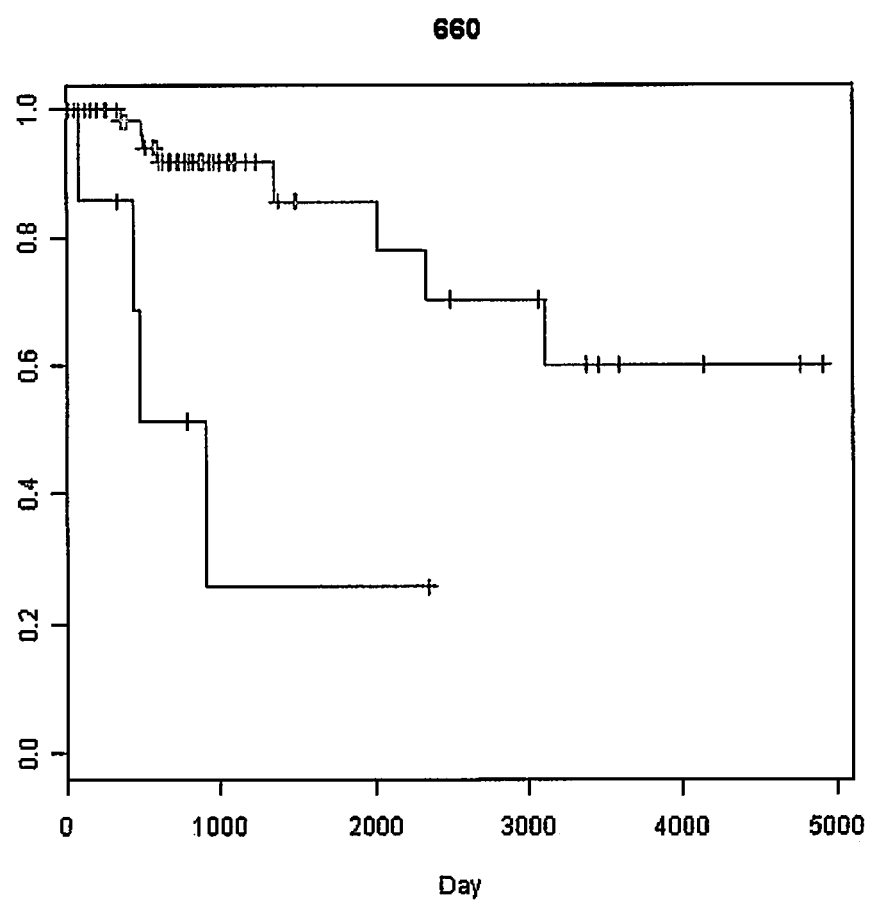
FIG. 20 is a Kaplan-Meier plot showing the overall survival (OS) in days for a 78 patient cohort with NSCLC stage Ia-IIa, classified by presence or absence of a copy number gain in Chr 8, 6.9-8.8 Mb. [marker 15]

FIG. 20 is a Kaplan-Meier plot showing the overall survival (OS) in days for a 78 patient cohort with NSCLC stage Ia-IIa, classified by presence or absence of a copy number gain in Chr 8, 6.9-8.8 Mb. [marker 15]. FDR p-value=0.0166. 7 samples: 3 copy.

Figure 21:
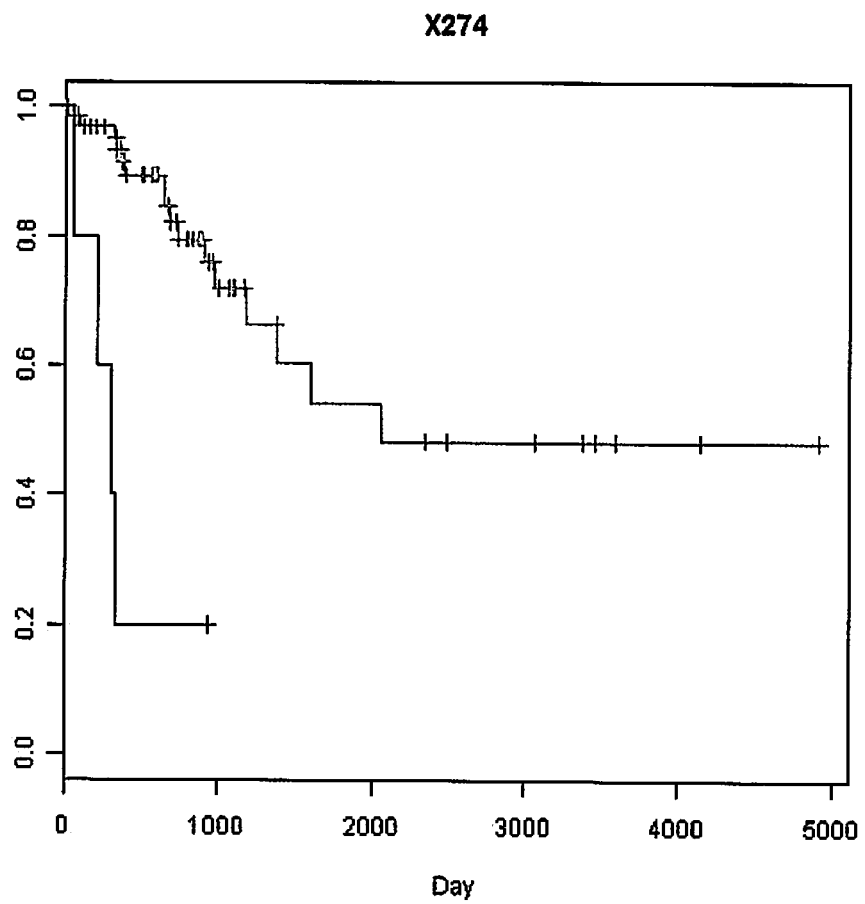
FIG. 21 is a Kaplan-Meier plot showing the time to recurrence (TTR) in days for a 74 patient cohort with NSCLC stage Ia-IIa, classified by presence or absence of a copy number gain in Chr 2, 159.9-161.4 Mb. [marker 16]

FIG. 21 is a Kaplan-Meier plot showing the time to recurrence (TTR) in days for a 74 patient cohort with NSCLC stage Ia-IIa, classified by presence or absence of a copy number gain in Chr 2, 159.9-161.4 Mb. [marker 16]. FDR p-value=0.0013. 4 samples: 3 copies, 1 sample: 4 copies.

Figure 22:
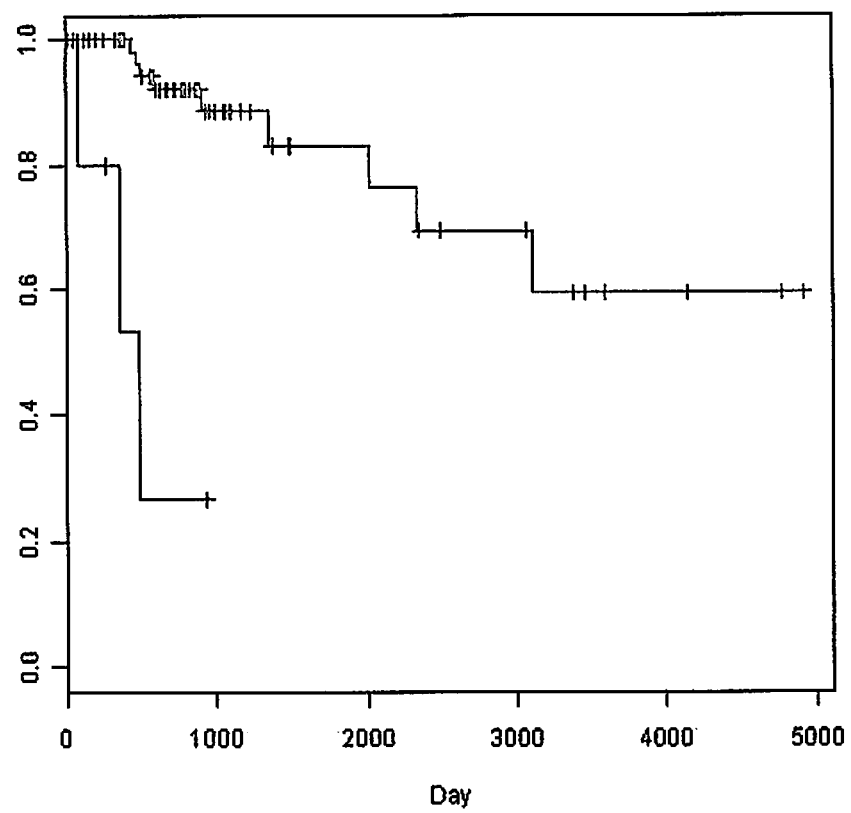
FIG. 22 is a Kaplan-Meier plot showing the overall survival (OS) in days for a 78 patient cohort with NSCLC stage Ia-IIa, classified by presence or absence of a copy number gain in Chr 2, 159.9-161.4 Mb. [marker 16]

FIG. 22 is a Kaplan-Meier plot showing the overall survival (OS) in days for a 78 patient cohort with NSCLC stage Ia-IIa, classified by presence or absence of a copy number gain in Chr 2, 159.9-161.4 Mb. [marker 16]. FDR p-value=0.0001. 4 samples: 3 copy, 1 sample: 4 copies.

Figure 23:
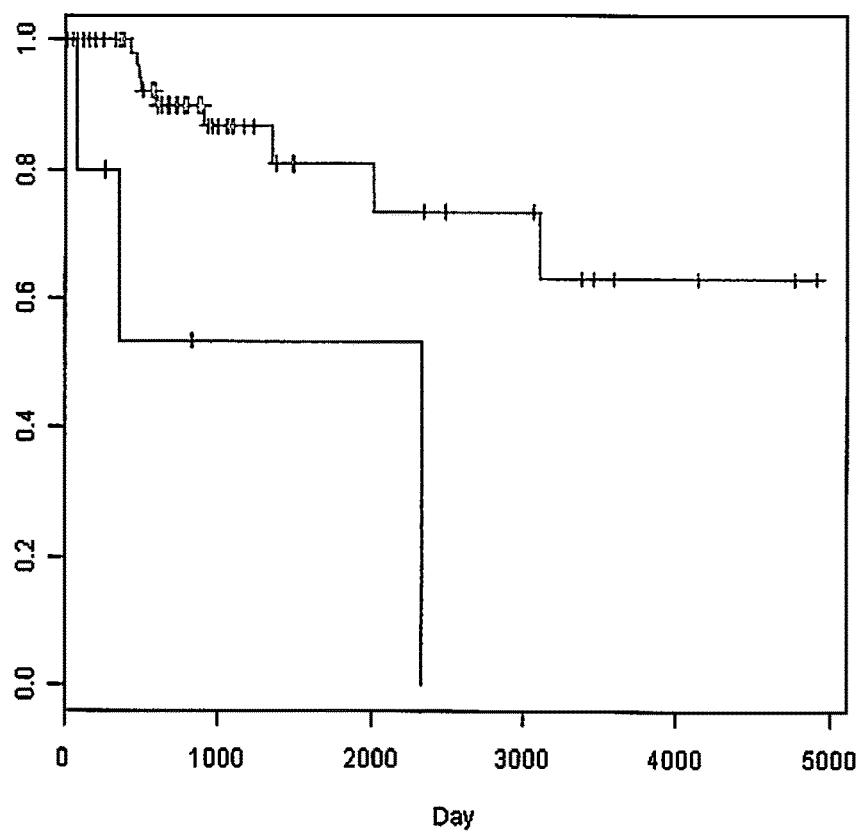
FIG. 23 is a Kaplan-Meier plot showing the overall survival (OS) in days for a 78 patient cohort with NSCLC stage Ia-IIa, classified by presence or absence of a copy number gain in Chr 2, 200.9-204.2 Mb. [marker 17]

FIG. 23 is a Kaplan-Meier plot showing the overall survival (OS) in days for a 78 patient cohort with NSCLC stage Ia-IIa, classified by presence or absence of a copy number gain in Chr 2, 200.9-204.2 Mb. [marker 17]. FDR p-value=0.0398. 6 samples: 3 copies.

Figure 24:
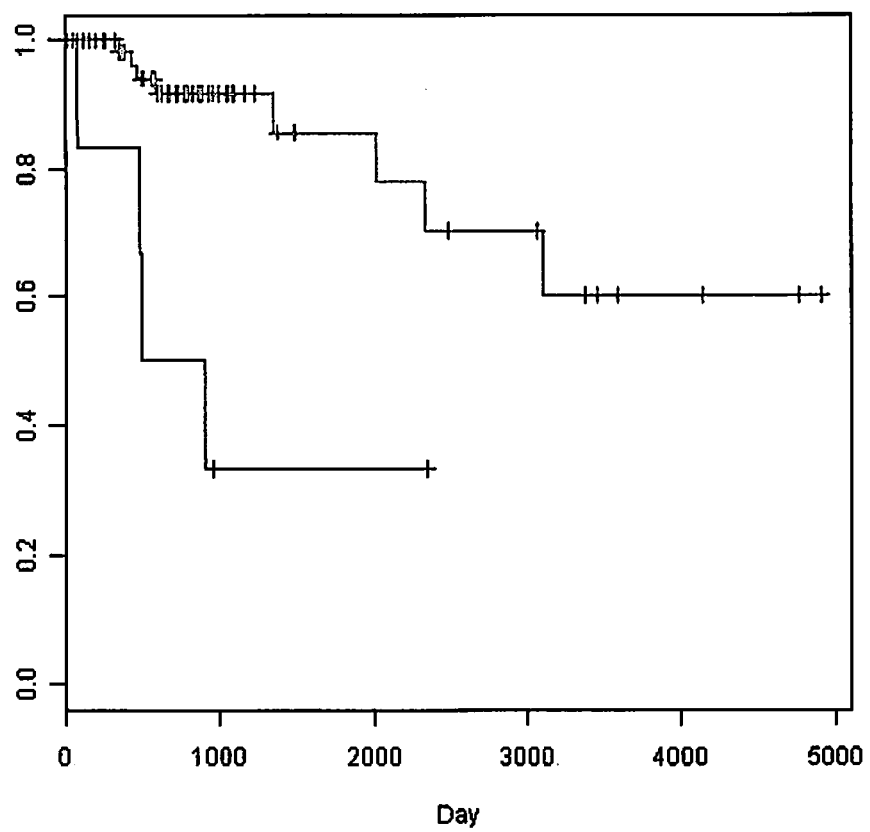
FIG. 24 is a Kaplan-Meier plot showing the overall survival (OS) in days for a 78 patient cohort with NSCLC stage Ia-IIa, classified by presence or absence of a copy number gain in Chr 6, 36.3-36.7 Mb. [marker 18]

FIG. 24 is a Kaplan-Meier plot showing the overall survival (OS) in days for a 78 patient cohort with NSCLC stage Ia-IIa, classified by presence or absence of a copy number gain in Chr 6, 36.3-36.7 Mb. [marker 18]. FDR p-value 0.0347. 6 samples: 3 copies.

Figure 25:
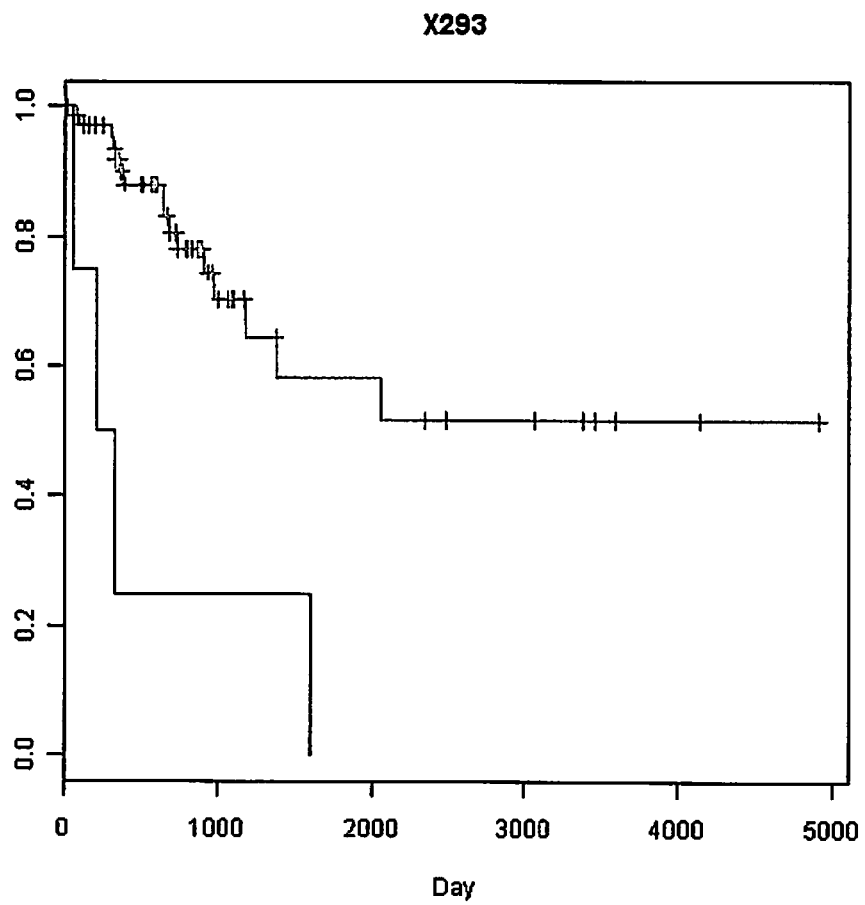
FIG. 25 is a Kaplan-Meier plot showing the time to recurrence (TTR) in days for a 74 patient cohort with NSCLC stage Ia-IIa, classified by presence or absence of a copy number gain in Chr 2, 205.9-208.1 Mb. [marker 19]

FIG. 25 is a Kaplan-Meier plot showing the time to recurrence (TTR) in days for a 74 patient cohort with NSCLC stage Ia-IIa, classified by presence or absence of a copy number gain in Chr 2, 205.9-208.1 Mb. [marker 19]. FDR p-value=0.04. 5 samples: 3 copies.

Figure 26:
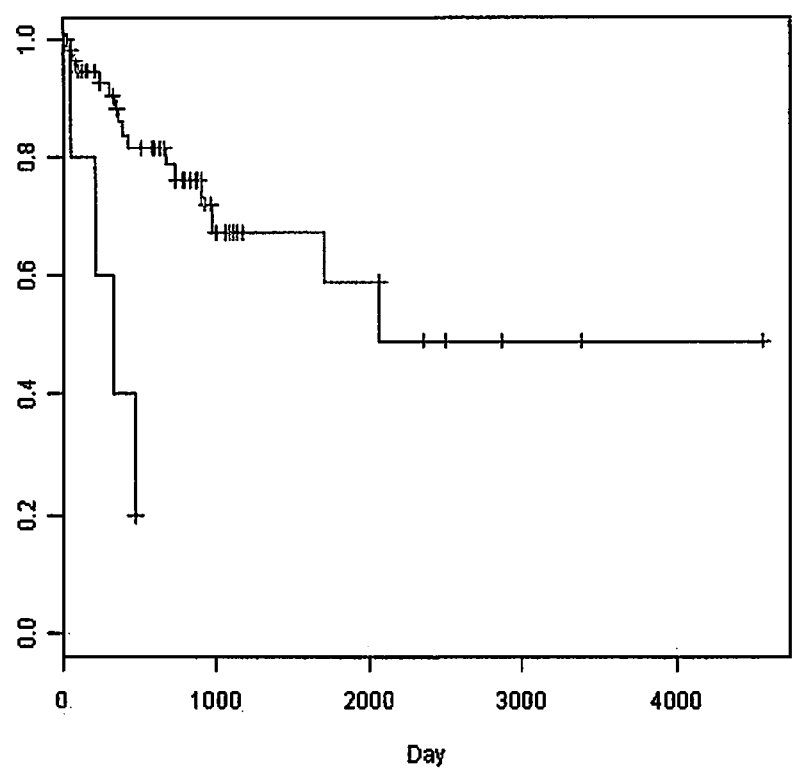
FIG. 26 is a Kaplan-Meier plot showing the time to recurrence (TTR) in days for a 66 patient cohort with NSCLC stage Ib-IIb, classified by presence or absence of a copy number gain in Chr 2, 205.9-208.1 Mb. [marker 19]

FIG. 26 is a Kaplan-Meier plot showing the time to recurrence (TTR) in days for a 66 patient cohort with NSCLC stage Ib-IIb, classified by presence or absence of a copy number gain in Chr 2, 205.9-208.1 Mb. [marker 19]. FDR p-value=0.0351. 6 samples: 3 copies.

Figure 27:
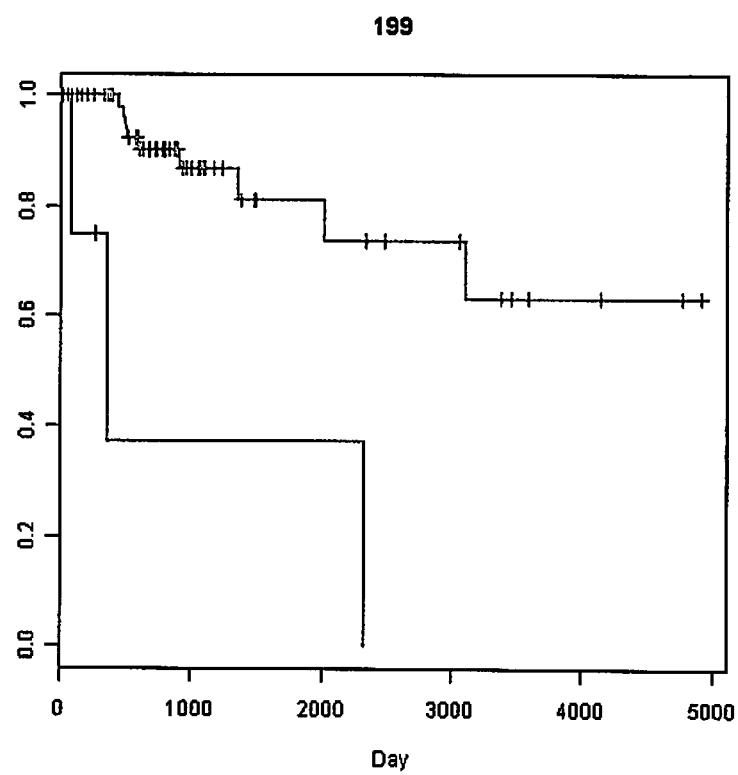
FIG. 27 is a Kaplan-Meier plot showing the overall survival (OS) in days for a 78 patient cohort with NSCLC stage Ia-IIa, classified by presence or absence of a copy number gain in Chr 2, 205.9-208.1 Mb. [marker 19]

FIG. 27 is a Kaplan-Meier plot showing the overall survival (OS) in days for a 78 patient cohort with NSCLC stage Ia-IIa, classified by presence or absence of a copy number gain in Chr 2, 205.9-208.1 Mb. [marker 19]. FDR p-value=0.0075. 5 samples: 3 copies.

Figure 28:
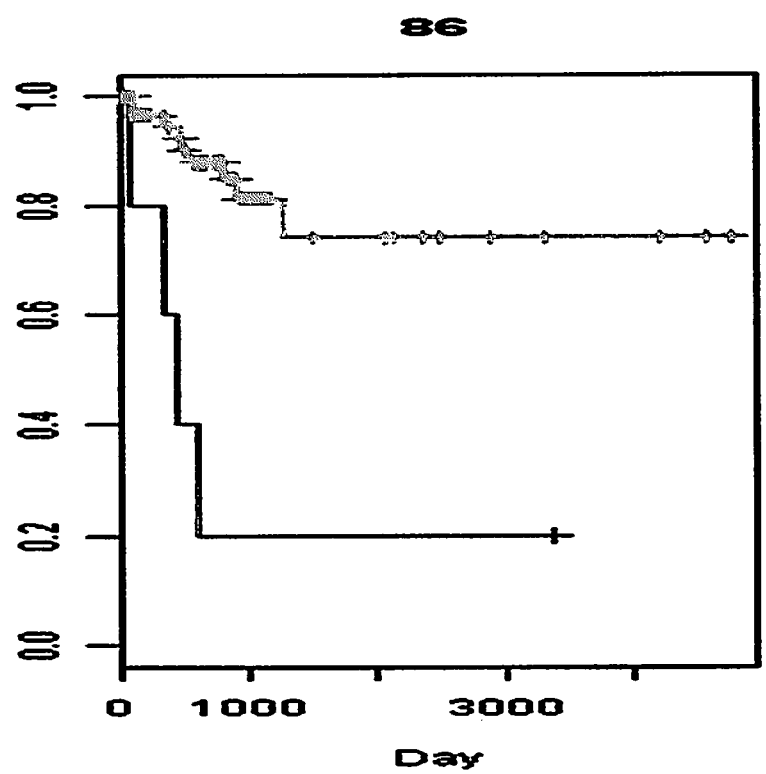
FIG. 28 is a Kaplan-Meier plot showing the overall survival (OS) in days for a 71 patient cohort with NSCLC stage Ib-IIb, classified by presence or absence of a copy number gain in Chr 1, 109.5-111.1 Mb. [marker 20]

FIG. 28 is a Kaplan-Meier plot showing the overall survival (OS) in days for a 71 patient cohort with NSCLC stage Ib-IIb, classified by presence or absence of a copy number gain in Chr 1, 109.5-111.1 Mb. [marker 20]. FDR p-value=0.0224. 5 samples: 3 copies.

Figure 29:
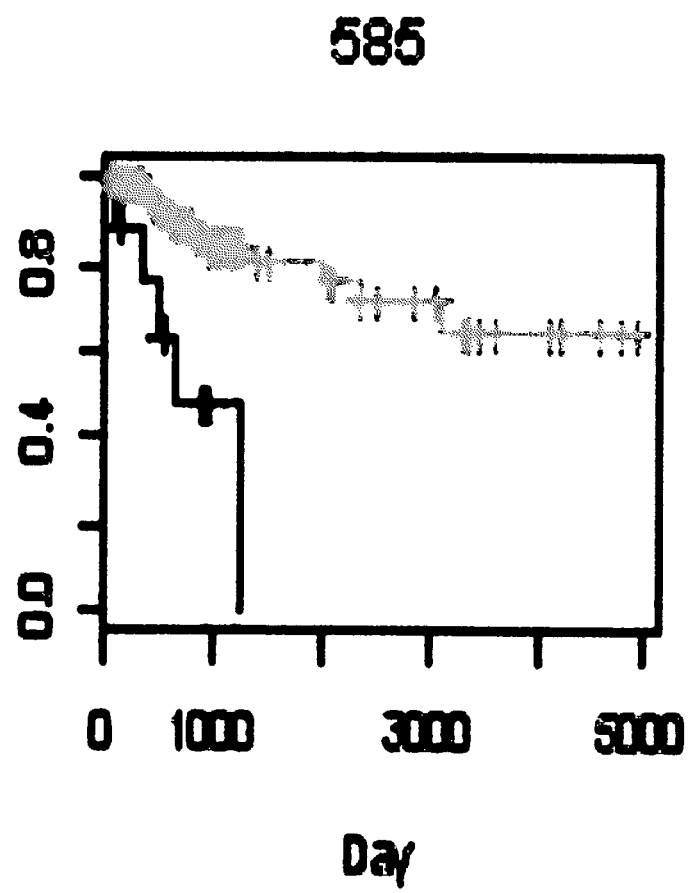
FIG. 29 is a Kaplan-Meier plot showing the overall survival (OS) in days for a 102 patient cohort with NSCLC stage Ia-IIb, classified by presence or absence of a copy number loss (deletion) of Chr 5, 62.9-67.8 Mb. [deletion marker 1]

FIG. 29 is a Kaplan-Meier plot showing the overall survival (OS) in days for a 102 patient cohort with NSCLC stage Ia-IIb, classified by presence or absence of a copy number loss (deletion) of Chr 5, 62.9-67.8 Mb. [deletion marker 1]. FDR p-value=0.0282. Deleted in 10 samples.

Figure 30:
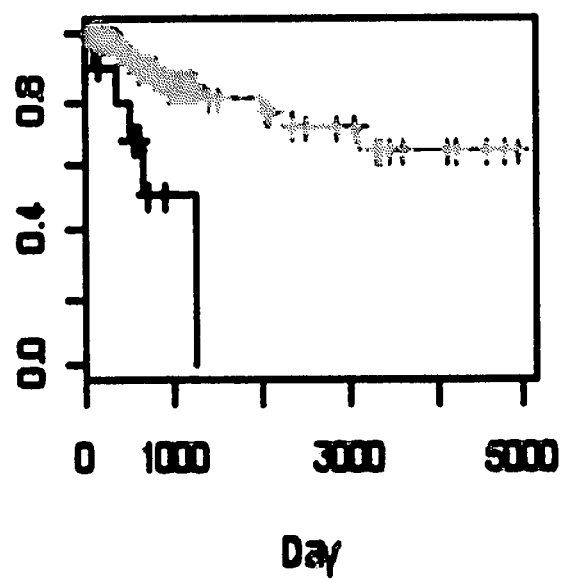
FIG. 30 is a Kaplan-Meier plot showing the overall survival (OS) in days for a 102 patient cohort with NSCLC stage Ia-IIb, classified by presence or absence of a copy number loss (deletion) of Chr 5, 53.3-53.8 Mb. [deletion marker 2]

FIG. 30 is a Kaplan-Meier plot showing the overall survival (OS) in days for a 102 patient cohort with NSCLC stage Ia-IIb, classified by presence or absence of a copy number loss (deletion) of Chr 5, 53.3-53.8 Mb. [deletion marker 2]. FDR p-value=0.0409. Deleted in 12 samples.

Figure 31:
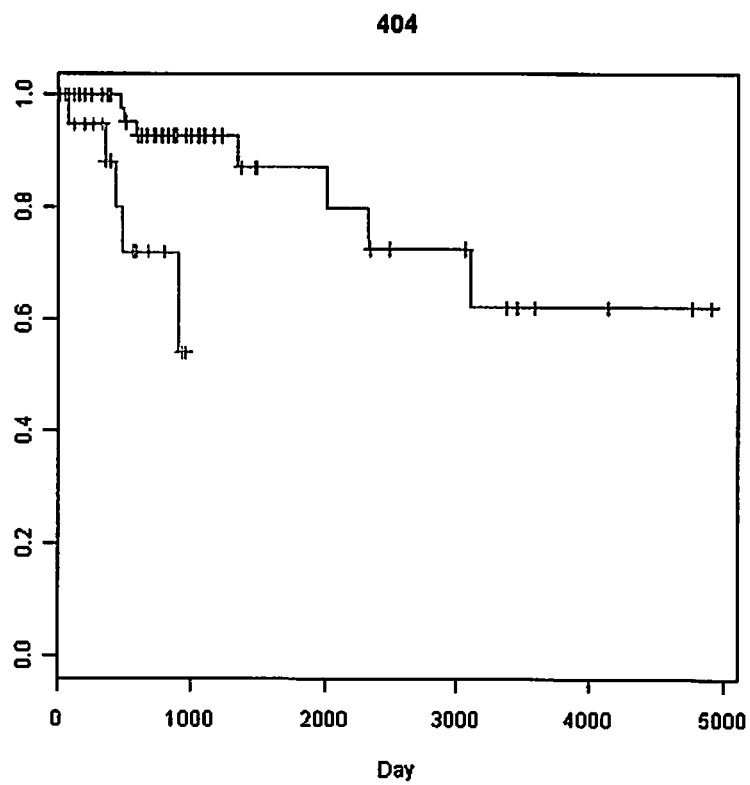
FIG. 31 is a Kaplan-Meier plot showing the overall survival (OS) in days for a 78 patient cohort with NSCLC stage Ia-IIa, classified by presence or absence of a copy number loss (deletion) of Chr 4, 105.8-107.2 Mb. [deletion marker 3]

FIG. 31 is a Kaplan-Meier plot showing the overall survival (OS) in days for a 78 patient cohort with NSCLC stage Ia-IIa, classified by presence or absence of a copy number loss (deletion) of Chr 4, 105.8-107.2 Mb. [deletion marker 3]. FDR p-value=0.0469. Deleted in 21 samples.

Figure 32:
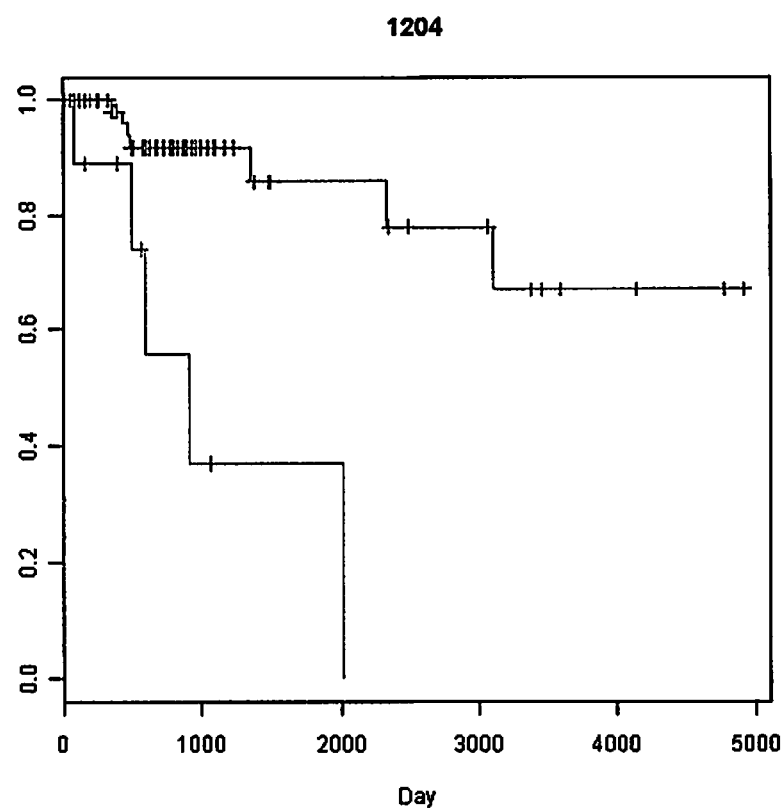
FIG. 32 is a Kaplan-Meier plot showing the overall survival (OS) in days for a 78 patient cohort with NSCLC stage Ia-IIa, classified by presence or absence of a copy number loss (deletion) of Chr 16, 45.8-46.3 Mb. [deletion marker 4]

FIG. 32 is a Kaplan-Meier plot showing the overall survival (OS) in days for a 78 patient cohort with NSCLC stage Ia-IIa, classified by presence or absence of a copy number loss (deletion) of Chr 16, 45.8-46.3 Mb. [deletion marker 4]. FDR p-value=0.0039. Deleted in 11 samples.

Figure 33:
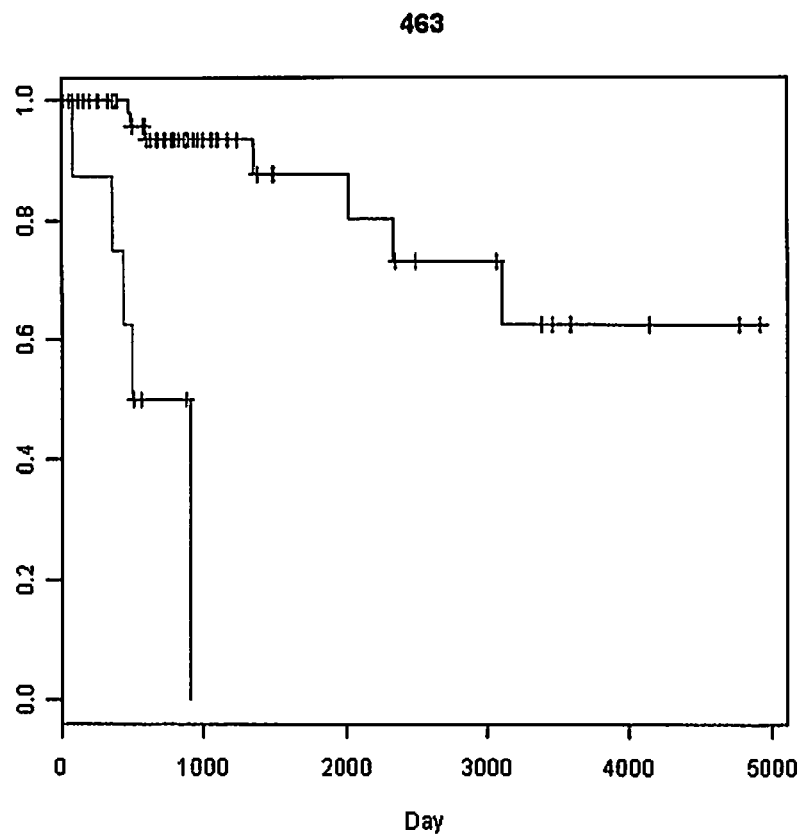
FIG. 33 is a Kaplan-Meier plot showing the overall survival (OS) in days for a 78 patient cohort with NSCLC stage Ia-IIa, classified by presence or absence of a copy number loss (deletion) of Chr 5, 50.7-52.0 Mb. [deletion marker 5]

FIG. 33 is a Kaplan-Meier plot showing the overall survival (OS) in days for a 78 patient cohort with NSCLC stage Ia-IIa, classified by presence or absence of a copy number loss (deletion) of Chr 5, 50.7-52.0 Mb. [deletion marker 5]. FDR p-value=0.0000. Deleted in 10 samples.

Figure 34:
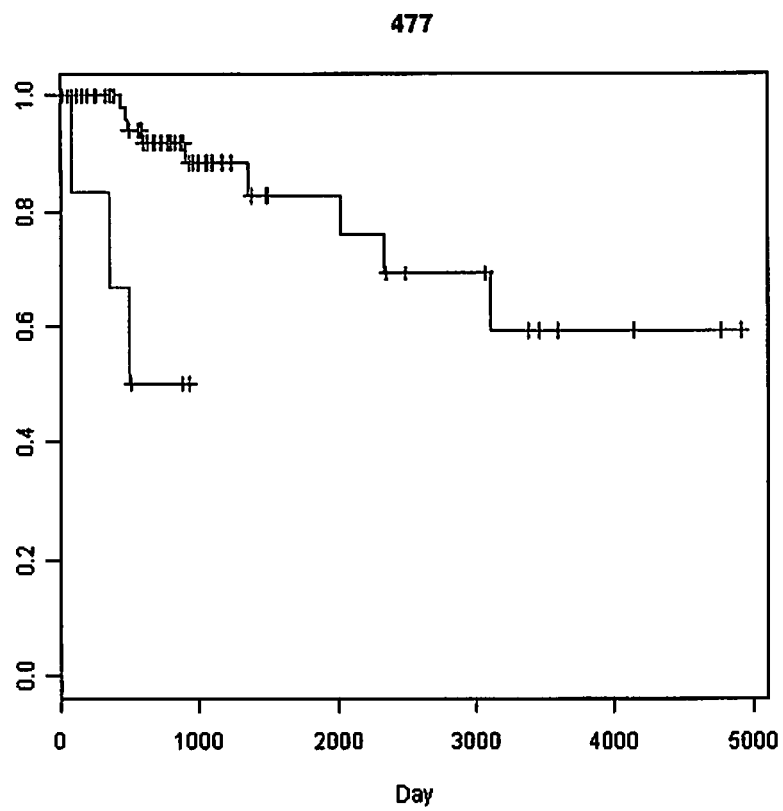
FIG. 34 is a Kaplan-Meier plot showing the overall survival (OS) in days for a 78 patient cohort with NSCLC stage Ia-IIa, classified by presence or absence of a copy number loss (deletion) of Chr 5, 94.2-96.1 Mb. [deletion marker 6]

FIG. 34 is a Kaplan-Meier plot showing the overall survival (OS) in days for a 78 patient cohort with NSCLC stage Ia-IIa, classified by presence or absence of a copy number loss (deletion) of Chr 5, 94.2-96.1 Mb. [deletion marker 6]. FDR p-value=0.0202. Deleted in 7 samples.

Figure 35:
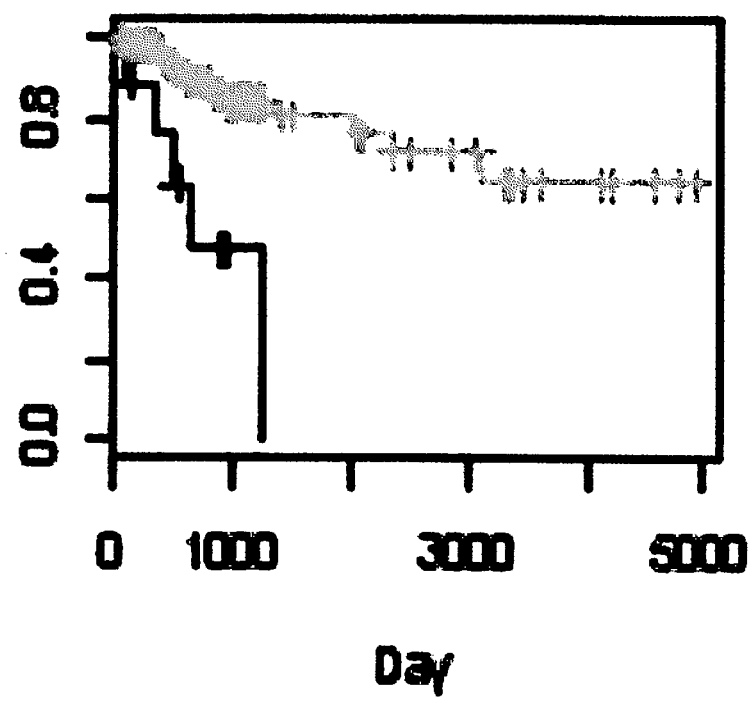
FIG. 35 is a Kaplan-Meier plot showing the overall survival (OS) in days for a 102 patient cohort with NSCLC stage Ia-IIb, classified by presence or absence of a copy number loss (deletion) of Chr 5, 94.2-96.1 Mb. [deletion marker 6]

FIG. 35 is a Kaplan-Meier plot showing the overall survival (OS) in days for a 102 patient cohort with NSCLC stage Ia-IIb, classified by presence or absence of a copy number loss (deletion) of Chr 5, 94.2-96.1 Mb. [deletion marker 6]. FDR p-value=0.0282. Deleted in 10 samples.

Figure 36:
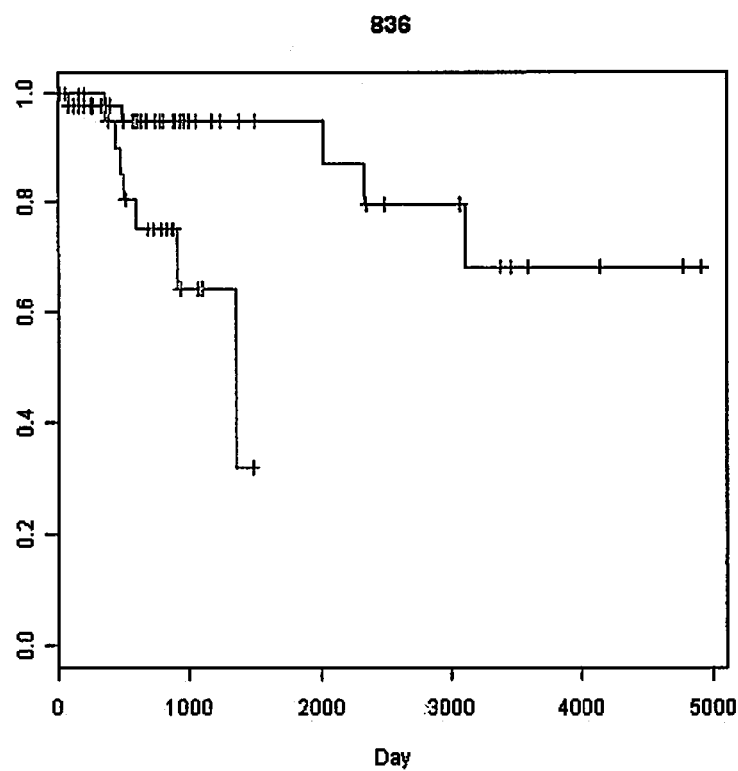
FIG. 36 is a Kaplan-Meier plot showing the overall survival (OS) in days for a 78 patient cohort with NSCLC stage Ia-IIa, classified by presence or absence of a copy number loss (deletion) of Chr 9, 36.1-37.0 Mb. [deletion marker 7]

FIG. 36 is a Kaplan-Meier plot showing the overall survival (OS) in days for a 78 patient cohort with NSCLC stage Ia-IIa, classified by presence or absence of a copy number loss (deletion) of Chr 9, 36.1-37.0 Mb. [deletion marker 7]. FDR p-value=0.0468. Deleted in 24 samples.

Figure 37:
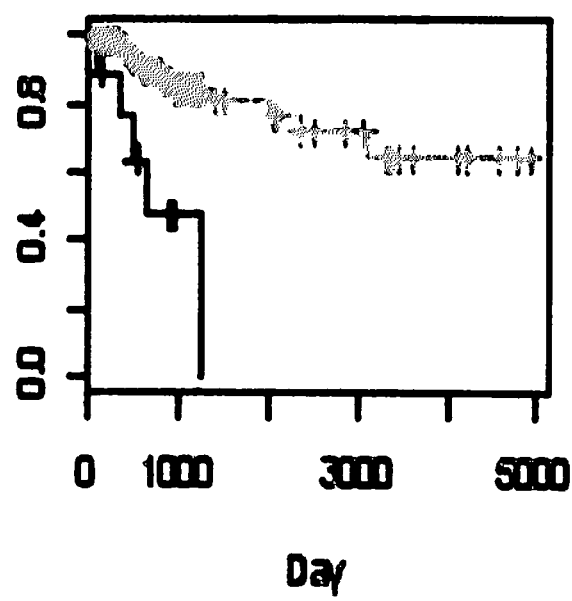
FIG. 37 is a Kaplan-Meier plot showing the overall survival (OS) in days for a 102 patient cohort with NSCLC stage Ia-IIb, classified by presence or absence of a copy number loss (deletion) of Chr 5, 94.2-96.1 Mb. [deletion marker 8]

FIG. 37 is a Kaplan-Meier plot showing the overall survival (OS) in days for a 102 patient cohort with NSCLC stage Ia-IIb, classified by presence or absence of a copy number loss (deletion) of Chr 5, 94.2-96.1 Mb. [deletion marker 8]. FDR p-value=0.0282. Deleted in 10 samples.

Figure 38:
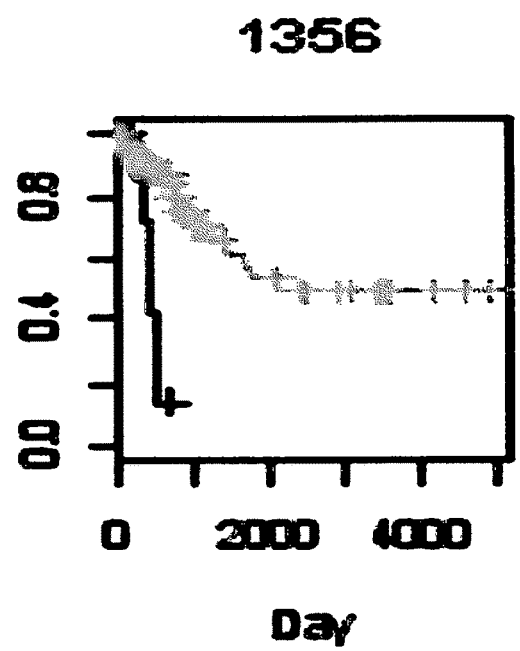
FIG. 38 is a Kaplan-Meier plot showing the time to recurrence (TTR) in days for a 97 patient cohort with NSCLC stage Ia-IIb, classified by presence or absence of a copy number loss (deletion) of Chr14, 51.1-52.8 Mb. [deletion marker 9]

FIG. 38 is a Kaplan-Meier plot showing the time to recurrence (TTR) in days for a 97 patient cohort with NSCLC stage Ia-IIb, classified by presence or absence of a copy number loss (deletion) of Chr14, 51.1-52.8 Mb. [deletion marker 9]. FDR p-value=0.0008. Deleted in 9 samples.

Figure 39:
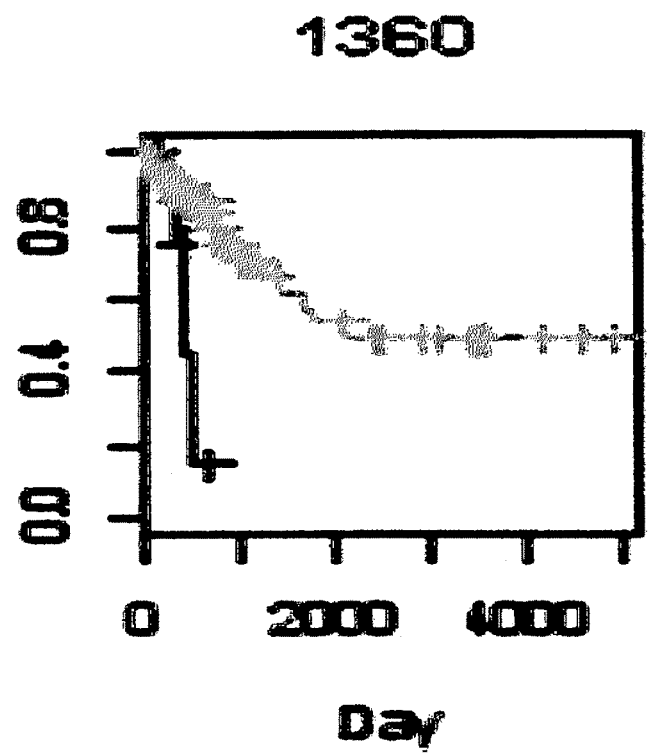
FIG. 39 is a Kaplan-Meier plot showing the time to recurrence (TTR) in days for a 97 patient cohort with NSCLC stage Ia-IIb, classified by presence or absence of a copy number loss (deletion) of Chr 14, 61.5-68.6 Mb. [deletion marker 10]

FIG. 39 is a Kaplan-Meier plot showing the time to recurrence (TTR) in days for a 97 patient cohort with NSCLC stage Ia-IIb, classified by presence or absence of a copy number loss (deletion) of Chr 14, 61.5-68.6 Mb. [deletion marker 10]. FDR p-value=0.0034. Deleted in 9 samples.

Figure 40:
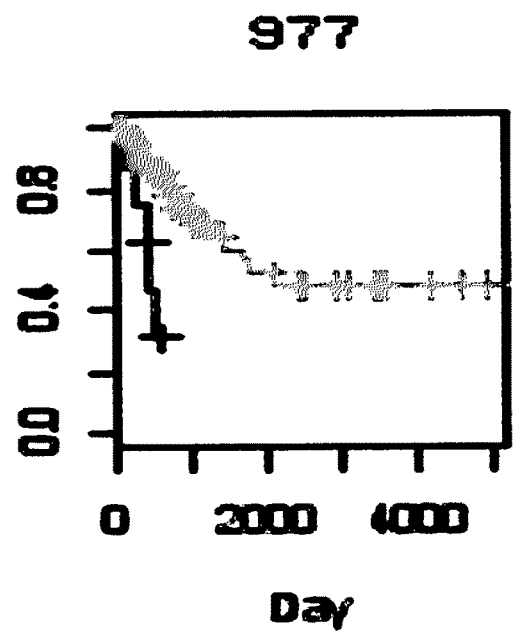
FIG. 40 is a Kaplan-Meier plot showing the time to recurrence (TTR) in days for a 97 patient cohort with NSCLC stage Ia-IIb, classified by presence or absence of a copy number loss (deletion) of Chr 9, 28.1 Mb. [deletion marker 11]

FIG. 40 is a Kaplan-Meier plot showing the time to recurrence (TTR) in days for a 97 patient cohort with NSCLC stage Ia-IIb, classified by presence or absence of a copy number loss (deletion) of Chr 9, 28.1 Mb. [deletion marker 11]. FDR p-value=0.0270. Deleted in 9 samples.

Figure 41:
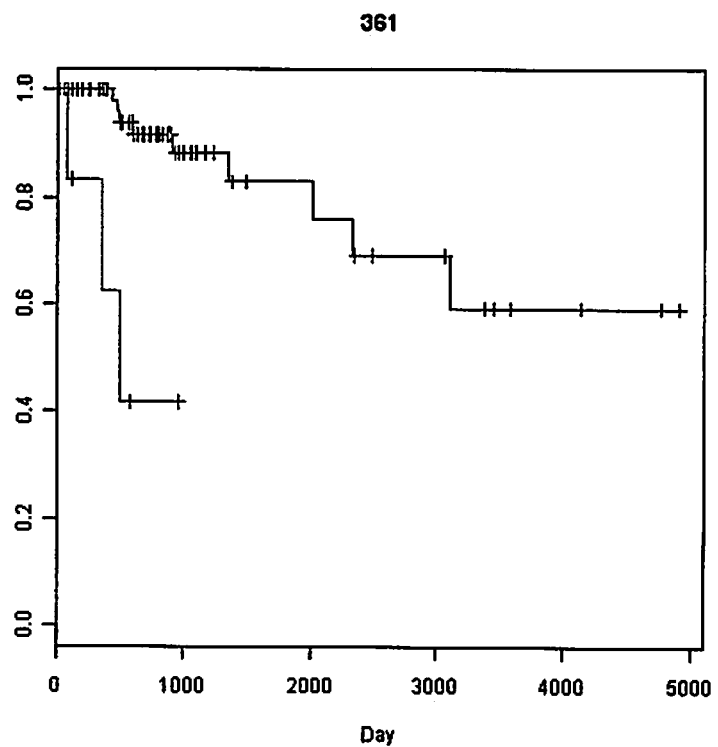
FIG. 41 is a Kaplan-Meier plot showing the overall survival (OS) in days for a 78 patient cohort with NSCLC stage Ia-IIa, classified by presence or absence of a copy number loss (deletion) of Chr 4, 43.7-44.2 Mb. [deletion marker 12]

FIG. 41 is a Kaplan-Meier plot showing the overall survival (OS) in days for a 78 patient cohort with NSCLC stage Ia-IIa, classified by presence or absence of a copy number loss (deletion) of Chr 4, 43.7-44.2 Mb. [deletion marker 12]. FDR p-value=0.0053. Deleted in 8 samples.

Figure 42:
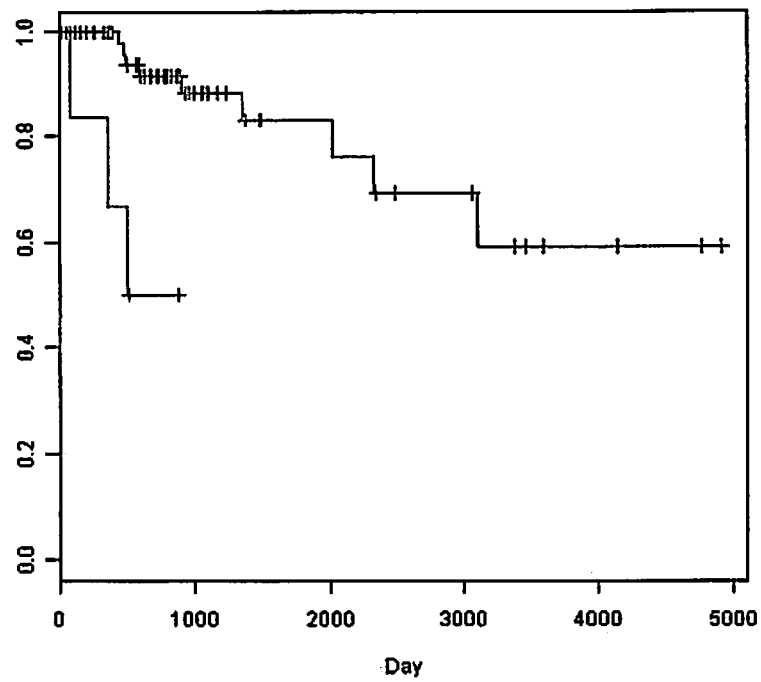
FIG. 42 is a Kaplan-Meier plot showing the overall survival (OS) in days for a 78 patient cohort with NSCLC stage Ia-IIa, classified by presence or absence of a copy number loss (deletion) of Chr 5, 60.8-62.9 Mb. [deletion marker 13]

FIG. 42 is a Kaplan-Meier plot showing the overall survival (OS) in days for a 78 patient cohort with NSCLC stage Ia-IIa, classified by presence or absence of a copy number loss (deletion) of Chr 5, 60.8-62.9 Mb. [deletion marker 13]. FDR p-value=0.0121. Deleted in 7 samples.

Figure 43:
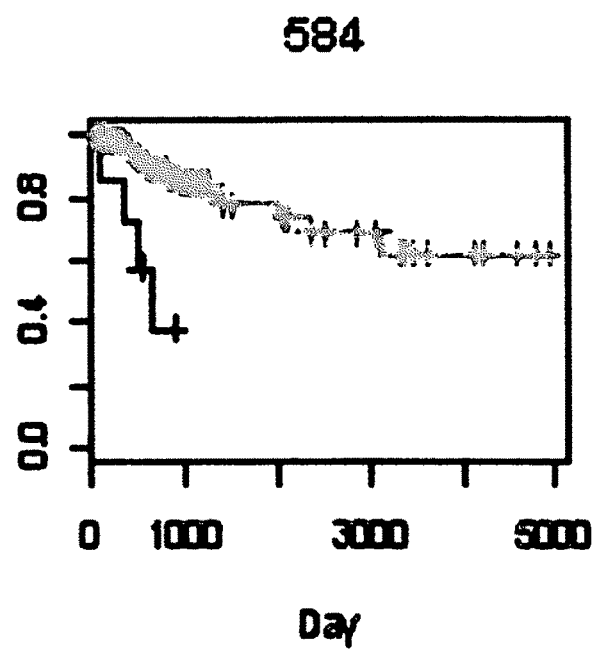
FIG. 43 is a Kaplan-Meier plot showing the overall survival (OS) in days for a 102 patient cohort with NSCLC stage Ia-IIb, classified by presence or absence of a copy number loss (deletion) of Chr 5, 60.8-62.9 Mb. [deletion marker 13]

FIG. 43 is a Kaplan-Meier plot showing the overall survival (OS) in days for a 102 patient cohort with NSCLC stage Ia-IIb, classified by presence or absence of a copy number loss (deletion) of Chr 5, 60.8-62.9 Mb. [deletion marker 13]. FDR p-value=0.0425. Deleted in 8 samples.

Figure 44:
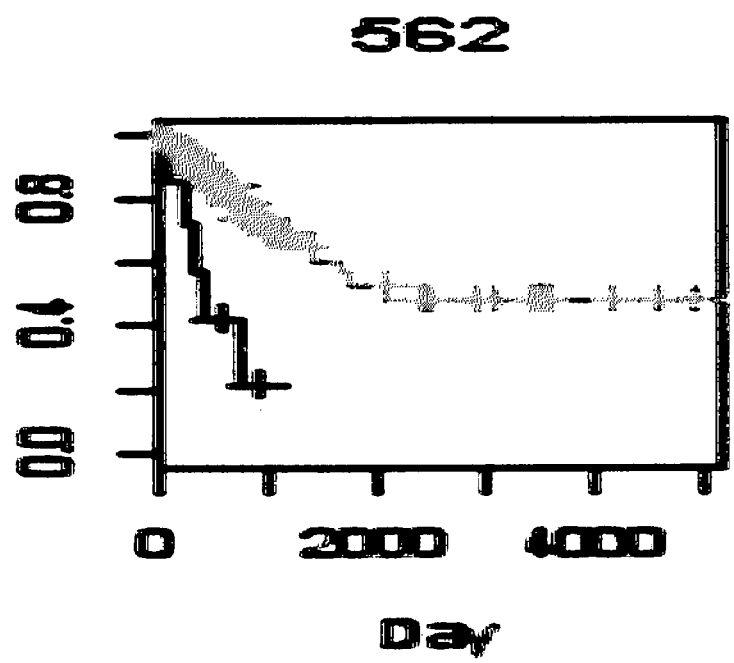
FIG. 44 is a Kaplan-Meier plot showing the time to recurrence (TTR) in days for a 97 patient cohort with NSCLC stage Ia-IIb, classified by presence or absence of a copy number loss (deletion) of Chr 5, 60.8-62.9 Mb. [deletion marker 13]

FIG. 44 is a Kaplan-Meier plot showing the time to recurrence (TTR) in days for a 97 patient cohort with NSCLC stage Ia-IIb, classified by presence or absence of a copy number loss (deletion) of Chr 5, 60.8-62.9 Mb. [deletion marker 13]. FDR p-value=0.0320. Deleted in 8 samples.

Figure 45:
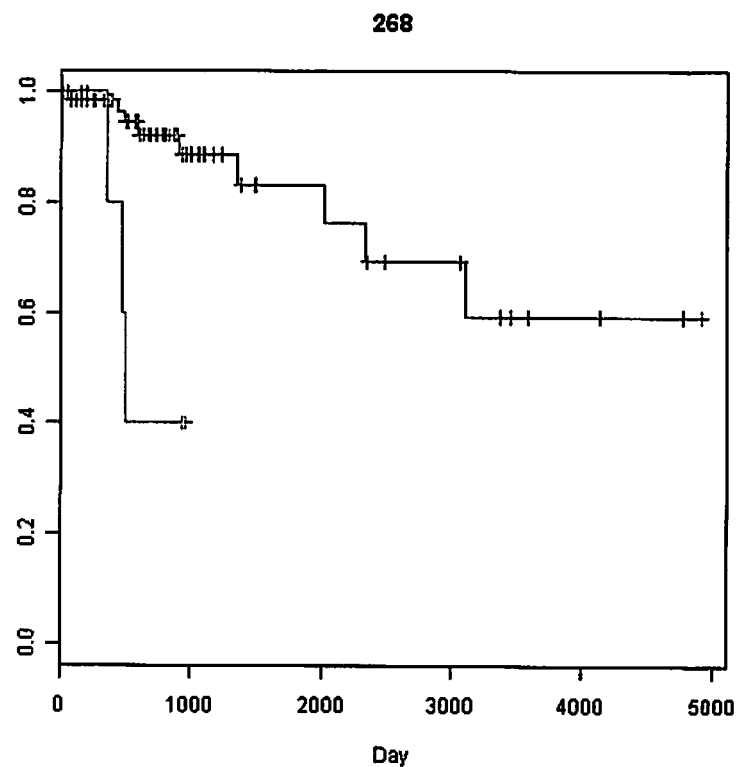
FIG. 45 is a Kaplan-Meier plot showing the overall survival (OS) in days for a 78 patient cohort with NSCLC stage Ia-IIa, classified by presence or absence of a copy number loss (deletion) of Chr 3, 120.0-121.1 Mb. [deletion marker 14]

FIG. 45 is a Kaplan-Meier plot showing the overall survival (OS) in days for a 78 patient cohort with NSCLC stage Ia-IIa, classified by presence or absence of a copy number loss (deletion) of Chr 3, 120.0-121.1 Mb. [deletion marker 14]. FDR p-value=0.0228. Deleted in 8 samples.

Figure 46:
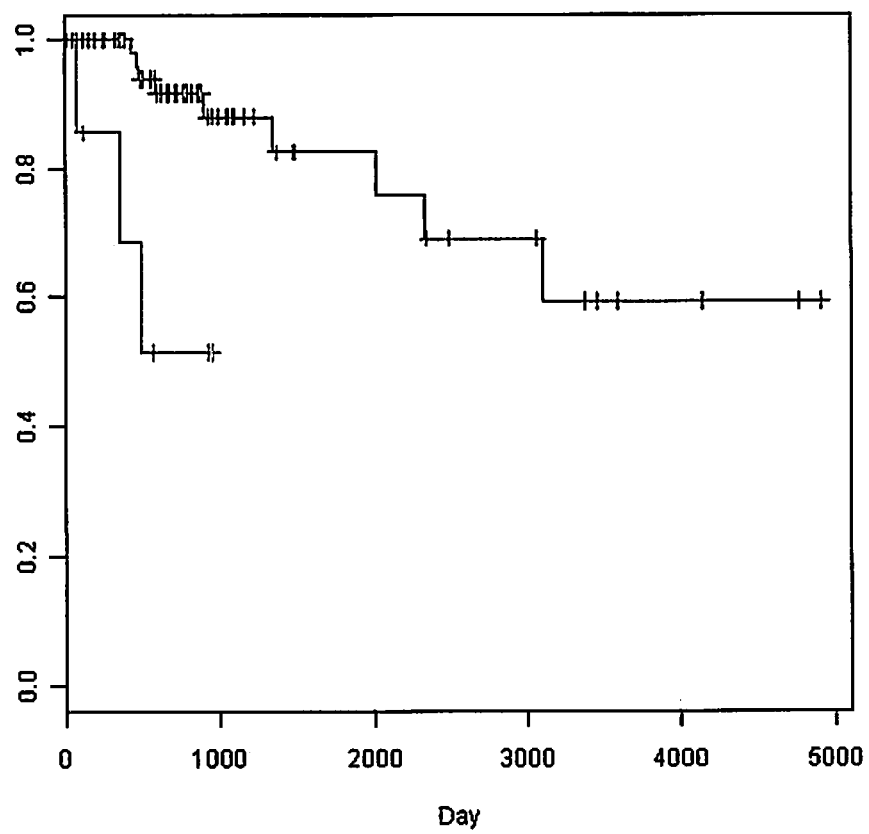
FIG. 46 is a Kaplan-Meier plot showing the overall survival (OS) in days for a 78 patient cohort with NSCLC stage Ia-IIa, classified by presence or absence of a copy number loss (deletion) of Chr 4, 46.2-48.0 Mb. [deletion marker 15]

FIG. 46 is a Kaplan-Meier plot showing the overall survival (OS) in days for a 78 patient cohort with NSCLC stage Ia-IIa, classified by presence or absence of a copy number loss (deletion) of Chr 4, 46.2-48.0 Mb. [deletion marker 15]. FDR p-value=0.0341. Deleted in 8 samples.

Figure 47:
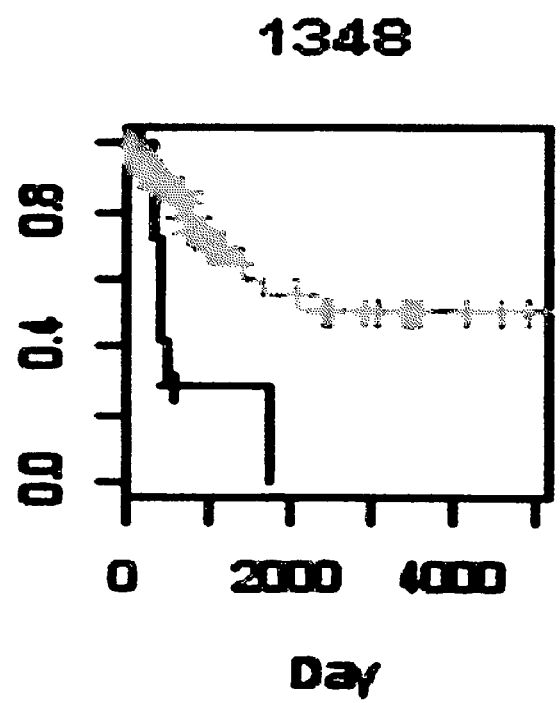
FIG. 47 is a Kaplan-Meier plot showing the time to recurrence (TTR) in days for a 97 patient cohort with NSCLC stage Ia-IIb, classified by presence or absence of a copy number loss (deletion) of Chr 14, 38.9-40.0 Mb. [deletion marker 16]

FIG. 47 is a Kaplan-Meier plot showing the time to recurrence (TTR) in days for a 97 patient cohort with NSCLC stage Ia-IIb, classified by presence or absence of a copy number loss (deletion) of Chr 14, 38.9-40.0 Mb. [deletion marker 16]. FDR p-value=0.0451. Deleted in 8 samples.

Figure 48:
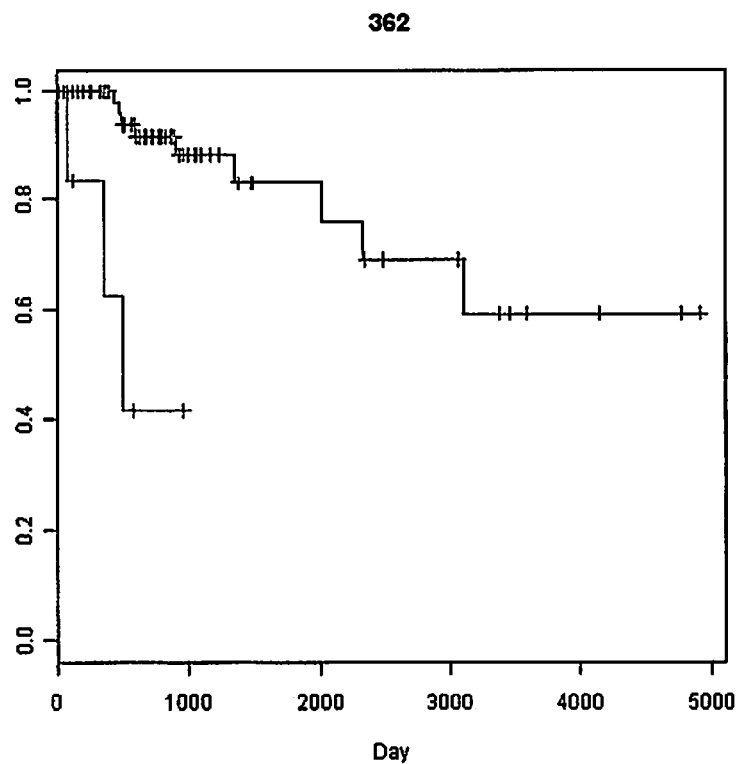
FIG. 48 is a Kaplan-Meier plot showing the overall survival (OS) in days for a 78 patient cohort with NSCLC stage Ia-IIa, classified by presence or absence of a copy number loss (deletion) of Chr 4, 44.2-44.6 Mb. [deletion marker 17]

FIG. 48 is a Kaplan-Meier plot showing the overall survival (OS) in days for a 78 patient cohort with NSCLC stage Ia-IIa, classified by presence or absence of a copy number loss (deletion) of Chr 4, 44.2-44.6 Mb. [deletion marker 17]. FDR p-value=0.0053. Deleted in 7 samples.

Figure 49:
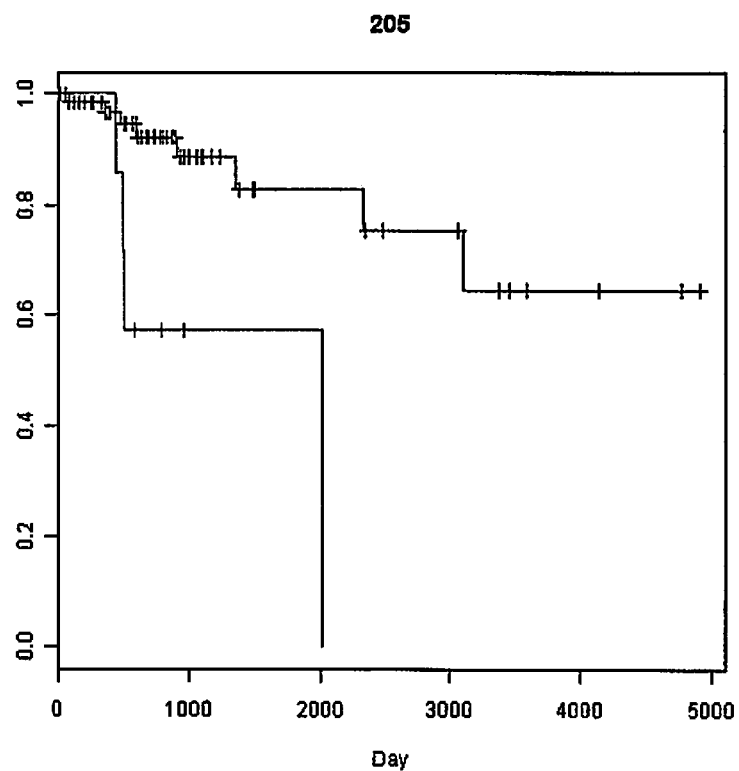
FIG. 49 is a Kaplan-Meier plot showing the overall survival (OS) in days for a 78 patient cohort with NSCLC stage Ia-IIa, classified by presence or absence of a copy number loss (deletion) of Chr 2, 213.7-214.3 Mb. [deletion marker 18]

FIG. 49 is a Kaplan-Meier plot showing the overall survival (OS) in days for a 78 patient cohort with NSCLC stage Ia-IIa, classified by presence or absence of a copy number loss (deletion) of Chr 2, 213.7-214.3 Mb. [deletion marker 18]. FDR p-value=0.0286. Deleted in 7 samples.

Figure 50:
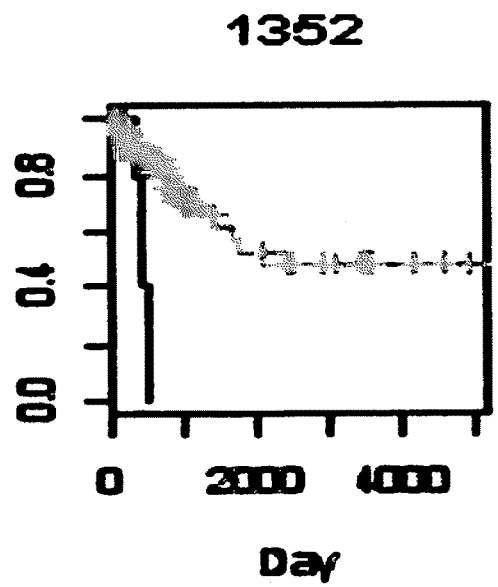
FIG. 50 is a Kaplan-Meier plot showing the time to recurrence (TTR) in days for a 97 patient cohort with NSCLC stage Ia-IIb, classified by presence or absence of a copy number loss (deletion) of Chr14, 43.9-46.6 Mb. [deletion marker 19]

FIG. 50 is a Kaplan-Meier plot showing the time to recurrence (TTR) in days for a 97 patient cohort with NSCLC stage Ia-IIb, classified by presence or absence of a copy number loss (deletion) of Chr14, 43.9-46.6 Mb. [deletion marker 19]. FDR p-value=0.0009. Deleted in 6 samples.

Figure 51:
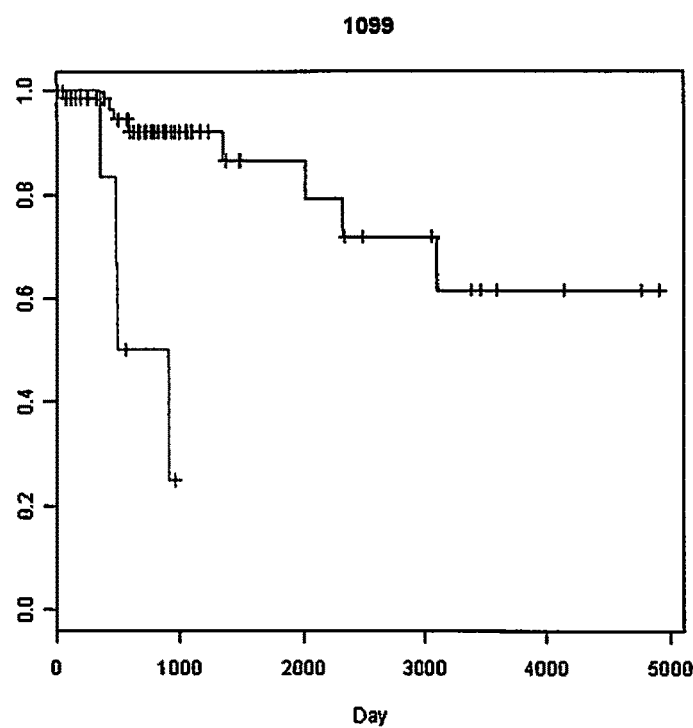
FIG. 51 is a Kaplan-Meier plot showing the overall survival (OS) in days for a 78 patient cohort with NSCLC stage Ia-IIa, classified by presence or absence of a copy number loss (deletion) of Chr 14, 27.6-28.6 Mb. [deletion marker 20]

FIG. 51 is a Kaplan-Meier plot showing the overall survival (OS) in days for a 78 patient cohort with NSCLC stage Ia-IIa, classified by presence or absence of a copy number loss (deletion) of Chr 14, 27.6-28.6 Mb. [deletion marker 20]. FDR p-value=0.0021. Deleted in 6 samples.

Figure 52:
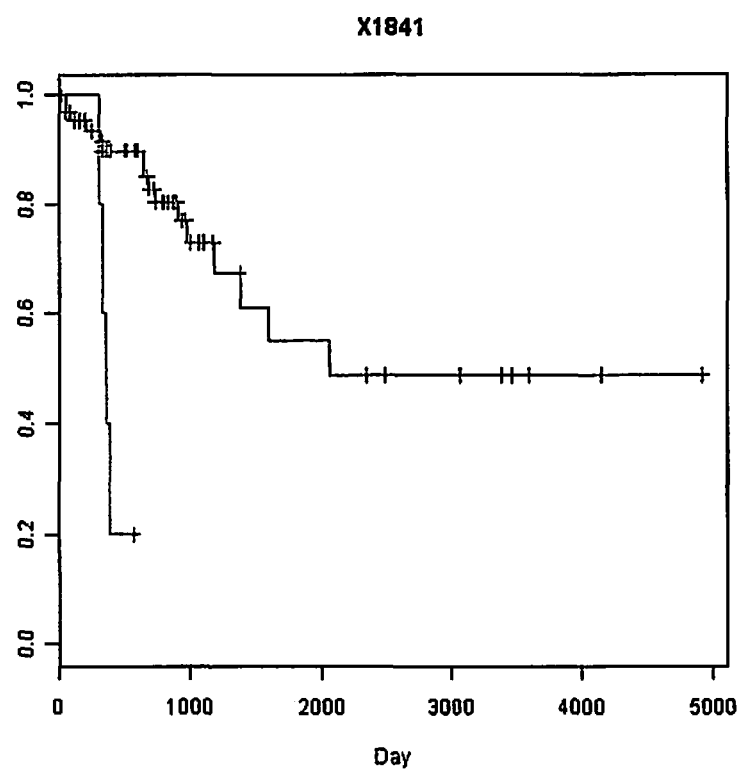
FIG. 52 is a Kaplan-Meier plot showing the time to recurrence (TTR) in days for a 74 patient cohort with NSCLC stage Ia-IIa, classified by presence or absence of a copy number loss (deletion) of Chr 14, 27.6-28.6 Mb. [deletion marker 20]

FIG. 52 is a Kaplan-Meier plot showing the time to recurrence (TTR) in days for a 74 patient cohort with NSCLC stage Ia-IIa, classified by presence or absence of a copy number loss (deletion) of Chr 14, 27.6-28.6 Mb. [deletion marker 20]. FDR p-value=0.0101. Deleted in 5 samples.

Figure 53:
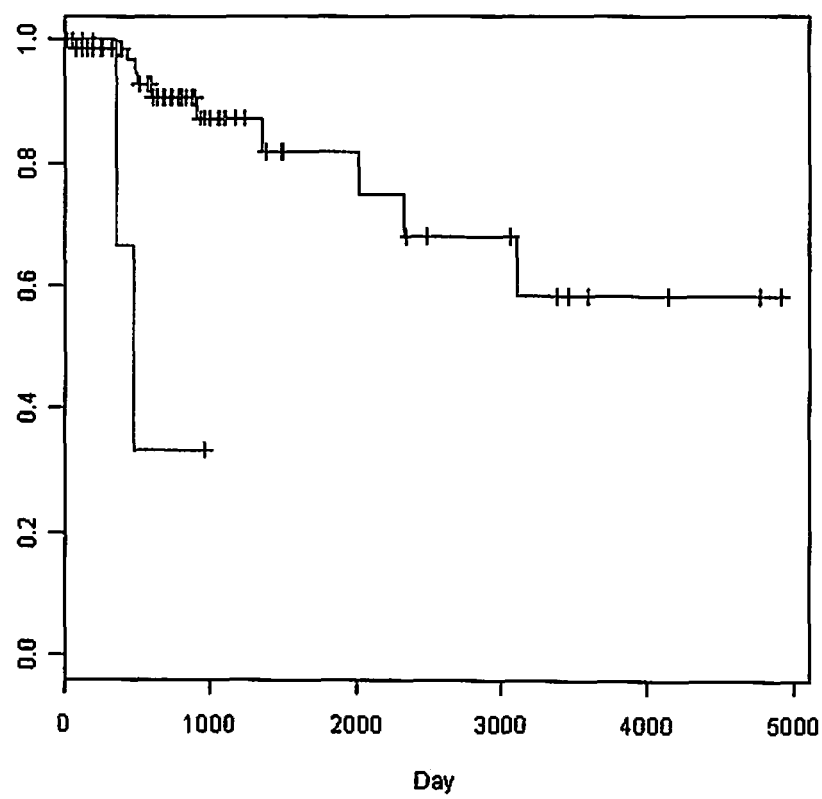
FIG. 53 is a Kaplan-Meier plot showing the overall survival (OS) in days for a 78 patient cohort with NSCLC stage Ia-IIa, classified by presence or absence of a copy number loss (deletion) of Chr 3, 98.0-98.3 Mb. [deletion marker 21]

FIG. 53 is a Kaplan-Meier plot showing the overall survival (OS) in days for a 78 patient cohort with NSCLC stage Ia-IIa, classified by presence or absence of a copy number loss (deletion) of Chr 3, 98.0-98.3 Mb. [deletion marker 21]. FDR p-value=0.0316. Deleted in 6 samples.

Figure 54:
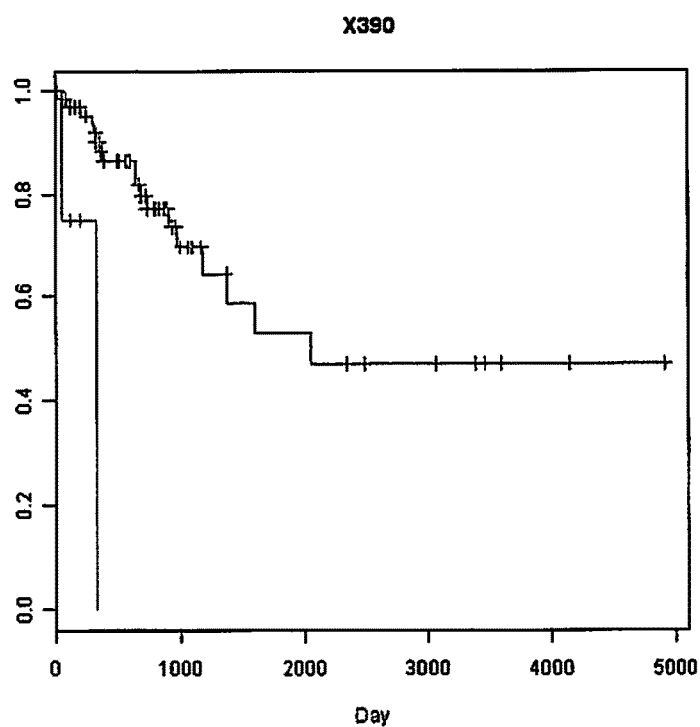
FIG. 54 is a Kaplan-Meier plot showing the time to recurrence (TTR) in days for a 74 patient cohort with NSCLC stage Ia-IIa, classified by presence or absence of a copy number loss (deletion) of Chr 3, 98.0-98.3 Mb. [deletion marker 21]

FIG. 54 is a Kaplan-Meier plot showing the time to recurrence (TTR) in days for a 74 patient cohort with NSCLC stage Ia-IIa, classified by presence or absence of a copy number loss (deletion) of Chr 3, 98.0-98.3 Mb. [deletion marker 21]. FDR p-value=0.0416. Deleted in 5 samples.

Figure 55:
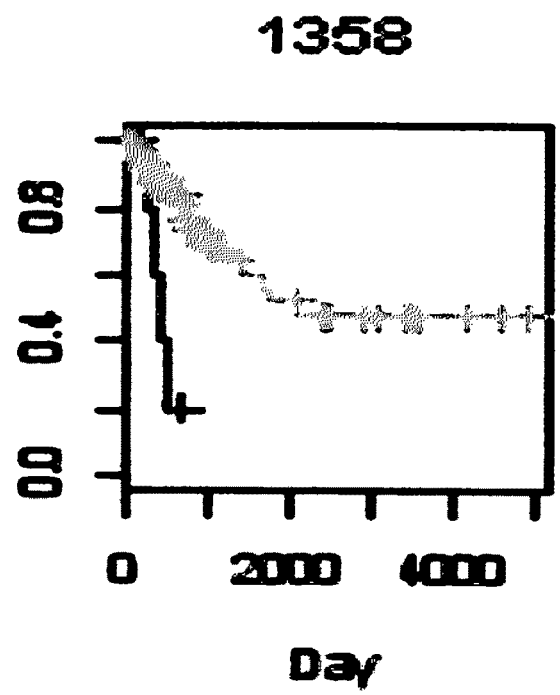
FIG. 55 is a Kaplan-Meier plot showing the time to recurrence (TTR) in days for a 97 patient cohort with NSCLC stage Ia-IIb, classified by presence or absence of a copy number loss (deletion) of Chr14, 55.2-60.0 Mb. [deletion marker 22]

FIG. 55 is a Kaplan-Meier plot showing the time to recurrence (TTR) in days for a 97 patient cohort with NSCLC stage Ia-IIb, classified by presence or absence of a copy number loss (deletion) of Chr14, 55.2-60.0 Mb. [deletion marker 22]. FDR p-value=0.0345. Deleted in 6 samples.

Figure 56:
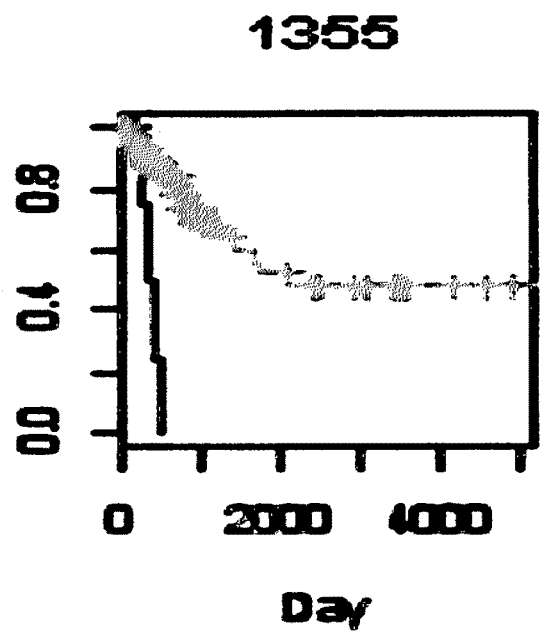
FIG. 56 is a Kaplan-Meier plot showing the time to recurrence (TTR) in days for a 97 patient cohort with NSCLC stage Ia-IIb, classified by presence or absence of a copy number loss (deletion) of Chr14, 48.7-51.1 Mb. [deletion marker 23]

FIG. 56 is a Kaplan-Meier plot showing the time to recurrence (TTR) in days for a 97 patient cohort with NSCLC stage Ia-IIb, classified by presence or absence of a copy number loss (deletion) of Chr14, 48.7-51.1 Mb. [deletion marker 23]. FDR p-value=0.0006. Deleted in 5 samples.

Figure 57:
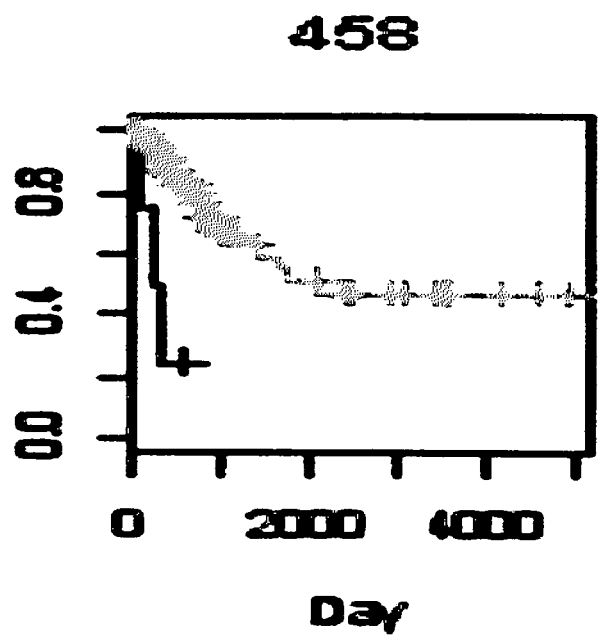
FIG. 57 is a Kaplan-Meier plot showing the time to recurrence (TTR) in days for a 97 patient cohort with NSCLC stage Ia-IIb, classified by presence or absence of a copy number loss (deletion) of Chr 4, 81.4-83.2 Mb. [deletion marker 24]

FIG. 57 is a Kaplan-Meier plot showing the time to recurrence (TTR) in days for a 97 patient cohort with NSCLC stage Ia-IIb, classified by presence or absence of a copy number loss (deletion) of Chr 4, 81.4-83.2 Mb. [deletion marker 24]. FDR p-value=0.0047. Deleted in 5 samples.

Figure 58:
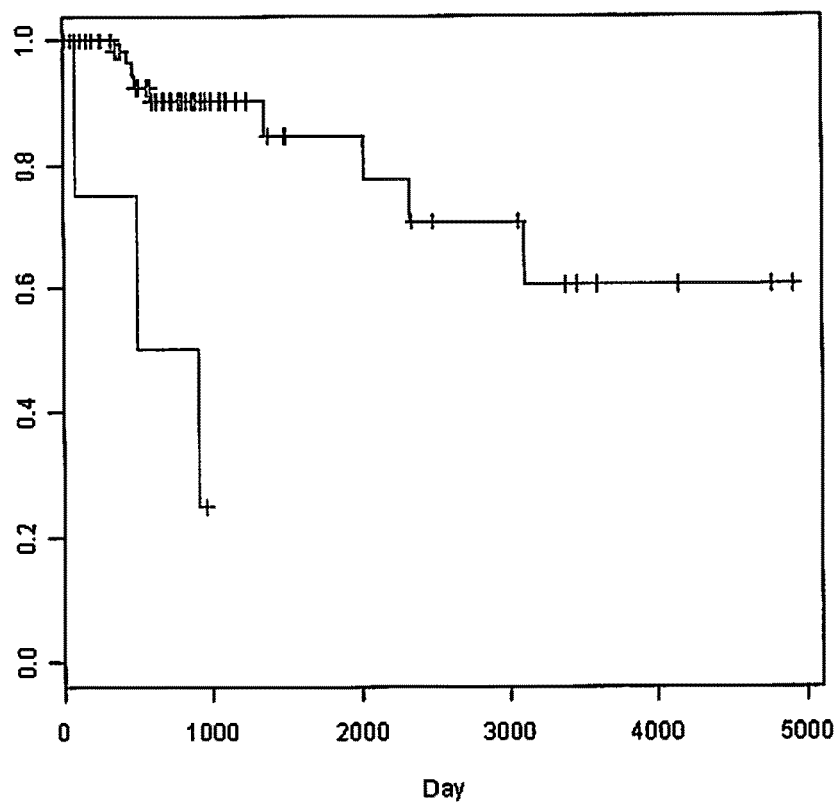
FIG. 58 is a Kaplan-Meier plot showing the overall survival (OS) in days for a 78 patient cohort with NSCLC stage Ia-IIa, classified by presence or absence of a copy number loss (deletion) of Chr 10, 51.9-54.2 Mb. [deletion marker 25]

FIG. 58 is a Kaplan-Meier plot showing the overall survival (OS) in days for a 78 patient cohort with NSCLC stage Ia-IIa, classified by presence or absence of a copy number loss (deletion) of Chr 10, 51.9-54.2 Mb. [deletion marker 25]. FDR p-value=0.0067. Deleted in 5 samples.

Figure 59:
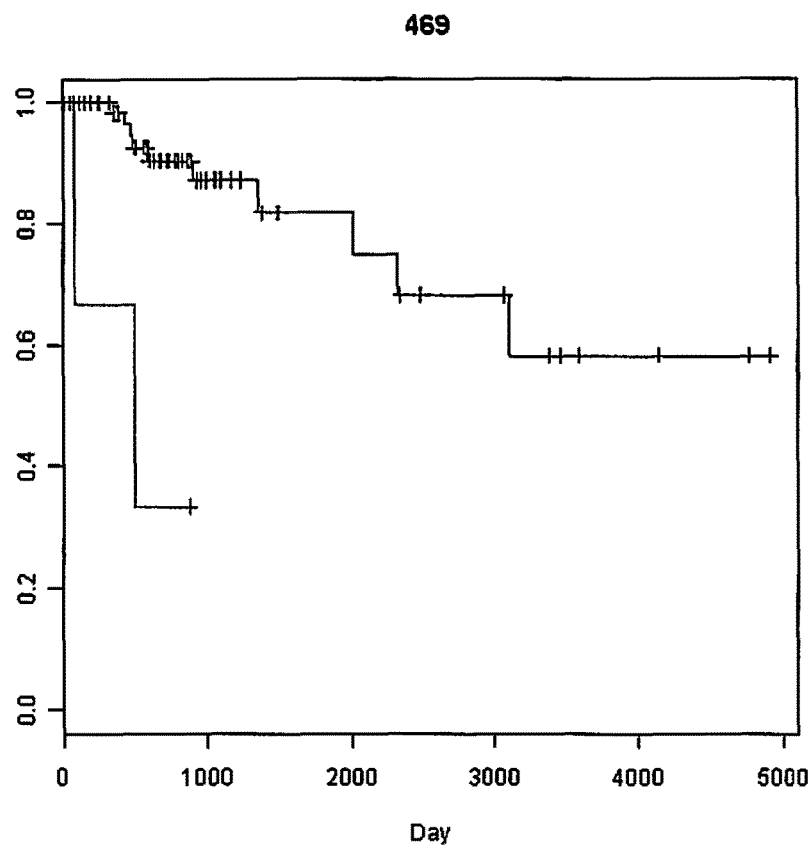
FIG. 59 is a Kaplan-Meier plot showing the overall survival (OS) in days for a 78 patient cohort with NSCLC stage Ia-IIa, classified by presence or absence of a copy number loss (deletion) of Chr 5, 55.2-58.6 Mb. [deletion marker 26]

FIG. 59 is a Kaplan-Meier plot showing the overall survival (OS) in days for a 78 patient cohort with NSCLC stage Ia-IIa, classified by presence or absence of a copy number loss (deletion) of Chr 5, 55.2-58.6 Mb. [deletion marker 26]. FDR p-value=0.0130 Deleted in 5 samples.

Figure 60:
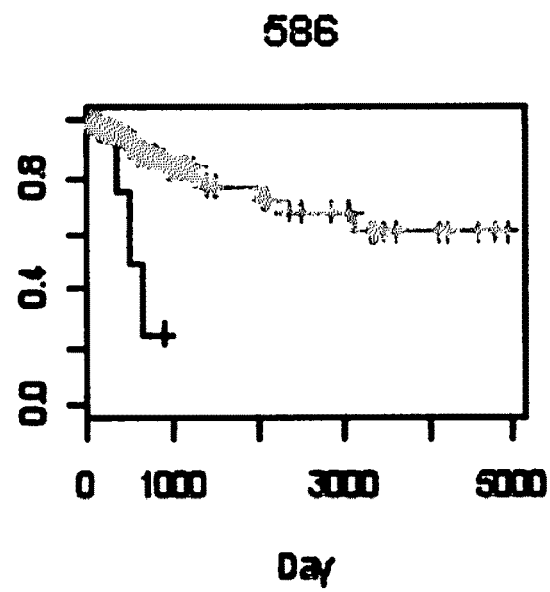
FIG. 60 is a Kaplan-Meier plot showing the overall survival (OS) in days for a 102 patient cohort with NSCLC stage Ia-IIb, classified by presence or absence of a copy number loss (deletion) of Chr 5, 67.8-68.5 Mb. [deletion marker 27].

FIG. 60 is a Kaplan-Meier plot showing the overall survival (OS) in days for a 102 patient cohort with NSCLC stage Ia-IIb, classified by presence or absence of a copy number loss (deletion) of Chr 5, 67.8-68.5 Mb. [deletion marker 27]. FDR p-value=0.0475 Deleted in 5 samples.

As can be seen from the Kaplan-Meier plots in FIGS. 1-60, copy number alterations in the specified markers are associated with short OS and/or shorter TTR in NSCLC stage I-II patients. Table 4 lists overall survival data for several markers. (Markers for which data is shown in red are shared between different clinical stages).

TABLE 4

Overall Survival for markers on Chr1, Chr2, Chr6, Chr8, Chr11, Chr12, Chr17, and Chr19

| Stages | chrom | start.pos | length.seg | FDR | n.amp | mean.amp | n.SNP |
|---|---|---|---|---|---|---|---|
| 1a-2a | 2 | 147604021 | 3513659 | 0.0233 | 7 | 2.8516132 | 166 |
| | 2 | 159911944 | 1511940 | 0.0001 | 5 | 3.2498274 | 67 |
| | 2 | 200924525 | 3320890 | 0.0398 | 6 | 3.006085 | 79 |
| | 2 | 205893481 | 2160144 | 0.0075 | 5 | 2.9990652 | 101 |
| | 3 | 88399682 | 386599 | 0.0140 | 5 | 3.5534647 | 12 |
| | 6 | 36255222 | 423122 | 0.0347 | 6 | 2.9201916 | 8 |
| | 6 | 39088059 | 762306 | 0.0356 | 15 | 3.1071308 | 30 |
| | 6 | 123724457 | 11850520 | 0.0377 | 7 | 2.9452862 | 667 |
| | 8 | 4115551 | 55428 | 0.0126 | 7 | 2.8073117 | 19 |
| | 8 | 6895465 | 1889190 | 0.0166 | 7 | 3.0262839 | 36 |
| | 11 | 61374252 | 2935902 | 0.0004 | 9 | 3.2120357 | 46 |
| | 11 | 64310154 | 493823 | 0.0040 | 12 | 3.5343537 | 6 |
| | 11 | 64803977 | 880941 | 0.0004 | 7 | 3.6506583 | 9 |
| | 12 | 93683 | 1774306 | 0.0493 | 11 | 3.604318 | 50 |
| | 17 | 43477124 | 1455714 | 0.0219 | 7 | 3.1622542 | 24 |
| | 17 | 51532820 | 1678229 | 0.0054 | 10 | 3.1730034 | 54 |
| | 17 | 69173224 | 2131396 | 0.0304 | 23 | 3.1612824 | 32 |
| | 19 | 32693527 | 387442 | 0.0183 | 18 | 4.0913848 | 8 |
| | 19 | 33195577 | 113123 | 0.0459 | 22 | 3.841479 | 6 |

TABLE 4-continued

Overall Survival for markers on Chr1, Chr2, Chr6, Chr8, Chr11, Chr12, Chr17, and Chr19

| Stages | chrom | start.pos | length.seg | FDR | n.amp | mean.amp | n.SNP |
|---|---|---|---|---|---|---|---|
|  | 19 | 34722418 | 921516 | 0.0299 | 27 | 4.1530261 | 20 |
|  | 19 | 38853838 | 1895624 | 0.0085 | 24 | 3.895232 | 34 |
|  | 19 | 57033283 | 5156456 | 0.0091 | 14 | 3.1469281 | 83 |
| 1b-2b | 1 | 109538586 | 1580066 | 0.0224 | 5 | 2.9805551 | 58 |
|  | 6 | 70761833 | 382704 | 0.0116 | 17 | 3.2107404 | 28 |
| 1a-2b | 6 | 70761833 | 382704 | 0.0110 | 24 | 3.0754468 | 28 |

Table 5 lists the genes and miRNA's that are encoded by nucleotide sequences within each cancer outcome marker sequence. In any of the methods, the cancer outcome marker can be selected from among those listed in Table 5. Those markers designated "M1" through "M20" are each a region of chromosomal DNA, the amplification of which produces a copy number gain in the cancer outcome marker, wherein the copy number gain is associated with a poor disease outcome. Those markers designated "DM1" through "DM27" are each a region of chromosomal DNA, the deletion of which produces a copy number loss in the cancer outcome marker, wherein the copy number loss is associated with a poor disease outcome.

TABLE 5

Cancer outcome markers and corresponding genes and miRNA's

| ID No. | Cancer outcome marker | Genes and miRNA's |
|---|---|---|
| M1 | Chr 19, 34.7 Mb-35.6 Mb; | C19orf12; C19orf12; cyclin E1; PLEKHF1; POP4; and ZNF536 |
| M2 | Chr 19, 38.9-40.7 Mb; | ATP4A ATPase; CHST8, DMKN FAR1, 2, 3; FXYD1, 3, 5, 7; GAPDHS; GPI; GPR42; GRAMD1A; HAMP; HPN; KCTD15 KIAA0355; KRTDAP; LGI4; LSM14A; LSR; MAG; PDCD2L; SAE2 SUMO1; SBSN; SCN1B; TMEM147, 162; USF2; WTIP; and ZNF181, 30, 302, 599, 792 |
| M3 | Chr 17, 69.2-71.3 Mb; | ARMC7 (armadillo repeat containing 7); ATP5H ATP synthase (H+ transporting, mitochondrial F0 complex, subunit d); CASKIN2 (CASK interacting protein 2); CD300A (CD300a molecule); CD300C (CD300c molecule); CD300E (CD300e molecule); CD300LB (CD300 molecule-like family member b); CD300LF (CD300 molecule-like family member f); CDR2L (cerebellar degeneration-related protein 2-like); DNAI2 (dynein, axonemal, intermediate chain 2); (FADS6 fatty acid desaturase domain family, member 6); FDXR (ferredoxin reductase); GALK1 (galactokinase 1); GGA3 (golgi associated, gamma adaptin ear containing, ARF binding protein): GPR142 (G protein-coupled receptor 142); GPRC5C (G protein-coupled receptor, family C, group 5, member C); GRB2 (growth factor receptor-bound protein 2); GRIN2C (glutamate receptor, ionotropic, N-methyl D-aspartate 2C); H3F3B (H3 histone, family 3B (H3.3B)); HN1 (hematological and neurological expressed 1 ICT1 immature colon carcinoma transcript 1); ITGB4 (integrin, beta 4); KCTD2 (potassium channel tetramerisation domain containing 2); KIAA0195; KIF19 (kinesin family member 19); LLGL2 (lethal giant larvae homolog 2 (*Drosophila*)); LOC388419 (galectin-3-binding protein-like); MIF4GD (MIF4G domain containing); MRPS7 (mitochondrial ribosomal protein S7); NAT9 (N-acetyltransferase 9); NT5C (5',3'-nucleotidase, cytosolic); NUP85 (nucleoporin 85 kDa); OTOP2 (otopetrin 2); OTOP3 (otopetrin 3); RAB37 (RAB37, member RAS oncogene family); RECQL5 (RecQ protein-like 5); RPL38 ribosomal protein L38; SAP30BP (SAP30 binding protein); SLC16A5 (solute carrier family 16, member 5 (monocarboxylic acid transporter 6)); SLC25A19 (solute carrier family 25 (mitochondrial thiamine pyrophosphate carrier), member 19); SLC9A3R1 (solute carrier family 9 (sodium/hydrogen exchanger), member 3 regulator 1); SUMO2 (SMT3 suppressor of mif two 3 homolog 2 (*S. cerevisiae*)); TMEM104 (transmembrane protein 104); TTYH2 (tweety homolog 2 (*Drosophila*)); UNK (unkempt homolog (*Drosophila*)); and USH1G (Usher syndrome 1G (autosomal recessive) |

TABLE 5-continued

Cancer outcome markers and corresponding genes and miRNA's

| ID No. | Cancer outcome marker | Genes and miRNA's |
|---|---|---|
| M4 | Chr 6, 70.8-71.1 Mb; | COL19A1 (collagen, type XIX, alpha 1), and COL9A1 (collagen, type IX, alpha 1) |
| M5 | Chr 12, 93.7 kb-1.9 Mb; | ADIPOR2 (adiponectin receptor 2); B4GALNT3 (beta-1,4-N-acetyl-galactosaminyl transferase 3); CACNA2D4 (calcium channel, voltage-dependent, alpha 2/delta subunit 4); CCDC77 (coiled-coil domain containing 77); ERC1 (ELKS/RAB6-interacting/CAST family member 1); FBXL14 (F-box and leucine-rich repeat protein 14); HSN2 (hereditary sensory neuropathy, type II); IQSEC3 (IQ motif and Sec7 domain 3); JARID1A (jumonji, AT rich interactive domain 1A); LRTM2 (leucine-rich repeats and transmembrane domains 2); NINJ2 (ninjurin 2); RAD52 (RAD52 homolog (*S. cerevisiae*)); SLC6A12 (solute carrier family 6 (neurotransmitter transporter, betaine/GABA), member 12); SLC6A13 (solute carrier family 6 (neurotransmitter transporter, GABA), member 13); WNK1 (WNK lysine deficient protein kinase 1); and WNT5B (wingless-type MMTV integration site family, member 5B) |
| M6 | Chr 11, 64.3-64.8 Mb; | ARL2 (ADP-ribosylation factor-like 2); ATG2A ATG2 (autophagy related 2 homolog A (*S. cerevisiae*)); BATF2 (basic leucine zipper transcription factor, ATF-like 2; CAPN1 calpain 1, (mu/I) large subunit); CDC42BPG (CDC42 binding protein kinase gamma (DMPK-like)); CDCA5 (cell division cycle associated 5); EHD1 (EH-domain containing 1); FAU (Finkel-Biskis-Reilly murine sarcoma virus (FBR-MuSV) ubiquitously expressed); GPHA2 (glycoprotein hormone alpha 2); MAP4K2 mitogen-activated protein kinase kinase kinase kinase 2<br>MEN1 multiple endocrine neoplasia I<br>MRPL49 mitochondrial ribosomal protein L49<br>NAALADL1 N-acetylated alpha-linked acidic dipeptidase-like 1<br>POLA2 polymerase (DNA directed), alpha 2 (70 kD subunit)<br>PPP2R5B protein phosphatase 2, regulatory subunit B', beta isoform<br>SAC3D1 SAC3 domain containing 1<br>SLC22A20 solute carrier family 22, member 20<br>SNX15 sorting nexin 15<br>SPDYC speedy homolog C (*Drosophila*)<br>SYVN1 synovial apoptosis inhibitor 1, synoviolin<br>TM7SF2 transmembrane 7 superfamily member 2<br>ZFPL1 zinc finger protein-like 1<br>ZNHIT2 zinc finger, HIT type 2;<br>hsa-mir-192; and<br>hsa-mir-194-2 |
| M7 | Chr 19, 57.0-62.2 Mb; | BIRC8 (baculoviral IAP repeat-containing 8);<br>BRSK1 (BR serine/threonine kinase 1);<br>CACNG6, 7, 8 calcium channel, voltage-dependent, gamma subunit 6, 7, 8<br>CCDC106 coiled-coil domain containing 106<br>CDC42EP5 CDC42 effector protein (Rho GTPase binding) 5<br>CNOT3 CCR4-NOT transcription complex, subunit 3<br>COX6B2 cytochrome c oxidase subunit VIb polypeptide 2 (testis)<br>DPRX divergent-paired related homeobox<br>EPN1 epsin 1<br>EPS8L1 EPS8-like 1<br>FCAR Fc fragment of IgA, receptor for<br>FIZ1 FLT3-interacting zinc finger 1<br>GALP galanin-like peptide<br>GP6 glycoprotein VI (platelet)<br>HSPBP1 hsp70-interacting protein<br>IL11 interleukin 11<br>ISOC2 isochorismatase domain containing 2<br>KIR2DL1, KIR2DL4, KIR2DS4 KIR3DL1, KIR3DL3, KIR3DX1 killer cell immunoglobulin-like receptor<br>LAIR1, 2 leukocyte-associated immunoglobulin-like receptor 1, 2<br>LENG1, 4, 8, 9 leukocyte receptor cluster (LRC) member 1, 4, 8, 9<br>LILRA2, 3, 4 leukocyte immunoglobulin-like receptor, subfamily A (with TM domain), member 2, 3, 4<br>LILRB1, 2, 3, 4, 5 leukocyte immunoglobulin-like receptor, subfamily B (with TM and ITIM domains), member 1, 2, 3, 4, 5<br>MYADM myeloid-associated differentiation marker<br>NAT14 N-acetyltransferase 14<br>NCR1 natural cytotoxicity triggering receptor 1<br>NDUFA3 NADH dehydrogenase (ubiquinone) 1 alpha subcomplex, 3, 9 kDa |

TABLE 5-continued

Cancer outcome markers and corresponding genes and miRNA's

| ID No. | Cancer outcome marker | Genes and miRNA's |
|---|---|---|
| | | NLRP2, 4, 5, 7, 8, 9, 11, 12, 13 NLR family, pyrin domain containing 2, 4, 5, 7, 8, 9, 11, 12, 13. |
| | | OSCAR osteoclast associated, immunoglobulin-like receptor |
| | | PEG3 paternally expressed 3 |
| | | PPP1R12C protein phosphatase 1, regulatory (inhibitor) subunit 12C |
| | | PPP2R1A protein phosphatase 2 (formerly 2A), regulatory subunit A, alpha isoform |
| | | PRKCG protein kinase C, gamma |
| | | PRPF31 PRP31 pre-mRNA processing factor 31 homolog (*S. cerevisiae*) |
| | | PTPRH protein tyrosine phosphatase, receptor type, H |
| | | RDH13 retinol dehydrogenase 13 (all-trans/9-cis) |
| | | RPL28 ribosomal protein L28 |
| | | RPS9 ribosomal protein S9 |
| | | SAPS1 SAPS domain family, member 1 |
| | | SUV420H2 suppressor of variegation 4-20 homolog 2 (*Drosophila*) |
| | | SYT5 synaptotagmin V |
| | | TFPT TCF3 (E2A) fusion partner (in childhood Leukemia) |
| | | TMC4 transmembrane channel-like 4 |
| | | TMEM190 transmembrane protein 190 |
| | | TMEM86B transmembrane protein 86B |
| | | TNNI3 troponin I type 3 (cardiac) |
| | | TNNT1 troponin T type 1 (skeletal, slow) |
| | | TSEN34 tRNA splicing endonuclease 34 homolog (*S. cerevisiae*) |
| | | TTYH1 tweety homolog 1 (*Drosophila*) |
| | | U2AF2 U2 small nuclear RNA auxiliary factor 2 |
| | | UBE2S ubiquitin-conjugating enzyme E2S |
| | | VN1R2 vomeronasal 1 receptor 2 |
| | | VN1R4 vomeronasal 1 receptor 4 |
| | | VSTM1 V-set and transmembrane domain containing 1 |
| | | ZNF28, 160, 320, 321, 331, 347, 350, 415, 432, 444, 468, 470 zinc finger protein 28, 160, 320, 321, 331, 347, 350, 415, 432, 444, 468, 470; and miRNA's including hsa-mir-643, hsa-mir-512-1, hsa-mir-512-2, hsa-mir-498, hsa-mir-520e, hsa-mir-515-1, hsa-mir-519e, hsa-mir-520f, hsa-mir-515-2, hsa-mir-519c, hsa-mir-520a, hsa-mir-526b, hsa-mir-519b, hsa-mir-525, hsa-mir-523, hsa-mir-518f, hsa-mir-520b, hsa-mir-518b, hsa-mir-526a-1, hsa-mir-520c, hsa-mir-518c, hsa-mir-524, hsa-mir-517a, hsa-mir-519d, hsa-mir-521-2, hsa-mir-520d, hsa-mir-517b, hsa-mir-520g, hsa-mir-516-3, hsa-mir-526a-2, hsa-mir-518e, hsa-mir-518a-1, hsa-mir-518d, hsa-mir-516-4, hsa-mir-518a-2, hsa-mir-517c, hsa-mir-520h, hsa-mir-521-1, hsa-mir-522, hsa-mir-519a-1, hsa-mir-527, hsa-mir-516-1, hsa-mir-516-2, hsa-mir-519a-2, hsa-mir-371, hsa-mir-372, hsa-mir-373, hsa-mir-516a-1, hsa-mir-516a-2, hsa-mir-516b-1, hsa-mir-516b-2, hsa-mir-517a-1, hsa-mir-517a-2, hsa-mir-520c-1, hsa-mir-520c-2 |
| M8 | Chr 6, 39.1-39.9 Mb; | C6orf64 (chromosome 6 open reading frame 64); DNAH8 dynein, axonemal, heavy chain 8 GLP1R glucagon-like peptide 1 receptor KCNK16 potassium channel, subfamily K, member 16 KCNK17 potassium channel, subfamily K, member 17 KCNK5 potassium channel, subfamily K, member 5 KIF6 kinesin family member 6. |
| M9 | Chr 11, 64.8-65.7 Mb; | BANF1 (barrier to autointegration factor 1); CATSPER1 cation channel, sperm associated 1 CCDC85B coiled-coil domain containing 85B CDC42EP2 CDC42 effector protein (Rho GTPase binding) 2 CFL1 cofilin 1 (non-muscle) CST6 cystatin E/M CTSW cathepsin W DPF2 D4, zinc and double PHD fingers family 2 DRAP1 DR1-associated protein 1 (negative cofactor 2 alpha) EFEMP2 EGF-containing fibulin-like extracellular matrix protein 2 EHBP1L1 EH domain binding protein 1-like 1 FAM89B family with sequence similarity 89, member B FIBP fibroblast growth factor (acidic) intracellular binding protein FOSL1 FOS-like antigen 1 FRMD8 FERM domain containing 8 GAL3ST3 galactose-3-O-sulfotransferase 3 |

TABLE 5-continued

Cancer outcome markers and corresponding genes and miRNA's

| ID No. | Cancer outcome marker | Genes and miRNA's |
|---|---|---|
| | | HTATIP HIV-1 Tat interacting protein, 60 kDa. KCNK7 potassium channel, subfamily K, member 7<br>LTBP3 latent transforming growth factor beta binding protein 3<br>MAP3K11 mitogen-activated protein kinase kinase kinase 11<br>MGC11102 hypothetical protein MGC11102<br>MUS81 MUS81 endonuclease homolog (*S. cerevisiae*)<br>OVOL1 ovo-like 1(*Drosophila*)<br>PACS1 phosphofurin acidic cluster sorting protein 1<br>PCNXL3 pecanex-like 3 (*Drosophila*)<br>POLA2 polymerase (DNA directed), alpha 2 (70 kD subunit)<br>RELA v-rel reticuloendotheliosis viral oncogene homolog A, nuclear factor of kappa light polypeptide gene enhancer in B-cells 3, p65 (avian)<br>RNASEH2C ribonuclease H2, subunit C<br>SART1 squamous cell carcinoma antigen recognized by T cells<br>SCYL1 SCY1-like 1 (*S. cerevisiae*)<br>SF3B2 splicing factor 3b, subunit 2, 145 kDa<br>SIPA1 signal-induced proliferation-associated gene 1<br>SLC25A45 solute carrier family 25, member 45<br>SSSCA1 Sjogren syndrome/scleroderma autoantigen 1<br>TIGD3 tigger transposable element derived 3<br>TSGA10IP testis specific, 10 interacting protein |
| M10 | Chr 11, 61.4-64.3 Mb; | AHNAK (AHNAK nucleoprotein);<br>ASRGL1 asparaginase like 1<br>B3GAT3 beta-1,3-glucuronyltransferase 3 (glucuronosyltransferase I)<br>BAD BCL2-antagonist of cell death<br>BEST1 bestrophin 1<br>BSCL2 Bernardinelli-Seip congenital lipodystrophy 2 (seipin)<br>CCDC88B coiled-coil domain containing 88B<br>CHRM1 cholinergic receptor, muscarinic 1<br>COX8A cytochrome c oxidase subunit 8A (ubiquitous)<br>DKFZP564J0863 DKFZP564J0863 protein<br>DKFZP566E164 DKFZP566E164 protein<br>DNAJC4 DnaJ (Hsp40) homolog, subfamily C, member 4<br>EEF1G eukaryotic translation elongation factor 1 gamma<br>EML3 echinoderm microtubule associated protein like 3<br>ESRRA estrogen-related receptor alpha<br>FADS2, 3 fatty acid desaturase 2, 3<br>FKBP2 FK506 binding protein 2, 13 kDa<br>FLRT1 fibronectin leucine rich transmembrane protein 1<br>FTH1 ferritin, heavy polypeptide 1<br>GANAB glucosidase, alpha; neutral AB<br>GNG3 guanine nucleotide binding protein (G protein), gamma 3<br>GPR137 G protein-coupled receptor 137<br>HRASLS2, 3, 5 HRAS-like suppressor 2, 3, 5<br>INCENP inner centromere protein antigens 135/155 kDa<br>INTS5 integrator complex subunit 5<br>KCNK4 potassium channel, subfamily K, member 4<br>LGALS12 lectin, galactoside-binding, soluble, 12 (galectin 12)<br>MACROD1 MACRO domain containing 1<br>MARK2 MAP/microtubule affinity-regulating kinase 2<br>MGC3196 hypothetical protein MGC3196<br>MTA2 metastasis associated 1 family, member 2<br>NAT11 N-acetyltransferase 11<br>NRXN2 neurexin 2<br>NUDT22 nudix (nucleoside diphosphate linked moiety X)-type motif 22<br>NXF1 nuclear RNA export factor 1<br>OTUB1 OTU domain, ubiquitin aldehyde binding 1<br>PLCB3 phospholipase C, beta 3 (phosphatidylinositol-specific)<br>POLR2G polymerase (RNA) II (DNA directed) polypeptide G<br>PPP1R14B protein phosphatase 1, regulatory (inhibitor) subunit 14B<br>PRDX5 peroxiredoxin 5<br>PYGM phosphorylase, glycogen; muscle (McArdle syndrome, glycogen storage disease type V)<br>RAB3IL1 RAB3A interacting protein (rabin3)-like 1<br>RARRES3 retinoic acid receptor responder (tazarotene induced) 3<br>RASGRP2 RAS guanyl releasing protein 2 (calcium and DAG-regulated)<br>RCOR2 REST corepressor 2<br>ROM1 retinal outer segment membrane protein 1<br>RPS6KA4 ribosomal protein S6 kinase, 90 kDa, polypeptide 4<br>RTN3 reticulon 3<br>SCGB1A1, 1D1, 1D2, 1D4, 2A1, 2A1 secretoglobin, family<br>SF1 splicing factor 1 |

TABLE 5-continued

Cancer outcome markers and corresponding genes and miRNA's

| ID No. | Cancer outcome marker | Genes and miRNA's |
|---|---|---|
| | | SLC22A10, 11, 12, 6, 8, 9 solute carrier family 22 (organic anion/cation transporter) SLC3A2 solute carrier family 3 (activators of dibasic and neutral amino acid transport), member 2
STIP1 stress-induced-phosphoprotein 1 (Hsp70/Hsp90-organizing protein)
STX5 syntaxin 5
TAF6L TAF6-like RNA polymerase II, p300/CBP-associated factor (PCAF)-associated factor, 65 kDa
TRPT1 tRNA phosphotransferase 1
TTC9C tetratricopeptide repeat domain 9C
TUT1 terminal uridylyl transferase 1, U6 snRNA-specific
URP2 UNC-112 related protein 2
UST6 putative UST1-like organic anion transporter
VEGFB vascular endothelial growth factor B
WDR74 WD repeat domain 74; and
ZBTB3 zinc finger and BTB domain containing 3 |
| M11 | Chr 17, 51.5-53.2 Mb; | AKAP1 (A kinase (PRKA) anchor protein 1);
ANKFN1 (ankyrin-repeat and fibronectin type III domain containing 1);
C17orf67 chromosome 17 open reading frame 67
COIL coilin
DGKE diacylglycerol kinase, epsilon 64 kDa
MSI2 musashi homolog 2 (*Drosophila*)
NOG noggin
SCPEP1 serine carboxypeptidase 1; and
TRIM25 tripartite motif-containing 25 |
| M12 | Chr 17, 43.5-44.9 Mb; | hsa-mir-10a; hsa-mir-196a-1; ABI3 (ABI gene family, member 3); ATP5G1 (ATP synthase, H+ transporting, mitochondrial F0 complex, subunit C1 (subunit 9));
B4GALNT2 beta-1,4-N-acetyl-galactosaminyl transferase 2
CALCOCO2 calcium binding and coiled-coil domain 2
CBX1 chromobox homolog 1 (HP1 beta homolog *Drosophila*)
GIP gastric inhibitory polypeptide
GNGT2 guanine nucleotide binding protein (G protein), gamma transducing activity polypeptide 2
HOXB1, 2, 3, 4, 5, 6, 7, 8, 9, 13 homeobox B1, 2, 3, 4, 5, 6, 7, 8, 9, 13
IGF2BP1 insulin-like growth factor 2 mRNA binding protein 1
NFE2L1 nuclear factor (erythroid-derived 2)-like 1
NGFR nerve growth factor receptor (TNFR superfamily, member 16)
PHB prohibitin
PHOSPHO1 phosphatase, orphan 1
PRAC small nuclear protein PRAC
SKAP1 src kinase associated phosphoprotein 1
SNF8 SNF8, ESCRT-II complex subunit, homolog (*S. cerevisiae*)
SNX11 sorting nexin 11
TTLL6 tubulin tyrosine ligase-like family, member 6
UBE2Z (ubiquitin-conjugating enzyme E2Z); and
ZNF652 (zinc finger protein 652). |
| M13 | Chr 2, 147.6-151.1 Mb; | ACVR2A activin A receptor, type IIA; C2orf25 chromosome 2 open reading frame 25
EPC2 enhancer of polycomb homolog 2 (*Drosophila*)
KIF5C kinesin family member 5C
LOC130576 hypothetical protein LOC130576
LYPD6 LY6/PLAUR domain containing 6
MBD5 methyl-CpG binding domain protein 5
ORC4L origin recognition complex, subunit 4-like (yeast)
RND3 Rho family GTPase 3 |
| M14 | Chr 6, 123.7-135.6 Mb; | hsa-mir-588;
AKAP7 (A kinase (PRKA) anchor protein 7);
ALDH8A1 aldehyde dehydrogenase 8 family, member A1
ARG1 arginase, liver
ARHGAP18 Rho GTPase activating protein 18
CTGF connective tissue growth factor
ECHDC1 enoyl Coenzyme A hydratase domain containing 1
ENPP1, 3 ectonucleotide pyrophosphatase/phosphodiesterase 1, 3
EPB41L2 erythrocyte membrane protein band 4.1-like 2
EYA4 eyes absent homolog 4 (*Drosophila*)
HDDC2 HD domain containing 2
HEY2 hairy/enhancer-of-split related with YRPW motif 2
HINT3 histidine triad nucleotide binding protein 3
KIAA1913 KIAA1913
LAMA2 laminin, alpha 2 (merosin, congenital muscular dystrophy) |

TABLE 5-continued

Cancer outcome markers and corresponding genes and miRNA's

| ID No. | Cancer outcome marker | Genes and miRNA's |
|---|---|---|
| | | MED23 mediator complex subunit 23<br>MOXD1 monooxygenase, DBH-like 1<br>MYB v-myb myeloblastosis viral oncogene homolog (avian)<br>NCOA7 nuclear receptor coactivator 7<br>NKAIN2 Na+/K+ transporting ATPase interacting 2<br>OR2A4 olfactory receptor, family 2, subfamily A, member 4<br>PTPRK protein tyrosine phosphatase, receptor type, K. RNF146<br>ring finger protein 146<br>RNF217 ring finger protein 217<br>RPS12 ribosomal protein S12<br>SAMD3 sterile alpha motif domain containing 3<br>SGK serum/glucocorticoid regulated kinase<br>SLC2A12 solute carrier family 2 (facilitated glucose<br>transporter), member 12<br>STX7 syntaxin 7<br>TAAR1, 2, 5, 6, 8, 9 trace amine associated receptor 1, 2, 5, 6, 8, 9<br>TBPL1 TBP-like 1<br>TCF21 transcription factor 21<br>TPD52L1 tumor protein D52-like 1<br>TRDN triadin<br>TRMT11 tRNA methyltransferase 11 homolog (*S. cerevisiae*));<br>and VNN1, 2, 3 (vanin 1, 2, 3). |
| M15 | Chr 8, 6.9-8.8 Mb; | CLDN23 claudin 23;<br>DEFA5 defensin, alpha 5, Paneth cell-specific;<br>DEFB103B defensin, beta 103B<br>DEFB104A defensin, beta 104A<br>DEFB104B defensin, beta 104B<br>DEFB105B defensin, beta 105B<br>DEFB106A defensin, beta 106A<br>DEFB106B defensin, beta 106B<br>DEFB107A defensin, beta 107A<br>DEFB107B defensin, beta 107B<br>DEFB4 defensin, beta 4<br>MFHAS1 malignant fibrous histiocytoma amplified sequence 1<br>PRAGMIN homolog of rat pragma of Rnd2<br>SPAG11A sperm associated antigen 11A; and<br>SPAG11B sperm associated antigen 11B |
| M16 | Chr 2, 159.9-161.4 Mb; | BAZ2B bromodomain adjacent to zinc finger domain, 2B;<br>CD302 CD302 molecule<br>ITGB6 integrin, beta 6<br>LY75 lymphocyte antigen 75<br>MARCH7 (membrane-associated ring finger (C3HC4) 7);<br>PLA2R1 (phospholipase A2 receptor 1, 180 kDa); and<br>RBMS1 (RNA binding motif, single stranded interacting protein 1). |
| M17 | Chr 2, 200.9-204.2 Mb; | ABI2 abl interactor 2;<br>ALS2 amyotrophic lateral sclerosis 2 (juvenile)<br>ALS2CR2, 4, 7, 8, 11, 12, 13 amyotrophic lateral sclerosis 2<br>(juvenile) chromosome region, candidate 2, 4, 7, 8, 11, 12, 13<br>AOX1 aldehyde oxidase 1<br>BMPR2 bone morphogenetic protein receptor, type II<br>(serine/threonine kinase)<br>BZW1 basic leucine zipper and W2 domains 1<br>CASP10 caspase 10, apoptosis-related cysteine peptidase<br>CASP8 caspase 8, apoptosis-related cysteine peptidase<br>CFLAR CASP8 and FADD-like apoptosis regulator<br>CLK1 CDC-like kinase 1<br>CYP20A1 cytochrome P450, family 20, subfamily A,<br>polypeptide 1<br>FAM126B family with sequence similarity 126, member B<br>FZD7 frizzled homolog 7 (*Drosophila*) ICA1L islet cell<br>autoantigen 1, 69 kDa-like<br>KCTD18 potassium channel tetramerisation domain containing 18<br>LOC26010 viral DNA polymerase-transactivated protein 6<br>MPP4 membrane protein, palmitoylated 4 (MAGUK p55<br>subfamily member 4). NBEAL1 neurobeachin-like 1<br>NDUFB3 NADH dehydrogenase (ubiquinone) 1 beta<br>subcomplex, 3, 12 kDa<br>NIF3L1 NIF3 NGG1 interacting factor 3-like 1 (*S. pombe*)<br>NOP5/NOP58 nucleolar protein NOP5/NOP58<br>ORC2L origin recognition complex, subunit 2-like (yeast)<br>PPIL3 peptidylprolyl isomerase (cyclophilin)-like 3<br>RAPH1 Ras association (RalGDS/AF-6) and pleckstrin<br>homology domains 1 |

TABLE 5-continued

Cancer outcome markers and corresponding genes and miRNA's

| ID No. | Cancer outcome marker | Genes and miRNA's |
|---|---|---|
| | | SGOL2 shugoshin-like 2 (*S. pombe*)<br>SUMO1 SMT3 suppressor of mif two 3 homolog 1 (*S. cerevisiae*)<br>TRAK2 trafficking protein, kinesin binding 2; and<br>WDR12 (WD repeat domain 12) |
| M18 | Chr 6, 36.3-36.7 Mb; | BRPF3 (bromodomain and PHD finger containing, 3)<br>DKFZp779B1540 hypothetical protein DKFZp779B1540<br>ETV7 ets variant gene 7 (TEL2 oncogene)<br>KCTD20 potassium channel tetramerisation domain containing 20<br>PNPLA1 patatin-like phospholipase domain containing 1<br>PXT1 peroxisomal, testis specific 1<br>SFRS3 splicing factor, arginine/serine-rich 3; and<br>STK38 (serine/threonine kinase 38) |
| M19 | Chr 2, 205.9-208.1 Mb; and | ADAM23 (ADAM metallopeptidase domain 23); CPO carboxypeptidase O;<br>DYTN dystrotelin<br>EEF1B2 eukaryotic translation elongation factor 1 beta 2<br>FASTKD2 FAST kinase domains 2<br>FLJ20309 hypothetical protein FLJ20309<br>GPR1 G protein-coupled receptor 1<br>KLF7 Kruppel-like factor 7 (ubiquitous)<br>MDH1B malate dehydrogenase 1B, NAD (soluble)<br>NDUFS1 NADH dehydrogenase (ubiquinone) Fe—S protein 1, 75 kDa (NADH-coenzyme Q reductase)<br>NRP2 neuropilin 2<br>PARD3B par-3 partitioning defective 3 homolog B (*C. elegans*)<br>ZDBF2 (zinc finger, DBF-type containing 2); and<br>HCG_1657980 hCG1657980 |
| M20 | Chr 1, 109.5-111.1 Mb. | hsa-mir-197;<br>AHCYL1 S-adenosylhomocysteine hydrolase-like 1);<br>ALX3 aristaless-like homeobox 3<br>AMIGO1 adhesion molecule with Ig-like domain 1<br>AMPD2 adenosine monophosphate deaminase 2 (isoform L)<br>ATXN7L2 ataxin 7-like 2<br>CELSR2 cadherin, EGF LAG seven-pass G-type receptor 2 (flamingo homolog, *Drosophila*)<br>CSF1 colony stimulating factor 1 (macrophage)<br>CYB561D1 cytochrome b-561 domain containing 1<br>EPS8L3 EPS8-like 3<br>FAM40A family with sequence similarity 40, member A<br>GNAI3 guanine nucleotide binding protein (G protein), alpha inhibiting activity polypeptide 3<br>GNAT2 guanine nucleotide binding protein (G protein), alpha transducing activity polypeptide 2<br>GPR61 G protein-coupled receptor 61<br>GSTM1, M2, M3, M4, M5 glutathione S-transferase M1, M2 (muscle), M3 (brain), M4, M5<br>HBXIP hepatitis B virus x interacting protein<br>KCNA2, 3, 4, 10 potassium voltage-gated channel, shaker-related subfamily, member 2, 3, 4, 10; KIAA1324 KIAA1324<br>MYBPHL myosin binding protein H-like<br>PROK1 prokineticin 1<br>PSMA5 proteasome (prosome, macropain) subunit, alpha type, 5<br>PSRC1 proline/serine-rich coiled-coil 1<br>RBM15 RNA binding motif protein 15<br>SARS seryl-tRNA synthetase<br>SLC16A4 solute carrier family 16, member 4 (monocarboxylic acid transporter 5)<br>SLC6A17 solute carrier family 6, member 17<br>SORT1 sortilin 1<br>SYPL2 synaptophysin-like 2<br>UBL4B (ubiquitin-like 4B) |
| DM1 | Chr 5, 62.9-67.8 Mb | ADAMTS6 ADAM metallopeptidase with thrombospondin type 1 motif, 6<br>CD180 CD180 molecule<br>CENPK centromere protein K<br>ERBB2IP erbb2 interacting protein<br>FLJ13611 hypothetical protein FLJ13611<br>HTR1A 5-hydroxytryptamine (serotonin) receptor 1A<br>MAST4 microtubule associated serine/threonine kinase family member 4<br>NLN neurolysin (metallopeptidase M3 family)<br>P18SRP P18SRP protein<br>PIK3R1 phosphoinositide-3-kinase, regulatory subunit 1 (p85 alpha) |

TABLE 5-continued

Cancer outcome markers and corresponding genes and miRNA's

| ID No. | Cancer outcome marker | Genes and miRNA's |
|---|---|---|
| | | PPWD1 peptidylprolyl isomerase domain and WD repeat containing 1<br>RGS7BP regulator of G-protein signaling 7 binding protein<br>RNF180 ring finger protein 180<br>SDCCAG10 serologically defined colon cancer antigen 10<br>SFRS12 splicing factor, arginine/serine-rich 12<br>SGTB small glutamine-rich tetratricopeptide repeat (TPR)-containing, beta0; and<br>TRIM23 tripartite motif-containing 23. |
| DM2 | Chr 5, 53.3-53.8 Mb | ARL15 (ADP-ribosylation factor-like 15); HSPB3 (heat shock 27 kDa protein 3) and hsa-miR-581. |
| DM3 | Chr 4, 105.8-107.2 Mb | FLJ20184 (hypothetical protein FLJ20184);<br>GSTCD (glutathione S-transferase, C-terminal domain containing);<br>INTS12 integrator complex subunit 12<br>KIAA1546 KIAA1546<br>MGC16169 hypothetical protein MGC16169<br>NPNT (nephronectin); and<br>PPA2 pyrophosphatase (inorganic) 2. |
| DM4 | Chr 16, 45.8-46.3 Mb | ITFG1 (integrin alpha FG-GAP repeat containing 1) and PHKB (phosphorylase kinase, beta). |
| DM5 | Chr 5, 50.7-52.0 Mb | ISL1 (ISL LIM homeobox). |
| DM6 | Chr 5, 94.2-96.1 Mb | ARSK (arylsulfatase family, member K);<br>CAST (calpastatin);<br>ELL2 (elongation factor, RNA polymerase II, 2);<br>FAM81B family with sequence similarity 81, member B<br>GLRX glutaredoxin (thioltransferase)<br>GPR150 G protein-coupled receptor 150<br>KIAA0372 KIAA0372<br>MCTP1 multiple C2 domains, transmembrane 1<br>PCSK1 proprotein convertase subtilisin/kexin type 1<br>RFESD (Rieske (Fe—S) domain containing)<br>RHOBTB3 Rho-related BTB domain containing 3<br>SPATA9 (spermatogenesis associated 9); and<br>hsa-miR-583. |
| DM7 | Chr 9, 36.1-37.0 Mb | C9orf19 chromosome 9 open reading frame 19<br>CCIN calicin<br>CLTA clathrin, light chain (Lca)<br>GNE glucosamine (UDP-N-acetyl)-2-epimerase/N-acetylmannosamine kinase<br>MELK maternal embryonic leucine zipper kinase<br>PAX5 paired box 5<br>RECK reversion-inducing-cysteine-rich protein with kazal motifs<br>RNF38 ring finger protein 38. |
| DM8 | Chr 5, 94.2-96.1 Mb | ARSK arylsulfatase family, member K<br>CAST calpastatin<br>ELL2 elongation factor, RNA polymerase II, 2<br>FAM81B family with sequence similarity 81, member B<br>GLRX glutaredoxin (thioltransferase)<br>GPR150 G protein-coupled receptor 150<br>KIAA0372 KIAA0372<br>MCTP1 multiple C2 domains, transmembrane 1<br>PCSK1 proprotein convertase subtilisin/kexin type 1<br>RFESD Rieske (Fe—S) domain containing<br>RHOBTB3 Rho-related BTB domain containing 3<br>SPATA9 spermatogenesis associated |
| DM9 | Chr14, 51.1-52.8 Mb | C14orf166 chromosome 14 open reading frame 166;<br>DDHD1 DDHD domain containing 1<br>ERO1L ERO1-like (*S. cerevisiae*)<br>FRMD6 FERM domain containing 6<br>GNG2 guanine nucleotide binding protein (G protein), gamma 2<br>GNPNAT1 glucosamine-phosphate N-acetyltransferase 1<br>GPR137C G protein-coupled receptor 137C<br>NID2 nidogen 2 (osteonidogen)<br>PLEKHC1 pleckstrin homology domain containing, family C (with FERM domain) member 1<br>PSMC6 proteasome (prosome, macropain) 26S subunit, ATPase, 6<br>PTGDR prostaglandin D2 receptor (DP)<br>PTGER2 prostaglandin E receptor 2 (subtype EP2), 53 kDa<br>STYX serine/threonine/tyrosine interacting protein<br>TXNDC16 thioredoxin domain containing 16. |

TABLE 5-continued

Cancer outcome markers and corresponding genes and miRNA's

| ID No. | Cancer outcome marker | Genes and miRNA's |
| --- | --- | --- |
| DM10 | Chr 14, 61.5-68.6 Mb | ACTN1 actinin, alpha 1<br>AKAP5 A kinase (PRKA) anchor protein 5<br>ARG2 arginase, type II<br>ATP6V1D ATPase, H+ transporting, lysosomal 34 kDa, V1 subunit D<br>C14orf50 chromosome 14 open reading frame 50<br>C14orf54 chromosome 14 open reading frame 54<br>C14orf83 chromosome 14 open reading frame 83<br>CHURC1 churchill domain containing 1<br>EIF2S1 eukaryotic translation initiation factor 2, subunit 1 alpha, 35 kDa<br>ESR2 estrogen receptor 2 (ER beta)<br>FLJ39779 FLJ39779 protein<br>FNTB farnesyltransferase, CAAX box, beta<br>FUT8 fucosyltransferase 8 (alpha (1, 6) fucosyltransferase)<br>GPHB5 glycoprotein hormone beta 5<br>GPHN gephyrin<br>GPX2 glutathione peroxidase 2 (gastrointestinal)<br>HSPA2 heat shock 70 kDa protein 2<br>KCNH5 potassium voltage-gated channel, subfamily H (eag-related), member 5<br>MAX MYC associated factor X<br>MPP5 membrane protein, palmitoylated 5 (MAGUK p55 subfamily member 5)<br>MTHFD1 methylenetetrahydrofolate dehydrogenase (NADP+ dependent) 1, methenyltetrahydrofolate cyclohydrolase, formyltetrahydrofolate synthetase<br>PIGH phosphatidylinositol glycan anchor biosynthesis, class H<br>PLEK2 pleckstrin 2<br>PLEKHG3 pleckstrin homology domain containing, family G (with RhoGef domain) member 3<br>PLEKHH1 pleckstrin homology domain containing, family H (with MyTH4 domain) member 1<br>PPP2R5E protein phosphatase 2, regulatory subunit B', epsilon isoform.<br>RAB15 RAB15, member RAS oncogene family<br>RAD51L1 RAD51-like 1 (*S. cerevisiae*)<br>RDH11 retinol dehydrogenase 11 (all-trans/9-cis/11-cis)<br>RDH12 retinol dehydrogenase 12 (all-trans/9-cis/11-cis)<br>RHOJ ras homolog gene family, member J<br>SGPP1 sphingosine-1-phosphate phosphatase 1<br>SPTB spectrin, beta, erythrocytic (includes spherocytosis, clinical type I)<br>SYNE2 spectrin repeat containing, nuclear envelope 2<br>SYT16 synaptotagmin XVI<br>VTI1B vesicle transport through interaction with t-SNAREs homolog 1B (yeast)<br>WDR22 WD repeat domain 22<br>WDR89 WD repeat domain 89<br>ZBTB1 zinc finger and BTB domain containing 1<br>ZBTB25 zinc finger and BTB domain containing 25<br>ZFP36L1 zinc finger protein 36, C3H type-like 1<br>ZFYVE26 zinc finger, FYVE domain containing 26 and hsa-miR-625. |
| DM11 | Chr 9, 28.1 Mb | LINGO2 (leucine rich repeat and Ig domain containing 2). |
| DM12 | Chr 4, 43.7-44.2 Mb | KCTD8 (potassium channel tetramerisation domain containing 8). |
| DM13 | Chr 5, 60.8-62.9 Mb | DIMT1L DIM1 dimethyladenosine transferase 1-like (*S. cerevisiae*)<br>FLJ37543 hypothetical protein FLJ37543<br>IPO11 importin 11<br>ISCA1L iron-sulfur cluster assembly 1 homolog (*S. cerevisiae*)-like<br>KIF2A kinesin heavy chain member 2A. |
| DM14 | Chr 3, 120.0-121.1 Mb | ADPRH ADP-ribosylarginine hydrolase;<br>B4GALT4 UDP-Gal:betaGlcNAc beta 1,4-galactosyltransferase, polypeptide 4<br>C3orf1 chromosome 3 open reading frame 1<br>C3orf15 chromosome 3 open reading frame 15<br>C3orf30 chromosome 3 open reading frame 30<br>CD80 CD80 molecule<br>CDGAP Cdc42 GTPase-activating protein<br>COX17 COX17 cytochrome c oxidase assembly homolog (*S. cerevisiae*)<br>GSK3B glycogen synthase kinase 3 beta<br>IGSF11 immunoglobulin superfamily, member 11<br>KTELC1 KTEL (Lys-Tyr-Glu-Leu) containing 1 |

TABLE 5-continued

Cancer outcome markers and corresponding genes and miRNA's

| ID No. | Cancer outcome marker | Genes and miRNA's |
|---|---|---|
| | | NR1I2 nuclear receptor subfamily 1, group I, member 2 |
| | | PLA1A phospholipase A1 member A |
| | | POPDC2 popeye domain containing 2 |
| | | TMEM39A transmembrane protein 39A; and |
| | | UPK1B uroplakin 1B. |
| DM15 | Chr 4, 46.2-48.0 Mb | CLDN23 claudin 23; |
| | | DEFA5 defensin, alpha 5, Paneth cell-specific; |
| | | DEFB103B defensin, beta 103B |
| | | DEFB104A defensin, beta 104A |
| | | DEFB104B defensin, beta 104B |
| | | DEFB105B defensin, beta 105B |
| | | DEFB106A defensin, beta 106A |
| | | DEFB106B defensin, beta 106B |
| | | DEFB107A defensin, beta 107A |
| | | DEFB107B defensin, beta 107B |
| | | DEFB4 defensin, beta 4 |
| | | MFHAS1 malignant fibrous histiocytoma amplified sequence 1 |
| | | PRAGMIN homolog of rat pragma of Rnd2 |
| | | SPAG11A sperm associated antigen 11A; and |
| | | SPAG11B sperm associated antigen 11B. |
| DM16 | Chr 14, 38.9-40.0 Mb | FBXO33 (F-box protein 33). |
| DM17 | Chr 4, 44.2-44.6 Mb | GNPDA2 (glucosamine-6-phosphate deaminase 2); |
| | | GUF1 (GUF1 GTPase homolog (*S. cerevisiae*)); and |
| | | YIPF7 (Yip1 domain family, member 7). |
| DM18 | Chr 2, 213.7-214.3 Mb | IKZF2 IKAROS family zinc finger 2 (Helios) |
| | | SPAG16 sperm associated antigen 16. |
| DM19 | Chr14, 43.9-46.6 Mb | C14orf106 chromosome 14 open reading frame 106 |
| | | C14orf155 chromosome 14 open reading frame 155 |
| | | C14orf28 chromosome 14 open reading frame 28 |
| | | FANCM Fanconi anemia, complementation group M |
| | | FKBP3 FK506 binding protein 3, 25 kDa |
| | | KIAA0423 KIAA0423 |
| | | KLHL28 kelch-like 28 (*Drosophila*) |
| | | MDGA2 MAM domain containing glycosylphosphatidylinositol anchor 2 |
| | | PRPF39 PRP39 pre-mRNA processing factor 39 homolog (*S. cerevisiae*) |
| | | RPL10L ribosomal protein L10-like. |
| DM20 | Chr 14, 27.6-28.6 Mb | FOXG1 (forkhead box G1). |
| DM21 | Chr 3, 98.0-98.3 Mb | EPHA6 (EPH receptor A6). |
| DM22 | Chr14, 55.2-60.0 Mb | ACTR10 actin-related protein 10 homolog (*S. cerevisiae*) |
| | | ARID4A AT rich interactive domain 4A (RBP1-like) |
| | | C14orf100 chromosome 14 open reading frame 100 |
| | | C14orf101 chromosome 14 open reading frame 101 |
| | | C14orf105 chromosome 14 open reading frame 105 |
| | | C14orf108 chromosome 14 open reading frame 108 |
| | | C14orf135 chromosome 14 open reading frame 135 |
| | | C14orf149 chromosome 14 open reading frame 149 |
| | | C14orf37 chromosome 14 open reading frame 37 |
| | | C14orf39 chromosome 14 open reading frame 39 |
| | | DAAM1 dishevelled associated activator of morphogenesis 1 |
| | | DACT1 dapper, antagonist of beta-catenin, homolog 1 (*Xenopus laevis*) |
| | | DHRS7 dehydrogenase/reductase (SDR family) member 7 |
| | | EXOC5 exocyst complex component 5 |
| | | GPR135 G protein-coupled receptor 135 |
| | | KIAA0586 KIAA0586 |
| | | NAT12 N-acetyltransferase 12 |
| | | OTX2 orthodenticle homeobox 2 |
| | | PELI2 pellino homolog 2 (*Drosophila*) |
| | | PPM1A protein phosphatase 1A (formerly 2C), magnesium-dependent, alpha isoform |
| | | PSMA3 proteasome (prosome, macropain) subunit, alpha type, 3 |
| | | RTN1 reticulon 1 |
| | | SLC35F4 solute carrier family 35, member F4 |
| | | TIMM9 translocase of inner mitochondrial membrane 9 homolog (yeast) |
| | | UNQ9438 TIMM. |
| DM23 | Chr14, 48.7-51.1 Mb | ABHD12B abhydrolase domain containing 12B |
| | | ARF6 ADP-ribosylation factor 6 |
| | | ATP5S ATP synthase, H+ transporting, mitochondrial F0 complex, subunit s (factor B) |
| | | C14orf104 chromosome 14 open reading frame 104 |
| | | C14orf138 chromosome 14 open reading frame 138 |
| | | CDKL1 cyclin-dependent kinase-like 1 (CDC2-related kinase) |

TABLE 5-continued

Cancer outcome markers and corresponding genes and miRNA's

| ID No. | Cancer outcome marker | Genes and miRNA's |
|---|---|---|
| | | FRMD6 FERM domain containing 6
KLHDC1 kelch domain containing 1
KLHDC2 kelch domain containing 2
L2HGDH L-2-hydroxyglutarate dehydrogenase
LOC196913 hypothetical protein LOC196913
LOC283551 hypothetical protein LOC283551
MAP4K5 mitogen-activated protein kinase kinase kinase kinase 5
MGAT2 mannosyl (alpha-1,6-)-glycoprotein beta-1,2-N-acetylglucosaminyltransferase
NIN ninein (GSK3B interacting protein)
POLE2 polymerase (DNA directed), epsilon 2 (p59 subunit)
PPIL5 peptidylprolyl isomerase (cyclophilin)-like 5
PYGL phosphorylase, glycogen; liver (Hers disease, glycogen storage disease type VI)
RPL36AL ribosomal protein L36a-like
RPS29 ribosomal protein S29. |
| DM24 | Chr 4, 81.4-83.2 Mb | BMP3 bone morphogenetic protein 3 (osteogenic)
C4orf22 chromosome 4 open reading frame 22
FGF5 fibroblast growth factor 5
PRKG2 protein kinase, cGMP-dependent, type II
RASGEF1B RasGEF domain family, member 1B. |
| DM25 | Chr 10, 51.9-54.2 Mb | ACF apobec-1 complementation factor
ASAH2B N-acylsphingosine amidohydrolase (non-lysosomal ceramidase) 2B
CSTF2T cleavage stimulation factor, 3' pre-RNA, subunit 2, 64 kDa, tau variant
DKK1 dickkopf homolog 1 (*Xenopus laevis*)
MBL2 mannose-binding lectin (protein C) 2, soluble (opsonic defect)
PRKG1 protein kinase, cGMP-dependent, type I
SGMS1 sphingomyelin synthase 1
hsa-miR-605. |
| DM26 | Chr 5, 55.2-58.6 Mb | ANKRD55 ankyrin repeat domain 55
C5orf29 chromosome 5 open reading frame 29
C5orf35 chromosome 5 open reading frame 35
DKFZp686D0972 similar to RIKEN cDNA 4732495G21 gene
GPBP1 GC-rich promoter binding protein 1
IL31RA interleukin 31 receptor A
IL6ST interleukin 6 signal transducer (gp130, oncostatin M receptor)
MAP3K1 mitogen-activated protein kinase kinase kinase 1
MIER3 mesoderm induction early response 1, family member 3
PDE4D phosphodiesterase 4D, cAMP-specific (phosphodiesterase E3 dunce homolog, *Drosophila*)
PLK2 polo-like kinase 2 (*Drosophila*)
RAB3C RAB3C, member RAS oncogene family. |
| DM27 | Chr 5, 67.8-68.5 Mb. | CCNB1 (cyclin B1) and SLC30A5 (solute carrier family 30 (zinc transporter), member 5). |

Table 6 lists the coordinates for each cancer outcome marker, using the same reference numerals listed in Table 5. All coordinates are based on human genome assembly hg18 (NCBI Build 36).

TABLE 6

| MarkerID | chrom | start.pos | end.pos |
|---|---|---|---|
| M1 | chr19 | 34722418 | 35643933 |
| M2 | chr19 | 38853838 | 40749461 |
| M3 | chr17 | 69173224 | 71304619 |
| M4 | chr6 | 70761833 | 71144537 |
| M5 | chr12 | 93683 | 1867988 |
| M6 | chr11 | 64310154 | 64803976 |
| M7 | chr19 | 57033283 | 62189738 |
| M8 | chr6 | 39088059 | 39850364 |
| M9 | chr11 | 64803977 | 65684917 |
| M10 | chr11 | 61374252 | 64310153 |
| M11 | chr17 | 51532820 | 53211048 |
| M12 | chr17 | 43477124 | 44932837 |
| M13 | chr2 | 147604021 | 151117679 |
| M14 | chr6 | 123724457 | 135574976 |

TABLE 6-continued

| MarkerID | chrom | start.pos | end.pos |
|---|---|---|---|
| M15 | chr8 | 6895465 | 8784654 |
| M16 | chr2 | 159911944 | 161423883 |
| M17 | chr2 | 200924525 | 204245414 |
| M18 | chr6 | 36255222 | 36678343 |
| M19 | chr2 | 205893481 | 208053624 |
| M20 | chr1 | 109538586 | 111118652 |
| DM1 | chr9 | 36056899 | 36988415 |
| DM2 | chr4 | 105818261 | 107238628 |
| DM3 | chr5 | 53264432 | 53790965 |
| DM4 | chr16 | 45791880 | 46313827 |
| DM5 | chr5 | 50706878 | 52008065 |
| DM6 | chr5 | 94204208 | 96112445 |
| DM7 | chr5 | 62942847 | 67798156 |
| DM9 | chr14 | 51108156 | 52752331 |
| DM10 | chr14 | 61456273 | 68632720 |
| DM11 | chr9 | 28057491 | 28114180 |
| DM12 | chr4 | 43689020 | 44161565 |
| DM13 | chr5 | 60797829 | 62942846 |
| DM14 | chr3 | 119993321 | 121112610 |
| DM15 | chr4 | 46246303 | 47955581 |

TABLE 6-continued

| MarkerID | chrom | start.pos | end.pos |
|---|---|---|---|
| DM16 | chr14 | 38939630 | 40021400 |
| DM17 | chr4 | 44161566 | 44606114 |
| DM18 | chr2 | 213677020 | 214308243 |
| DM19 | chr14 | 43899026 | 46591909 |
| DM20 | chr14 | 27646449 | 28630571 |
| DM21 | chr3 | 97988751 | 98257089 |
| DM22 | chr14 | 55249852 | 60045332 |
| DM23 | chr14 | 48734855 | 51108156 |
| DM24 | chr4 | 81371219 | 83187388 |
| DM25 | chr10 | 51929419 | 54199330 |
| DM26 | chr5 | 55221121 | 58648144 |
| DM27 | chr5 | 67798156 | 68516077 |

Unlike previously identified predictors (expression signatures), the biomarkers described herein represent DNA gains and losses (stable events measurable by FISH). FISH probes can be used to enable validation/use of the markers, and the markers are strong candidates for use as stratification biomarkers in clinical trials. They can be used for example to define molecular subgroups of disease with distinct outcomes. As such they are likely to correlate with drug response.

These data indicate that use of genomic copy number assessment of the genetic markers measured by FISH, and with use of an appropriate classifier, is of prognostic importance in early stage NSCLC. The classifier was able to produce statistically significant classification of patients who had been treated with surgery without neoadjuvant or follow-up chemotherapy into favorable and unfavorable recurrence categories. No present clinical in vitro diagnostic assay provides this capability. Thus, FISH assays to the listed markers performed on early stage NSCLC biopsy specimens or resected tumors appear valuable in decisions related to adjuvant therapy.

Example 2

Validation of Prognostic Markers Using a Korean Sample Set

To validate forty-six (46) of the biomarkers that correlated with the clinical outcome of low stage NSCLC patients, an additional set of low stage NSCLC tumor tissues was collected from the Samsung Cancer Center in Korea, together with associated clinical outcome information.

All samples were carefully dissected to maximize tumor/normal tissue ratio and verify histopathological type and stage. Only samples from patients with stage I and II samples were analyzed. All of these were from patients treated with surgical resection without any follow-up or neoadjuvant chemotherapy. Clinical information collected for each patient included age, sex, clinical stage, pathological stage, location, histology, differentiation, smoking status, chemotherapy status, radiation status, recurrence status, recurrence date, recurrence location, brain metastasis status, time to recurrence, date of last follow up, status at the last follow up, alive/dead, overall survival and cause of death. Time to Recurrence (TTR) and Overall Survival (OS) were chosen as the parameters of outcome. Other clinical parameters (node status, stage, etc) were considered as confounding variables. Times to recurrence of lung cancer and the overall survival times were obtained from the patient charts. Tables 7 and 8 provide the figures for Overall Survival and Total Time to Recurrence, respectively, for the patient cohort studied.

TABLE 7

| | OS | | |
|---|---|---|---|
| Stage | deaths | Alive (censored) | total |
| 1a | 0 | 10 | 10 |
| 1b | 22 | 33 | 55 |
| 2a | 0 | 0 | 0 |
| 2b | 6 | 2 | 8 |
| Total | 28 | 45 | 73 |

TABLE 8

| | TTR | | |
|---|---|---|---|
| Stage | recurred | Recurrence free (censored) | total |
| 1a | 0 | 10 | 10 |
| 1b | 24 | 31 | 55 |
| 2a | 0 | 0 | 0 |
| 2b | 6 | 2 | 8 |
| total | 30 | 43 | 73 |

The samples were processed, DNA extracted, amplified and hybridized to Affymetrix SNP 6.0 arrays (Affymetrix, Inc., Santa Clara, Calif.) which contains more than 906,600 single nucleotide polymorphisms (SNPs) and more than 946,000 probes for the detection of copy number variation with a median intermarker distance over all 1.8 million SNP and copy number markers combined of less than 700 bases. The microarrays were processed according to recommendations of the manufacturer (Affymetrix). Copy number of these tumors was calculated by comparing to a HapMap set of 270 normal controls. The copy number was segmented using Partek software 6.09.0310.

Figure 61:
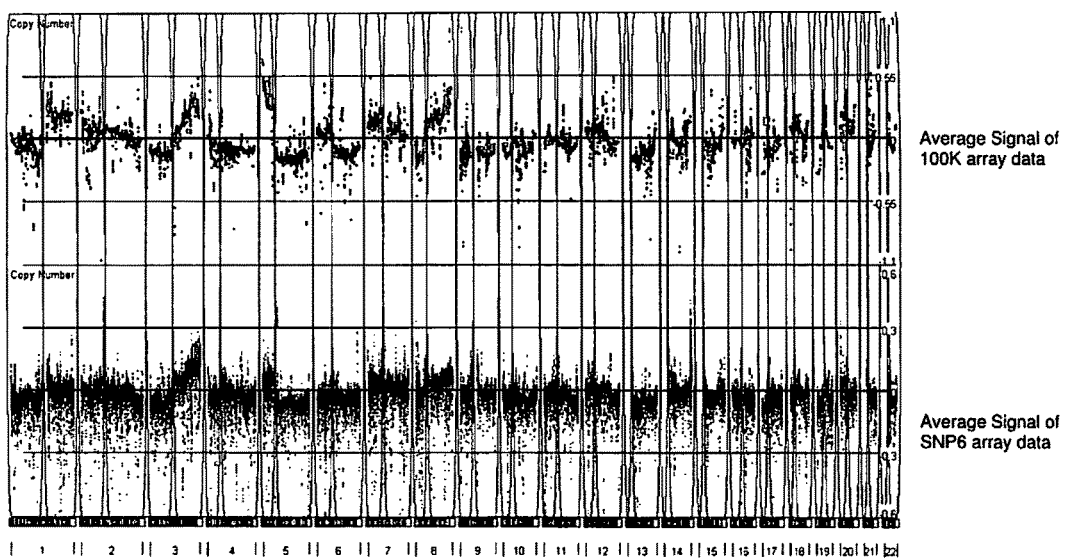
FIG. 61 is a plot indicating average copy number, comparing the average copy number pattern obtained using a training (100K array) data set and a validating (SNP 6.0 array) data set.

The average copy number of the validation set showed a pattern similar to the previous training data set, but with a much higher density, as shown in FIG. 61. FIG. 61 compares the average copy number pattern between training and validating data set. The log transformed copy numbers of each marker were averaged across all samples in the training (above) and testing (below) sets, where 0 represents the normal two copies, and red and blue represent on average gain or loss of copy numbers, respectively. Each dot represents one marker on the array, and the x-axis represents the genomic locations ranked by chromosome 1 to 22.

The validation data presented in this example is based on eighteen (18) times greater the coverage of SNPs and CNV markers as compared to the 100K microarray data generated and used to identify the diagnostic markers, and therefore more small scale copy number changing events could be identified. Therefore, instead of calculating the copy number of each biomarker, the copy number of each gene within these biomarkers was calculated, and then correlated to the Overall Survival or Time to Recurrence of the patients.

Figure 62:
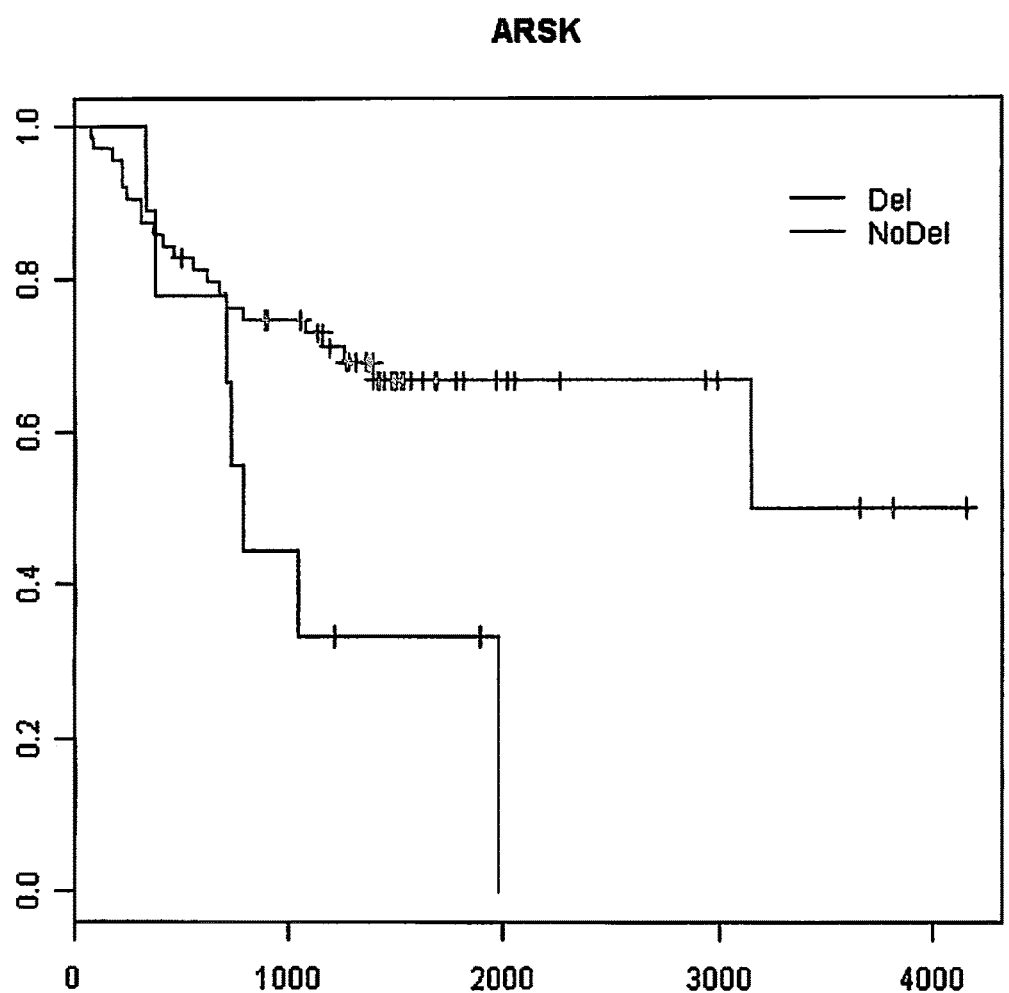
FIG. 62 is a Kaplan-Meier plot showing the overall survival (OS) in days for a 78 patient cohort with NSCLC stage Ia-IIa, classified by presence or absence of a copy number gain in ARSK.
Figure 63:
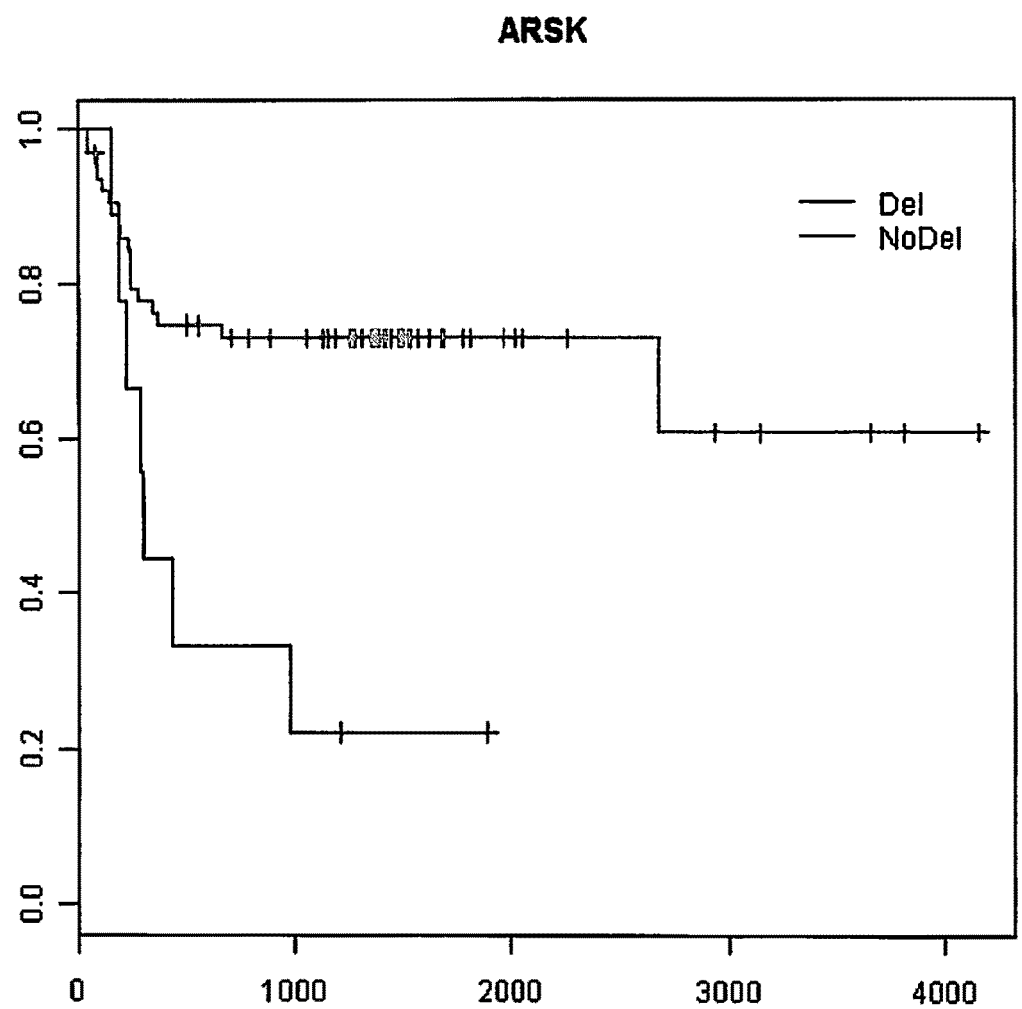
FIG. 63 is a Kaplan-Meier plot showing the time to recurrence (TTR) in days for a 74 patient cohort with NSCLC stage Ia-IIa, classified by presence or absence of a copy number gain in ARSK.
Figure 64:
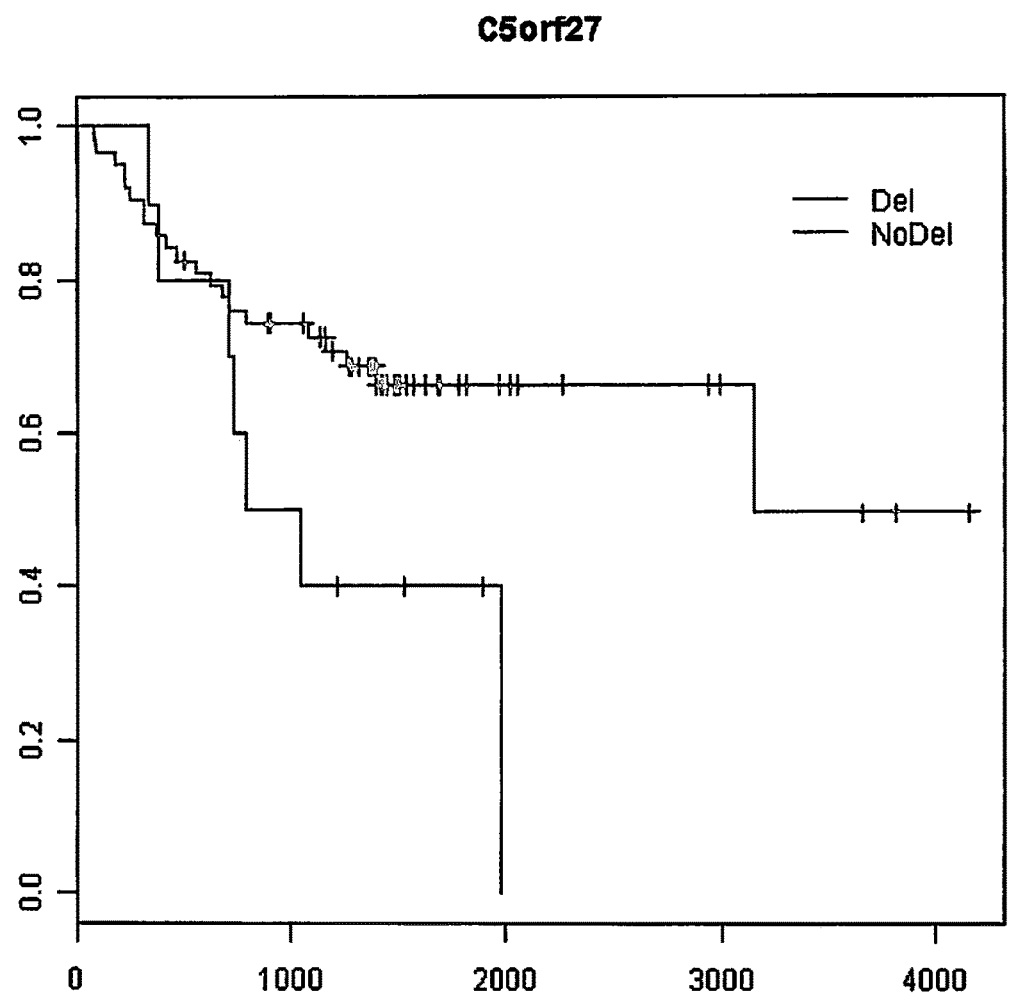
FIG. 64 is a Kaplan-Meier plot showing the overall survival (OS) in days for a 74 patient cohort with NSCLC stage Ia-IIa, classified by presence or absence of a copy number gain in C5orf27.
Figure 65:
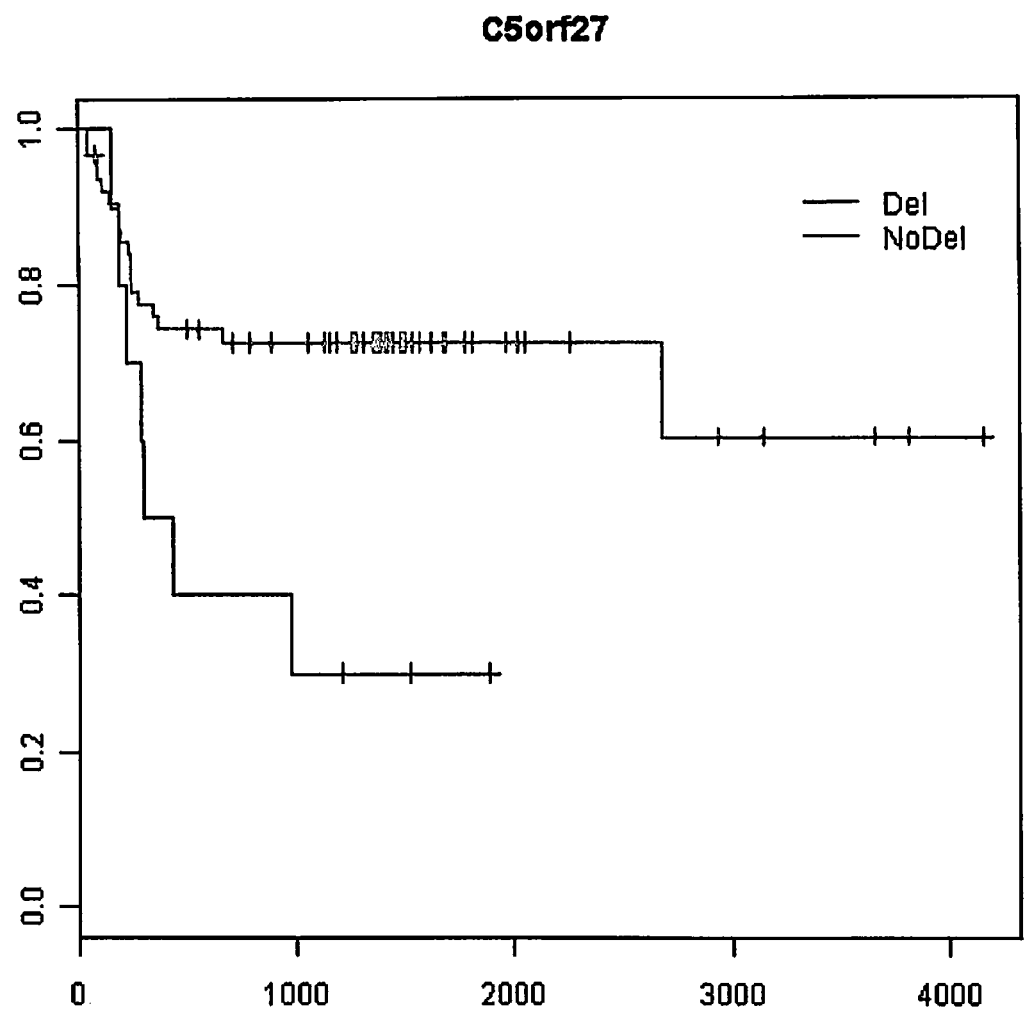
FIG. 65 is a Kaplan-Meier plot showing the time to recurrence (TTR) in days for a 74 patient cohort with NSCLC stage Ia-IIa, classified by presence or absence of a copy number gain in C5orf27.
Figure 66:
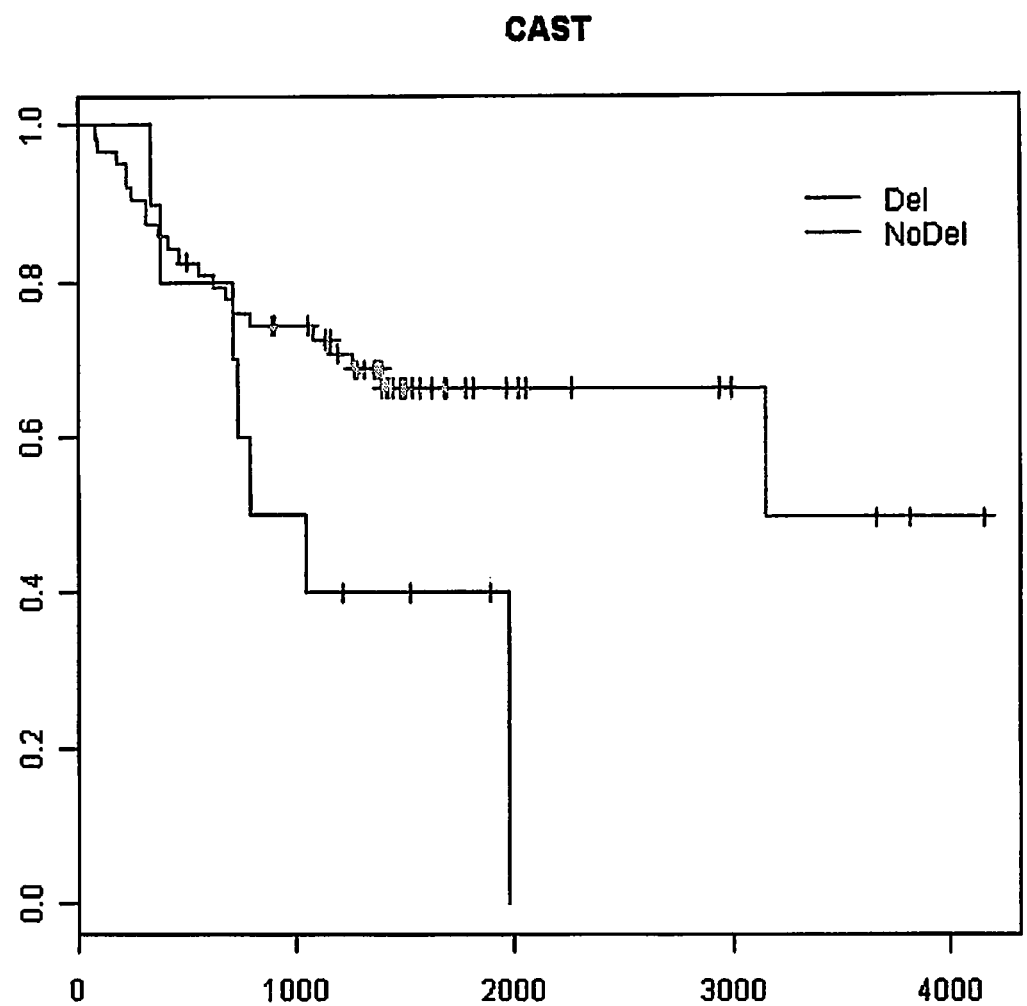
FIG. 66 is a Kaplan-Meier plot showing the overall survival (OS) in days for a 74 patient cohort with NSCLC stage Ia-IIa, classified by presence or absence of a copy number gain in CAST.
Figure 67:
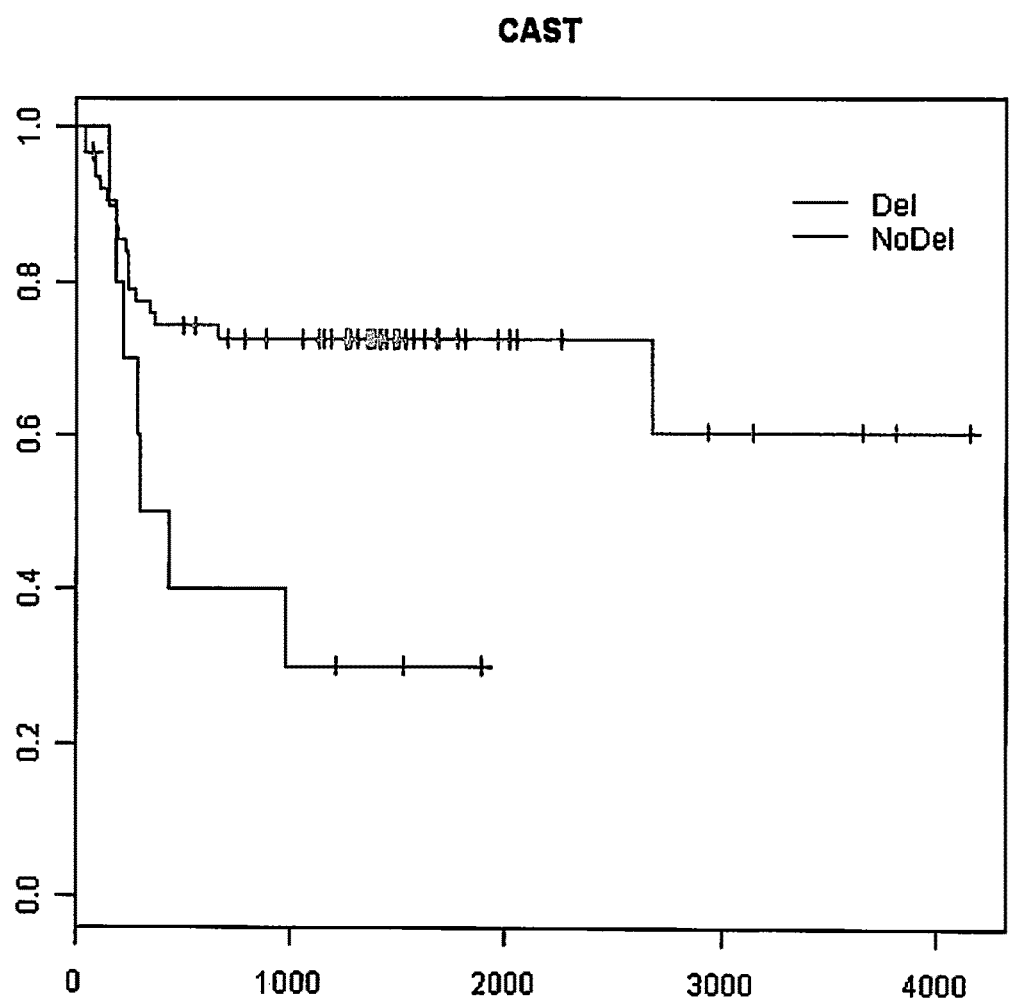
FIG. 67 is a Kaplan-Meier plot showing the time to recurrence (TTR) in days for a 74 patient cohort with NSCLC stage Ia-IIa, classified by presence or absence of a copy number gain in CAST.
Figure 68:
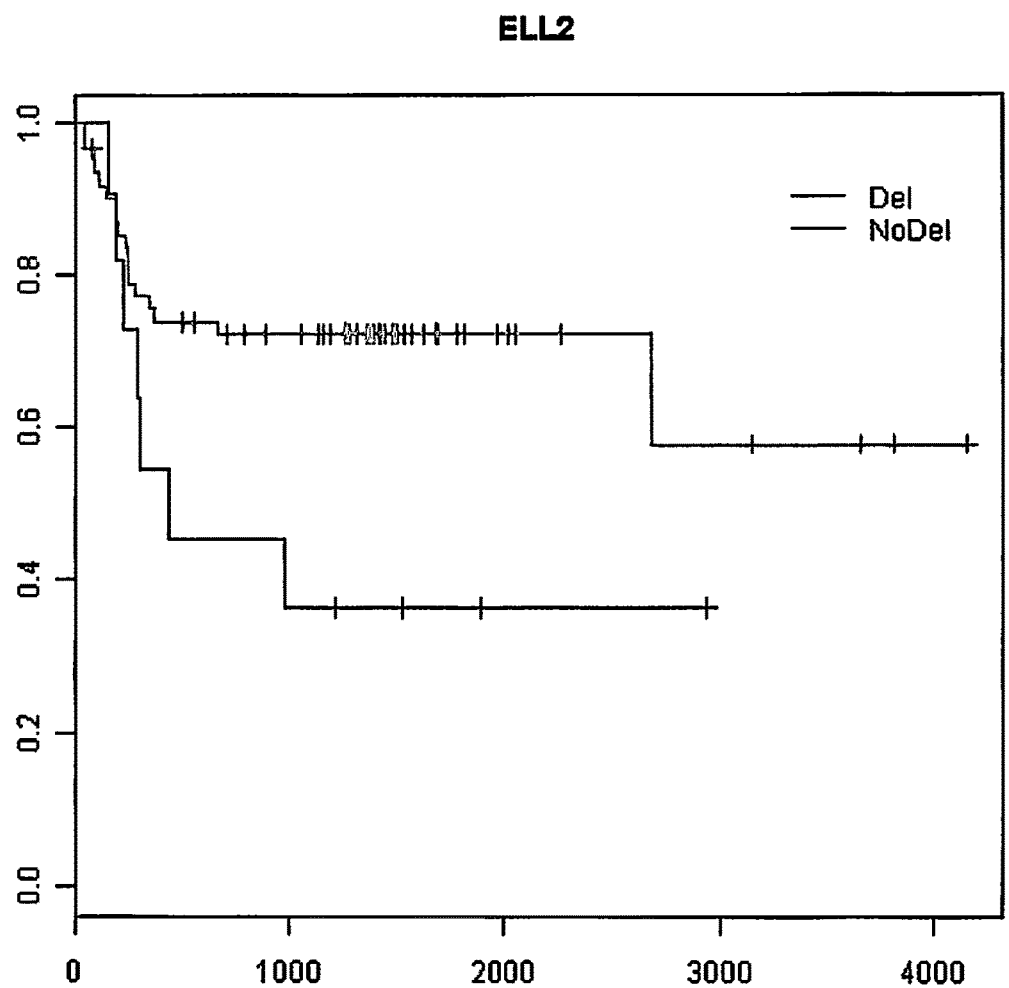
FIG. 68 is a Kaplan-Meier plot showing the time to recurrence (TTR) in days for a 74 patient cohort with NSCLC stage Ia-IIa, classified by presence or absence of a copy number gain in ELL2.
Figure 69:
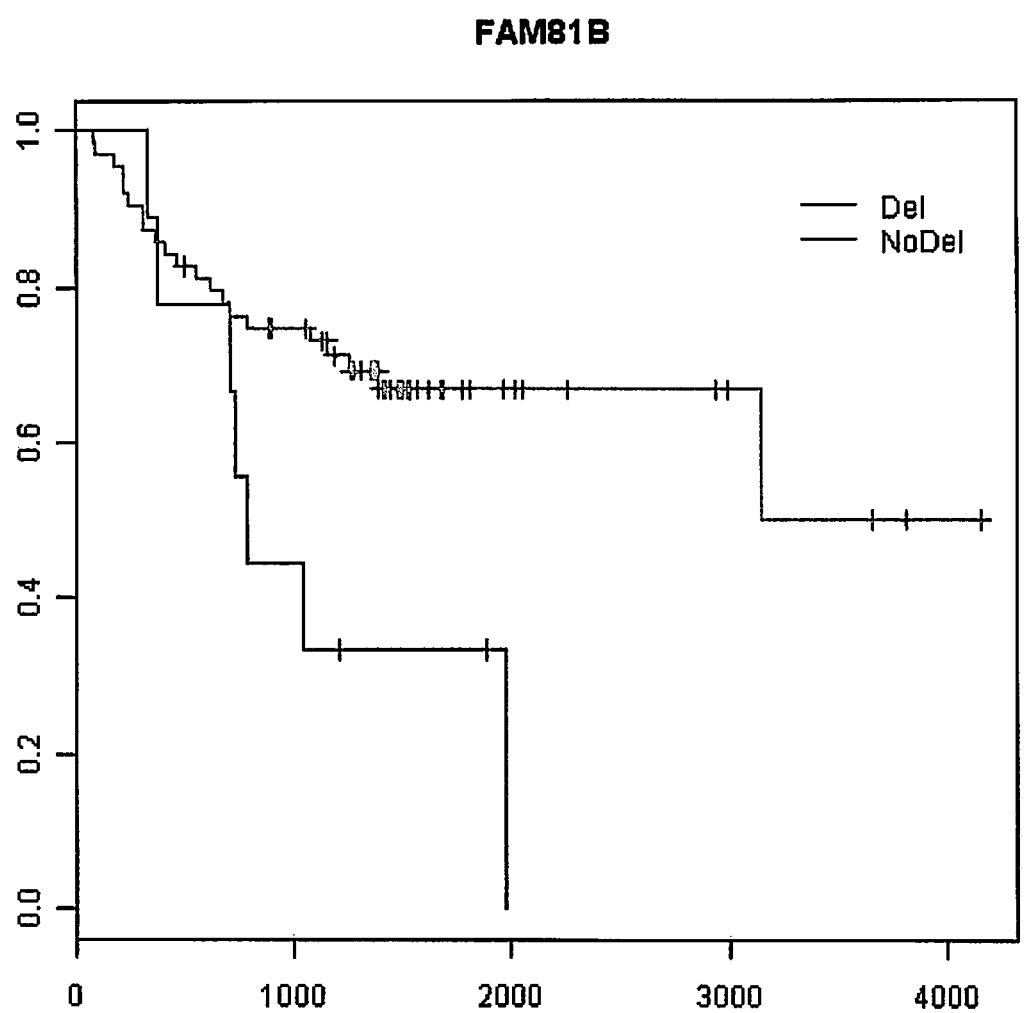
FIG. 69 is a Kaplan-Meier plot showing the overall survival (OS) in days for a 74 patient cohort with NSCLC stage Ia-IIa, classified by presence or absence of a copy number gain in FAM81B.
Figure 70:
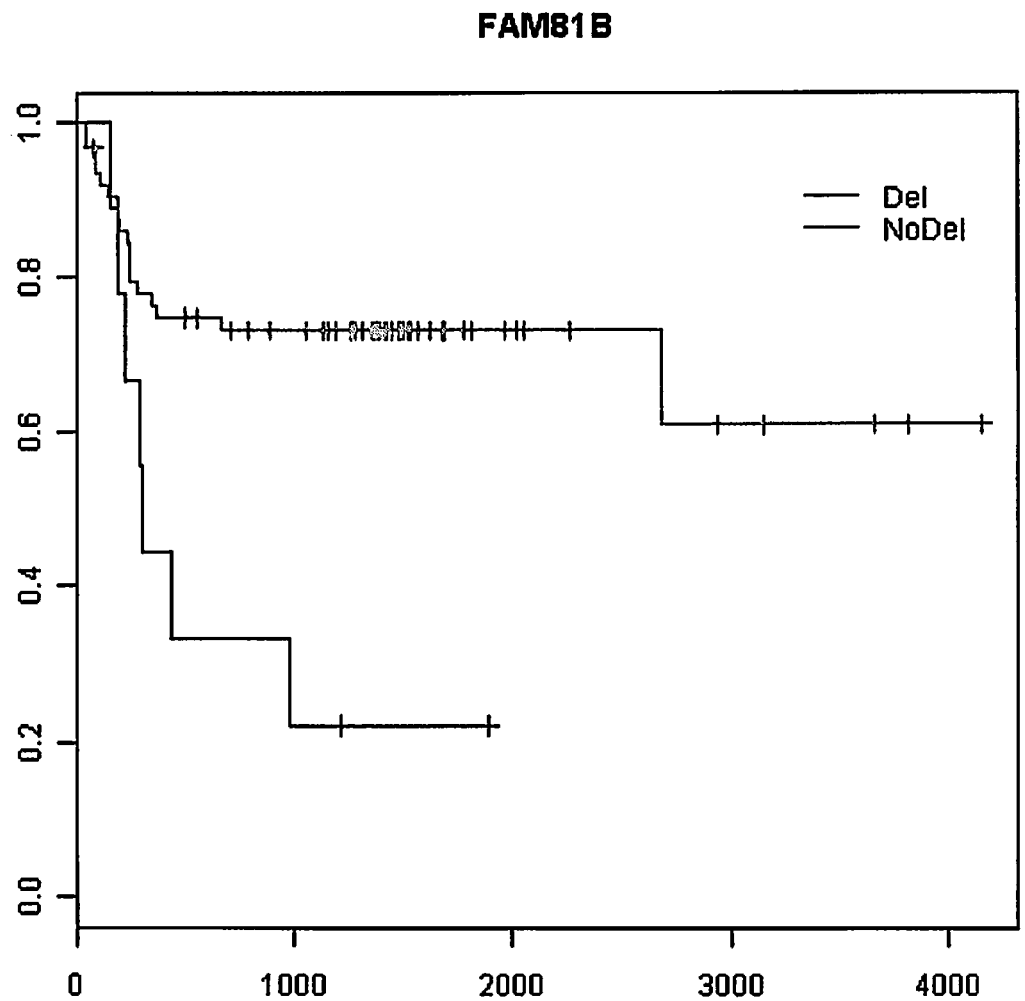
FIG. 70 is a Kaplan-Meier plot showing the time to recurrence (TTR) in days for a 74 patient cohort with NSCLC stage Ia-IIa, classified by presence or absence of a copy number gain in FAM81B.
Figure 71:
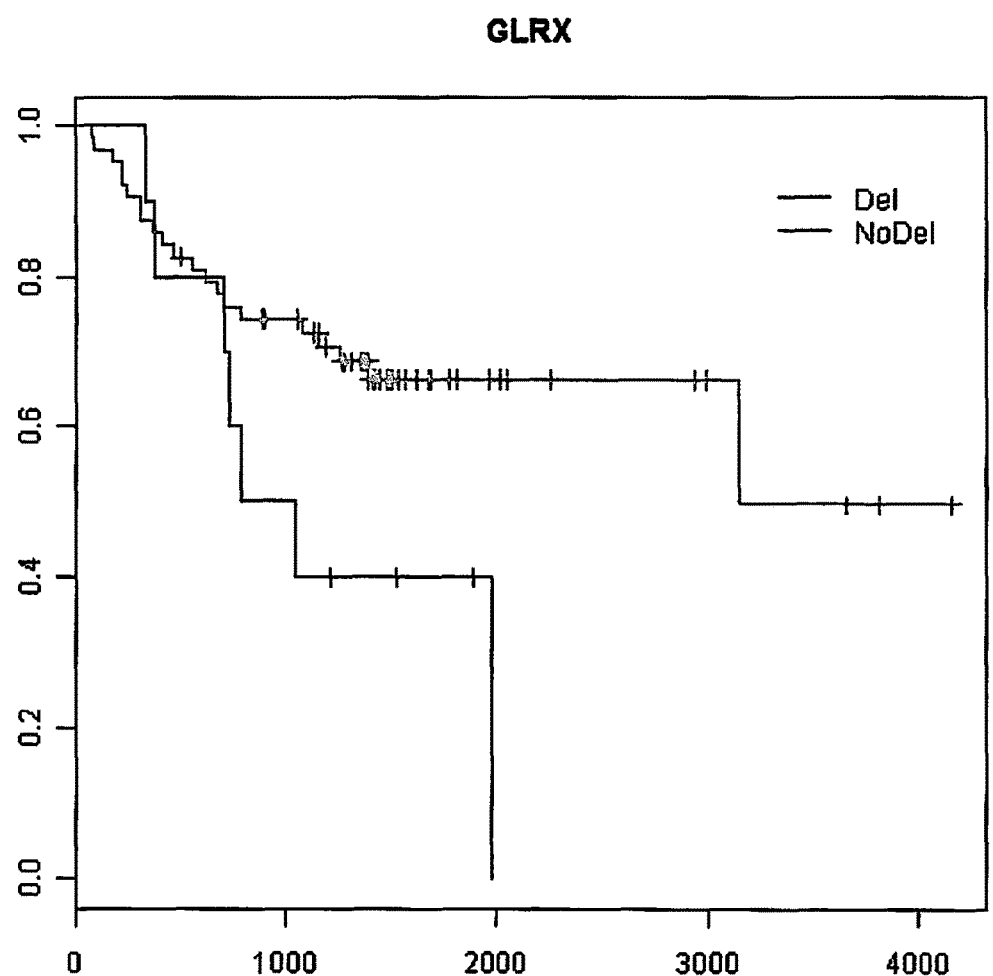
FIG. 71 is a Kaplan-Meier plot showing the overall survival (OS) in days for a 74 patient cohort with NSCLC stage Ia-IIa, classified by presence or absence of a copy number gain in GLRX.
Figure 72:
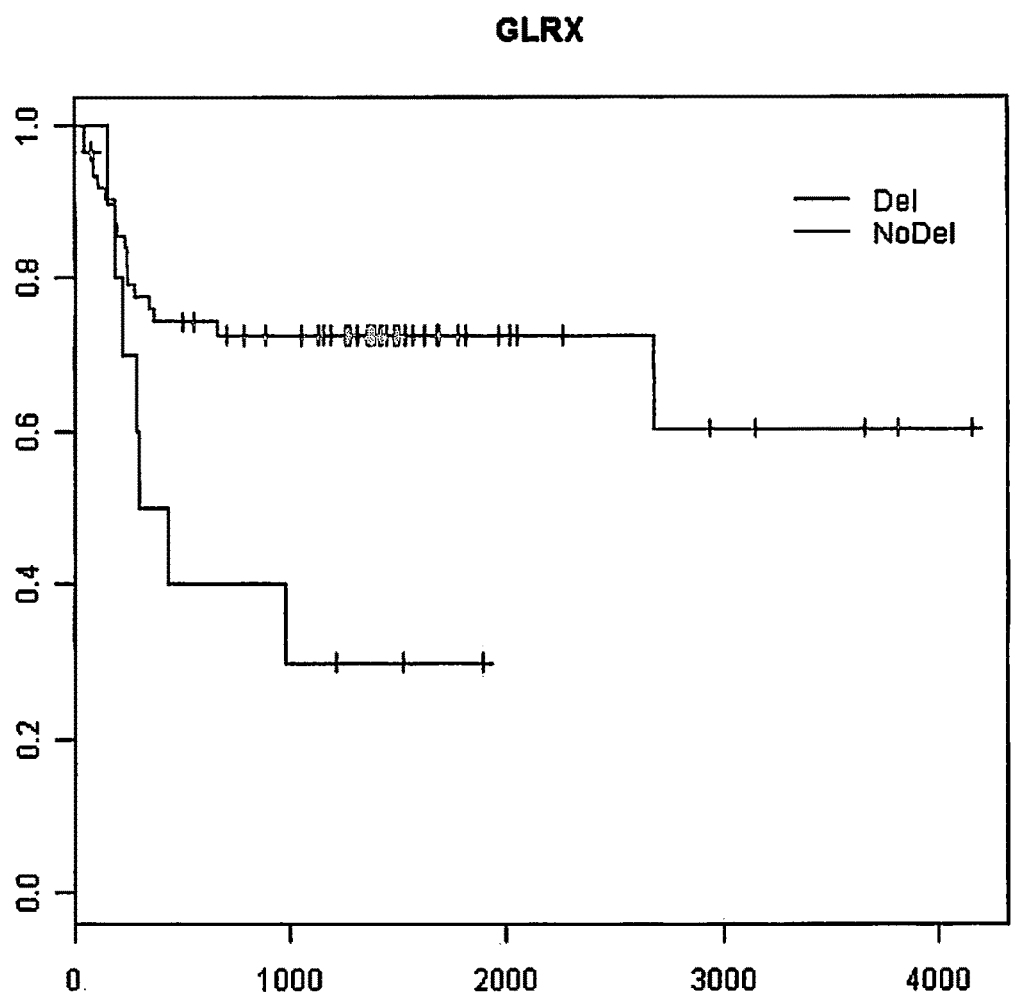
FIG. 72 is a Kaplan-Meier plot showing the time to recurrence (TTR) in days for a 74 patient cohort with NSCLC stage Ia-IIa, classified by presence or absence of a copy number gain in GLRX.
Figure 73:
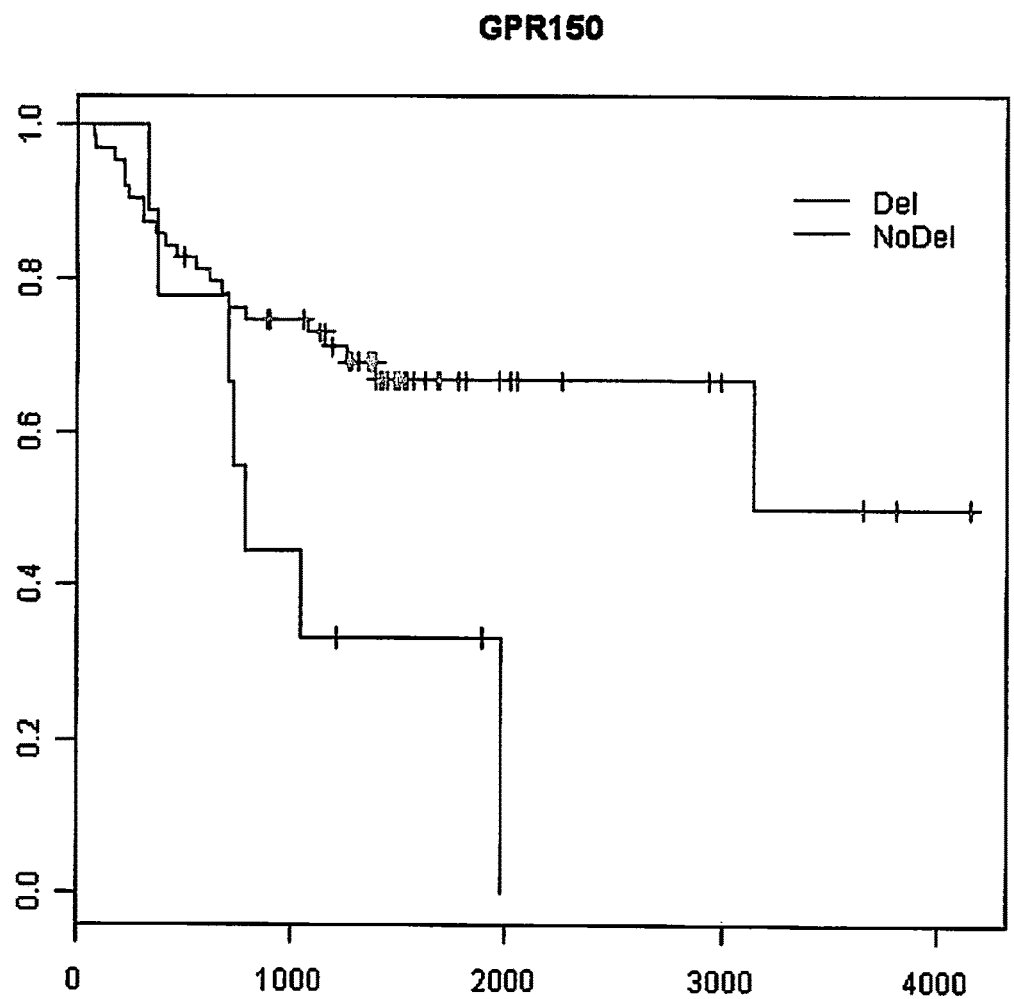
FIG. 73 is a Kaplan-Meier plot showing the overall survival (OS) in days for a 74 patient cohort with NSCLC stage Ia-IIa, classified by presence or absence of a copy number gain in GPR150.
Figure 74:
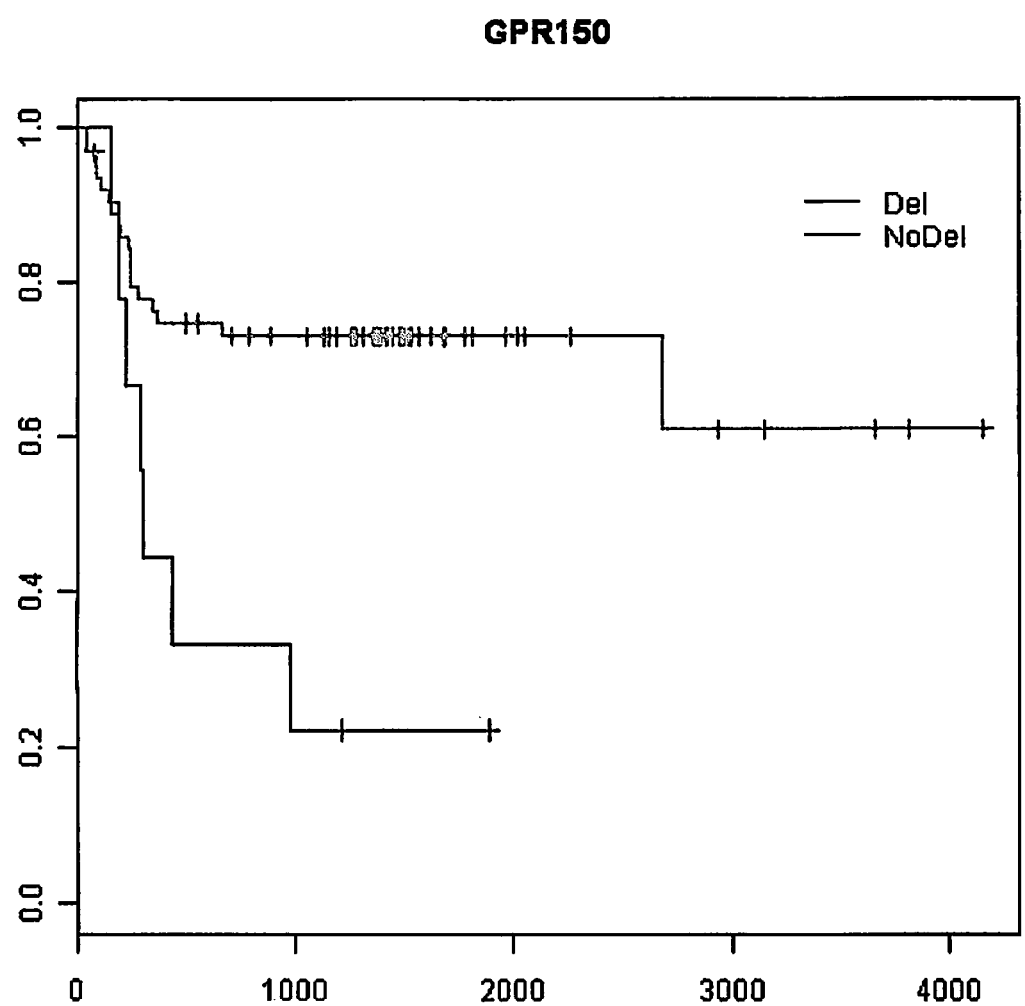
FIG. 74 is a Kaplan-Meier plot showing the time to recurrence (TTR) in days for a 74 patient cohort with NSCLC stage Ia-IIa, classified by presence or absence of a copy number gain in GPR150.
Figure 75:
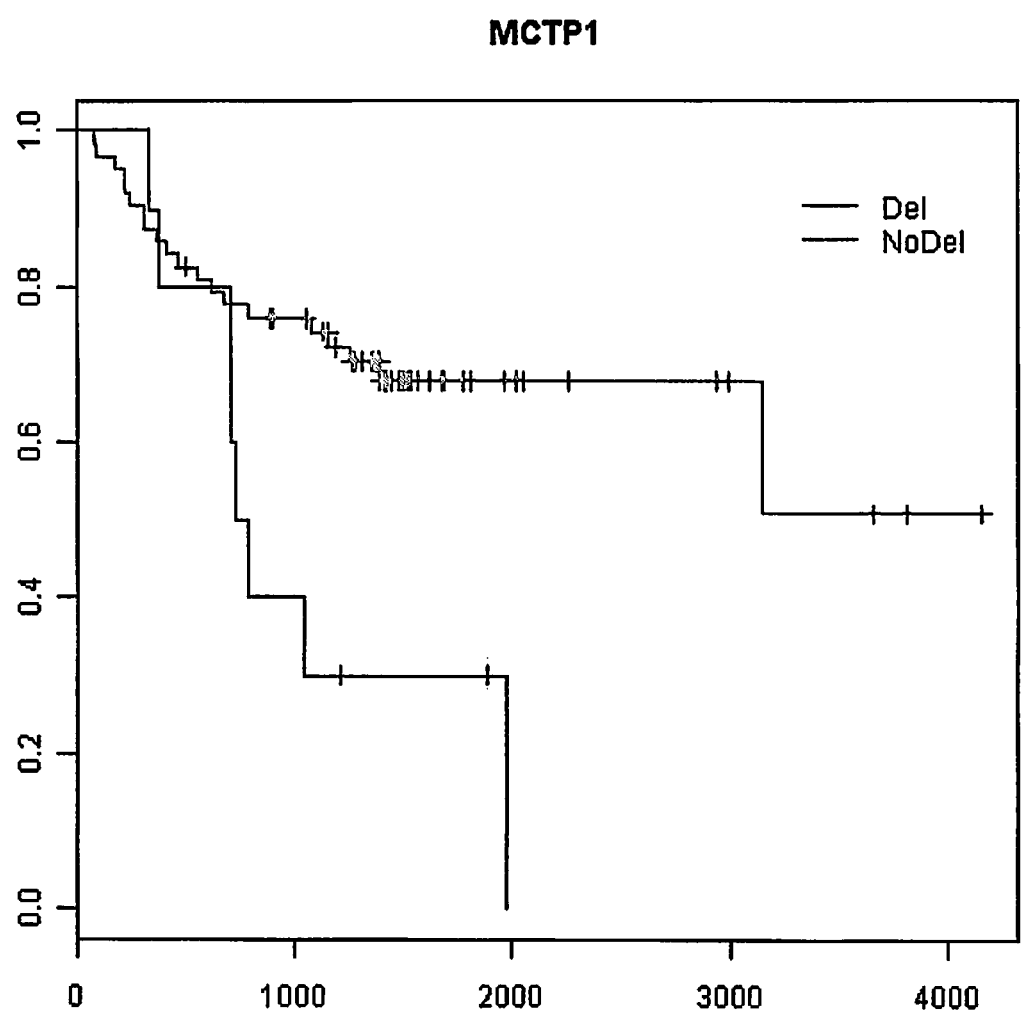
FIG. 75 is a Kaplan-Meier plot showing the overall survival (OS) in days for a 74 patient cohort with NSCLC stage Ia-IIa, classified by presence or absence of a copy number gain in MCTP1.
Figure 76:
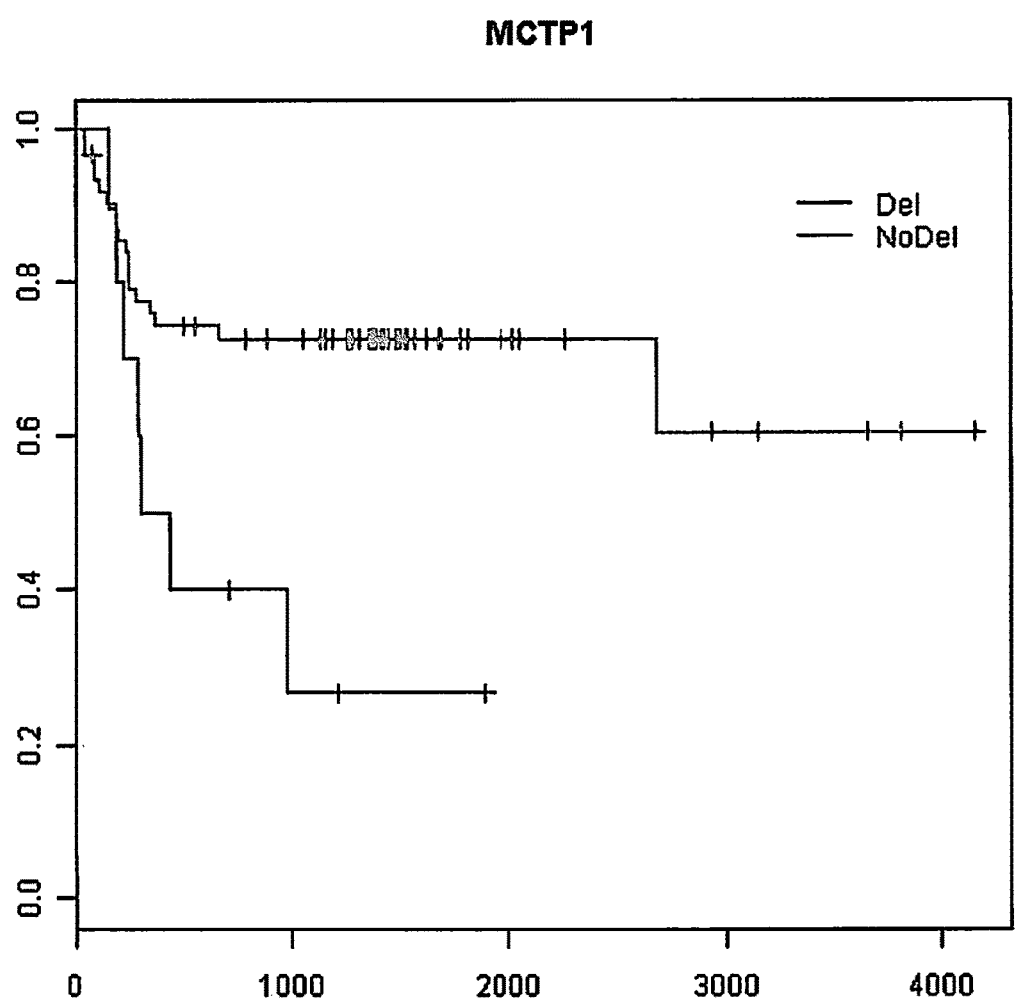
FIG. 76 is a Kaplan-Meier plot showing the time to recurrence (TTR) in days for a 74 patient cohort with NSCLC stage Ia-IIa, classified by presence or absence of a copy number gain in MCTP1.
Figure 77:
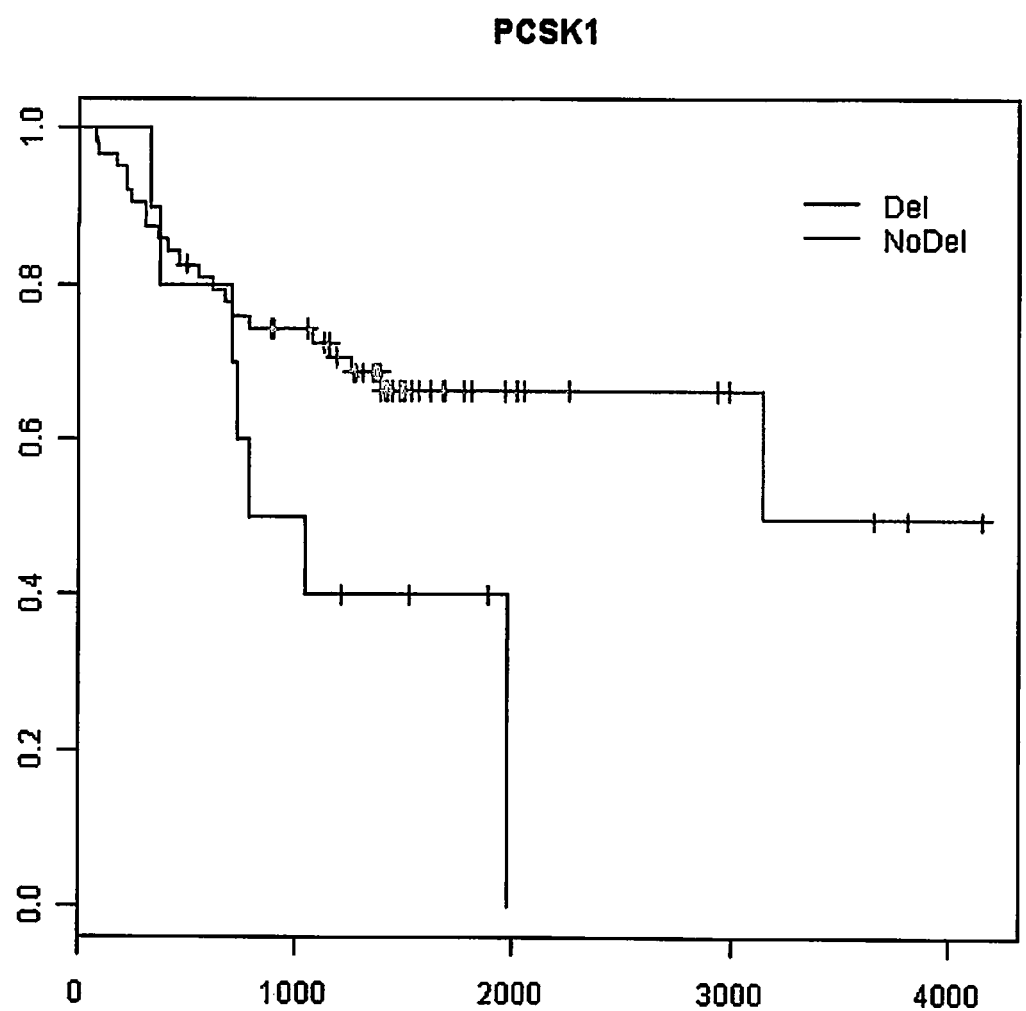
FIG. 77 is a Kaplan-Meier plot showing the overall survival (OS) in days for a 74 patient cohort with NSCLC stage Ia-IIa, classified by presence or absence of a copy number gain in PCSK1.
Figure 78:
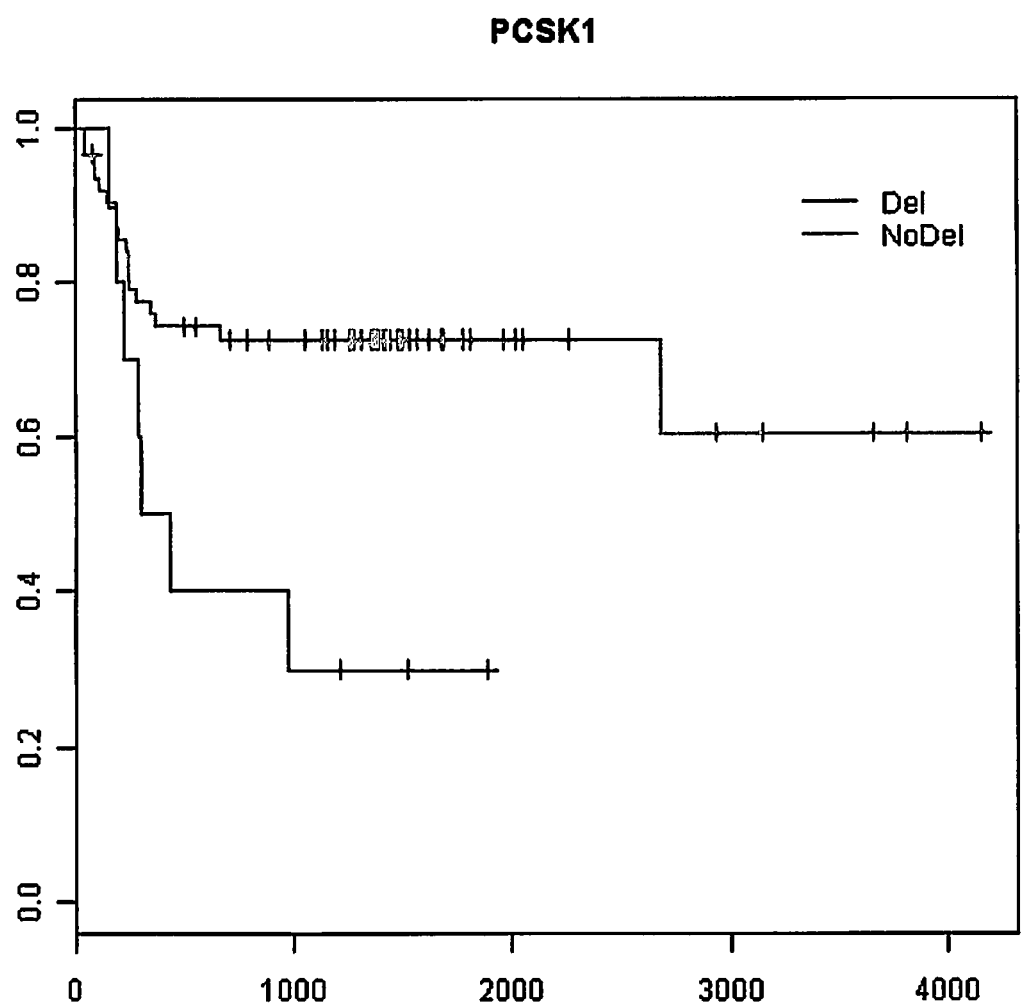
FIG. 78 is a Kaplan-Meier plot showing the time to recurrence (TTR) in days for a 74 patient cohort with NSCLC stage Ia-IIa, classified by presence or absence of a copy number gain in PCSK1.
Figure 79:
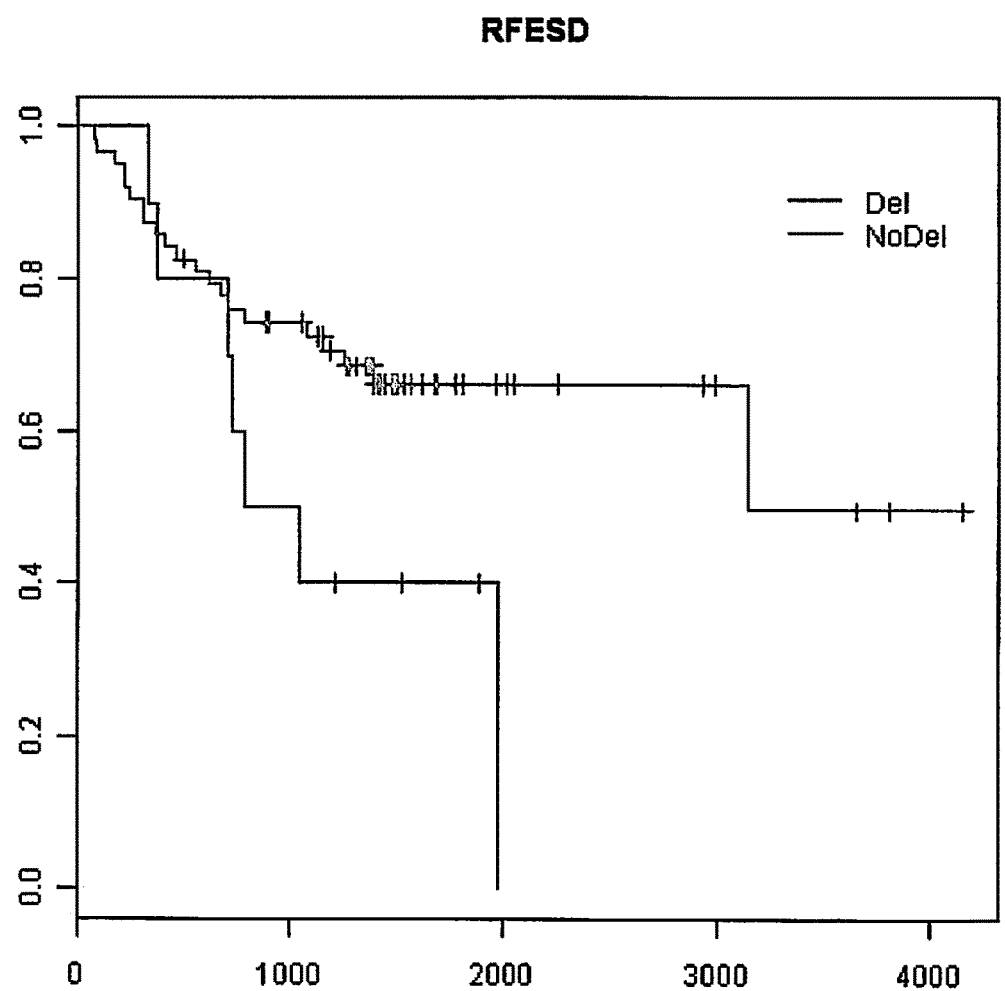
FIG. 79 is a Kaplan-Meier plot showing the overall survival (OS) in days for a 74 patient cohort with NSCLC stage Ia-IIa, classified by presence or absence of a copy number gain in RFESD.
Figure 80:
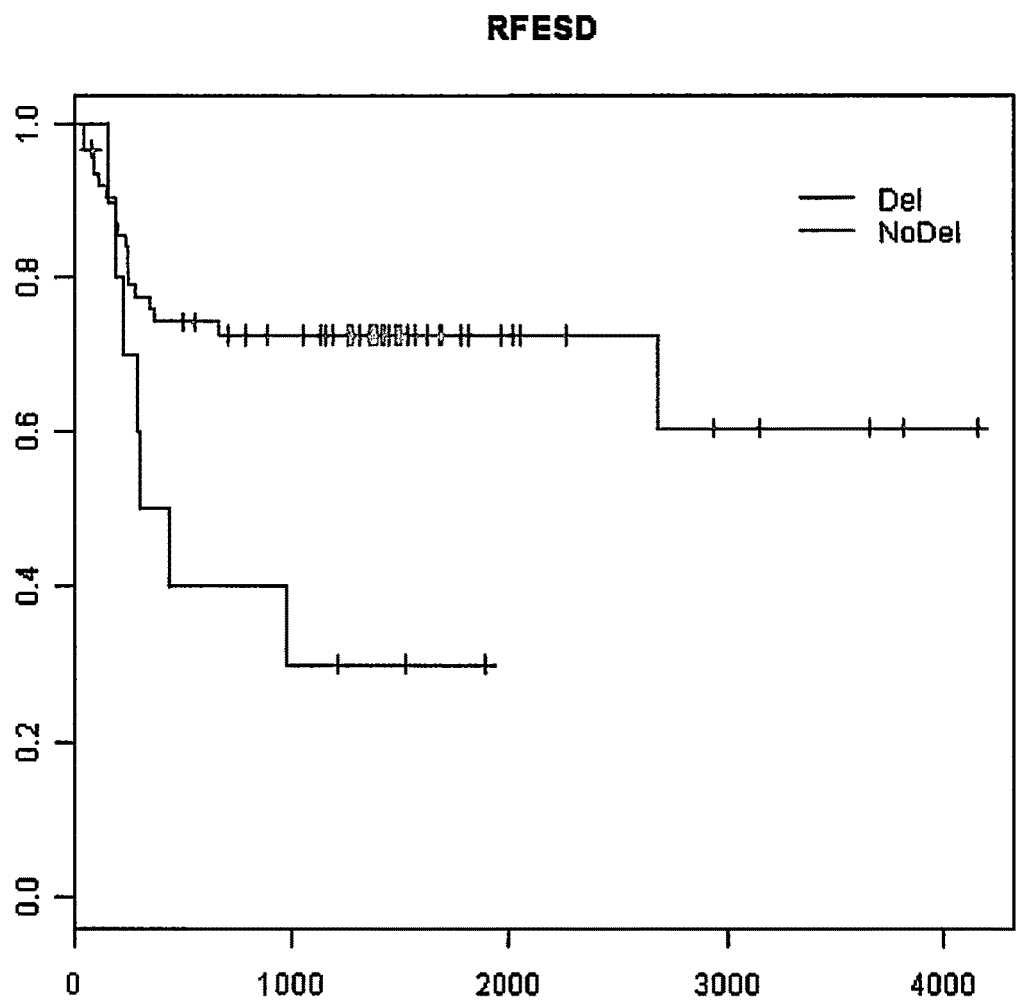
FIG. 80 is a Kaplan-Meier plot showing the time to recurrence (TTR) in days for a 74 patient cohort with NSCLC stage Ia-IIa, classified by presence or absence of a copy number gain in RFESD.
Figure 81:
FIG. 81 is a Kaplan-Meier plot showing the overall survival (OS) in days for a 74 patient cohort with NSCLC stage Ia-IIa, classified by presence or absence of a copy number gain in RHOBTB3.
Figure 82:
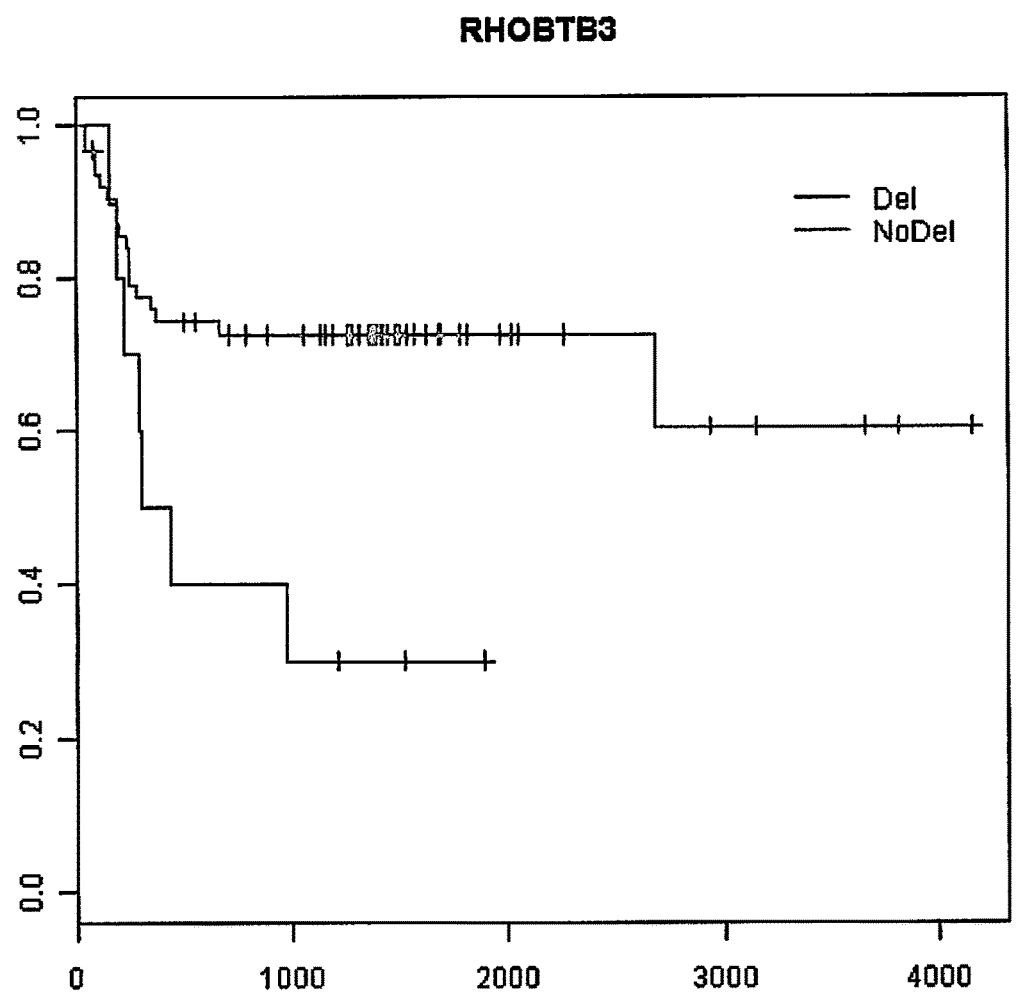
FIG. 82 is a Kaplan-Meier plot showing the time to recurrence (TTR) in days for a 74 patient cohort with NSCLC stage Ia-IIa, classified by presence or absence of a copy number gain in RHOBTB3.
Figure 83:
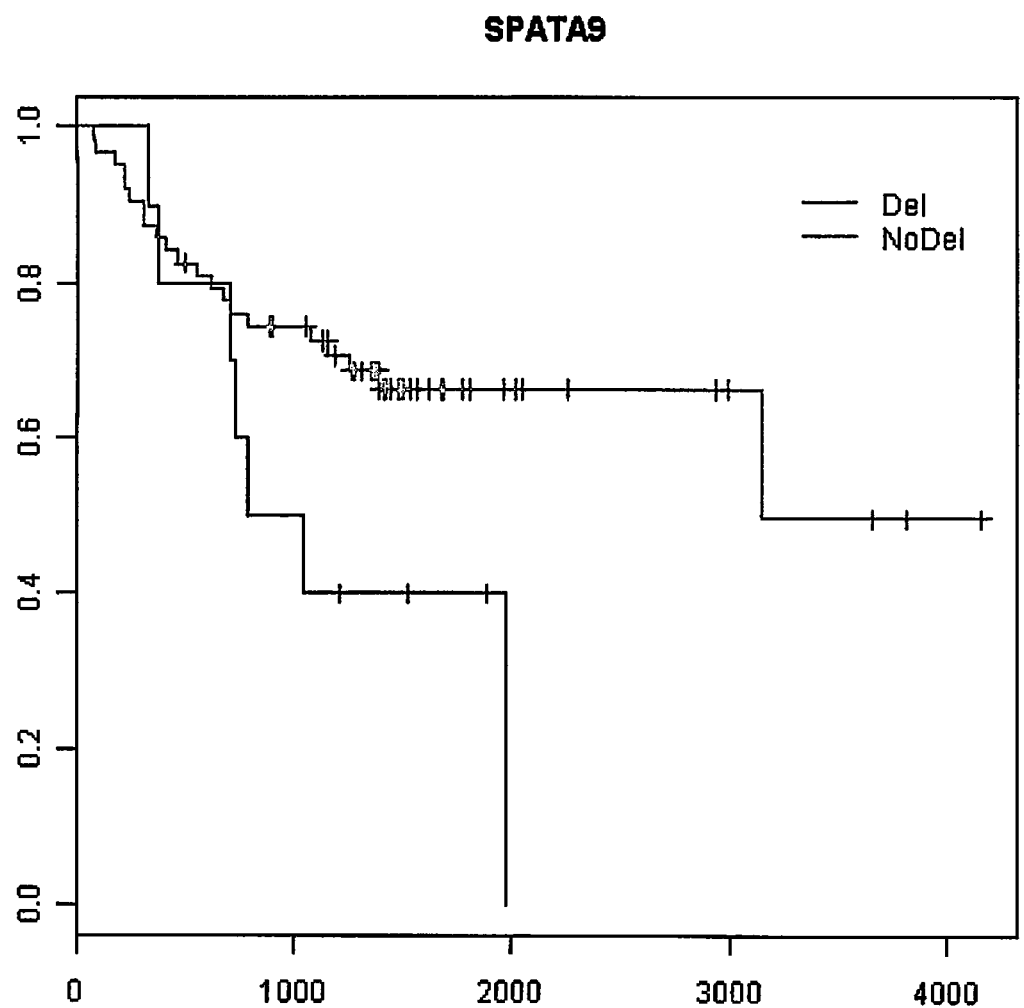
FIG. 83 is a Kaplan-Meier plot showing the overall survival (OS) in days for a 74 patient cohort with NSCLC stage Ia-IIa, classified by presence or absence of a copy number gain in SPATA9.
Figure 84:
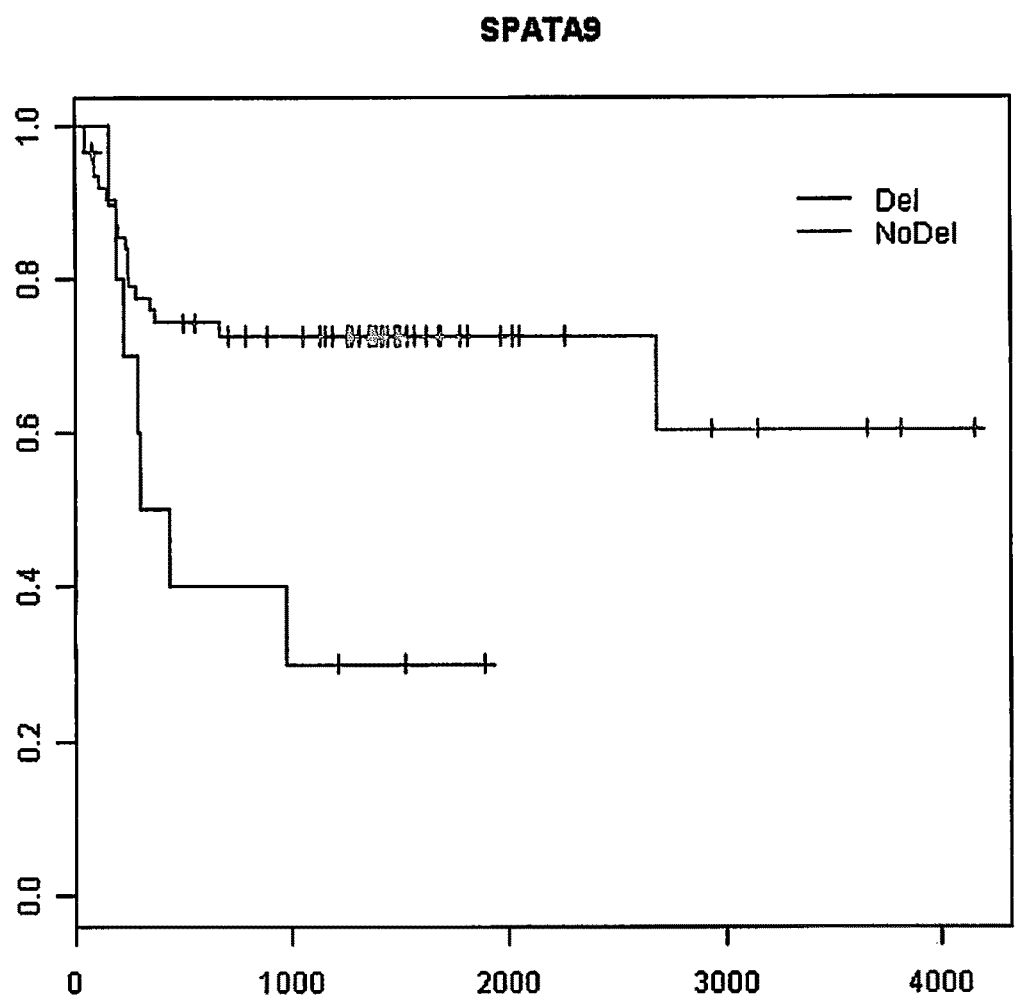
FIG. 84 is a Kaplan-Meier plot showing the time to recurrence (TTR) in days for a 74 patient cohort with NSCLC stage Ia-IIa, classified by presence or absence of a copy number gain in SPATA9.
Figure 85:
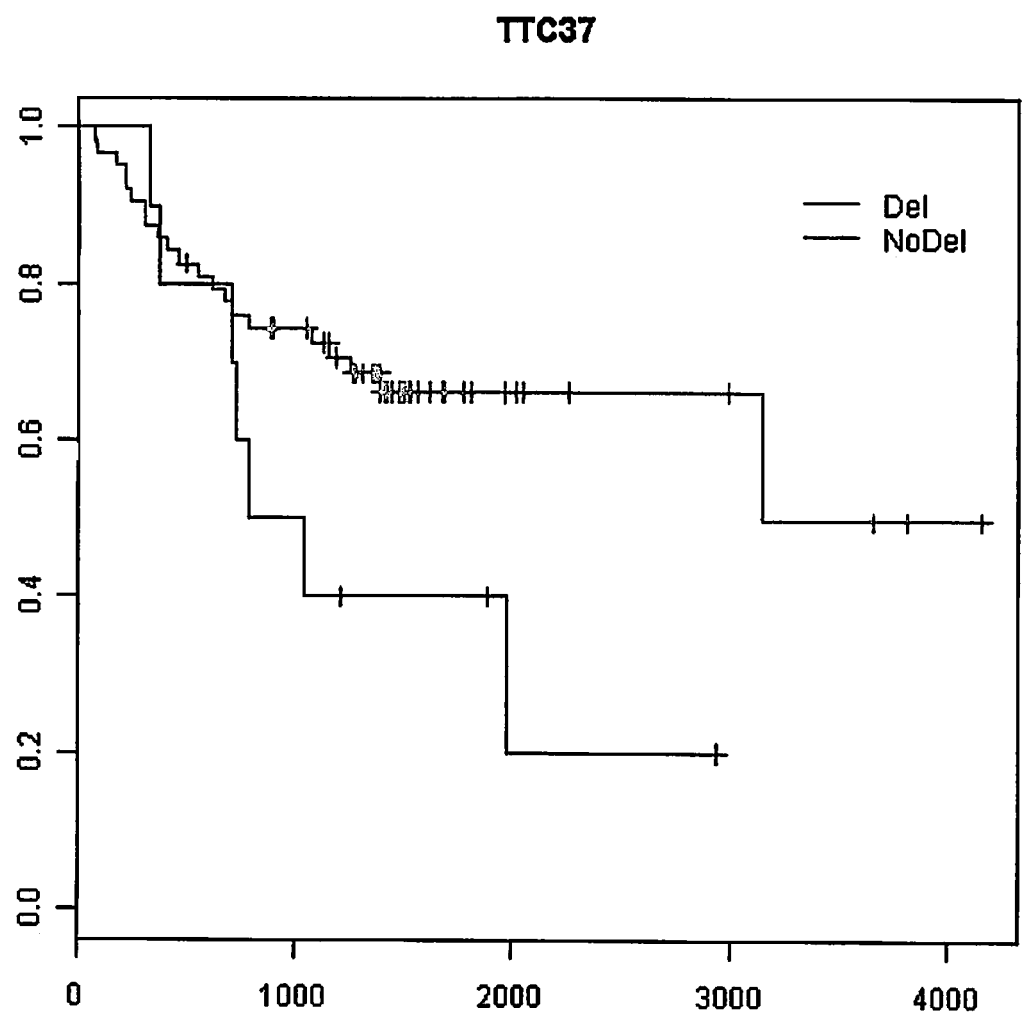
FIG. 85 is a Kaplan-Meier plot showing the overall survival (OS) in days for a 74 patient cohort with NSCLC stage Ia-IIa, classified by presence or absence of a copy number gain in TTC37.
Figure 86:
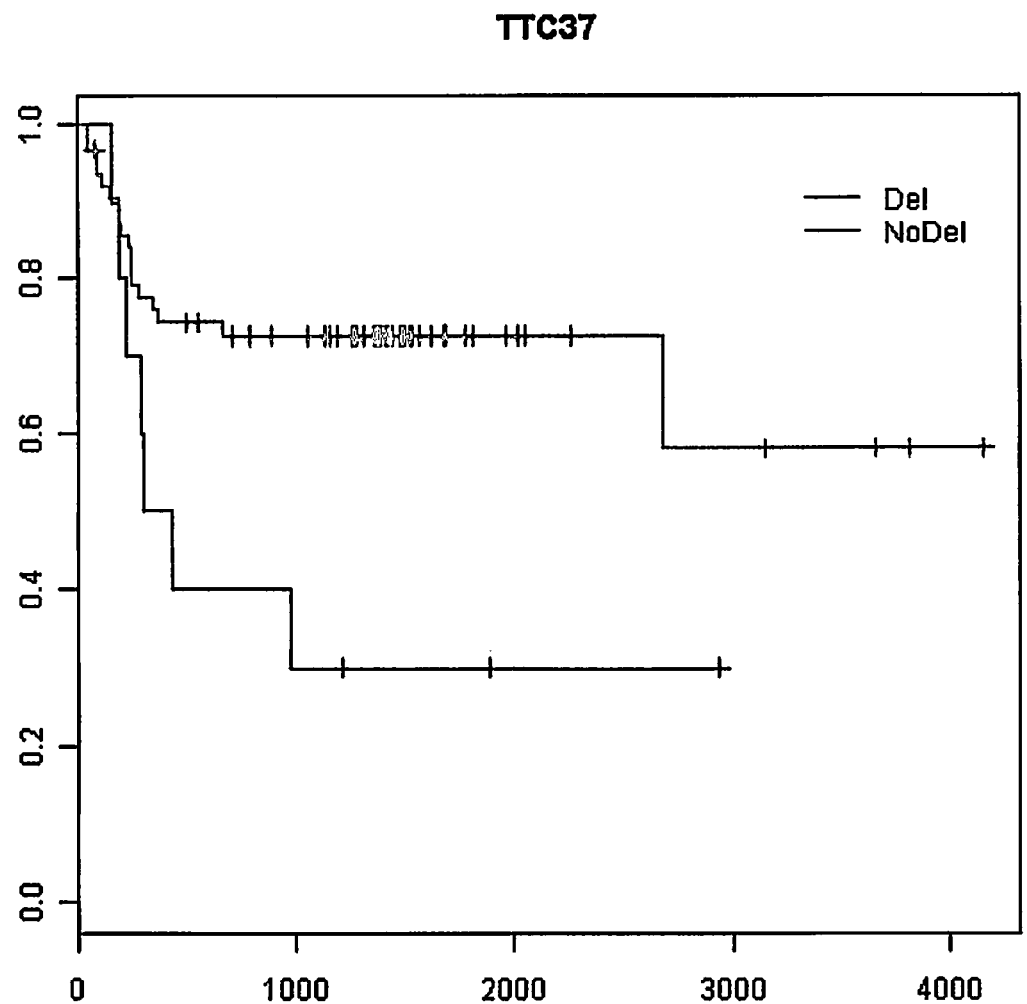
FIG. 86 is a Kaplan-Meier plot showing the time to recurrence (TTR) in days for a 74 patient cohort with NSCLC stage Ia-IIa, classified by presence or absence of a copy number gain in TTC37.
Figure 87:
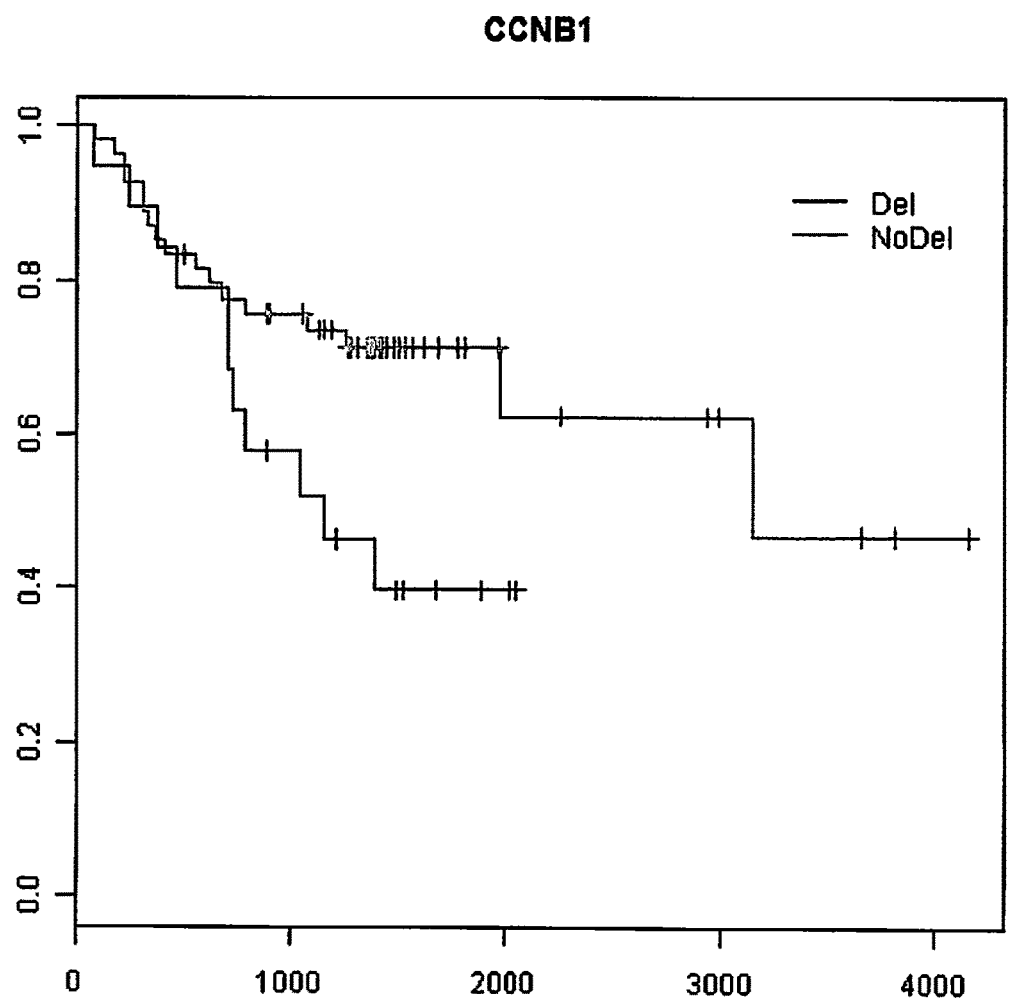
FIG. 87 is a Kaplan-Meier plot showing the overall survival (OS) in days for a 74 patient cohort with NSCLC stage Ia-IIa, classified by presence or absence of a copy number gain in CCNB1.
Figure 88:
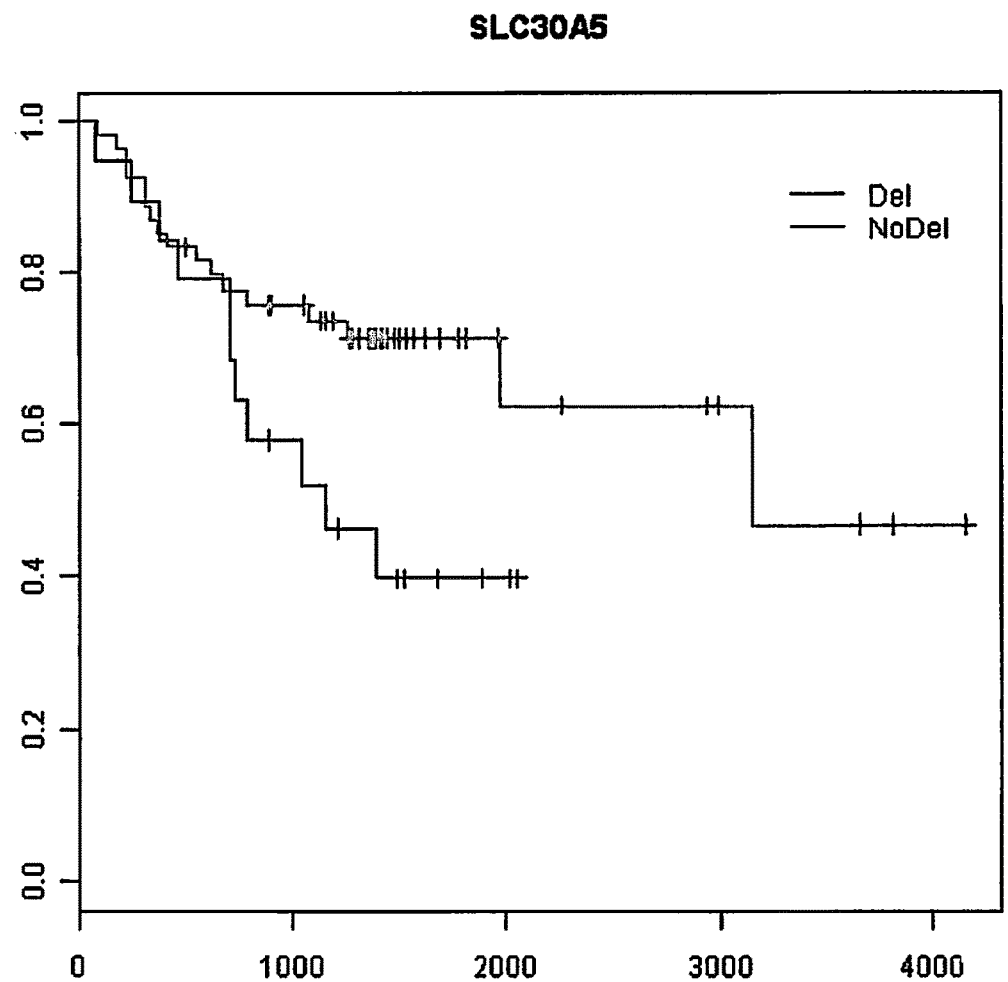
FIG. 88 is a Kaplan-Meier plot showing the overall survival (OS) in days for a 74 patient cohort with NSCLC stage Ia-IIa, classified by presence or absence of a copy number gain in SLC30A5.
Figure 89:
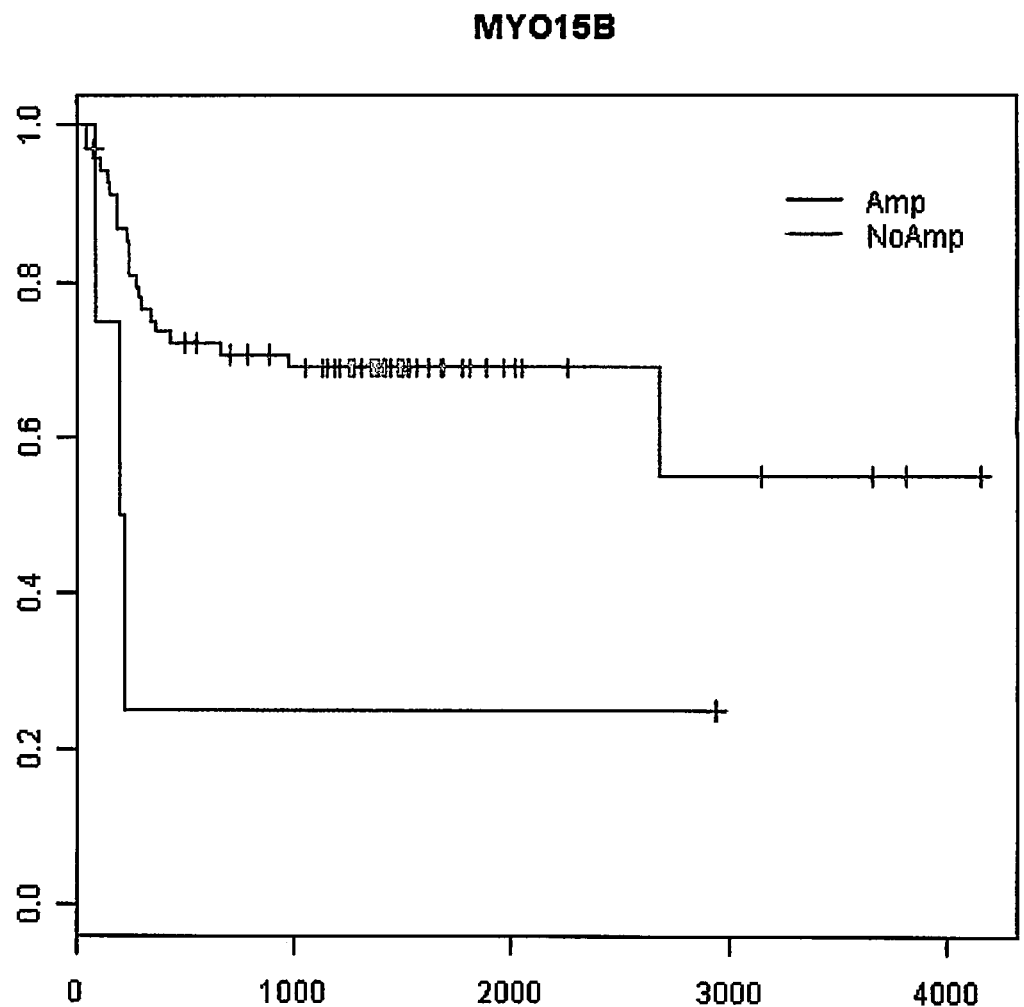
FIG. 89 is a Kaplan-Meier plot showing the time to recurrence (TTR) in days for a 74 patient cohort with NSCLC stage Ia-IIa, classified by presence or absence of a copy number gain in MYO15B.
Figure 90:
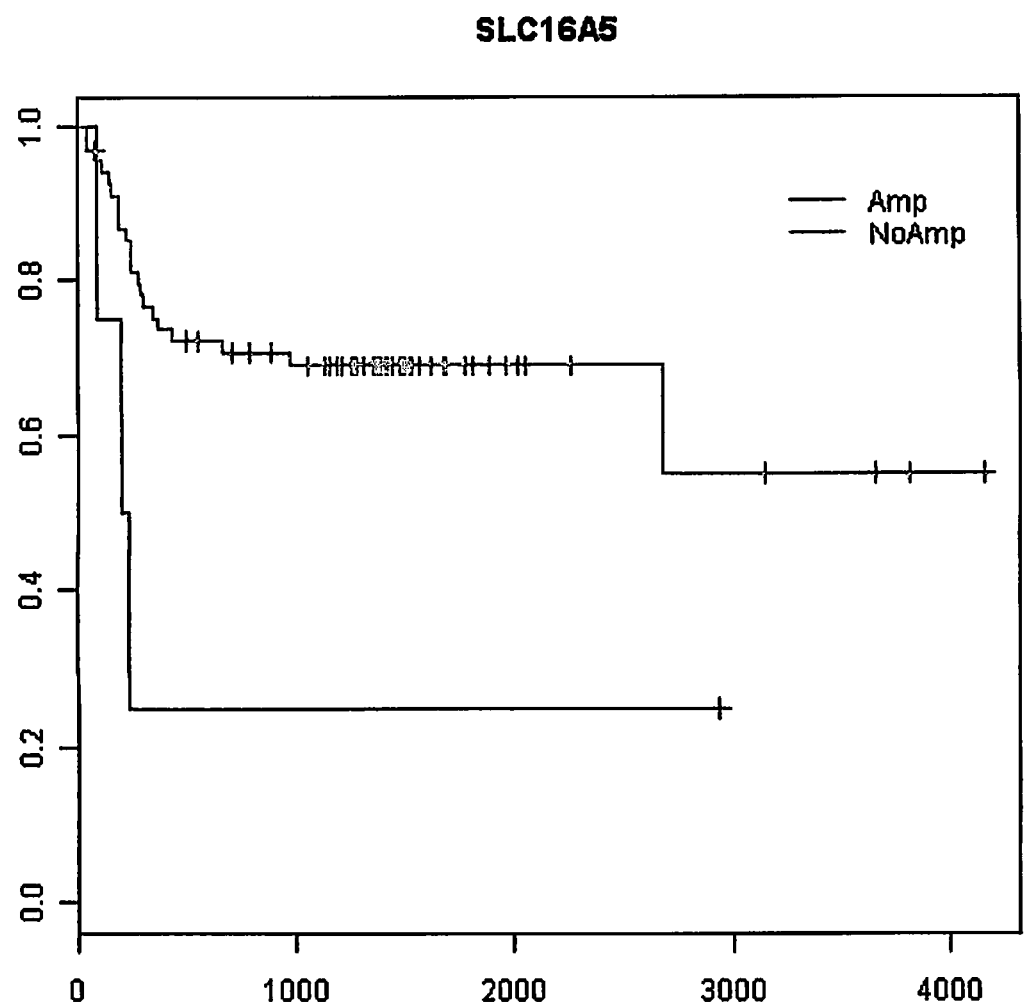
FIG. 90 is a Kaplan-Meier plot showing the time to recurrence (TTR) in days for a 74 patient cohort with NSCLC stage Ia-IIa, classified by presence or absence of a copy number gain in SLC16A5.
Figure 91:
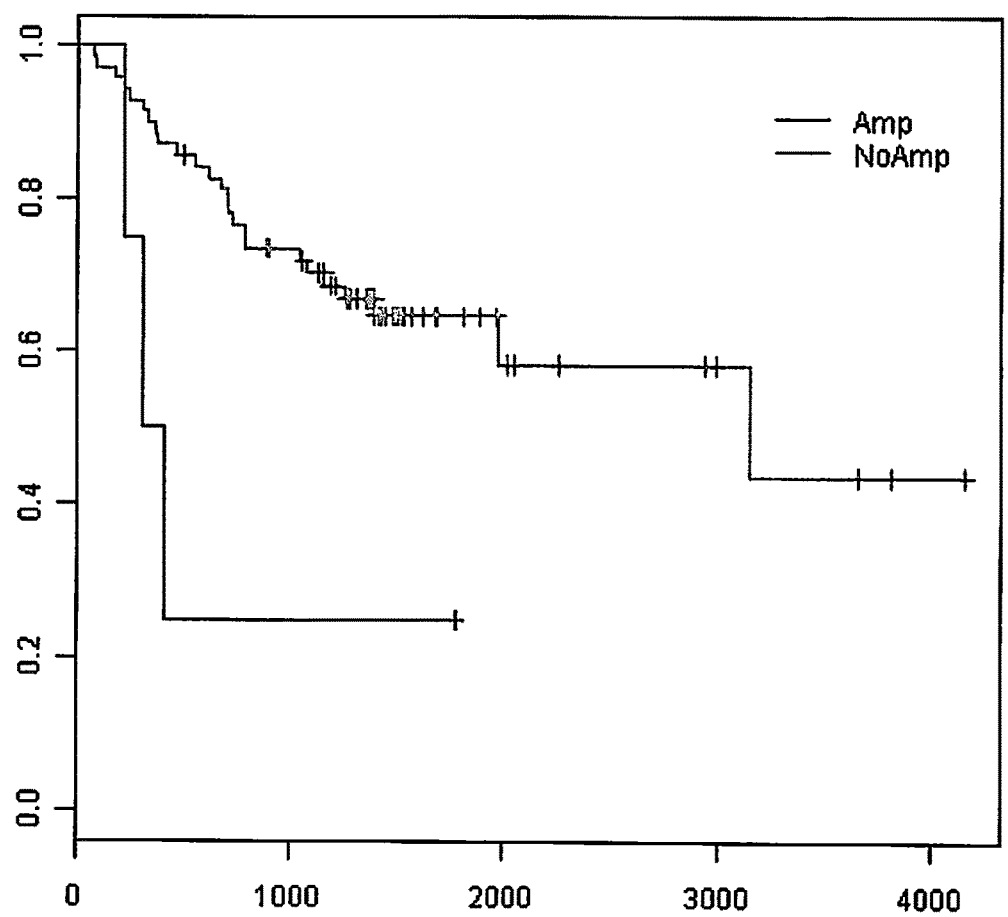
FIG. 91 is a Kaplan-Meier plot showing the overall survival (OS) in days for a 74 patient cohort with NSCLC stage Ia-IIa, classified by presence or absence of a copy number gain in DKFZp761E198.
Figure 92:
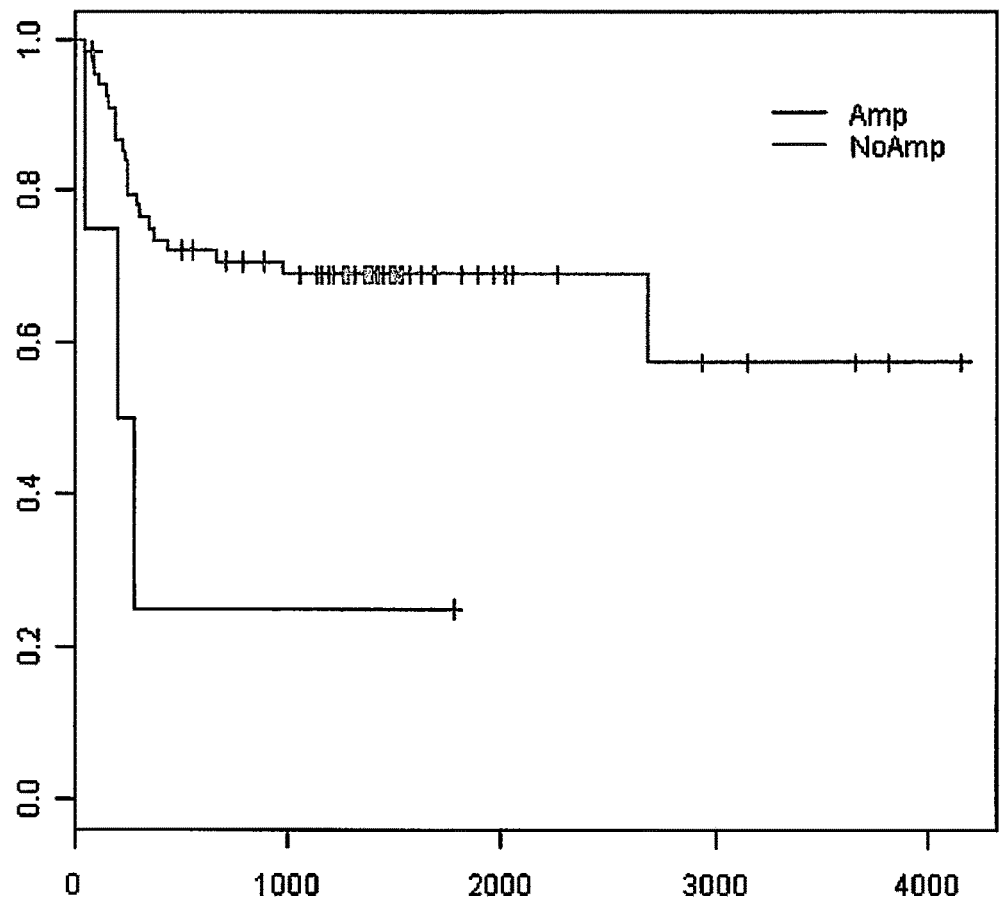
FIG. 92 is a Kaplan-Meier plot showing the time to recurrence (TTR) in days for a 74 patient cohort with NSCLC stage Ia-IIa, classified by presence or absence of a copy number gain in DKFZp761E198.
Figure 93:
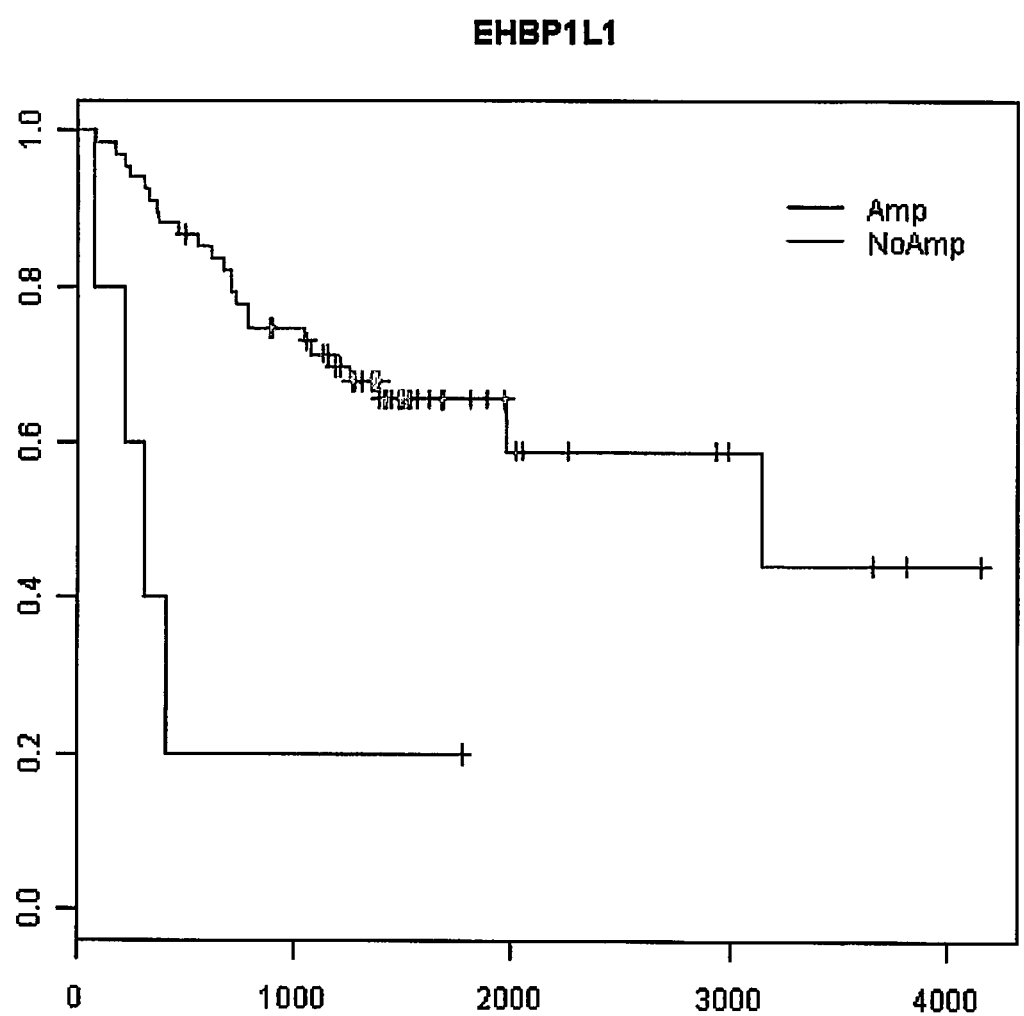
FIG. 93 is a Kaplan-Meier plot showing the overall survival (OS) in days for a 74 patient cohort with NSCLC stage Ia-IIa, classified by presence or absence of a copy number gain in EHBP1L1.
Figure 94:
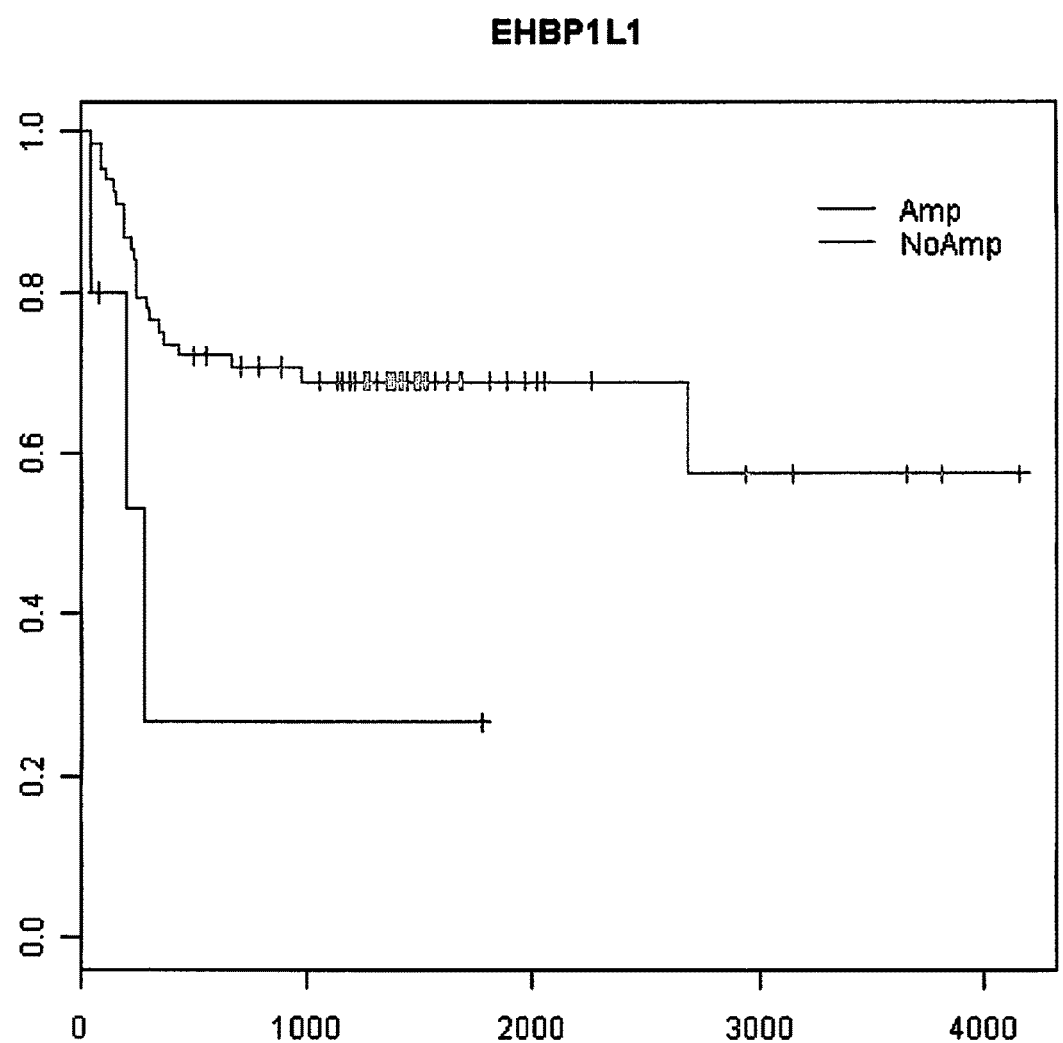
FIG. 94 is a Kaplan-Meier plot showing the time to recurrence (TTR) in days for a 74 patient cohort with NSCLC stage Ia-IIa, classified by presence or absence of a copy number gain in EHBP1L1.
Figure 95:
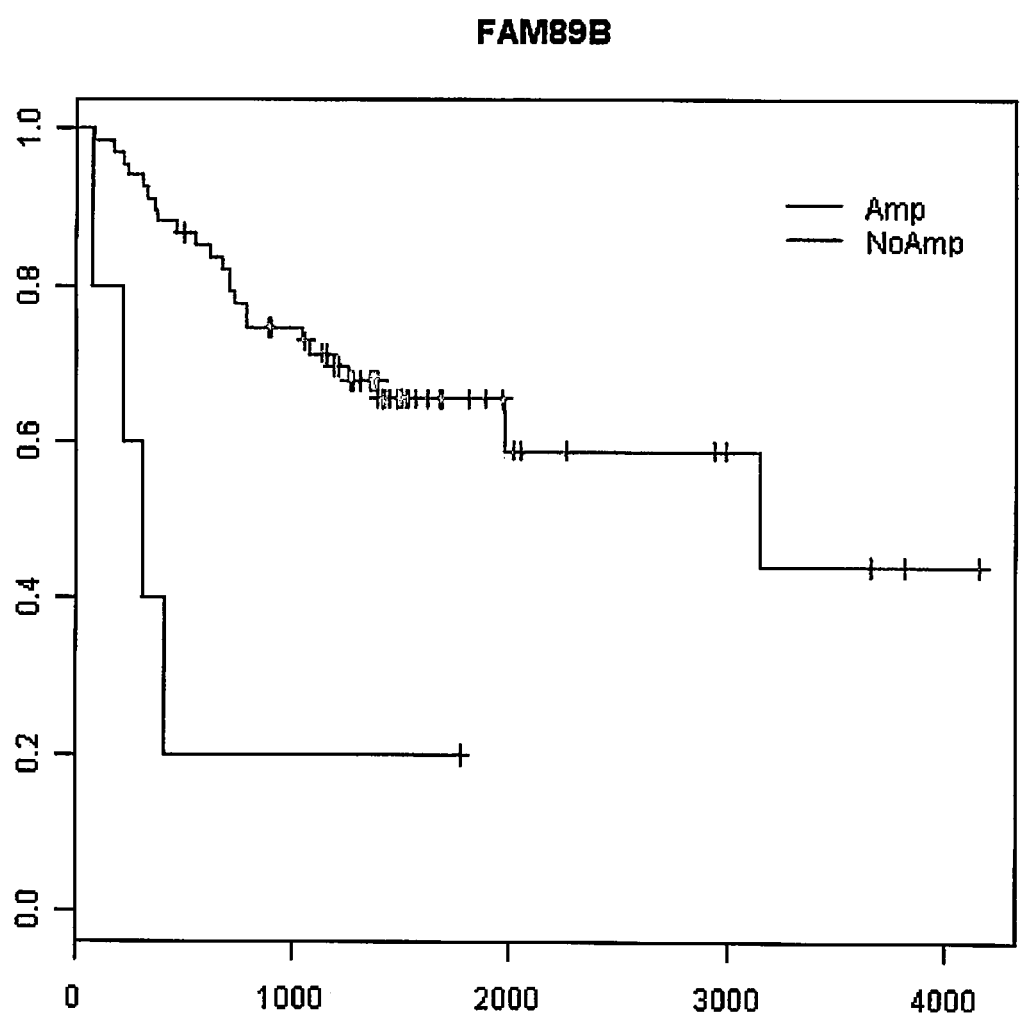
FIG. 95 is a Kaplan-Meier plot showing the overall survival (OS) in days for a 74 patient cohort with NSCLC stage Ia-IIa, classified by presence or absence of a copy number gain in FAM89B.
Figure 96:
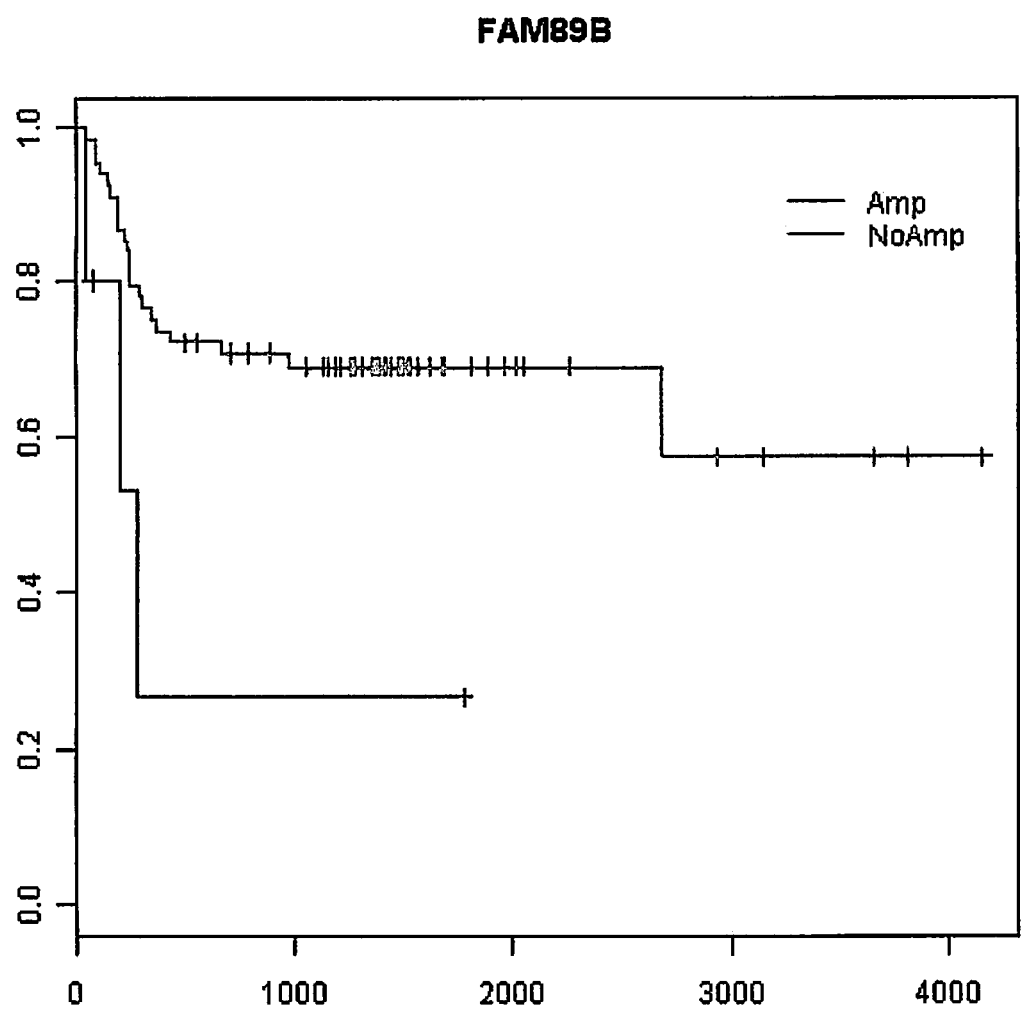
FIG. 96 is a Kaplan-Meier plot showing the time to recurrence (TTR) in days for a 74 patient cohort with NSCLC stage Ia-IIa, classified by presence or absence of a copy number gain in FAM89B.
Figure 97:
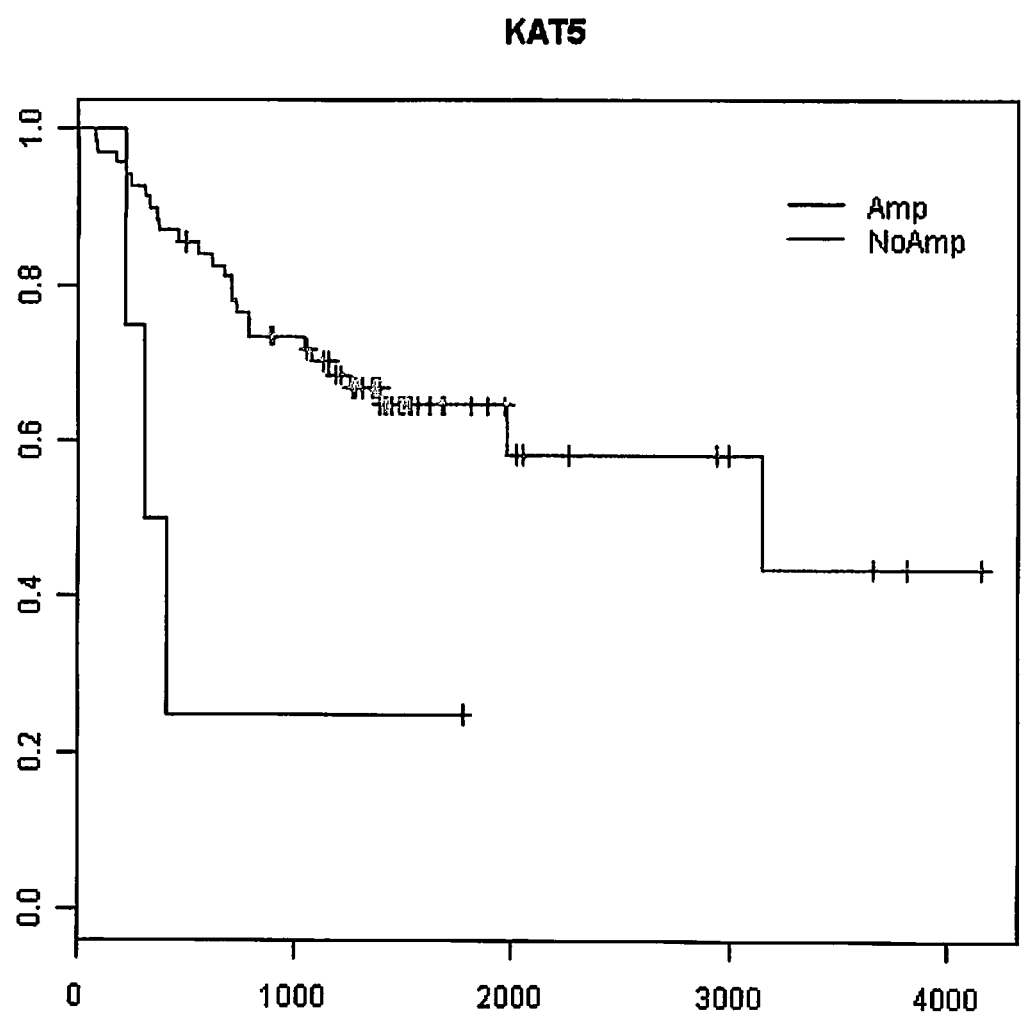
FIG. 97 is a Kaplan-Meier plot showing the overall survival (OS) in days for a 74 patient cohort with NSCLC stage Ia-IIa, classified by presence or absence of a copy number gain in KAT5.
Figure 98:
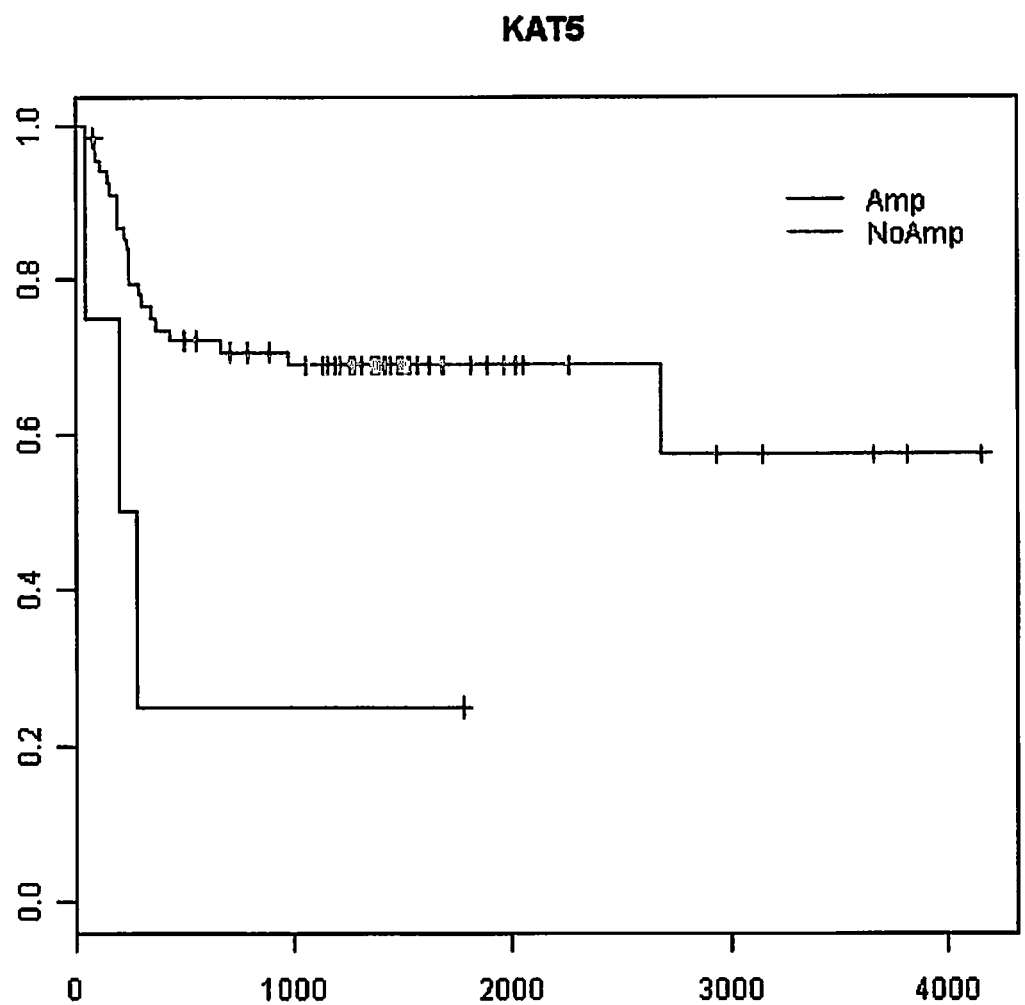
FIG. 98 is a Kaplan-Meier plot showing the time to recurrence (TTR) in days for a 74 patient cohort with NSCLC stage Ia-IIa, classified by presence or absence of a copy number gain in KAT5.
Figure 99:
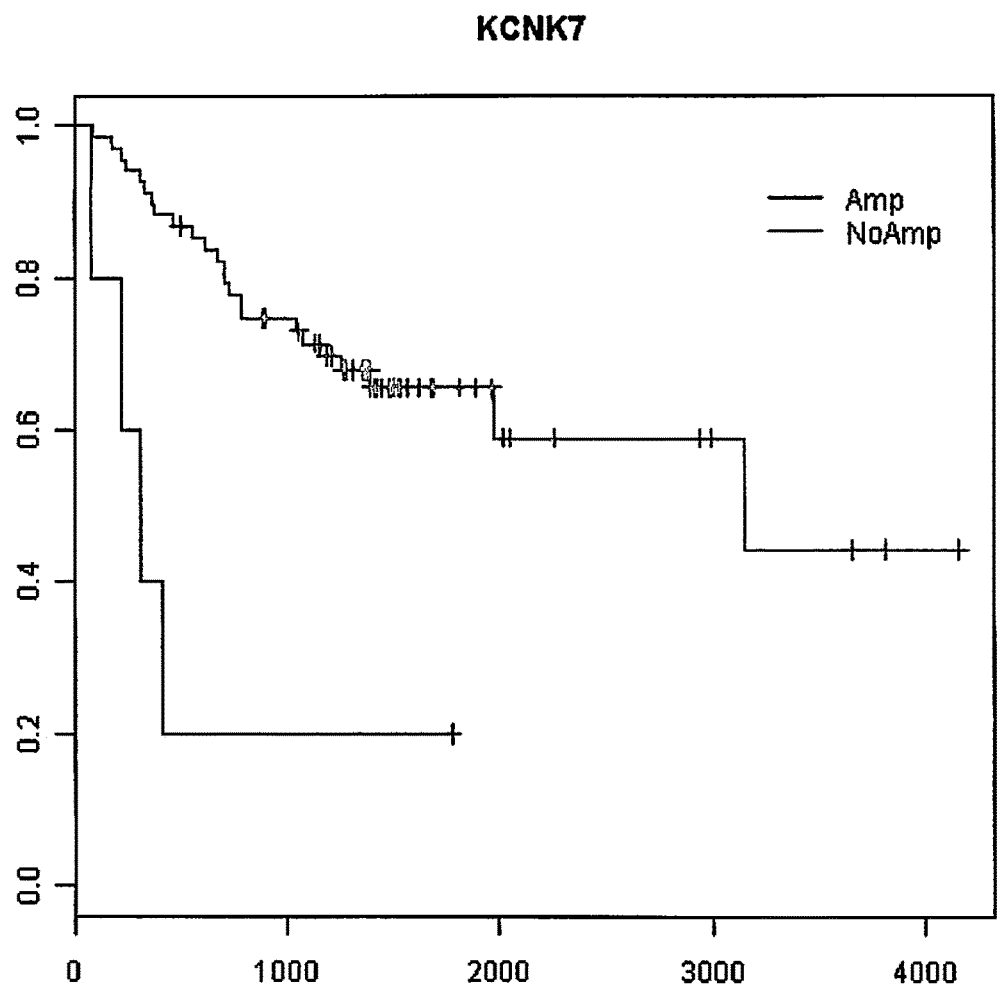
FIG. 99 is a Kaplan-Meier plot showing the overall survival (OS) in days for a 74 patient cohort with NSCLC stage Ia-IIa, classified by presence or absence of a copy number gain in KCNK7.
Figure 100:
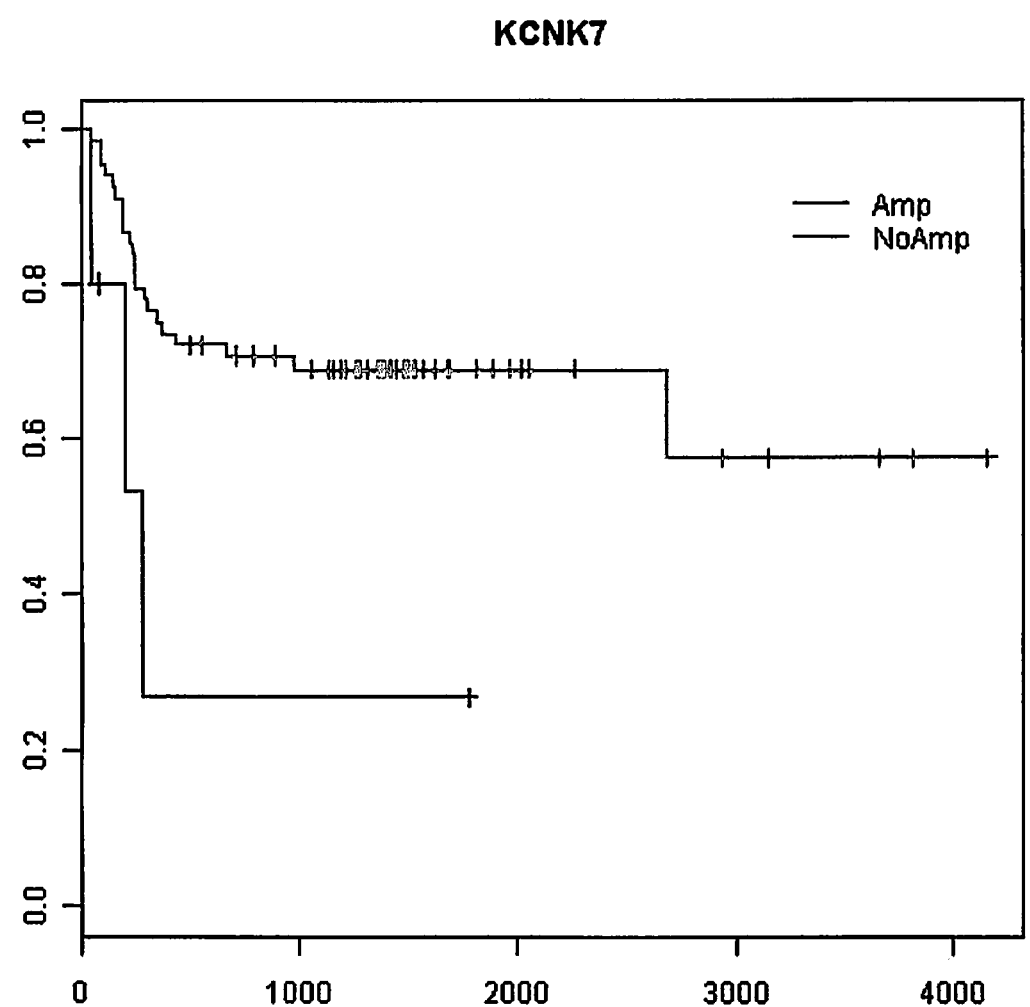
FIG. 100 is a Kaplan-Meier plot showing the time to recurrence (TTR) in days for a 74 patient cohort with NSCLC stage Ia-IIa, classified by presence or absence of a copy number gain in KCNK7.
Figure 101:
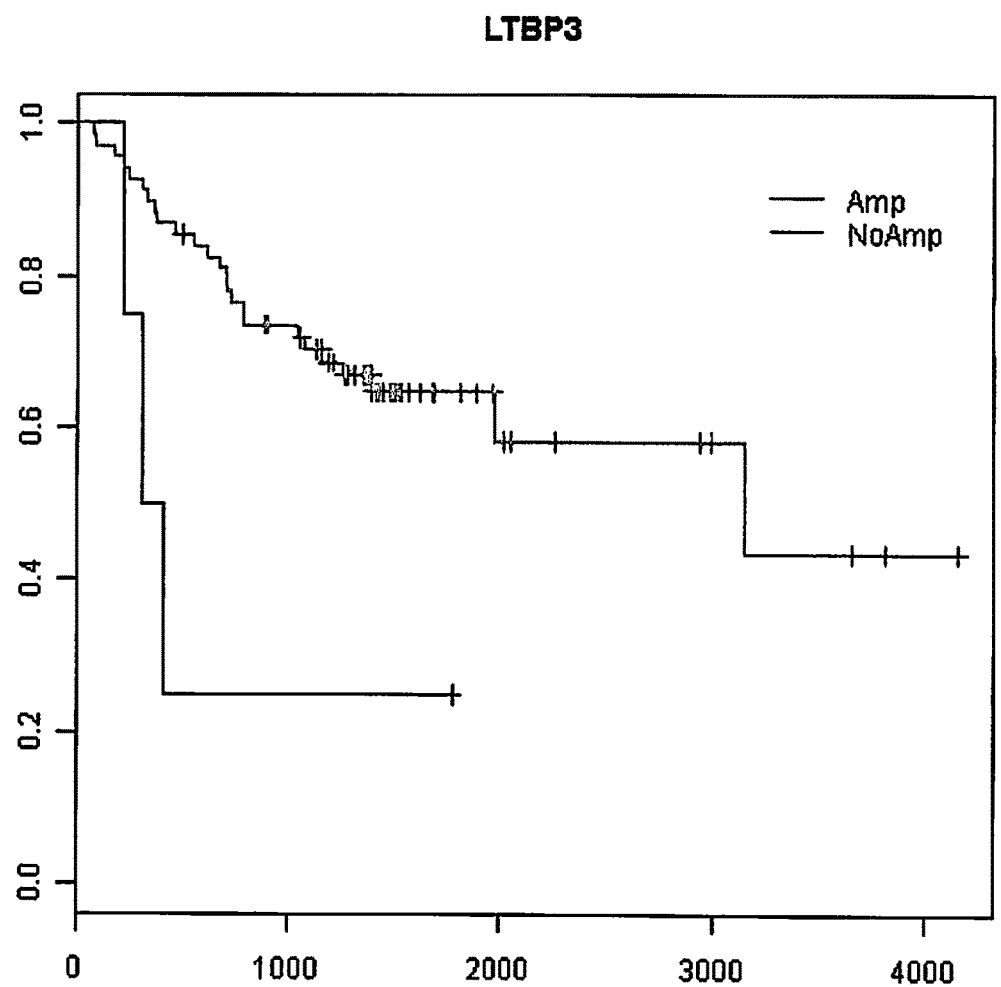
FIG. 101 is a Kaplan-Meier plot showing the overall survival (OS) in days for a 74 patient cohort with NSCLC stage Ia-IIa, classified by presence or absence of a copy number gain in LTBP3.
Figure 102:
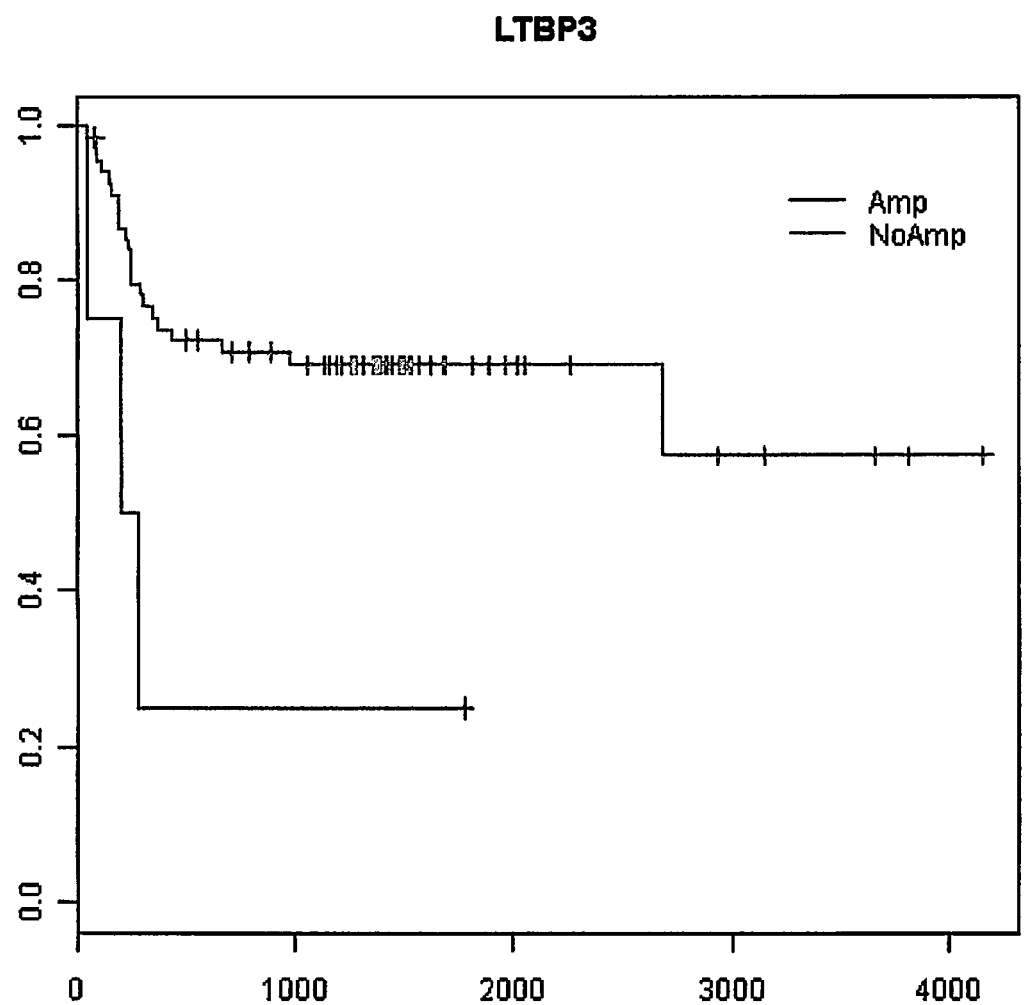
FIG. 102 is a Kaplan-Meier plot showing the time to recurrence (TTR) in days for a 74 patient cohort with NSCLC stage Ia-IIa, classified by presence or absence of a copy number gain in LTBP3.
Figure 103:
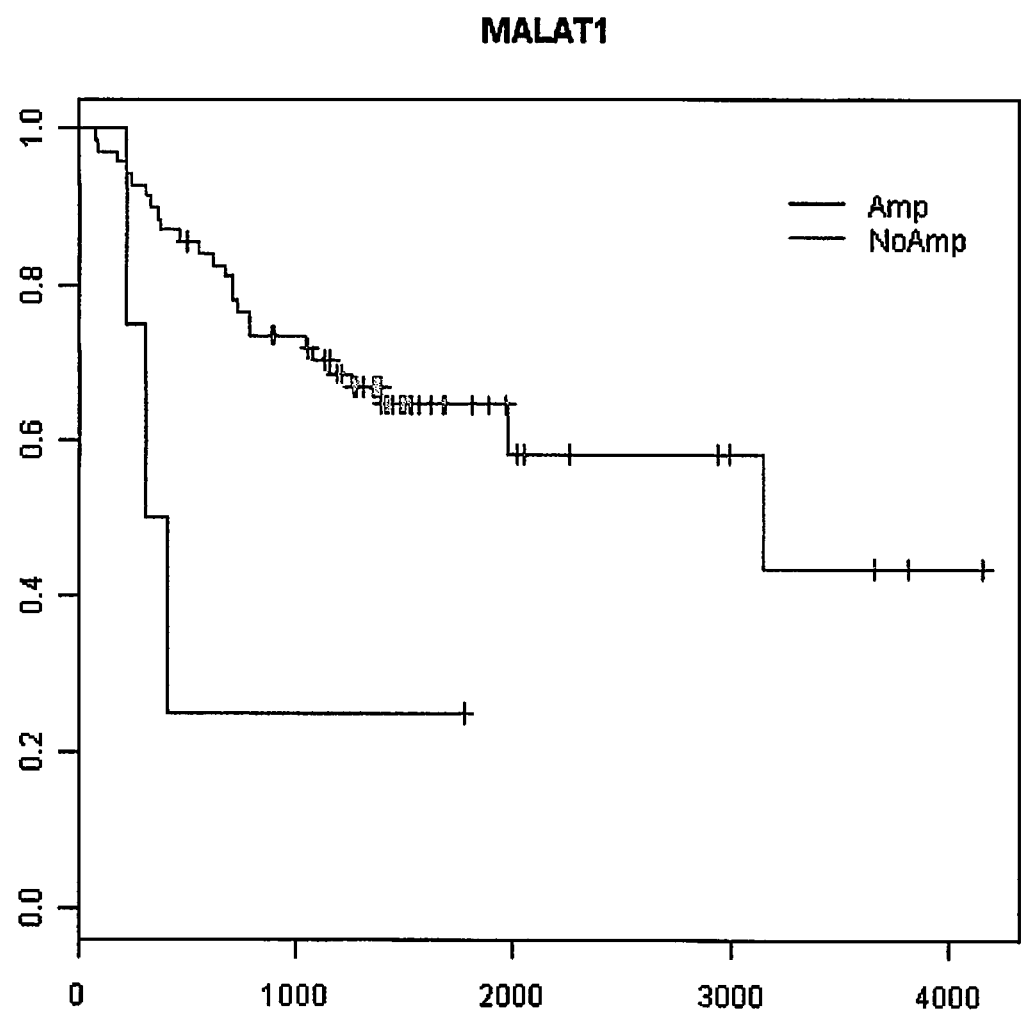
FIG. 103 is a Kaplan-Meier plot showing the overall survival (OS) in days for a 74 patient cohort with NSCLC stage Ia-IIa, classified by presence or absence of a copy number gain in MALAT1.
Figure 104:
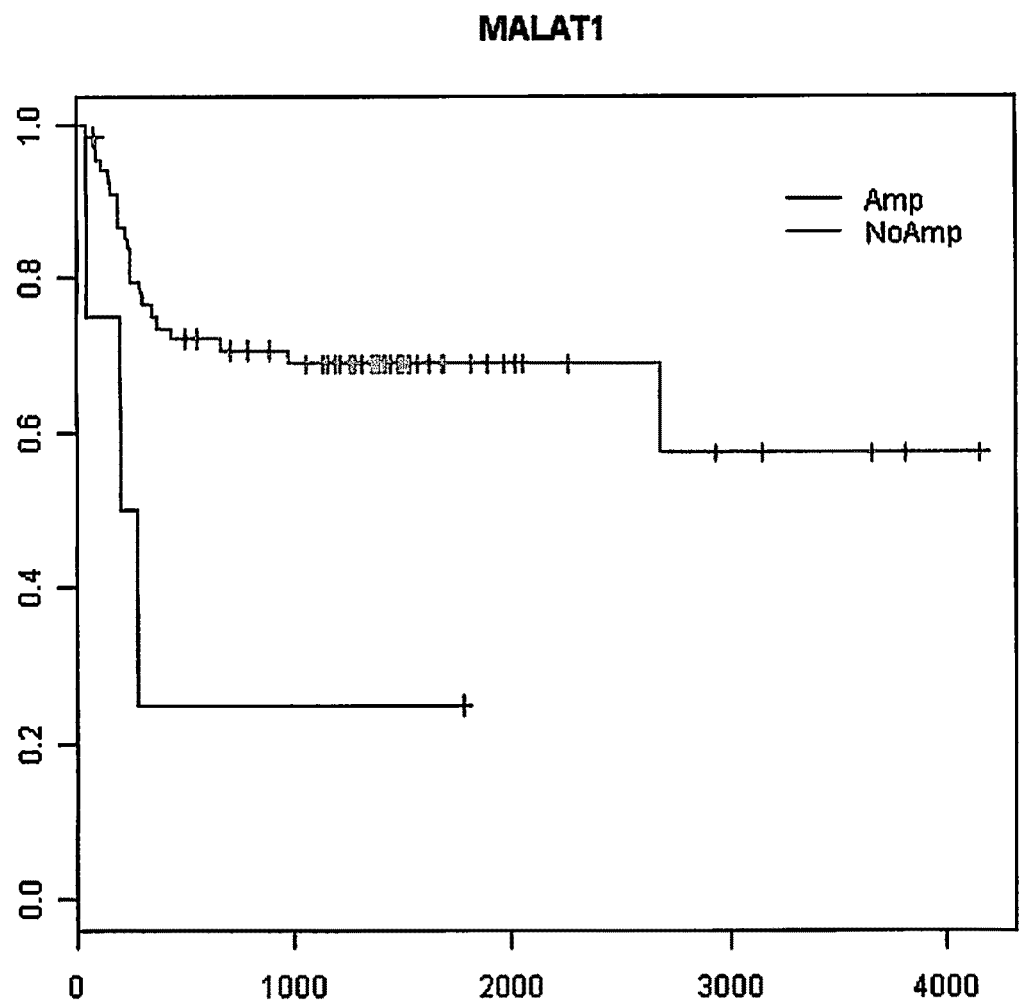
FIG. 104 is a Kaplan-Meier plot showing the time to recurrence (TTR) in days for a 74 patient cohort with NSCLC stage Ia-IIa, classified by presence or absence of a copy number gain in MALAT1.
Figure 105:
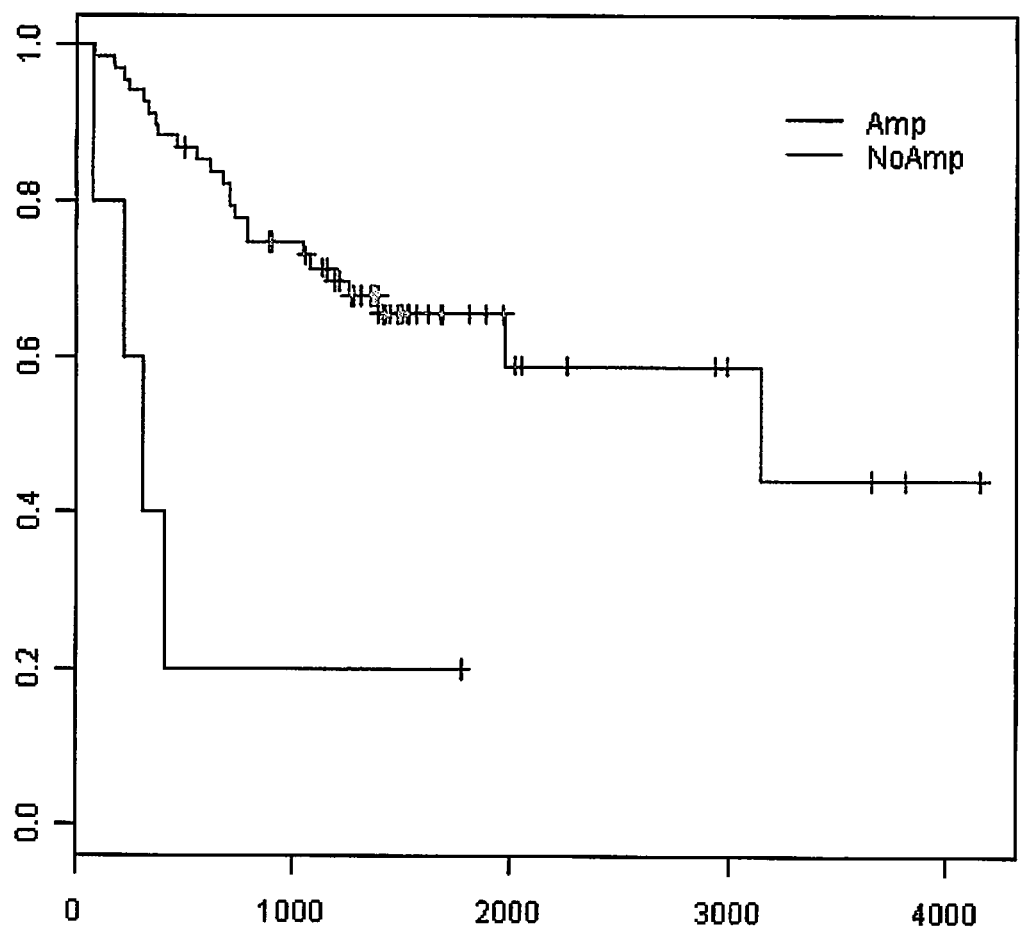
FIG. 105 is a Kaplan-Meier plot showing the overall survival (OS) in days for a 74 patient cohort with NSCLC stage Ia-IIa, classified by presence or absence of a copy number gain in MAP3K11.
Figure 106:
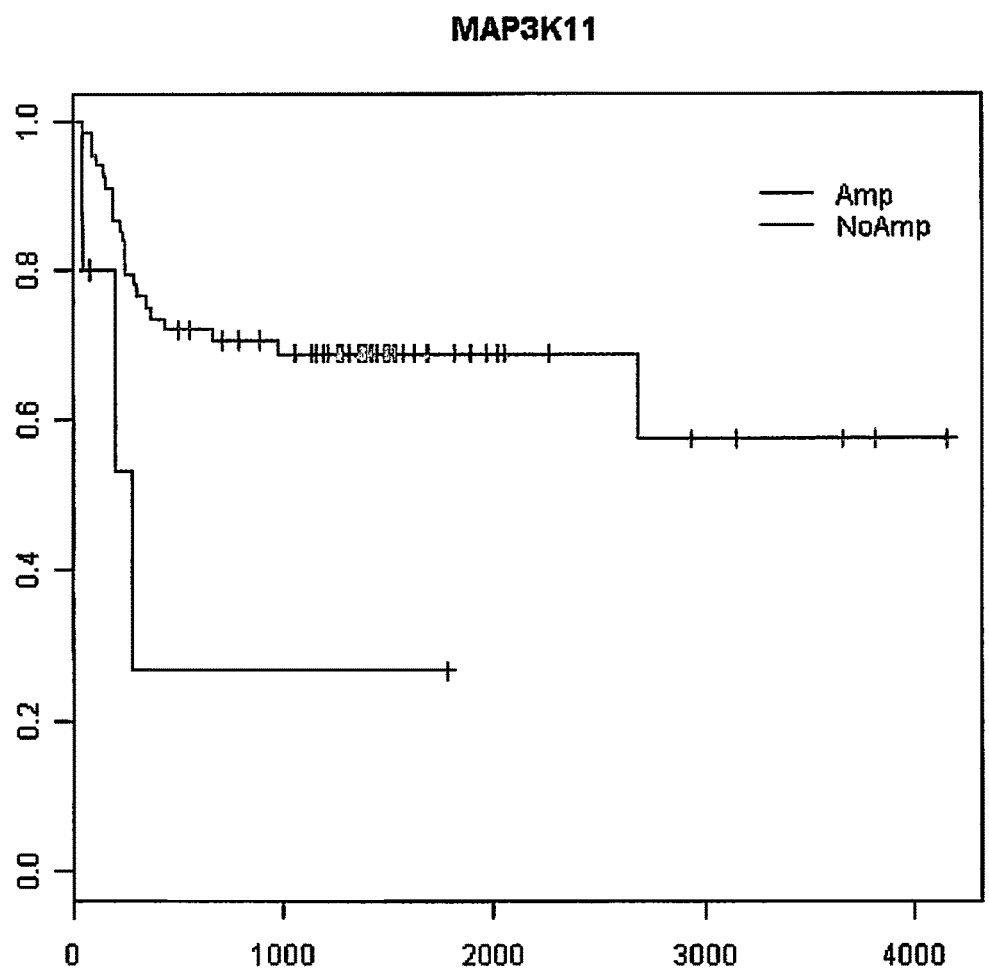
FIG. 106 is a Kaplan-Meier plot showing the time to recurrence (TTR) in days for a 74 patient cohort with NSCLC stage Ia-IIa, classified by presence or absence of a copy number gain in MAP3K11.
Figure 107:
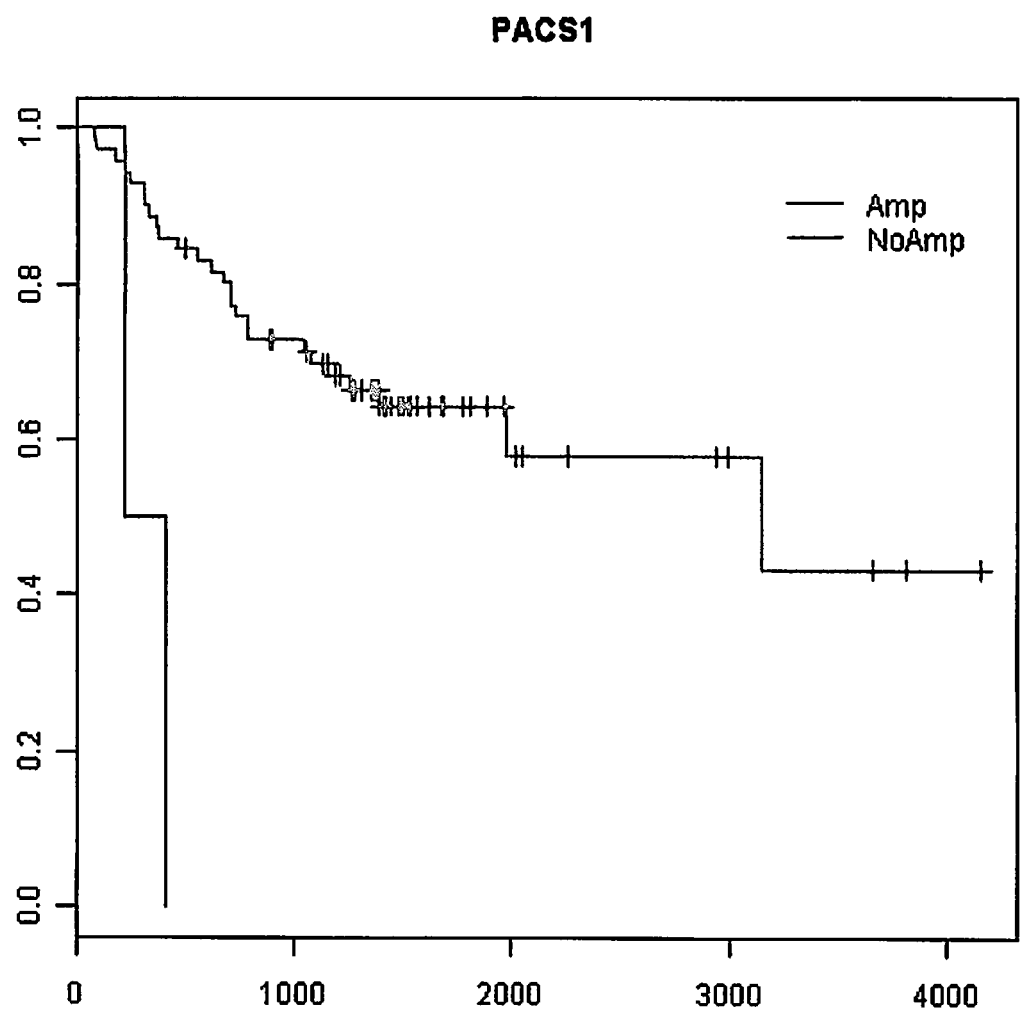
FIG. 107 is a Kaplan-Meier plot showing the overall survival (OS) in days for a 74 patient cohort with NSCLC stage Ia-IIa, classified by presence or absence of a copy number gain in PACS1.
Figure 108:
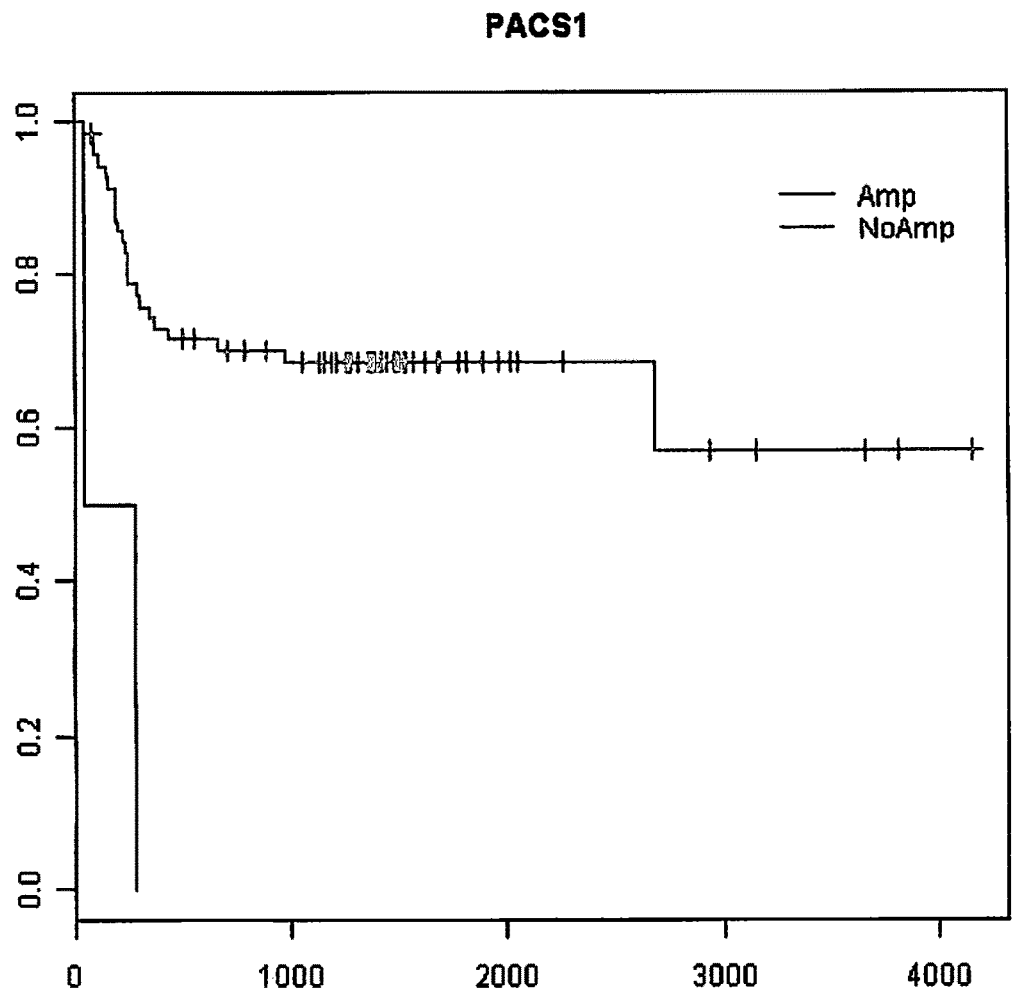
FIG. 108 is a Kaplan-Meier plot showing the time to recurrence (TTR) in days for a 74 patient cohort with NSCLC stage Ia-IIa, classified by presence or absence of a copy number gain in PACS1.
Figure 109:
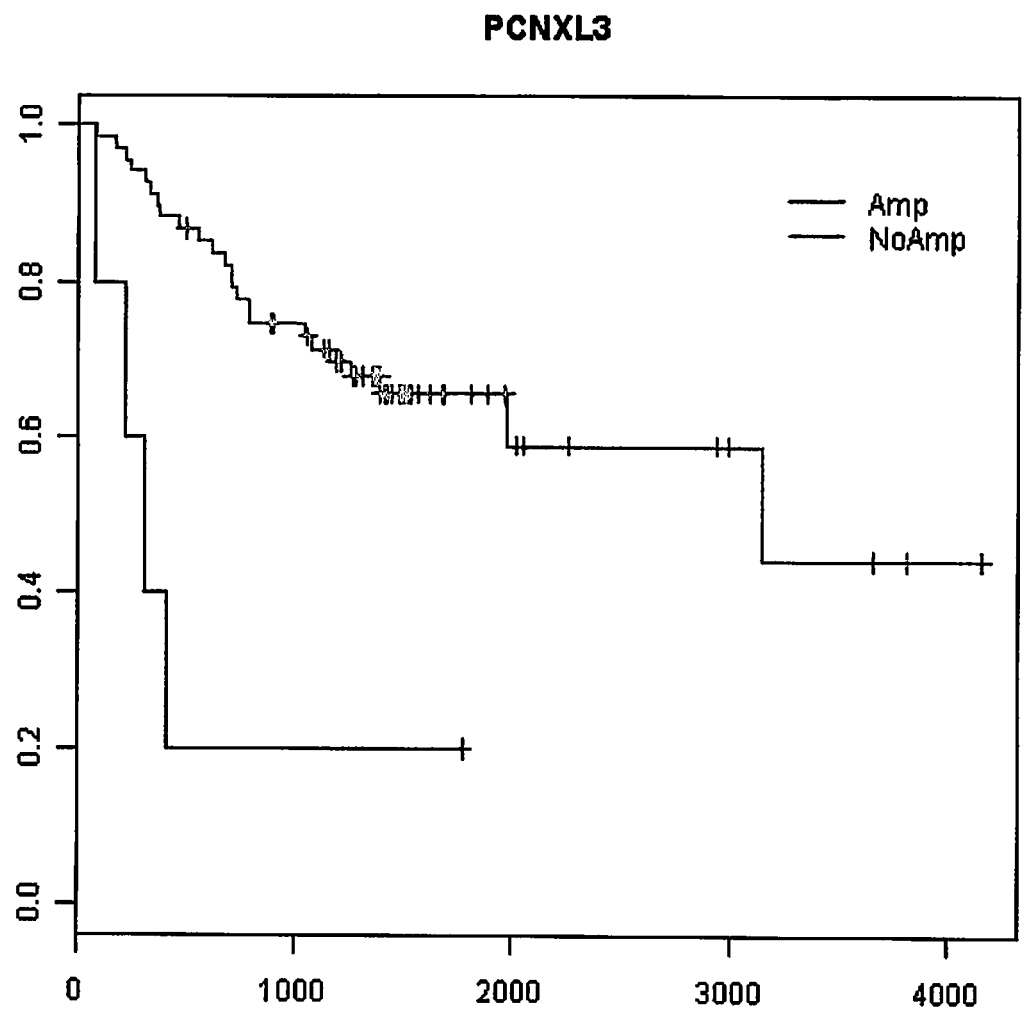
FIG. 109 is a Kaplan-Meier plot showing the overall survival (OS) in days for a 74 patient cohort with NSCLC stage Ia-IIa, classified by presence or absence of a copy number gain in PCNXL3.
Figure 110:
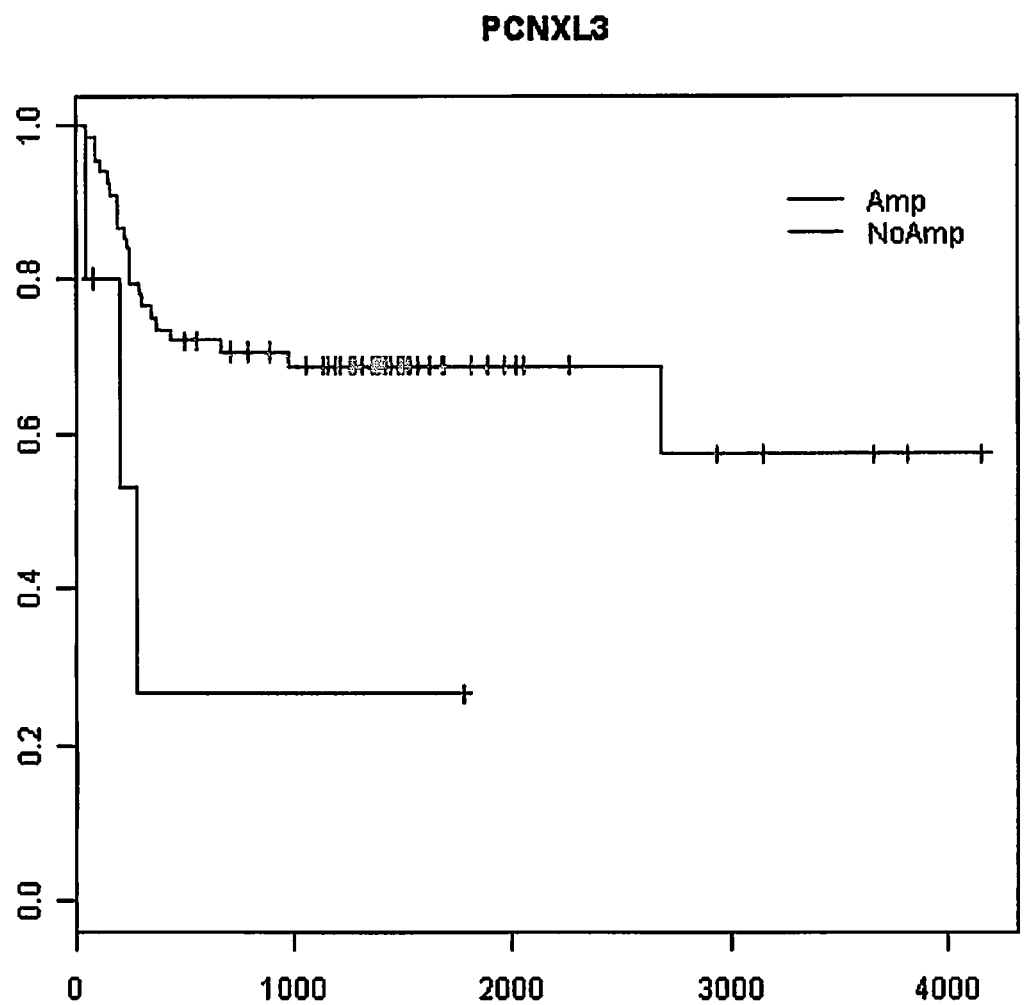
FIG. 110 is a Kaplan-Meier plot showing the time to recurrence (TTR) in days for a 74 patient cohort with NSCLC stage Ia-IIa, classified by presence or absence of a copy number gain in PCNXL3.
Figure 111:
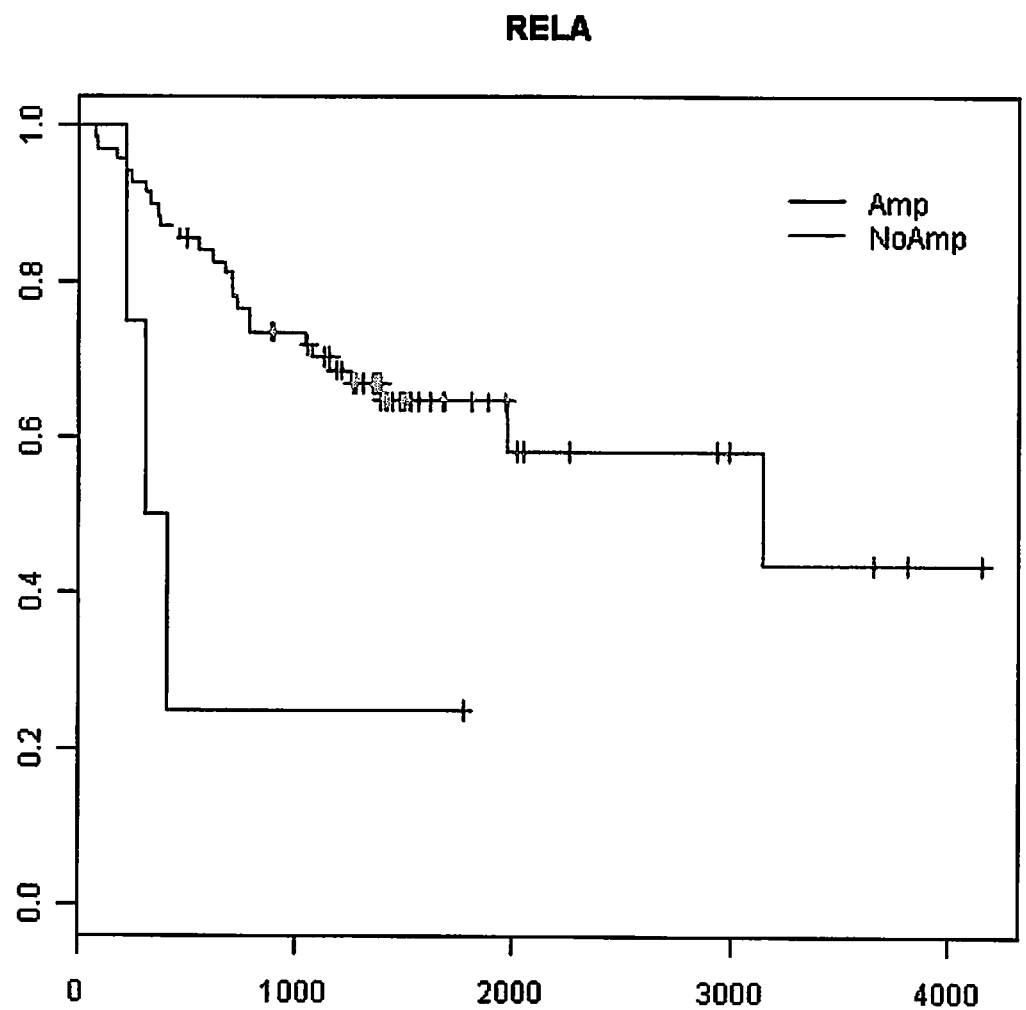
FIG. 111 is a Kaplan-Meier plot showing the overall survival (OS) in days for a 74 patient cohort with NSCLC stage Ia-IIa, classified by presence or absence of a copy number gain in RELA.
Figure 112:
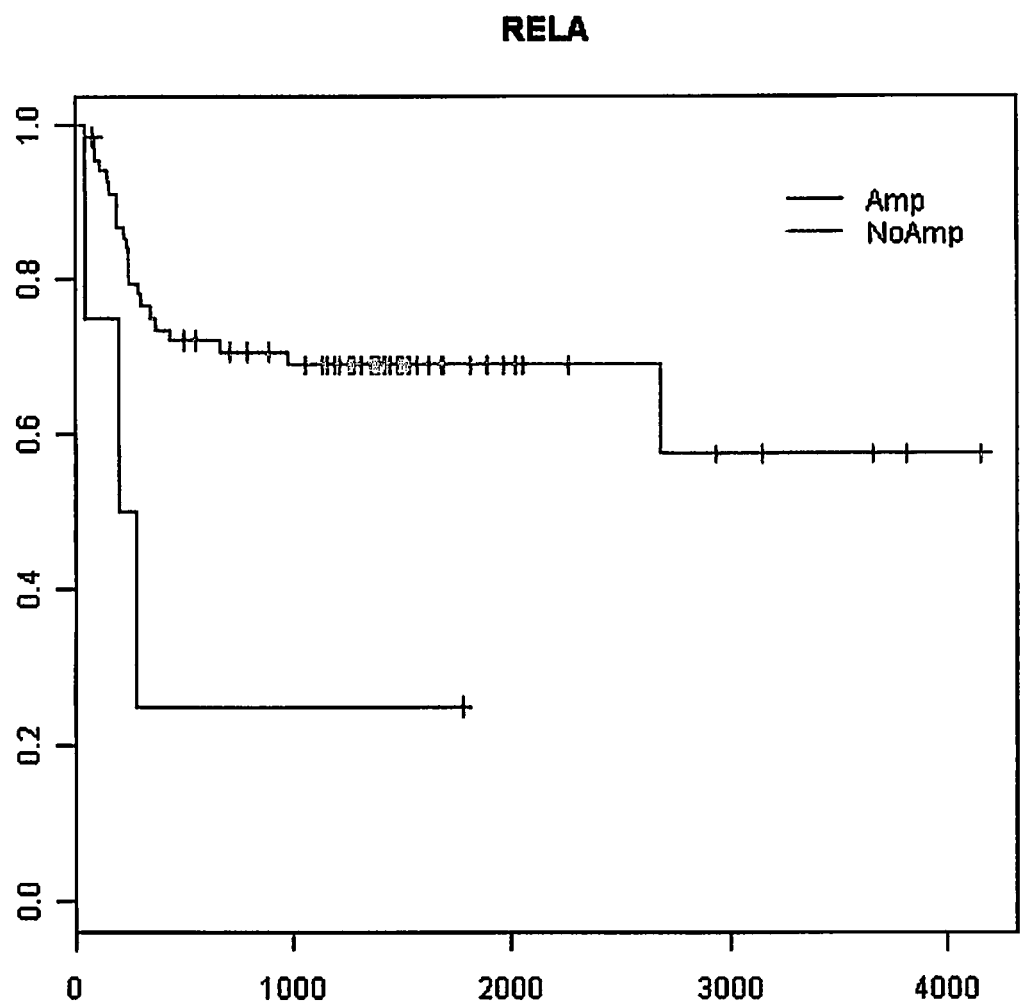
FIG. 112 is a Kaplan-Meier plot showing the time to recurrence (TTR) in days for a 74 patient cohort with NSCLC stage Ia-IIa, classified by presence or absence of a copy number gain in RELA.
Figure 113:
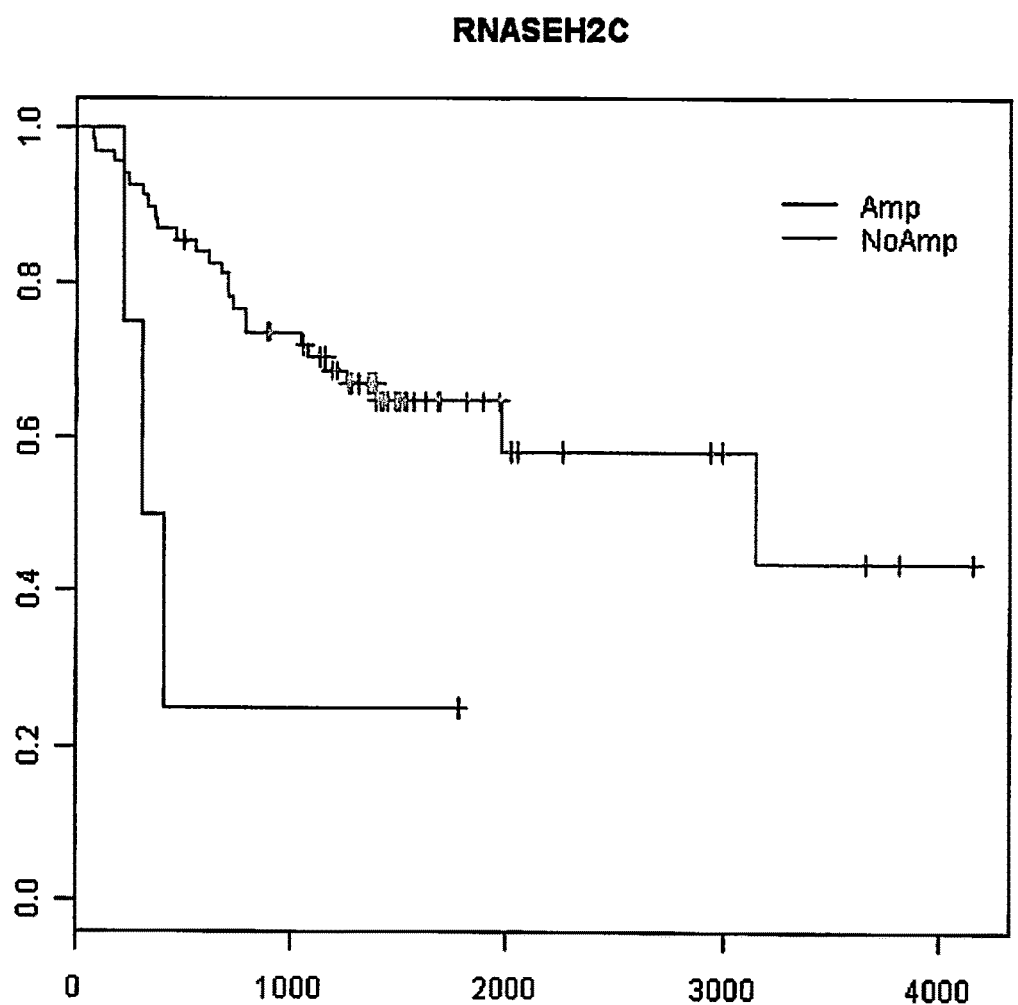
FIG. 113 is a Kaplan-Meier plot showing the overall survival (OS) in days for a 74 patient cohort with NSCLC stage Ia-IIa, classified by presence or absence of a copy number gain in RNASEH2C.
Figure 114:
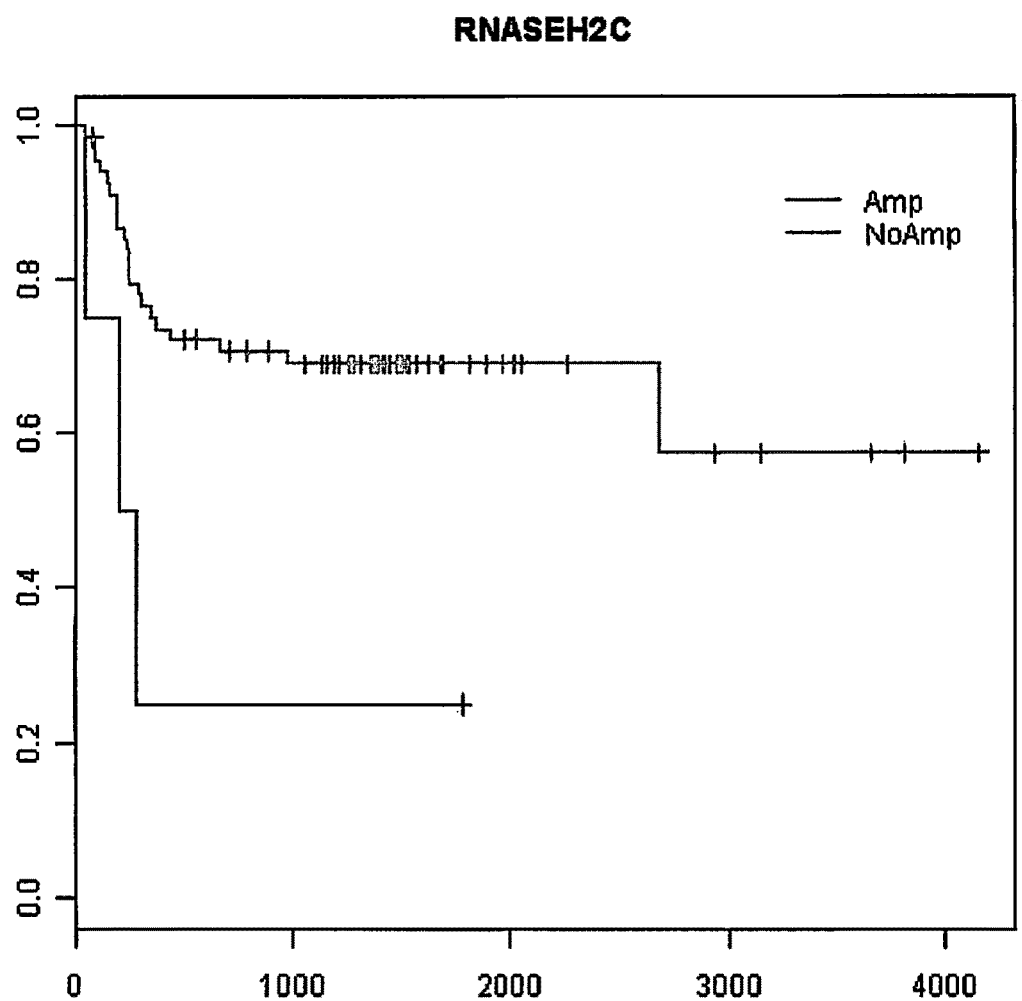
FIG. 114 is a Kaplan-Meier plot showing the time to recurrence (TTR) in days for a 74 patient cohort with NSCLC stage Ia-IIa, classified by presence or absence of a copy number gain in RNASEH2C.
Figure 115:
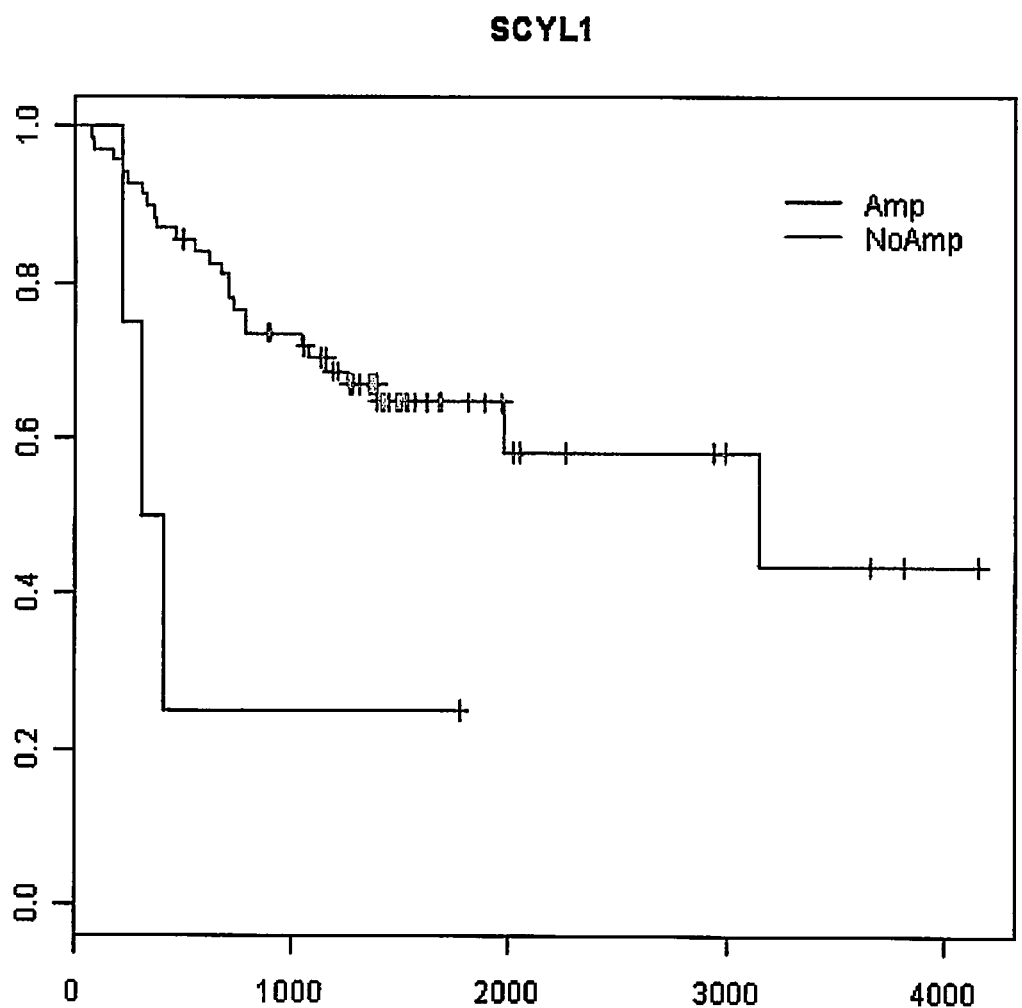
FIG. 115 is a Kaplan-Meier plot showing the overall survival (OS) in days for a 74 patient cohort with NSCLC stage Ia-IIa, classified by presence or absence of a copy number gain in SCYL1.
Figure 116:
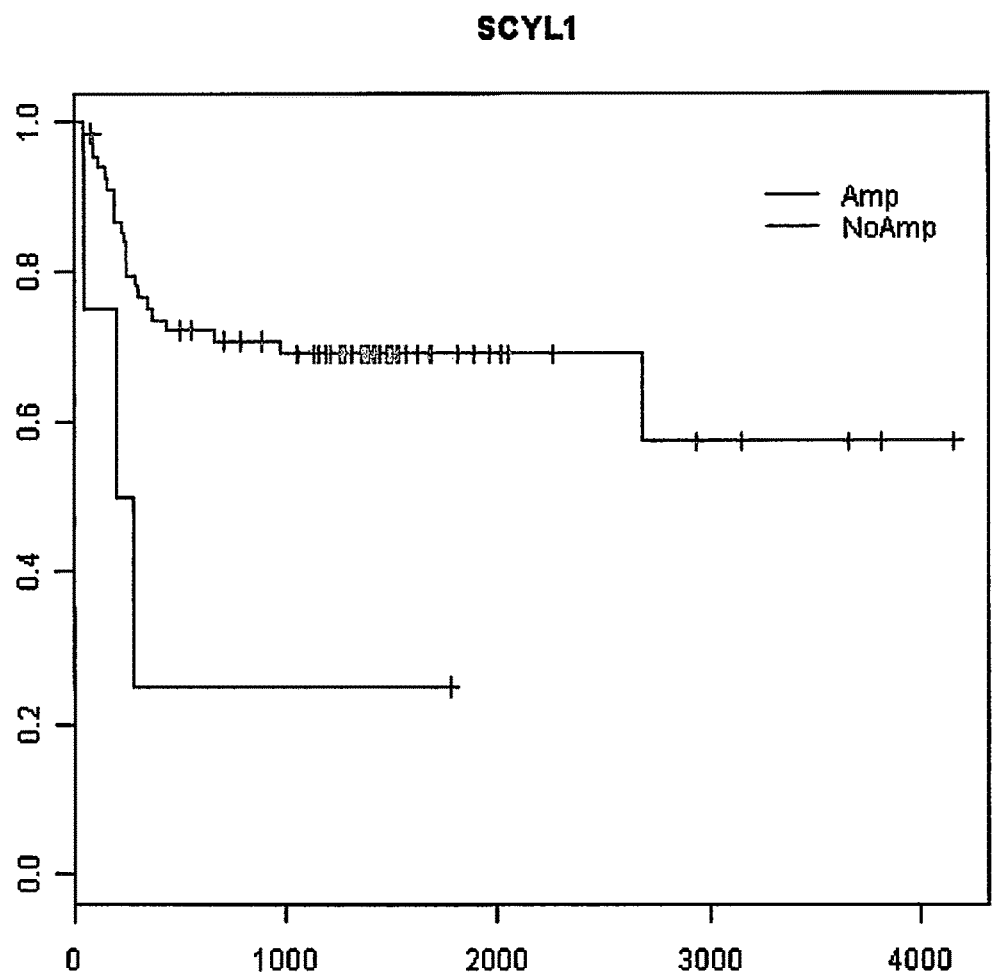
FIG. 116 is a Kaplan-Meier plot showing the time to recurrence (TTR) in days for a 74 patient cohort with NSCLC stage Ia-IIa, classified by presence or absence of a copy number gain in SCYL1.
Figure 117:
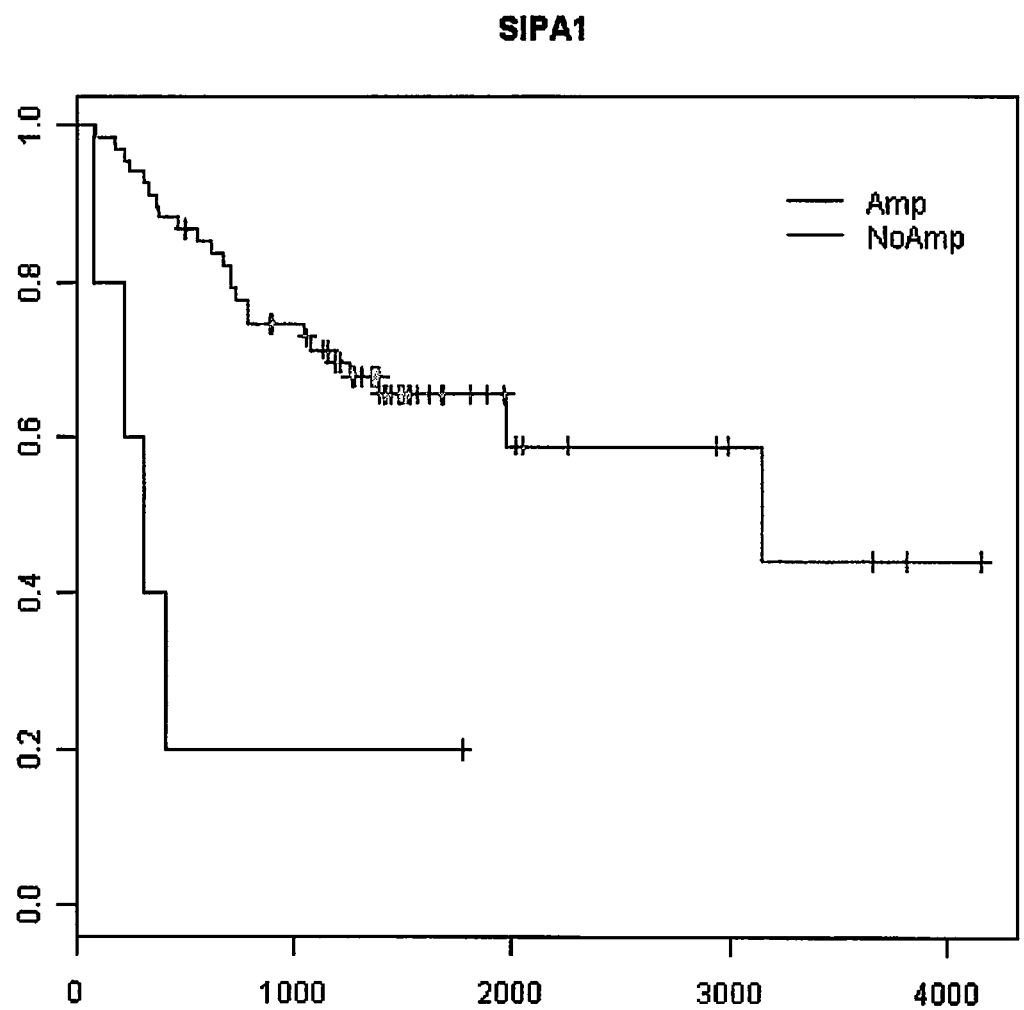
FIG. 117 is a Kaplan-Meier plot showing the overall survival (OS) in days for a 74 patient cohort with NSCLC stage Ia-IIa, classified by presence or absence of a copy number gain in SIPA1.
Figure 118:
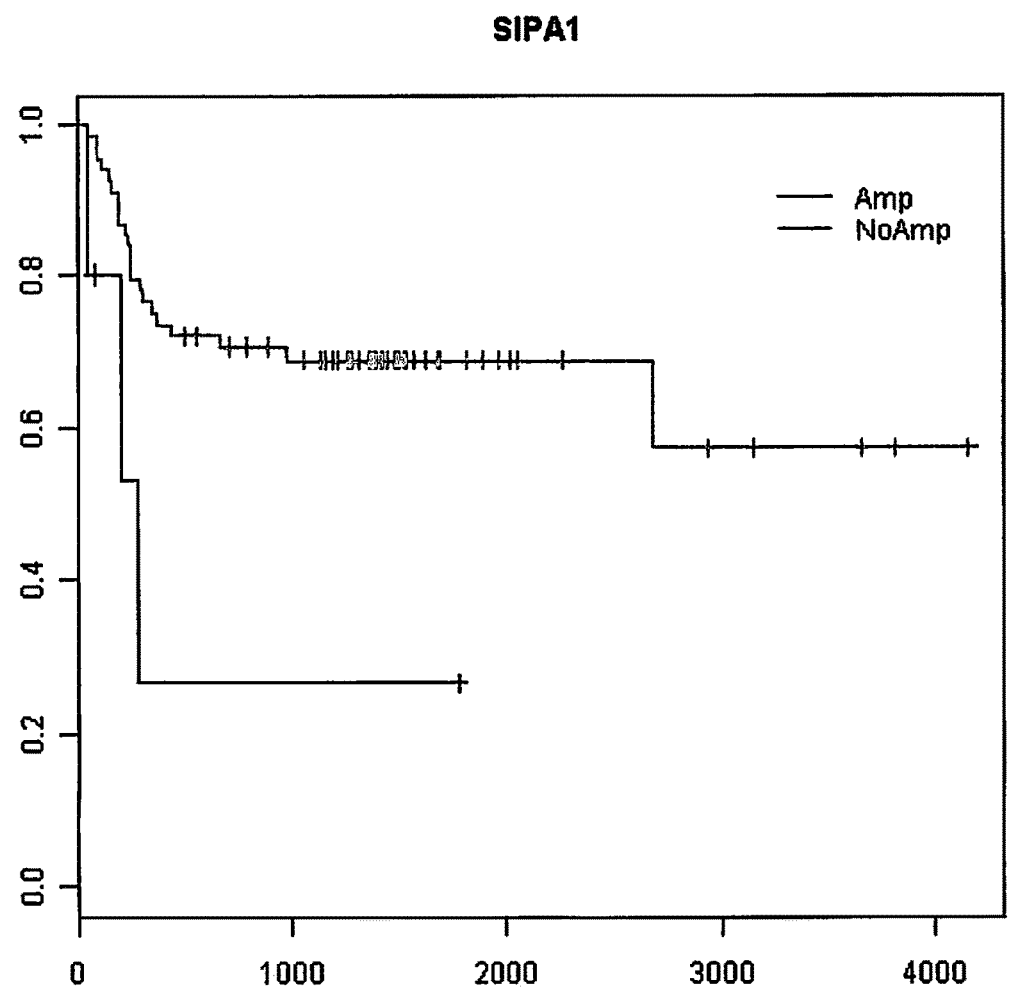
FIG. 118 is a Kaplan-Meier plot showing the time to recurrence (TTR) in days for a 74 patient cohort with NSCLC stage Ia-IIa, classified by presence or absence of a copy number gain in SIPA1.
Figure 119:
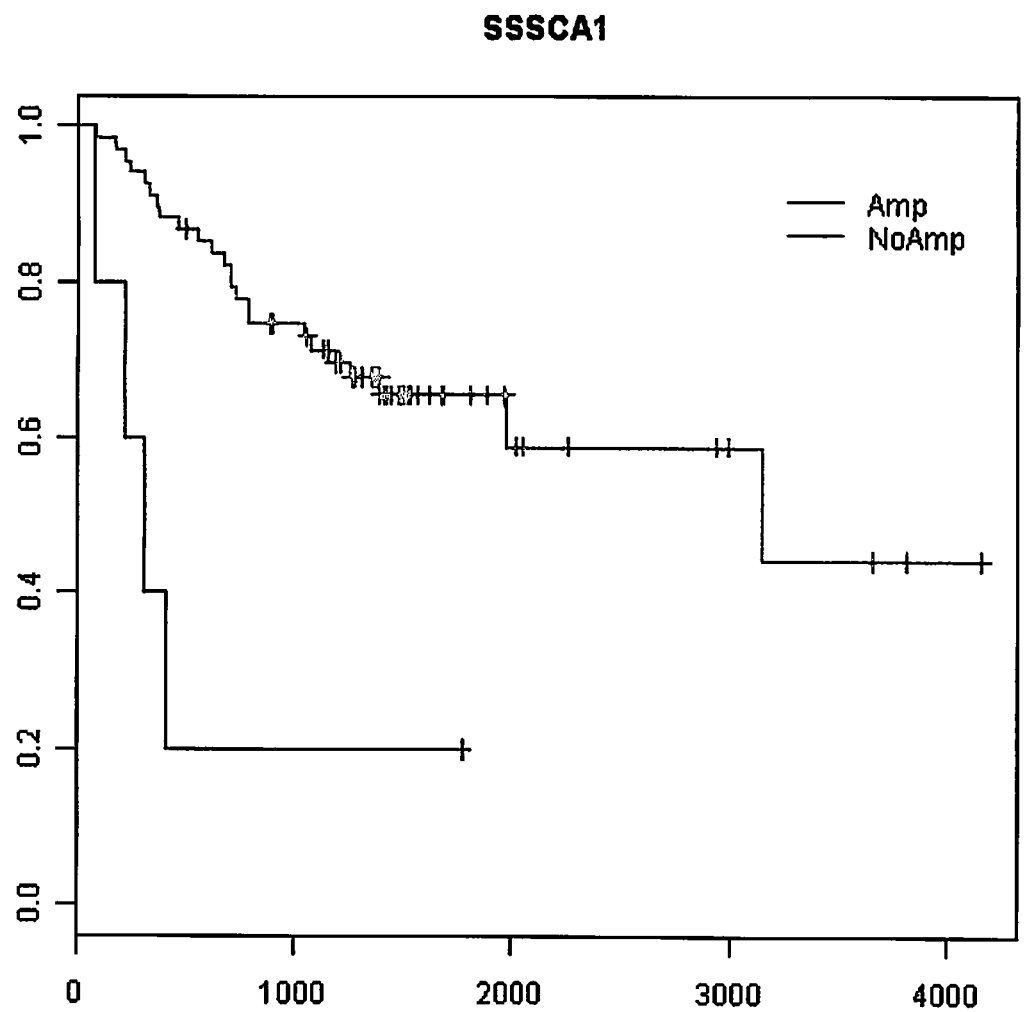
Figure 120:
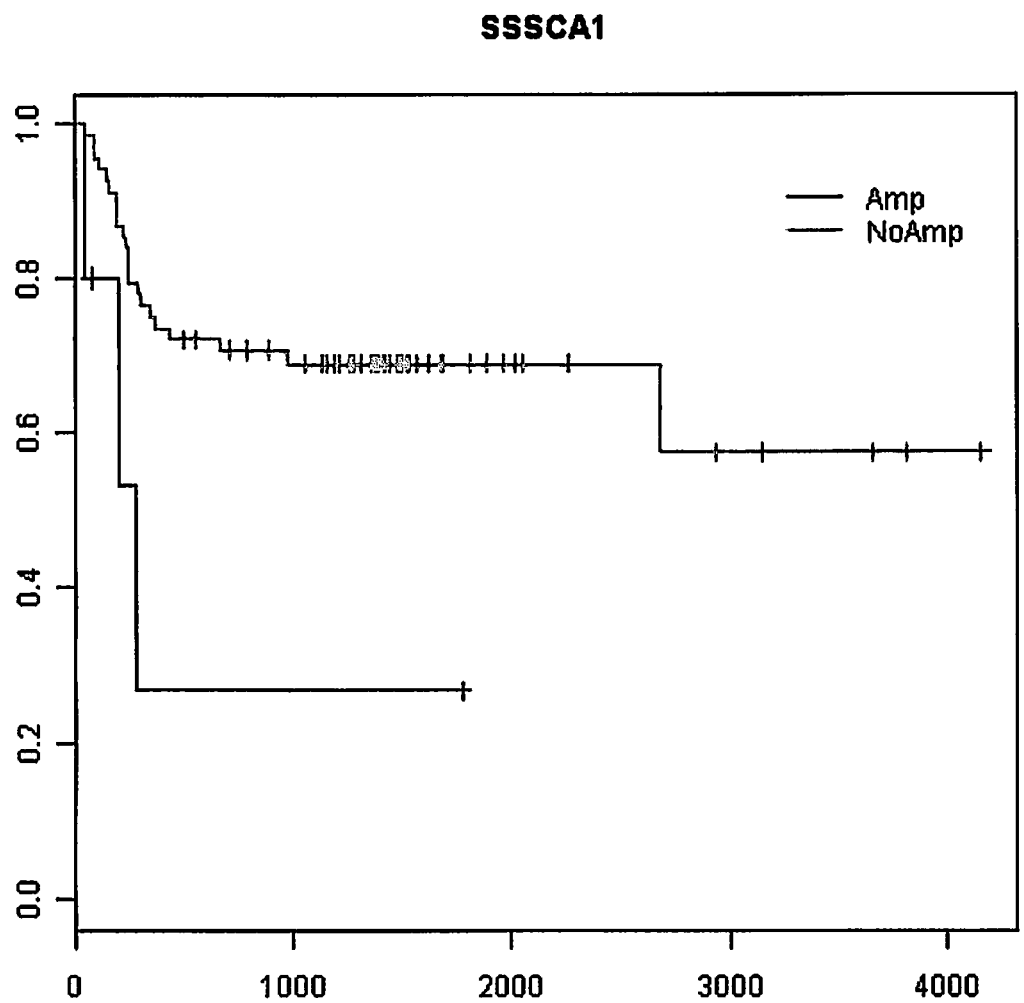
Figure 121:
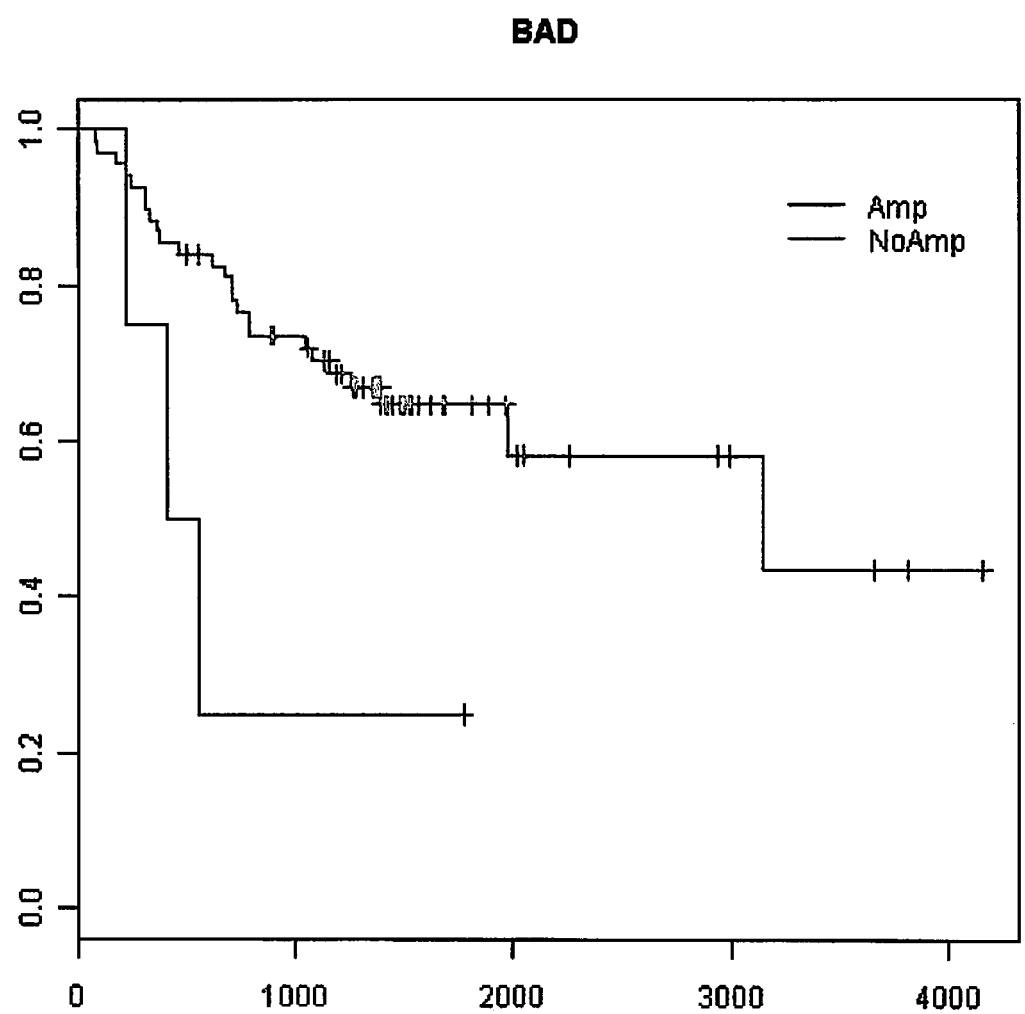
Figure 122:
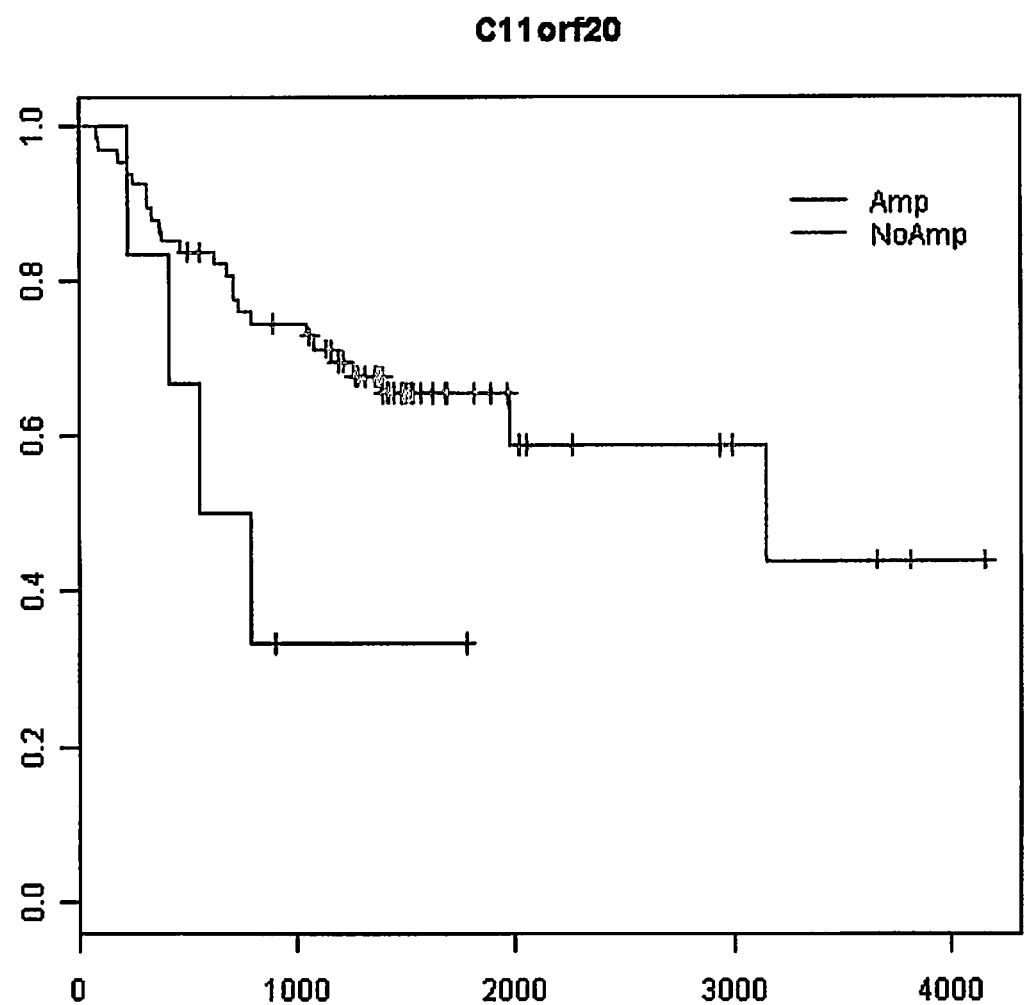
Figure 123:
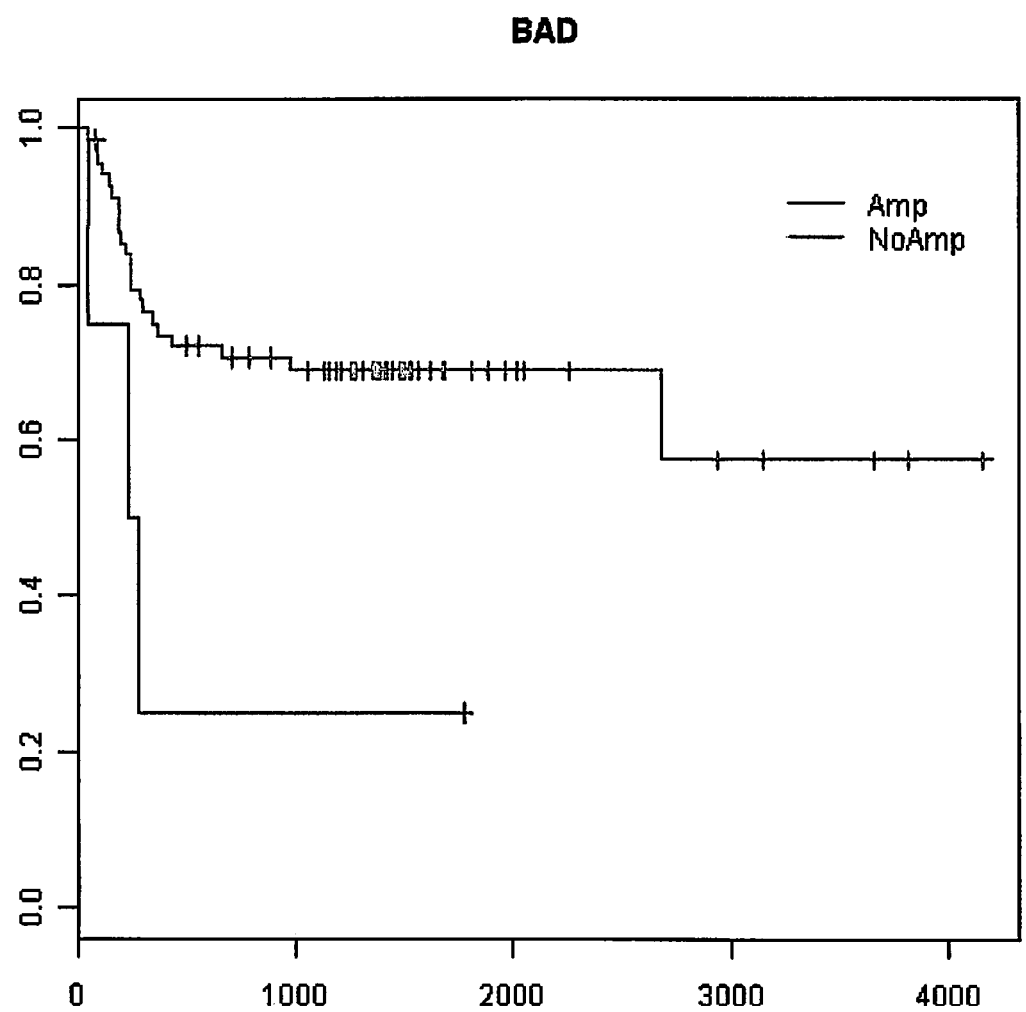
Figure 124:
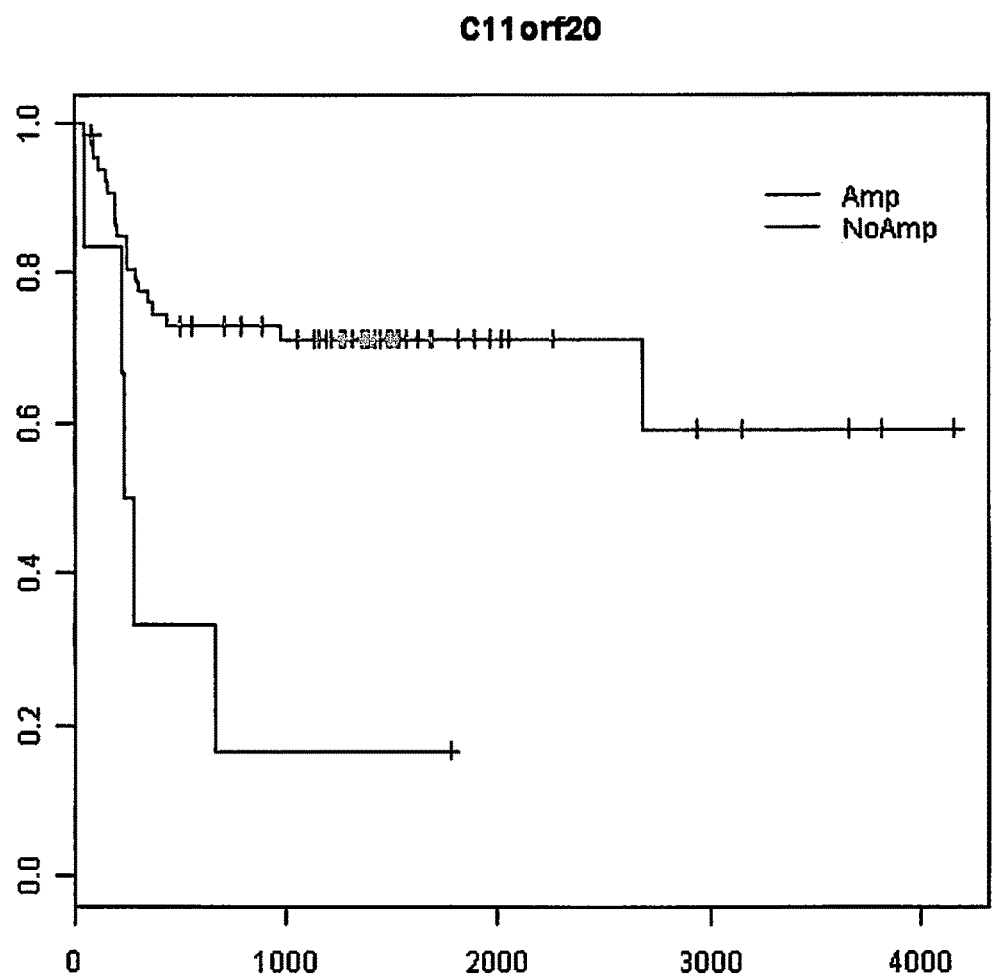
Figure 125:
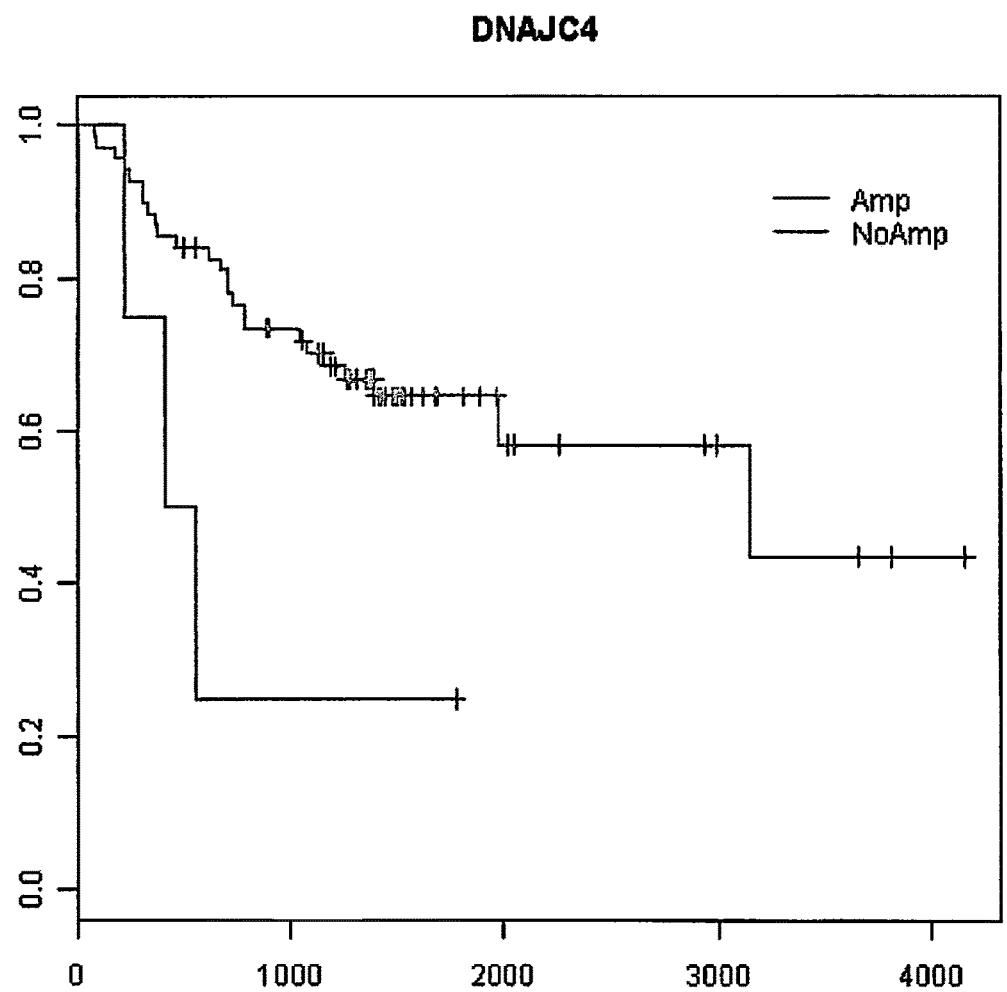
Figure 126:
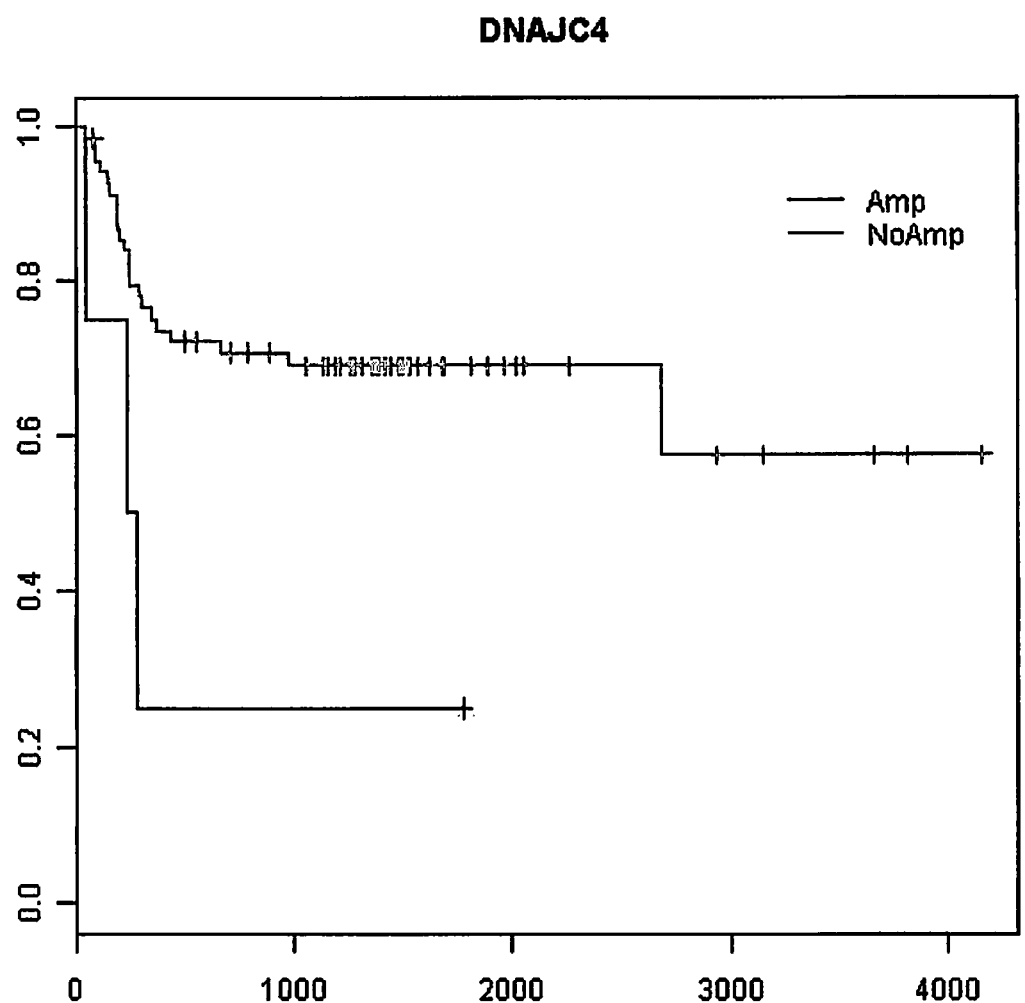
Figure 127:
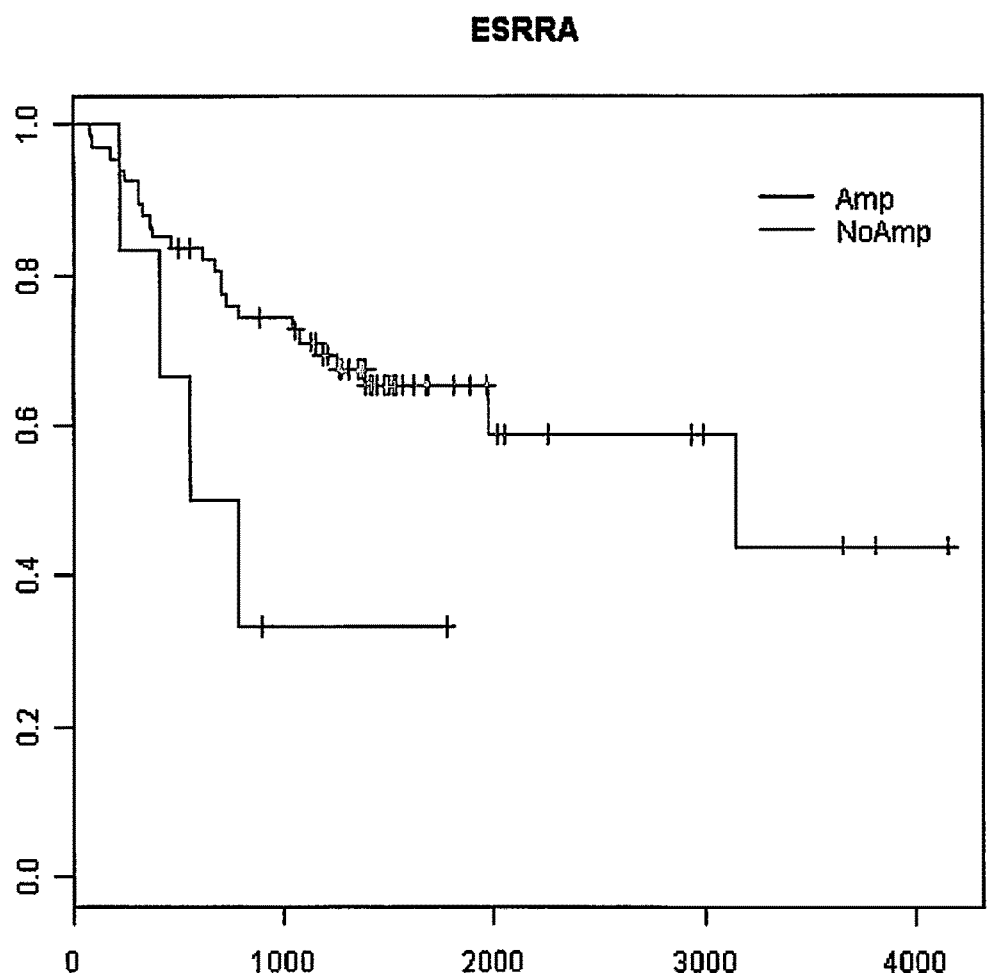
Figure 128:
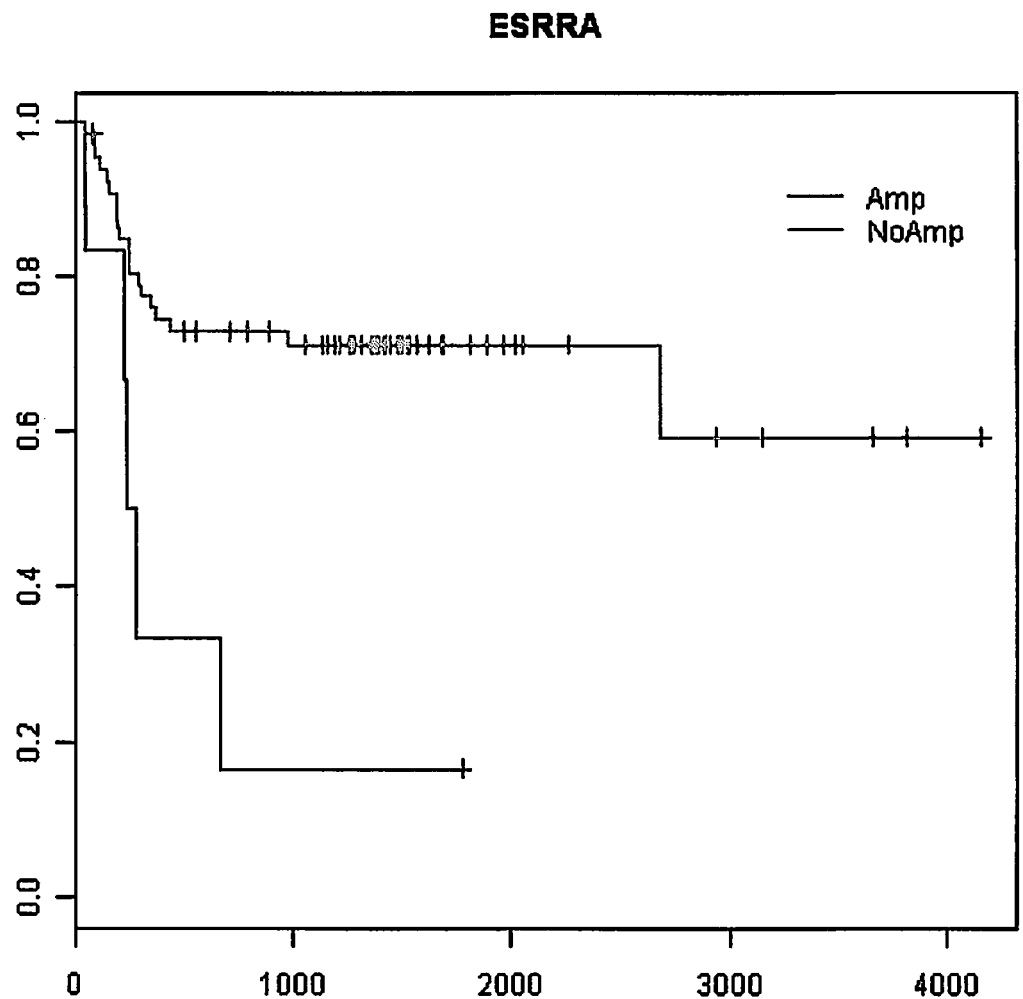
Figure 129:
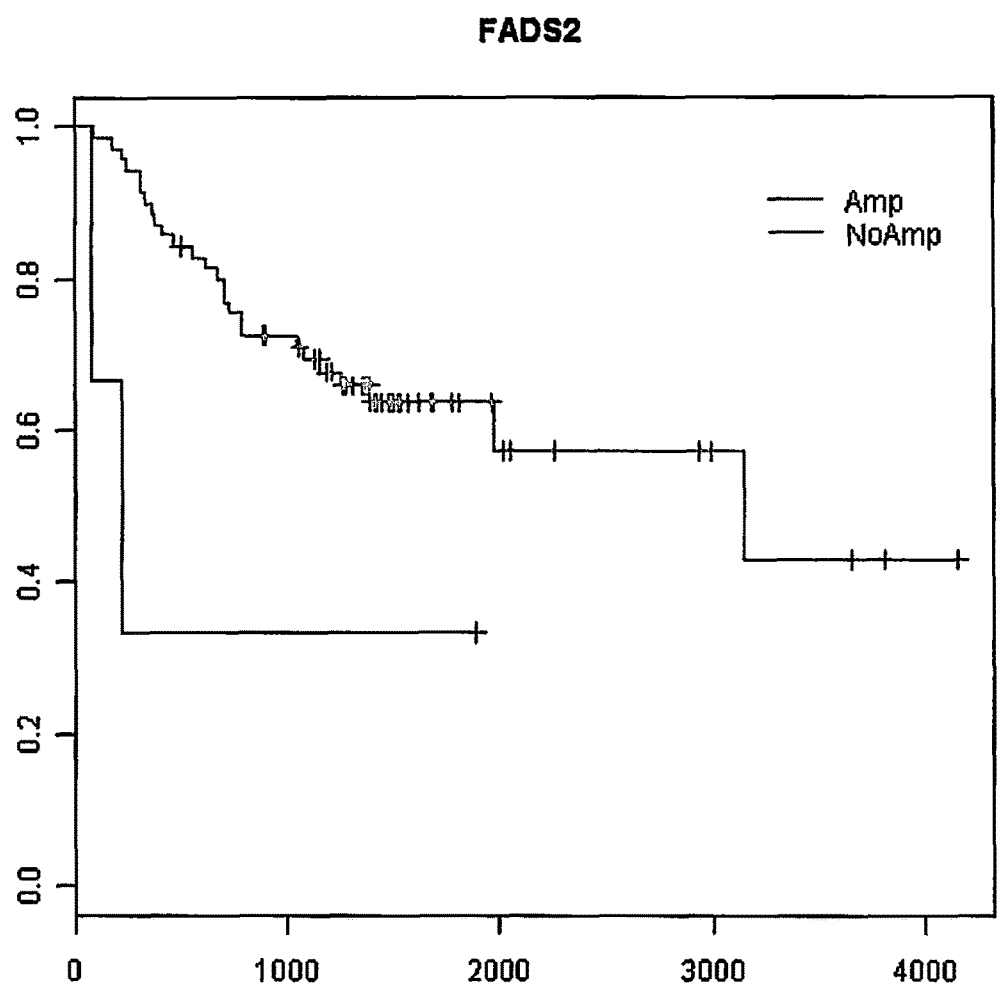
Figure 130:
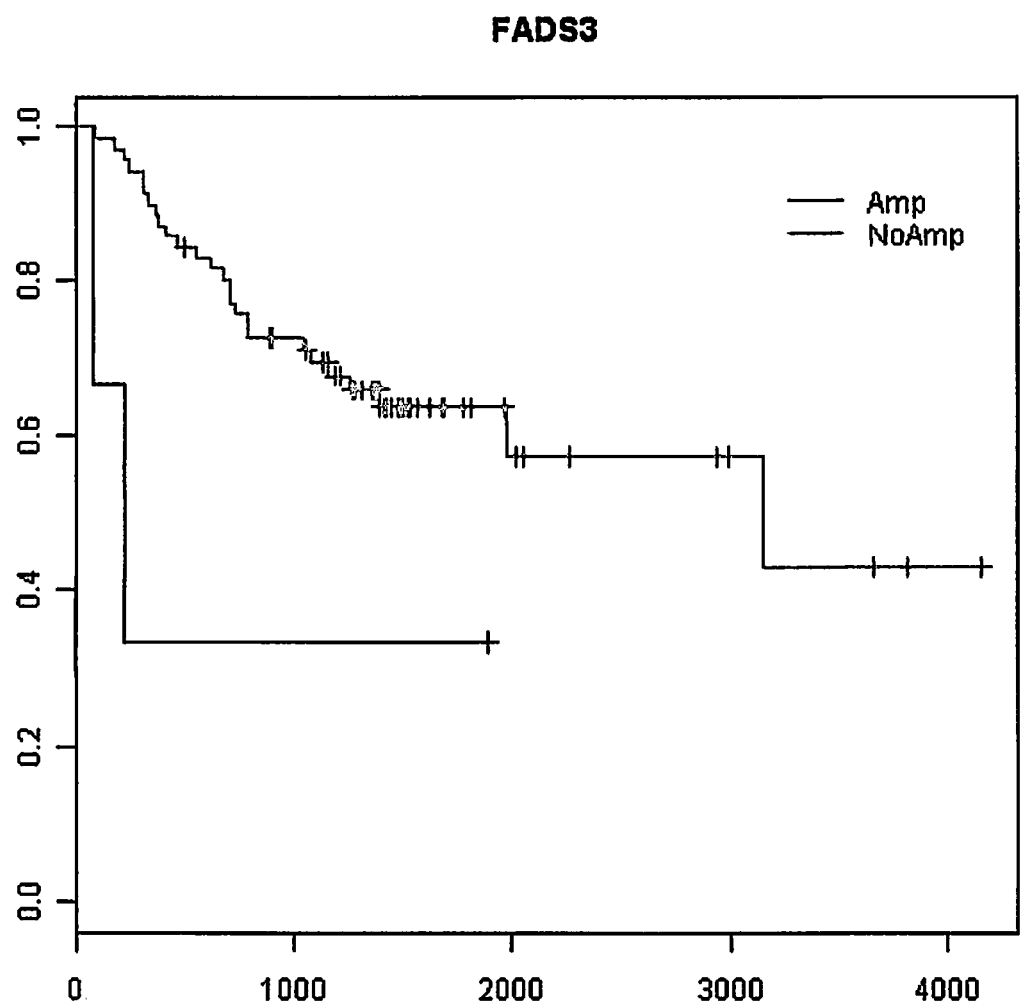

Sixty-one (61) genes in total, in six (6) different markers were validated with the criterion of p-value by logrank test below 0.05. The genes are listed in Table 9 with significant p-values underlined . FIGS. 62-162 are Kaplan-Meier plots showing the overall survival (OS) or the time to recurrence (TTR) in days for the 73 patient cohort classified by presence or absence of a copy number gain in the particular gene as indicated on each plot.

The number of markers ultimately validated as described is relatively small, which may be attributable in part to the fact that the two patient populations are from different ethnic groups. Previous large samplings were collected in Chicago, Ill., USA and included a mix of Asian, Caucasian, African and Hispanic patients, while the validation samples were collected in Korea from a homogeneously Asian population. Additionally, the two samples sets were processed at different locations, Abbott Park for the first sample set and the Samsung Cancer Center for the second sample set. Although the sample processing in both locations followed the same suggested protocol, potential systems bias cannot be totally ruled out. Also, the two sample sets were assayed using different versions of Affymetrix SNPs arrays, between which density differed by a factor of eighteen (18). The additional probes included in the new array may reveal more detailed copy number variation events that were not observed by the older version of SNPs arrays.

TABLE 9

Validated genes within the identified biomarkers that correlate to clinical outcome of NSCLC patients

| GeneSymbol | Chromosome | Type | MarkerID | Event | Normal | PvalTTR | PvalOS |
|---|---|---|---|---|---|---|---|
| C11orf20 | chr11 | Amp | Marker10 | 6 | 67 | 0.0024 | 0.0477 |
| ESRRA | chr11 | Amp | Marker10 | 6 | 67 | 0.0024 | 0.0477 |
| HSPC152 | chr11 | Amp | Marker10 | 6 | 67 | 0.0024 | 0.0477 |
| KCNK4 | chr11 | Amp | Marker10 | 6 | 67 | 0.0024 | 0.0477 |
| PRDX5 | chr11 | Amp | Marker10 | 6 | 67 | 0.0024 | 0.0477 |
| GPR137 | chr11 | Amp | Marker10 | 5 | 68 | 0.0132 | 0.1138 |
| BAD | chr11 | Amp | Marker10 | 4 | 69 | 0.0232 | 0.0278 |
| DNAJC4 | chr11 | Amp | Marker10 | 4 | 69 | 0.0232 | 0.0278 |
| FKBP2 | chr11 | Amp | Marker10 | 4 | 69 | 0.0232 | 0.0278 |
| NUDT22 | chr11 | Amp | Marker10 | 4 | 69 | 0.0232 | 0.0278 |
| PLCB3 | chr11 | Amp | Marker10 | 4 | 69 | 0.0232 | 0.0278 |
| PPP1R14B | chr11 | Amp | Marker10 | 4 | 69 | 0.0232 | 0.0278 |
| TRPT1 | chr11 | Amp | Marker10 | 4 | 69 | 0.0232 | 0.0278 |
| VEGFB | chr11 | Amp | Marker10 | 4 | 69 | 0.0232 | 0.0278 |
| FLRT1 | chr11 | Amp | Marker10 | 4 | 69 | 0.1288 | 0.0069 |
| FADS2 | chr11 | Amp | Marker10 | 3 | 70 | 0.4208 | 0.0482 |
| FADS3 | chr11 | Amp | Marker10 | 3 | 70 | 0.4208 | 0.0482 |
| RAB31L1 | chr11 | Amp | Marker10 | 3 | 70 | 0.4208 | 0.0482 |
| AKAP1 | chr17 | Amp | Marker11 | 3 | 70 | 0.0370 | 0.3782 |
| ANKFN1 | chr17 | Amp | Marker11 | 3 | 70 | 0.0370 | 0.3782 |
| C17orf67 | chr17 | Amp | Marker11 | 3 | 70 | 0.0370 | 0.3782 |
| COIL | chr17 | Amp | Marker11 | 3 | 70 | 0.0370 | 0.3782 |
| DGKE | chr17 | Amp | Marker11 | 3 | 70 | 0.0370 | 0.3782 |
| MSI2 | chr17 | Amp | Marker11 | 3 | 70 | 0.0370 | 0.3782 |
| MTVR2 | chr17 | Amp | Marker11 | 3 | 70 | 0.0370 | 0.3782 |
| NOG | chr17 | Amp | Marker11 | 3 | 70 | 0.0370 | 0.3782 |
| RNF126P1 | chr17 | Amp | Marker11 | 3 | 70 | 0.0370 | 0.3782 |
| SCPEP1 | chr17 | Amp | Marker11 | 3 | 70 | 0.0370 | 0.3782 |
| TRIM25 | chr17 | Amp | Marker11 | 3 | 70 | 0.0370 | 0.3782 |
| MYO15B | chr17 | Amp | Marker3 | 4 | 69 | 0.0342 | 0.1535 |
| SLC16A5 | chr17 | Amp | Marker3 | 4 | 69 | 0.0342 | 0.1126 |
| PACS1 | chr11 | Amp | Marker9 | 2 | 71 | 0.0015 | 0.0004 |
| DKFZp761E198 | chr11 | Amp | Marker9 | 4 | 69 | 0.0189 | 0.0136 |
| KAT5 | chr11 | Amp | Marker9 | 4 | 69 | 0.0189 | 0.0136 |
| LTBP3 | chr11 | Amp | Marker9 | 4 | 69 | 0.0189 | 0.0136 |
| MALAT1 | chr11 | Amp | Marker9 | 4 | 69 | 0.0189 | 0.0136 |
| RELA | chr11 | Amp | Marker9 | 4 | 69 | 0.0189 | 0.0136 |
| RNASEH2C | chr11 | Amp | Marker9 | 4 | 69 | 0.0189 | 0.0136 |
| SCYL1 | chr11 | Amp | Marker9 | 4 | 69 | 0.0189 | 0.0136 |
| EHBP1L1 | chr11 | Amp | Marker9 | 5 | 68 | 0.0224 | 0.0004 |
| FAM89B | chr11 | Amp | Marker9 | 5 | 68 | 0.0224 | 0.0004 |
| KCNK7 | chr11 | Amp | Marker9 | 5 | 68 | 0.0224 | 0.0004 |
| MAP3K11 | chr11 | Amp | Marker9 | 5 | 68 | 0.0224 | 0.0004 |
| PCNXL3 | chr11 | Amp | Marker9 | 5 | 68 | 0.0224 | 0.0004 |
| SIPA1 | chr11 | Amp | Marker9 | 5 | 68 | 0.0224 | 0.0004 |
| SSSCA1 | chr11 | Amp | Marker9 | 5 | 68 | 0.0224 | 0.0004 |
| CCNB1 | chr5 | Del | DelMarker27 | 19 | 54 | 0.3161 | 0.0495 |
| SLC30A5 | chr5 | Del | DelMarker27 | 19 | 54 | 0.3161 | 0.0495 |
| ARSK | chr5 | Del | DelMarker6 | 9 | 64 | 0.0033 | 0.0135 |
| FAM81B | chr5 | Del | DelMarker6 | 9 | 64 | 0.0033 | 0.0135 |
| GPR150 | chr5 | Del | DelMarker6 | 9 | 64 | 0.0033 | 0.0135 |
| MCTP1 | chr5 | Del | DelMarker6 | 10 | 63 | 0.0114 | 0.0051 |
| C5orf27 | chr5 | Del | DelMarker6 | 10 | 63 | 0.0122 | 0.0406 |
| CAST | chr5 | Del | DelMarker6 | 10 | 63 | 0.0122 | 0.0406 |
| GLRX | chr5 | Del | DelMarker6 | 10 | 63 | 0.0122 | 0.0406 |
| PCSK1 | chr5 | Del | DelMarker6 | 10 | 63 | 0.0122 | 0.0406 |
| RFESD | chr5 | Del | DelMarker6 | 10 | 63 | 0.0122 | 0.0406 |
| RHOBTB3 | chr5 | Del | DelMarker6 | 10 | 63 | 0.0122 | 0.0406 |
| SPATA9 | chr5 | Del | DelMarker6 | 10 | 63 | 0.0122 | 0.0406 |
| TTC37 | chr5 | Del | DelMarker6 | 10 | 63 | 0.0193 | 0.0491 |
| ELL2 | chr5 | Del | DelMarker6 | 11 | 62 | 0.0467 | 0.1066 |

It is to be understood that the foregoing description is intended to illustrate and not limit the scope of the invention. Other aspects, advantages, and modifications of the invention are within the intended scope of the claims set forth below.

What is claimed is:

1. A method comprising:
   (a) obtaining a lung tissue sample or a peripheral blood sample comprising circulating tumor cells from a patient, and
   (b) determining a copy number gain of the chromosome 11 markers Chr 11, 61.4-64.3 Mb, Chr 11, 64.3-64.8 Mb, and/or Chr 11, 64.8-65.7 in the lung tissue sample or peripheral blood sample using fluorescent in situ hybridization (FISH).

2. The method of claim 1, wherein the marker Chr 11, 61.4-64.3 Mb comprises nucleotide sequences encoding AHNAK (AHNAK nucleoprotein); ASRGL1(asparaginase like 1); B3GAT3 (beta-1,3-glucuronyltransferase 3 (glucuronosyltransferase I)); BAD (BCL2-antagonist of cell death); BEST1 (bestrophin 1); BSCL2 (Bernardinelli-Seip congenital lipodystrophy 2 (seipin)); CCDC88B (coiled-coil domain containing 88B); CHRM1 (cholinergic receptor, muscarinic 1); COX8A (cytochrome c oxidase subunit 8A (ubiquitous)); DKFZP564J0863 (DKFZP564J0863 protein); DKFZP566E164(DKFZP566E164 protein); DNAJC4 (DnaJ (Hsp40) homolog, subfamily C, member 4); EEF1G (eukaryotic translation elongation factor 1 gamma); EML3 (echinoderm microtubule associated protein like b 3); ESRRA (estrogen-related receptor alpha); FADS2,3 (fatty acid desaturase 2,3); FKBP2 (FK506 binding protein 2, 13 kDa); FLRT1 (fibronectin leucine rich transmembrane protein 1); FTH1 (ferritin, heavy polypeptide 1); GANAB (glucosidase, alpha; neutral AB); GNG3 (guanine nucleotide binding protein (G protein), gamma 3); GPR137 (G protein-coupled receptor 137); HRASLS2, 3, 5 (HRAS-like suppressor 2, 3, 5); INCENP (inner centromere protein antigens 135/155 kDa); INTS5 (integrator complex subunit 5); KCNK4 (potassium channel, subfamily K, member 4); LGALS12 (lectin, galactoside-binding, soluble, 12 (galectin 12)); MACROD1 (MACRO domain containing 1); MARK2 (MAP/microtubule affinity-regulating kinase 2); MGC3196 (hypothetical protein MGC3196); MTA2 (metastasis associated 1 family, member 2); NAT11 (N-acetyltransferase 11); NRXN2 (neurexin 2); NUDT22 (nudix (nucleoside diphosphate linked moiety X)-type motif 22); NXF1 (nuclear RNA export factor 1); OTUB1 (OTU domain, ubiquitin aldehyde binding 1); PLCB3 (phospholipase C, beta 3 (phosphatidylinositol-specific)); POLR2G (polymerase (RNA) II (DNA directed) polypeptide G); PPP1R14B (protein phosphatase 1, regulatory (inhibitor) subunit 14B); PRDX5 (peroxiredoxin 5); PYGM (phosphorylase, glycogen; muscle (McArdle syndrome, glycogen storage disease type V)); RAB3IL1(RAB3A interacting protein (rabin3)-like 1); RARRES3 (retinoic acid receptor responder (tazarotene induced) 3); RASGRP2 (RAS guanyl releasing protein 2 (calcium and DAG-regulated)); RCOR2REST (corepressor 2); ROM1 (retinal outer segment membrane protein 1); RPS6KA4 (ribosomal protein S6 kinase, 90 kDa, polypeptide 4 RTN3 reticulon 3); SCGB1A1, 1D1, 1D2, 1D4, 2A1, 2A1 (secretoglobin, family SF1 splicing factor 1); SLC22A10, 11, 12, 6, 8, 9 (solute carrier family 22 (organic anion/cation transporter) SLC3A2 solute carrier family 3 (activators of dibasic and neutral amino acid transport), member 2); STIP1 (stress-induced-phosphoprotein 1 (Hsp70/Hsp90-organizing protein)); STX5 (syntaxin 5); TAF6L (TAF6-like RNA polymerase II, p300/CBP-associated factor (PCAF)-associated factor, 65 kDa); TRPT1 (tRNA phosphotransferase 1); TTC9C (tetratricopeptide repeat domain 9C); TUT1 (terminal uridylyl transferase 1, U6 snRNA-specific URP2 UNC-112 related protein 2); UST6 (putative UST1-like organic anion transporter VEGFB vascular endothelial growth factor B); WDR74 (WD repeat domain 74); and ZBTB3 (zinc finger and BTB domain containing 3).

3. The method of claim 1, wherein the marker Chr 11, 64.3-64.8 Mb comprises nucleotide sequences encoding ARL2 (ADP-ribosylation factor-like 2); ATG2A ATG2 (autophagy related 2 homolog A (S. cerevisiae)); BATF2 (basic leucine zipper transcription factor, ATF-like 2; CAPN1 calpain 1, (mu/I) large subunit); CDC42BPG (CDC42 binding protein kinase gamma (DMPK-like)); CDCA5 (cell division cycle associated 5); EHD1 (EH-domain containing 1); FAU (Finkel-Biskis-Reilly murine sarcoma virus (FBR-MuSV) ubiquitously expressed); GPHA2 (glycoprotein hormone alpha 2); MAP4K2 (mitogen-activated protein kinase kinase kinase 2); MEN1 (multiple endocrine neoplasia I); MRPL49 (mitochondrial ribosomal protein L49); NAALADL1 (N-acetylated alpha-linked acidic dipeptidase-like 1); POLA2 (polymerase (DNA directed), alpha 2 (70 kD subunit)); PPP2R5B (protein phosphatase 2, regulatory subunit B', beta isoform); SAC3D1 SAC3 (domain containing 1); SLC22A20 (solute carrier family 22, member 20); SNX15 (sorting nexin 15); SPDYC (speedy homolog C (Drosophila)); SYVN1(synovial apoptosis inhibitor 1, synoviolin); TM7SF2 (transmembrane 7 superfamily member 2); ZFPL1 (zinc finger protein-like 1); ZNHIT2 (zinc finger, HIT type 2); (hsa-mir-192); and (hsa-mir-194-2).

4. The method of claim 1, wherein the marker Chr 11, 64.8-65.7 Mb comprises nucleotide sequences encoding BANF1 (barrier to autointegration factor 1); CATSPER1 (cation channel, sperm associated 1); CCDC85B (coiled-coil domain containing 85B); CDC42EP2CDC42 (effector protein (Rho GTPase binding) 2); CFL1 (cofilin 1 (non-muscle)); CST6 (cystatin E/M); CTSW (cathepsin W); DPF2 D4, (zinc and double PHD fingers family 2); DRAP1 (DR1-associated protein 1 (negative cofactor 2 alpha)); EFEMP2(EGF-containing fibulin-like extracellular matrix protein 2); EHBP1L1 (EH domain binding protein 1-like 1); FAM89B (family with sequence similarity 89, member B); FIBP (fibroblast growth factor (acidic) intracellular binding protein); FOSL1 (FOS-like antigen 1); FRMD8(FERM domain containing 8); GAL3ST3 (galactose-3-O-sulfotransferase 3); HTATIP (HIV-1 Tat interacting protein, 60 kDa); KCNK7 (potassium channel, subfamily K, member 7); LTBP3 (latent transforming growth factor beta binding protein 3); MAP3K11 (mitogen-activated protein kinase kinase kinase 11); MGC11102 (hypothetical protein MGC11102); MUS81 (endonuclease homolog (S. cerevisiae)); OVOL1 (ovo-like 1 (Drosophila)); PACS1(phosphofurin acidic cluster sorting protein 1); PCNXL3 (pecanex-like 3 (Drosophila)); POLA2 (polymerase (DNA directed), alpha 2 (70 kD subunit)); RELA (v-rel reticuloendotheliosis viral oncogene homolog A, nuclear factor of kappa light polypeptide gene enhancer in B-cells 3, p65 (avian)); RNASEH2C (ribonuclease H2, subunit C); SART1 (squamous cell carcinoma antigen recognized by T cells); SCYL1 (SCY1-like 1 (S. cerevisiae)); SF3B2 (splicing factor 3b, subunit 2, 145 kDa); SIPA1 (signal-induced proliferation-associated gene 1); SLC25A45 (solute carrier family 25, member 45); SSSCA1(Sjogren syndrome/scleroderma autoantigen 1); TIGD3 (tigger transposable element derived 3); and TSGA101P (testis specific, 10 interacting protein).

5. The method of claim 1, wherein the in situ hybridization is performed with at least one nucleic acid probe that is fluorescently labeled.

6. The method of claim 5, wherein the in situ hybridization is performed with at least two nucleic acid probes.

7. The method of claim 1, wherein the in situ hybridization is performed with a peptide nucleic acid probe.

8. The method of claim 1, which comprises obtaining a lung tissue sample from a patient.

9. The method of claim 8, wherein the lung tissue sample is a lung cancer sample.

10. The method of claim 9, wherein the lung cancer is non-small-cell lung cancer.

11. The method of claim 1, wherein the patient is being treated with chemotherapy, radiation, surgery, or any combination thereof.

\* \* \* \* \*